US00RE49816E

(19) United States
(12) Reissued Patent
Lin et al.

(10) Patent Number: US RE49,816 E
(45) Date of Reissued Patent: Jan. 30, 2024

(54) DIPEPTIDES AS INHIBITORS OF HUMAN IMMUNOPROTEASOMES

(71) Applicant: CORNELL UNIVERSITY, Ithaca, NY (US)

(72) Inventors: Gang Lin, Forest Hills, NY (US); Carl Nathan, Larchmont, NY (US); Aihao Ding, Riverdale, NY (US); Xiaojing Ma, Fort Lee, NJ (US)

(73) Assignee: CORNELL UNIVERSITY, Ithaca, NY (US)

(21) Appl. No.: 16/893,086

(22) Filed: Jun. 4, 2020

Related U.S. Patent Documents

Reissue of:
(64) Patent No.: 9,988,421
Issued: Jun. 5, 2018
Appl. No.: 15/110,000
PCT Filed: Jan. 12, 2015
PCT No.: PCT/US2015/011022
§ 371 (c)(1),
(2) Date: Jul. 6, 2016
PCT Pub. No.: WO2015/106200
PCT Pub. Date: Jul. 16, 2015

U.S. Applications:
(60) Provisional application No. 61/926,062, filed on Jan. 10, 2014.

(51) Int. Cl.

| | |
|---|---|
| ***C07K 5/072*** | (2006.01) |
| ***C07K 5/078*** | (2006.01) |
| ***C07K 5/062*** | (2006.01) |
| ***C07K 5/097*** | (2006.01) |
| ***C07K 5/083*** | (2006.01) |
| ***C07K 5/06*** | (2006.01) |
| ***C07K 5/068*** | (2006.01) |
| ***A61K 38/00*** | (2006.01) |

(52) U.S. Cl.
CPC ..... *C07K 5/06104* (2013.01); *C07K 5/0606* (2013.01); *C07K 5/06026* (2013.01); *C07K 5/06069* (2013.01); *C07K 5/06086* (2013.01); *C07K 5/06113* (2013.01); *C07K 5/06139* (2013.01); *C07K 5/06191* (2013.01); *C07K 5/0806* (2013.01); *C07K 5/0821* (2013.01); *A61K 38/00* (2013.01)

(58) Field of Classification Search
CPC ..... C07K 5/06104; C07K 5/06026; C07K 5/0606; C07K 5/06069; C07K 5/06086; C07K 5/06113; C07K 5/06139; C07K 5/06191; C07K 5/0806; C07K 5/0821; A61K 38/00
See application file for complete search history.

(56) References Cited

U.S. PATENT DOCUMENTS

| | | | | |
|---|---|---|---|---|
| 5,763,604 | A | 6/1998 | Ackermann et al. | |
| 7,001,921 | B1 | 2/2006 | Adams et al. | |
| 8,048,911 | B2 | 11/2011 | Ogata | |
| 8,367,668 | B2 | 2/2013 | Stieber et al. | |
| 11,066,397 | B2 | 7/2021 | Lin et al. | |
| 11,202,817 | B2 | 12/2021 | Lin et al. | |
| 11,203,613 | B2 | 12/2021 | Lin et al. | |
| 2005/0171146 | A1 | 8/2005 | Weber et al. | |
| 2006/0241056 | A1* | 10/2006 | Orlowski | C07K 5/06078 514/1.9 |
| 2007/0010515 | A1 | 1/2007 | Masuda et al. | |
| 2007/0244153 | A1 | 10/2007 | Kakimoto et al. | |
| 2009/0227601 | A1 | 9/2009 | Zhu et al. | |
| 2010/0249197 | A1 | 9/2010 | Watkins et al. | |
| 2010/0249400 | A1 | 9/2010 | Shiina | |
| 2013/0053303 | A1 | 2/2013 | Shenk et al. | |
| 2013/0072422 | A1 | 3/2013 | Shenk et al. | |
| 2014/0315786 | A1 | 10/2014 | Jirousek et al. | |
| 2018/0221431 | A1 | 8/2018 | Lin et al. | |
| 2018/0282317 | A1 | 10/2018 | Lin et al. | |
| 2020/0317729 | A1 | 10/2020 | Lin et al. | |
| 2021/0171514 | A1 | 6/2021 | Lin et al. | |
| 2022/0056073 | A1 | 2/2022 | Lin et al. | |
| 2022/0080022 | A1 | 3/2022 | Lin et al. | |

FOREIGN PATENT DOCUMENTS

| | | | |
|---|---|---|---|
| CN | 1984880 | A | 6/2007 |
| CN | 102807601 | A | 12/2012 |
| IN | 101506224 | A | 8/2009 |
| JP | 2006-298785 | A | 11/2006 |
| JP | 2008-512476 | A | 4/2008 |
| JP | 2014-091731 | | 5/2014 |

(Continued)

OTHER PUBLICATIONS

Rowe, R. C. Editor, Handbok of Pharmaceutical Excipients, Sixth Edition, 2009 (Year: 2009).*
International Search Report and Written Opinion for corresponding Application No. PCT/US2015/044876 (dated Nov. 13, 2015).
Pubchem. SID 132358420. Jan. 24, 2012, pp. 1-6 [online], [retrieved on Oct. 1, 2015] Retrieved from the Internet <URL: http://pubchem.ncbi.nih.gov/substance/132358420>; p. 3, formula.
Pubchem. SID 132071324. Jan. 24, 2012, pp. 1-6 [online], [retrieved on Oct. 1, 2015]. Retrieved from the Internet <URL: http://pubchem.ncbi.nih.gov/substance/132071324>;p. 3, formula.
Pubchem. SID 146191084. Oct. 10, 2012, pp. 1-6 [online]. [retrieved on Oct. 10, 2015]. Retrieved from the Internet <URL: http://pubchem.ncbi.nih.gov/substance/146191084>;p. 3, formula.

(Continued)

*Primary Examiner* — Dwayne C. Jones
*Assistant Examiner* — Sharon Turner
(74) *Attorney, Agent, or Firm* — Troutman Pepper Hamilton Sanders LLP (Rochester)

(57) ABSTRACT

The compounds of the present invention are represented by the following compounds having Formula (I) where the substituents $R^1$-$R^{10}$, X, Y, k, m, n, q, and s are as defined herein. These compounds are used in the treatment of cancer, immunologic disorders, autoimmune disorders, neurodegenerative disorders, or inflammatory disorders or for providing immunosuppression for transplanted organs or tissues.

76 Claims, 9 Drawing Sheets

(56) References Cited

FOREIGN PATENT DOCUMENTS

| | | | |
|---|---|---|---|
| JP | 2014-167005 | A | 9/2014 |
| WO | 98/29387 | A1 | 7/1998 |
| WO | 2006/009134 | A1 | 1/2006 |
| WO | 2006/029210 | A2 | 3/2006 |
| WO | 2006/065826 | A2 | 6/2006 |
| WO | 2006/099261 | A2 | 9/2006 |
| WO | 2007/083394 | A1 | 7/2007 |
| WO | 2007/149512 | A2 | 12/2007 |
| WO | 2009/051581 | A1 | 4/2009 |
| WO | 2010/036357 | A1 | 4/2010 |
| WO | 2010/038200 | A1 | 4/2010 |
| WO | 2011/123502 | A1 | 10/2011 |
| WO | 2012/065891 | A1 | 5/2012 |
| WO | 2012/116440 | A1 | 9/2012 |
| WO | 2013/005045 | A1 | 1/2013 |
| WO | 2013/092979 | A1 | 6/2013 |
| WO | 2014/095773 | A1 | 6/2014 |
| WO | 2015/076359 | A1 | 5/2015 |
| WO | 2015/106200 | A2 | 7/2015 |
| WO | 2016/028571 | A2 | 2/2016 |
| WO | 2017/066763 | A1 | 4/2017 |
| WO | 2019/075252 | A1 | 4/2019 |

OTHER PUBLICATIONS

Pubchem. SID 144773390. Oct. 18, 2012, pp. 1-6 [online], [retrieved on Oct. 1, 2015]. Retrieved from the Internet <URL: http://pubchem.ncbi.nih.gov/substance/144773390>; p. 3, formula.

Allen et al., "Analysis of the Cytosolic Proteome in a Cell Culture Model of Familial Amyotrophic Lateral Sclerosis Reveals Alterations to the Proteasome, Antioxidant Defenses, and Nitric Oxide Synthetic Pathways," J. Biol. Chem. 278:6371-6383 (2003).

Basler et al., "Prevention of Experimental Colitis by a Selective Inhibitor of the Immunoproteasome," J. Immunol. 185:634-641 (2010).

Basler et al., "Inhibition of the Immunoproteasome Ameliorates Experimental Autoimmune Encephalomyelitis," EMBO Mol. Med. 6:226-238 (2014).

Baumeister et al., "The Proteasome: Paradigm of a Self-Compartmentalizing Protease," Cell 92:367-380 (1998).

Bedford et al., "Ubiquitin-Like Protein Conjugation and the Ubiquitin-Proteasome System as Drug Targets," Nat. Rev. Drug Discov. 10:29-46 (2011).

Bontscho et al., "Myeloperoxidase-Specific Plasma Cell Depletion by Bortezomib Protects From Anti-Neutrophil Cytoplasmic Autoantibodies-Induced Glomerulonephritis," J. Am. Soc. Nephrol. 22:336-348 (2011).

Brun, "Proteasome Inhibition as a Novel Therapy in Treating Rheumatoid Arthritis," Med. Hypotheses 71:65-72 (2008).

Egerer et al., "Tissue-Specific Up-Regulation of the Proteasome Subunit beta5i (LMP7) in Sjogren's Syndrome," Arthritis Rheum. 54:1501-1508 (2006).

El-Hashim et al., "Effect of Inhibition of the Ubiquitin-Proteasome-System and IkappaB Kinase on Airway Inflammation and Hyperresponsiveness in a Murine Model of Asthma," Int. J. Immunopathol. Pharmacol. 24:33-42 (2011).

Elliott et al., "Proteasome Inhibition: A Novel Mechanism to Combat Asthma," J. Allergy Clin. Immunol. 104:294-300 (1999).

Goldberg, "Functions of the Proteasome: From Protein Degradation and Immune Surveillance to Cancer Therapy," Biochem. Soc. Trans. 35:12-17 (2007).

Guillaume et al., "Two Abundant Proteasome Subtypes That Uniquely Process Some Antigens Presented by HLA Class I Molecules," Proc. Natl. Acad. Sci. U.S.A. 107:18599-18604 (2010).

Henry et al., "Proteolytic Activity and Expression of the 20S Proteasome are Increased in Psoriasis Lesional Skin," Br. J. Dermatol. 165:311-320 (2011).

Hirai, et al., "Bortezomib Suppresses Function and Survival of Plasmacytoid Dendritic Cells by Targeting Intracellular Trafficking of Toll-Like Receptors and Endoplasmic Reticulum Homeostasis," Blood 117:500-509 (2011).

Huber et al., "Immuno- and Constitutive Proteasome Crystal Structures Reveal Differences in Substrate and Inhibitor Specificity," Cell 148:727-738 (2012).

Huber et al., "Inhibitors for the Immuno- and Constitutive Proteasome: Current and Future Trends in Drug Development," Angew Chem. Int. Ed Engl. 51:8708-8720 (2012).

Ichikawa et al., "Novel Proteasome Inhibitors Have a Beneficial Effect in Murine Lupus via the Dual Inhibition of Type I Interferon and Autoantibody-Secreting Cells," HHS Public Access Author Manuscript, Available in PMC Sep. 28, 2015, 19 pages, Published in final edited form as: Arthritis Rheum. 64(2):493-503 (2012).

Inoue et al., "The Effect of Proteasome Inhibitor MG132 on Experimental Inflammatory Bowel Disease," Clin. Exp. Immunol. 156:172-82 (2009).

Kincaid et al., "Mice Completely Lacking Immunoproteasomes Display Major Alternatives in Antigen Presentation," HHS Public Access Author Manuscript, Available in PMC Aug. 1, 2012, 18 pages, Published in final edited form as: Nat. Immunol. 13(2):129-135 (2012).

Lang et al., "The Early Marginal Zone B Cell-Initiated T-Independent Type 2 Response Resists the Proteasome Inhibitor Bortezomib," J. Immunol. 185:5637-5647 (2010).

Liang et al., "Proteasome Inhibition in Transplantation-Focusing on the Experience with Bortezomib," Curr. Pharm. Design 19:3299-3304.

Meng et al., "Epoxomicin, a Potent and Selective Proteasome Inhibitor, Exhibits in Vivo Antiinflammatory Activity," P. Natl. Acad. Sci. U.S.A. 96:10403-10408 (1999).

Minagar et al., "Plasma Ubiquitin-Proteasome System Profile in Patients With Multiple Sclerosis: Correlation With Clinical Features, Neuroimaging, and Treatment With Interferon-Beta-1 b," Neurol. Res. 34:611-618 (2012).

Muchamuel et al., "A Selective Inhibitor of the Immunoproteasome Subunit LMP7 Blocks Cytokine Production and Attenuates Progression of Experimental Arthritis," Nat. Med. 15:781-787 (2009).

Neubert et al., "The Proteasome Inhibitor Bortezomib Depletes Plasma Cells and Protects Mice With Lupus-Like Disease From Nephritis," Nat. Med. 14:748-755 (2008).

Niewerth et al., "Anti-Leukemic Activity and Mechanisms Underlying Resistance to the Novel Immunoproteasome Inhibitor PR-924," Biochem. Pharmacol. 89:43-51 (2014).

Padrissa-Altes et al., "The use of a Reversible Proteasome Inhibitor in a Model of Reduced-Size Orthotopic Liver Transplantation in Rats," Exp. Mol. Pathol. 93:99-110 (2012).

Perkins, "Integrating Cell-Signalling Pathways With NF-[kappa]B and IKK Function," Nat. Rev. Mol. Cell. Biol. 8:49-62 (2007).

Roccaro et al., "Selective Inhibition of Chymotrypsin-Like Activity of the Immunoproteasome and Constitutive Proteasome in Waldenstrom Macroglobulinemia," Blood 115:4051-4060 (2010).

Rock et al., "Proteases in MHC Class I Presentation and Cross-Presentation," NIH Public Access Author Manuscript, Available in PMC May 13, 2011, 16 pages, Published in final edited form as: J. Immunol. 184 (1):9-15 (2010).

Rock et al., "Inhibitors of the Proteasome Block the Degradation of Most Cell Proteins and the Generation of Peptides Presented on MHC Class I Molecules," Cell 78:761-771 (1994).

Rock et al., "Protein Degradation and the Generation of MHC Class I-Presented Peptides," Adv. Immunol 80:1-70 (2002).

Schmidt et al., "Targeting the Proteasome: Partial Inhibition of the Proteasome by Bortezomib or Deletion of the Immunosubunit LMP7 Attenuates Experimental Colitis," Gut 59:896-906 (2010).

Singh et al., "PR-924, a Selective Inhibitor of the Immunoproteasome Subunit LMP-7, Blocks Multiple Myeloma Cell Growth Both in Vitro and in Vivo," NIH Public Access Author Manuscript, Available in PMC Jan. 1, 2012, 15 pages, Published in final edited form as: Br. J. Haematol. 152:155-163 (2011).

Sureshkumar et al., "Proteasome Inhibition With Bortezomib: an Effective Therapy for Severe Antibody Mediated Rejection After Renal Transplantation," Clin. Nephrol. 77: 246-253 (2012).

Van der Heijden et al., "The Proteasome Inhibitor Bortezomib Inhibits the Release of NFkappaB-Inducible Cytokines and Induces Apoptosis of Activated T Cells From Rheumatoid Arthritis Patients," Clin. Exp. Rheumatol. 27:92-98 (2009).

(56) References Cited

OTHER PUBLICATIONS

Verbrugge et al., "Inactivating PSMB5 Mutations and P-glycoprotein (Multidrug Resistance-Associated Protein/ATP-Binding Cassette B1) Mediate Resistance to Proteasome Inhibitors: ex Vivo Efficacy of (Immuno)Proteasome Inhibitors in Mononuclear Blood Cells From Patients With Rheumatoid Arthritis," J. Pharmacol. Exp. Ther. 341:174-182 (2012).
Zhang et al., "In Vitro and in Vivo Therapeutic Efficacy of Carfilzomib in Mantle Cell Lymphoma: Targeting the Immunoproteasome," Mol. Cancer Ther. 12:2494-2504 (2013).
Zollner et al., "Proteasome Inhibition Reduces Superantigen-Mediated T Cell Activation and the Severity of Psoriasis in a SCID-hu Model," J. Clin. Invest. 109:671-679(2002).
DFHBI IT Datasheet (Lucerna).
International Preliminary Report on Patentability for Application No. PCT/US2015/044876 (dated Feb. 21, 2017).
Supplementary European Search Report dated Mar. 27, 2018 for EP Application Serial No. 15834073.7.
Fuchise et al., "Atlantic Cod Trypsin-Catalyzed Peptide Synthesis with Inverse Substrates as Acyl Donor Components," Chem. Pharm. Bull. 58(4):484-487 (2010).
Notice of Reasons for Rejection for Japanese Patent Application No. 2017-509632 (dated Jun. 5, 2019).
Coumar et al., "3-[2-((2S)-2-Cyano-pyrrolidin-1-yl)-2-oxo-ethylamino]-3-methyl-butyramide Analogues as Selective DPP-IV Inhibitors for the Treatment of Type-II Diabetes," Bioorg. Med. Chem. Lett. 17(5):1274-1279 (2007).
Drey et al., "Synthesis of β-Amino-Acid Peptides by Aminolysis of Substituted Di-hydro-1,3-oxazinones and Amino-Protected β-Lactams," Perkin Transactions 1, J. Chem. Soc. 17:2001-2006 17:2001-2006 (1973).
Liotta et al., "Antibody-Catalyzed Rearrangement of a Peptide Bond: Mechanistic and Kinetic Investigations," J. Am. Chem. Soc. 117(17):4729-4741 (1995).
Examination Report for Indian Patent Application No. 201747005687 (dated Aug. 29, 2019).
Singh et al., "Immunoproteasome β5i-Selective Dipeptidomimetic Inhibitors," ChemMedChem 11:1-6 (2016).
El-Naggar et al., "Synthesis and Biological Activity of Some New 4-(Aminoacyl)Aminopyridines and 2-(Aminoacyl) Aminopyrimidine Derivatives," Polish Journal of Chemistry, 56:1279-1285 (1982).
Yamazaki et al., "Two New Tryptamine Derivatives, Leptoclinidamide and (−)-Leptoclinidamine B, from an Indonesian Ascidian Leptoclinides dubius," Marine Drugs, 10(12):349-357 (2012).
Examination report for Europe Patent Application No. 15834073.7 (dated Mar. 25, 2020).
Database Registry Database accession No. 1299989-71-1.
Database Registry Database accession No. 1276335-00-2.
Database Registry Database accession No. 1060993-03-4.
Extended European Search Report for EP Application Serial No. 18867283.6 (dated Sep. 27, 2021).
El-Naggar et al., "Database CA [Online]: 'Synthesis and Biological Activity of Some New 4-(Aminoacyl) Aminopyridines and 2-(Aminoacyl)Aminopyrimidine Derivatives,'" Polish Journal of Chemistry, 56:1279-1285 (1982).
Office Action for U.S. Appl. No. 15/768,628 (dated Oct. 11, 2019).
CAS Registry No. 3641-55-2, Entered STN: Nov. 16, 1984.
CAS Registry No. 294889-15-9, Entered STN: Oct. 12, 2000.
CAS Registry No. 51219-75-1, Entered STN: Nov. 16, 1984.
CAS Registry No. 51219-69-3, Entered STN: Nov. 16, 1984.
CAS Registry No. 59973-55-6, Entered STN: Nov. 16, 1984.
Duke et al., "Synthesis and Biological Evaluation of Sparsomycin Analogues," J. Med. Chem. 26:1556-1561 (1983).
Baud et al., "Defining the Mechanism of Action and Enzymatic Selectivity of Psammaplin A against Its Epigenetic Targets," J. Med. Chem. 55:1731-1750 (2012).
CAS Registry No. 839730-13-1, Entered STN: Mar. 1, 2005.
CAS Registry No. 839730-22-2, Entered STN: Mar. 1, 2005.
CAS Registry No. 839730-21-1, Entered STN: Mar. 1, 2005.
CAS Registry No. 866779-17-1, Entered STN: Nov. 4, 2005.
CAS Registry No. 1461869-28-2, Entered STN: Oct. 21, 2013.
CAS Registry No. 50633-04-0, Entered STN: Nov. 16, 1984.
CAS Registry No. 87639-77-8, Entered STN: Nov. 16, 1984.
CAS Registry No. 120655-16-5, Entered STN: May 12, 1989.
Translation of the Office Action for Chinese Patent Application No. 201580056519.4 (dated Jun. 29, 2020).
Office Action for U.S. Appl. No. 15/110,000 (dated Jun. 5, 2017).
Beaumont et al. "Design of Ester Prodrugs to Enhance Oral Absorption of Poorly Permeable Compounds: Challenges to the Discovery Scientist" Curr. Drug Metab. 4:461-485. (2003).
Vippagunta et al. "Crystalline Solids" Advanced Drug Delivery Reviews 48:3-26. (2001).
Hook et al. "The Proteolytic Stability of 'Designed' [beta]-Peptides Containing [alpha]-Peptide-Bond Mimics and of Mixed [alpha, beta]-Peptides: Application to Construction of MHC-Binding Peptides" Chemistry & Biodiversity 2:591-632 (2005).
Office Action for U.S. Appl. No. 15/504,951 (dated Sep. 10, 2020).
Office Action in Chinese Patent Application No. 201680065296.2 (dated Sep. 28, 2020).
Office Action in European Application No. 16856412.8 (dated Sep. 16, 2020).
Notice of Reasons for Rejection for Japanese Patent Application No. 2018-519271 (dated Oct. 22, 2020).
Korshin et al., "Aminoamidines. 7.* 2-(Arylaminomethyl)imidazolines and Their Acylated Derivatives," Izvestiya Akademii Nauk, Seriya Khimicheskaya 3:472-479 (1994) with English translation as Korshin et al., "Aminoamidines. 7.* 2-(Arylaminomethyl)imidazolines and Their Acylated Derivatives," Russ. Chem. Bull. 43(3):431-438 (1994).
Grudzinski et al., "Studia nad Procesami Uwodornienia Aminonitryli. IX. Otrzymywanie N,N'-Dwuacylo-Trojmetylenodwuamin o Niejednakowych Resztach Kwasowych w Czateczce [Studies on the Hydrogenation of Aminonitriles. IX. Synthesis of N,N'-Diacyl-trimethylenediamines Containing Different Acyl Residues]," Acta Poloniae Pharmaceutica 22(6):485-490 (1965) (Article in Polish, English Title and Summary at pp. 489-490).
Restriction Requirement for U.S. Appl. No. 15/110,000 (dated Mar. 6, 2017).
Office Action for EP Application Serial No. 15834073.7 (dated Mar. 4, 2022).
Extended European Search Report for EP Application Serial No. 21216660.7 (dated Mar. 29, 2022).
Supplementary European Search Report for EP Application Serial No. 18867283.6 (dated Oct. 14, 2021).
Lei et al., "Structural Features and Binding Free Energies for Non-Covalent Inhibitors Interacting with Immunoproteasome by Molecular Modeling and Dynamics Simulations," Theor. Chem. Acc. 131:1-11 (2012).
Blackburn et al., "Characterization of a new Series of Non-Covalent Proteasome Inhibitors with Exquisite Potency and Selectivity for the 20S Beta5-Subunit," Biochem. J. 430:461-476 (2010).
Blackburn et al. "Optimization of a Series of Dipeptides with a P3 Beta-Neopentyl Asparagine Residue as Non-Covalent Inhibitors of the Chymotrypsin-Like Activity of the Human 20S Proteasome," Med. Chem. Commun. 3:710-719 (2012).
International Preliminary Report on Patentability and Written Opinion for PCT/US2015/011022 (dated Jul. 21, 2016).
Pubchem: Compound Summary for CID 269632 (Mar. 26, 2005).
Office Action for European Patent Application No. 15735399.6 (dated Jun. 11, 2018).
Pubchem. CID 17857389. Dec. 4, 2007, pp. 1-13[online], [retrieved on Feb. 27, 2017] Retrieved from the Internet <URL: https://pubchem.ncbi.nlm.nih.gov/compound/17857389; p. 4, formula.
PCT International Search Report and Written Opinion corresponding to PCT/US2016/057346, dated Mar. 23, 2017.
International Preliminary Report on Patentability for Application No. PCT/US2016/057346 (dated Apr. 17, 2018).
Extended European Search Report and Opinion for European Application No. 16856412.8 dated Mar. 22, 2019.
Solomon et al., "Synthesis and Antimalarial Activity of Novel Side Chain Modified Antimalarial Agents Derived From 4-Aminoquinoline," Medicinal Chemistry, 4:446-456 (2008).

(56) References Cited

OTHER PUBLICATIONS

Office Action in Chinese Patent Application No. 201680065296.2 (dated Dec. 4, 2019).
Pubchem CID 91250924, https://pubchem.ncbi.nlm.nih.gov/compound/91250924, Retrieved Nov. 24, 2019.
International Search Report and Written Opinion for corresponding Application No. PCT/2018/055482 (dated Feb. 8, 2019).
Pubchem CID 64894495, Oct. 23, 2012 (Accession date Nov. 29, 2018).
Pubchem CID 129847054, Sep. 13, 2017 (Accession date Jan. 18, 2019).
Restriction Requirement for U.S. Appl. No. 15/504,951 (dated Jun. 8, 2018).
Office Action for U.S. Appl. No. 15/504,951 (dated Jun. 11, 2019).
Office Action for U.S. Appl. No. 15/504,951 (dated Oct. 12, 2018).
Ettmayer et al., "Lessons Learned from Marketed and Investigational Prodrugs," J. Med. Chem. 47:2393-2404 (2004).
Han, Hyo-Kyung "Targeted Prodrug Design to Optimize Drug Delivery," AAPS Pharmsci 2:1-11 (2000).
Muller, Christa "Prodrug Approaches for Enhancing the Bioavailability of Drugs with Low Solubility," Chemistry & Biodiversity 6:2071-2083. (2009).
Singh et al., "Recent Trends in Targeted Anticancer Prodrug and Conjugate Design," NIH Public Access Author Manuscript, Available in PMC Jan. 5, 2010, 53 pages, Published in final edited form as: Curr. Med. Chem. 15 (18):1802-1826 (2008).
Testa, Bernard "Prodrug Research: Futile or Failure?" Biochemical Pharmacology 68:2097-2106 (2004).
Office Action for U.S. Appl. No. 15/768,628 (dated May 1, 2020).
Office Action for Chinese Patent Application No. 201580056519.4 (dated May 7, 2021).
Examination Report for Indian Patent Application No. 202048025018 (dated Jun. 3, 2021).
Partial Supplementary European Search Report for EP Application Serial No. 18867283.6 (dated Jun. 23, 2021).
O'Mahony et al., "A Practical Synthesis of 2'-Aminoacylamino-2'-Deoxyadenosines," Tetrahedron 63(29): 6901-6908 (2007).
Kataoka et al., "Formation of Heterocyclic Amine—Amino Acid Adducts by Heating in a Model System," Food Chemistry 130(3):725-729 (2012).
Restriction Requirement for U.S. Appl. No. 16/755,427 (dated Dec. 21, 2020).
Muchamuel et al., "A Selective Inhibitor of the Immunoproteasome Subunit LMP7 Blocks Cytokine Production and Attenuates Progression of Experimental Arthritis," Nature Medicine 15(7):781-787 (2009).
Ichikawa et al., "Beneficial Effect of Novel Proteasome Inhibitors in Murine Lupus via Dual Inhibition of Type I Interferon and Autoantibody-Secreting Cells," Arthritis & Rheumatism 64(2):493-503 (2012).
Mutlu et al., "Proteasomal Inhibition After Injury Prevents Fibrosis by Modulating TGF-b1 Signalling," Thorax 67:139-146 (2012).
Mitsiades et al., "Proteasome Inhibition as a New Therapeutic Principle in Hematological Malignancies," Current Drug Targets 7:1341-1347 (2006).
Orlowski "The Ubiquitin Proteasome Pathway from Bench to Bedside," Hematology 220-225 (2005).
Fisher et al., "Multicenter Phase II Study of Bortezomib in Patients With Relapsed or Refractory Mantle Cell Lymphoma," J. Clin. Oncol. 24(30):4867-4874 (2006).
Walsh et al., "Proteasome Inhibitor-Based Primary Therapy for Antibody-Mediated Renal Allograft Rejection," Transplantation 89(3):277-284 (2010).
Mateos-Mazon et al., "Use of Bortezomib in the Management of Chronic Graft-Versus-Host Disease Among Multiple Myeloma Patients Relapsing After Allogeneic Transplantation," Haematologica 92(9):1295-1296 (2007).
Kloda, "Systemic Sclerosis—Bortezomib—is it Wonder Drug?," MEDtube.net (2011) https://medtube.net/tribune/systemic-sclerosis-bortezomib-is-it-wonder-drug/.
Office Action for U.S. Appl. No. 15/504,951 (dated Mar. 26, 2021).
International Preliminary Report on Patentability for Application No. PCT/2018/055482 (dated Apr. 14, 2020).
Office Action in Chinese Patent Application No. 201680065296.2 (dated Apr. 30, 2021).
Office Action for U.S. Appl. No. 17/521,328 (dated Nov. 1, 2022).
Office Action for U.S. Appl. No. 17/177,729 (dated Mar. 21, 2022).
Notice of Reasons for Rejection for Japanese Patent Application No. 2021-176164 (dated Dec. 8, 2022).
Blackburn et al. Optimization of a series of dipeptides with a P3 beta-neopentyl asparagine residue as non-covalent inhibitors of the chymotrypsin-like activity of human 20S proteasome. Med Chem Commun, 2012 (published Apr. 19, 2012), vol. 3, pp. 710-719.*
International Preliminary Report on Patentability and Written Opinion for PCT/US2015/011022 (dated Jul. 12, 2016).
International Search Report and Written Opinion for corresponding Application No. PCT/US2015/011022 (dated Jun. 24, 2015).
PubChem: Compound Summary for CID 269632 (Mar. 26, 2005) https://pubchem.ncbi.nim.nih.gov/compound/269632?from=summary>.
Lin et al., "N,C-Capped Dipeptides with Selectivity for Mycobacterial Proteasome Over Human Proteasomes: Role of S3 and S1 Binding Pockets," J. Am. Chem. Soc. 135:9968-9971 (2013).
Supplementary European Search Report for European Patent Application No. 15735399.6 (dated Jun. 29, 2017).
Lei et al., "Structural Features and Binding Free Energies for Non-Covalent Inhibitors Interacting with Immunoproteasome by Molecular Modeling and Dynamics Simulations," Theor. Chem. Acc. 131:2-11 (2012).
Blackburn et al., "Chracterization of a new Series of Non-Covalent Proteasome Inhibitors with Exquisite Potency and Selectivity for the 20S Beta5-Subunit," Biochem. J. 430:461-476 (2010).
Siebler et al., "Molecular Mutil-Wavelength Optical Anion Sensors," Eur. J. Inorg. Chem. 523-527 (2010).
Ahlford et al., "Fine-Tuning Catalytic Activity and Selectivity-[Rh(Amino Acid Thioamide)] Complexes for Efficient Ketone Reduction," Tetrahedron Lett. 50:6321-6324 (2009).

* cited by examiner

A

B

C

A

DPLG-3 dose-dependently reduced the growth of 4T1 Tumor in mice

B

Tumor Weight (mg)

DIPEPTIDES AS INHIBITORS OF HUMAN IMMUNOPROTEASOMES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application *is an application for reissue of U.S. Pat. No. 9,988,421, issued Jun. 5, 2018, filed as U.S. patent application Ser. No. 15/110,000, which* is a national stage application under 35 U.S.C. § 371 of PCT Application No. PCT/US2015/011022, filed Jan. 12, 2015, which claims the benefit of U.S. Provisional Patent Application Ser. No. 61/926,062, filed Jan. 10, 2014, which are hereby incorporated by reference in their entirety.

FIELD OF THE INVENTION

The present invention relates to inhibitors of human immunoproteasomes.

BACKGROUND OF THE INVENTION

The proteasome is a large, ATP-dependent, multi-subunit, barrel-shaped N-terminal nucleophile hydrolase present in the cytosol and nucleus of eukaryotic cells, and is responsible for the degradation of the majority of cellular proteins (Baumeister et al., "The Proteasome: Paradigm of a Self-Compartmentalizing Protease," Cell 92:367-380 (1998); Goldberg, A. L., "Functions of the Proteasome: From Protein Degradation and Immune Surveillance to Cancer Therapy," Biochemical Society Transactions 35:12-17 (2007)). The proteasome not only controls many critical cellular checkpoints through degradation, but also generates peptides for antigen presentation (Goldberg, A. L., "Functions of the Proteasome: From Protein Degradation and Immune Surveillance to Cancer Therapy," Biochemical Society Transactions 35:12-17 (2007); Rock et al., "Inhibitors of the Proteasome Block the Degradation of Most Cell Proteins and the Generation of Peptides Presented on MHC Class I Molecules," Cell 78:761-771 (1994)). Highly specific proteasome inhibitors can markedly limit the overall supply of peptides for MHC class I molecules and thus block antigen presentation (Rock et al., "Protein Degradation and the Generation of MHC Class I-Presented Peptides," Advances in Immunology 80:1-70 (2002)). The constitutive proteasome core particle is called 20S (c-20S) because of its sedimentation properties. Inside the c-20S core reside two copies of each of three proteases with distinct specificities, β1 (caspase-like), β2 (tryptic-like) and β5 (chymotrypticlike) (Bedford et al., "Ubiquitin-Like Protein Conjugation and the Ubiquitin-Proteasome System as Drug Targets," Nature Reviews. Drug Discovery 10:29-46 (2011)). However, lymphocytes and cells that have responded to interferon-γ express a different proteasome, called the immunoproteasome (i-20S), in which the corresponding proteases are the products of different genes: β1i, β2i and P5i. Intermediate proteasomes that contain mixed β subunits are found in many cells, for example in the mucosa of the colon and small bowel (Guillaume et al., "Two Abundant Proteasome Subtypes that Uniquely Process Some Antigens Presented by HLA Class I Molecules," Proc. Nat'l Acad. Sci. USA 107:18599-18604 (2010)). The effects of replacement of constitutive subunits by immuno-β subunits include increased proteolytic activity and altered peptide preferences of the active sites (Rock et al., "Proteases in MHC Class I Presentation and Cross-Presentation," Journal of Immunology 184:9-15d (2010)). For example, the caspase-like β1 replacement, βi, preferentially cleaves after small hydrophobic residues rather than after aspartate (Huber et al., "Immuno- and Constitutive Proteasome Crystal Structures Reveal Differences in Substrate and Inhibitor Specificity," Cell 148:727-738 (2012)). This results in altered peptide products, such that mice with combined deficiency of β1i, β2i, and β5i are viable, fertile and healthy but express a different antigenic peptide repertoire than wild type mice, as evidenced by their rejection of syngeneic wild type splenocytes (Kincaid et al., "Mice Completely Lacking Immunoproteasomes Show Major Changes in Antigen Presentation," Nature Immunology 13:129-135 (2012)). Hu c-20S and i-20S appear to regulate cytokine production through different pathways (Muchamuel et al., "A Selective Inhibitor of the Immunoproteasome Subunit LMP7 Blocks Cytokine Production and Attenuates Progression of Experimental Arthritis," Nature Medicine 15:781-787 (2009)). Hu c-20S controls the activation of NF-κB via the degradation of IκB, the binding partner of NF-κB in the cytosol (Perkins, N.D., "Integrating Cell-Signalling Pathways with NF[Kappa]B and IKK Function," Nat. Rev. Mol. Cell Biol. 8:49-62 (2007)), and inhibition of c-20S blocks the activation of NF-κB (Meng et al., "Epoxomicin, a Potent and Selective Proteasome Inhibitor, Exhibits In Vivo Antiinflammatory Activity," Proc. Nat'l Acad. Sci. USA 96:10403-10408 (1999)). For its part, among other potential pathways, i-20S appears to control the co-translocation of TLR9 and Unc93B1, an endoplasmic reticulum (ER)-resident protein, to endosomes (Hirai et al., "Bortezomib Suppresses Function and Survival of Plasmacytoid Dendritic Cells by Targeting Intracellular Trafficking of Toll-Like Receptors and Endoplasmic Reticulum Homeostasis," Blood 117:500-509 (2011)). Proteasomes control diverse cellular functions, among them signal transduction for inflammatory cytokine release, antigen presentation, and the ability of plasma cells to secrete antibodies without dying from accumulation of misfolded immunoglobulins (Goldberg, A. L., "Functions of the Proteasome: From Protein Degradation and Immune Surveillance to Cancer Therapy," Biochemical Society Transactions 35:12-17 (2007); Bedford et al., "Ubiquitin-Like Protein Conjugation and the Ubiquitin-Proteasome System as Drug Targets," Nature Reviews. Drug Discovery 10:29-46 (2011); Neubert et al., "The Proteasome Inhibitor Bortezomib Depletes Plasma Cells and Protects Mice with Lupus-Like Disease from Nephritis," Nature Medicine 14:748-755 (2008)). Thus the proteasome could be a target for treating autoimmune and inflammatory diseases. For example, inhibition of the proteasome in plasmacytoid dendritic cells (pDCs) prevents the trafficking of TLRs, resulting in a block of nuclear translocation of IRF-7, consequently suppressing the production of IFNα (Hirai et al., "Bortezomib Suppresses Function and Survival of Plasmacytoid Dendritic Cells by Targeting Intracellular Trafficking of Toll-Like Receptors and Endoplasmic Reticulum Homeostasis," Blood 117:500-509 (2011)), a cytokine implicated in systemic lupus erythematosus (SLE). However, by the same token, widespread inhibition of proteasomes can be expected to be toxic and has proven toxic in the clinic.

Two proteasome inhibitors approved by the FDA for treatment of malignancy, Bortezomib and Carfilzomib, inhibit both the c-20S β5c and the i-20S β5i (Huber et al., "Inhibitors for the Immuno- and Constitutive Proteasome: Current and Future Trends in Drug Development," Angewandte Chemie 51:8708-8720 (2012)). Bortezomib, a dipeptidyl boronate, is a slow-binding, covalent but reversible inhibitor, whereas Carfilzomib is a peptide with an epoxyketone warhead that inhibits proteasomes irreversibly. In addition to treatment of malignancy, Bortezomib has been reported to be effective in inflammatory bowel disease (IBD), SLE, graft-versus-host disease, antibody-mediated graft rejection, rheumatoid arthritis (RA), and other immunologic, autoimmune and/or inflammatory conditions. However, such a broad-spectrum inhibitor is too toxic for chronic treatment of non-malignant diseases. ONX 0914, another peptide epoxyketone, has modest selectivity for i-20S β5i (Muchamuel et al., "A Selective Inhibitor of the Immunoproteasome Subunit LMP7 Blocks Cytokine Production and Attenuates Progression of Experimental Arthritis," Nature Medicine 15:781-787 (2009)) and is reported to have efficacy in rheumatoid arthritis (Muchamuel et al., "A Selective Inhibitor of the Immunoproteasome Subunit LMP7 Blocks Cytokine Production and Attenuates Progression of Experimental Arthritis," Nature Medicine 15:781-787 (2009)), SLE (Ichikawa et al., "Beneficial Effect of Novel Proteasome Inhibitors in Murine Lupus Via Dual Inhibition of Type I Interferon and Autoantibody-Secreting Cells," Arthritis and Rheumatism 64:493-503 (2012)), experimental colitis (Basler et al., "Prevention of Experimental Colitis by a Selective Inhibitor of the Immunoproteasome," Journal of Immunology 185:634-641 (2010)), and multiple sclerosis (Basler et al., "Inhibition of the immunoproteasome ameliorates experimental autoimmune encephalomyelitis," EMBO Mol. Med. 6:226-238 (2014)). Nonetheless, it, too, acts irreversibly and has considerable toxicity.

The present invention is directed to overcoming these and other deficiencies in the art.

SUMMARY OF THE INVENTION

One aspect of the present invention relates to a compound of Formula (I):

(I)

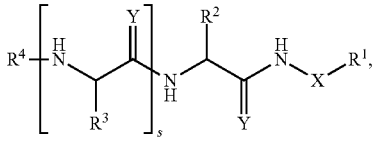

wherein $R^1$ is selected from the group consisting of monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein monocyclic and bicyclic aryl, biphenyl, monocyclic and bicyclic heteroaryl and bi-heteroaryl, monocyclic and bicyclic heterocyclyl and b-iheterocyclyl, and monocyclic and bicyclic non-aromatic heterocycle can be optionally substituted from 1 to 3 times with a substituent selected independently at each occurrence thereof from the group consisting of halogen, cyano, —$CF_3$, $C_{1-6}$ alkyl, and $C_{1-6}$ alkoxy;

$R^2$ is independently selected at each occurrence thereof from the group consisting of H, D, $C_{1-6}$ alkyl, —$CH_2OC_{1-6}$ alkyl, —$CH_2$Ar, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^3$ is independently selected at each occurrence thereof from the group consisting of H, D, —$CH_2OC_{1-6}$ alkyl, —$(CH_2)_mC(O)NHR^5$, and —$(CH_2)_mC(O)NR^6R^7$;

$R^4$ is selected from the group consisting of —$C(O)(CH_2)_1$Ph, —$C(O)CH_2NR^6R^7$, —$SO_2$Ar, —$SO_2C_{1-6}$ alkyl, —$SO_2C_{3-6}$cycloalkyl, —$C(O)(CH_2\mathbf{2}_n$,Het, —C(O)C(O)Het, —$C(O)C_{1-6}$ alkyl, —$C(O)OC_{1-6}$ alkyl, —$C(O)CF_3$, heteroaryl, —$C(O)R^{10}$, and —$(CH_2)_1NR^6R^7$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^5$ is selected from the group consisting of $C_{1-6}$ alkyl, $C_{1-6}$ alkoxy, non-aromatic heterocycle, —$NR^6R^7$, and —$CR^8R^9$;

$R^6$, $R^7$, $R^8$, and $R^9$ are each independently selected from the group consisting of H, D, $C_{1-6}$ alkyl, and $(—CH_2)_kOH$;

or $R^6$ and $R^7$ are taken together with the nitrogen to which they are attached to form a piperidine, pyrrolidine, or morpholine ring;

or $R^8$ and $R^9$ are taken together with the carbon to which they are attached to form an oxetane ring;

$R^{10}$ is monocyclic carbocycle or fused bicyclic carbocycle;

X is —$(CH_2)_q$—, —O—, or —$(CD_2)_q$—;

Y is O or S;

k is 1, 2, or 3;

m is 0, 1, 2, 3, 4, or 5;

n is 0, 1, 2, or 3;

q is 0, 1, or 2; and s is 0 or 1;

or an oxide thereof, a pharmaceutically acceptable salt thereof, a solvate thereof, or a prodrug thereof.

A second aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (I):

(I)

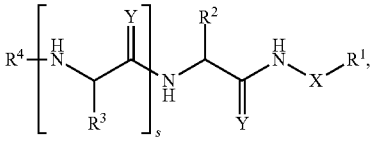

wherein $R^1$ is selected from the group consisting of monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —$CF_3$, $C_{1-6}$ alkyl, and $C_{1-6}$ alkoxy;

$R^2$ is independently selected at each occurrence thereof from the group consisting of H, D, $C_{1-6}$ alkyl, —$CH_2OC_{1-6}$ alkyl, —$CH_2$Ar, and $CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^3$ is independently selected at each occurrence thereof from the group consisting of H, D, —$CH_2OC_{1-6}$ alkyl, —$(CH_2)_mC(O)NHR^5$, and —$(CH_2)_mC(O)NR^6R^7$;

$R^4$ is selected from the group consisting of —$C(O)(CH_2)_1$Ph, —$C(O)CH_2NR^6R^7$, —$SO_2$Ar, —$SO_2C_{1-6}$ alkyl, —$SO_2C_{3-6}$cycloalkyl, —$C(O)(CH_2)_n$Het, —C(O)C(O)Het, —$C(O)C_{1-6}$ alkyl, —$C(O)OC_{1-6}$ alkyl, —$C(O)CF_3$, heteroaryl, —$C(O)R^{10}$, and —$(CH_2)_1NR^6R^7$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^5$ is selected from the group consisting of $C_{1-6}$ alkyl, $C_{1-6}$ alkoxy, non-aromatic heterocycle, —$NR^6R^7$, and —$CR^8R^9$;

$R^6$, $R^7$, $R^8$, and $R^9$ are each independently selected from the group consisting of H, D, $C_{1-6}$ alkyl, and —$(CH_2)_kOH$;

or $R^6$ and $R^7$ are taken together with the nitrogen to which they are attached to form a piperidine, pyrrolidine, or morpholine ring;

or $R^8$ and $R^9$ are taken together with the carbon to which they are attached to form an oxetane ring;

$R^{10}$ is monocyclic carbocycle or fused bicyclic carbocycle;

X is —$(CH_2)_q$—, —O—, or —$(CD_2)_q$—;

Y is O or S;

k is 1, 2, or 3;

m is 0, 1, 2, 3, 4, or 5;

n is 0, 1, 2, or 3;

q is 0, 1, or 2; and s is 0 or 1.

Selective inhibition of the i-20S is believed to impact the immune system but would otherwise be far less toxic than combined inhibition of both constitutive and immunoproteasomes. Here are presented the first inhibitors that act both with high selectivity and full reversibility on hu i-20S β5i over hu c-20S Inhibitors that are selective for the i-20S β5i are expected to be equally if not more efficacious in treating autoimmune disease, with less toxicity. These inhibitors could open a new path to the treatment of immunologic, autoimmune, inflammatory, neurodegenerative, and certain neoplastic disorders such as: systemic lupus erythematosis, chronic rheumatoid arthritis, inflammatory bowel disease, ulcerative colitis, Crohn's disease, multiple sclerosis, amyotrophic lateral sclerosis (ALS), atherosclerosis, scleroderma, systemic sclerosis, autoimmune hepatitis, Sjogren Syndrome, lupus nephritis, glomerulonephritis, rheumatoid arthritis, psoriasis, Myasthenia Gravis, Imunoglobuline A nephropathy, atherosclerosis, vasculitis, renal fibrosis, lung fibrosis, liver fibrosis, transplant rejection, idiopathic pulmonary fibrosis, asthma, and inflammation driven cancers such as: triple negative breast cancers.

BRIEF DESCRIPTION OF THE DRAWINGS

FIG. 1A shows schematic illustration of N,C-capped dipeptide. CapN represents the chemical cap on the amine terminus of the dipeptide. CapC represents the chemical cap on the carboxyl terminus of the dipeptide. P1-P4 refer to the moieties of an inhibitor, while S1-S4 refer to the subsites of the proteasome active site at which C-Cap, P2, P3 and N-Cap moieties bind, respectively. FIG. 1B shows the structure of DPLG-3.

FIG. 2A is a graph showing % body weight change relative to days post induction. For FIGS. 2B-D, first, chimeric mice with NOD2 deficiency either in the hematopoietic system or in the non-hematopoietic system were created by syngeneic bone marrow transplantation (BMT) (B6 WT→B6 $NOD2^{-/-}$ or B6 $NOD2^{-/-}$ →B6 WT). After 90 days (d), TNBS colitis was induced. Colons were harvested at day 3 after induction of colitis. Combined data from two independent experiments are shown; n=8/group. FIG. 2B is a graph showing % body weight change relative to days post induction. Greater weight loss of $NOD2^{-/-}$ →WT chimera versus WT→$NOD2^{-/-}$ chimera during colitis. FIG. 2C shows hematoxylin and eosin-stained images of the colon at day 3 after induction of colitis. Bar, 200 μm. FIG. 2D is a bar graph showing results of the histological scoring. Histological scoring showed increased colitis in the hematopoietic NOD2-deficient chimeras. Error bars show SEM.

FIG. 3A shows % body weight changes relative to days post TNBS. Neutralizing anti-IL-12/IL-23 [rat anti-mouse p40 monoclonal antibody (mAb) (C17.8)] was given intraperitoneally (i.p.) on days 0, 1, 2, and 3. The antibody was raised against p40, which is shared between IL-12 and IL-23. Sera from all mice in A were collected at the end and analyzed for p40 levels by ELISA. FIG. 3B shows p40 levels in sera. WT mice (4/group) were presensitized with TNBS (0.15 mg) at day −7, and treated with TNBS (3.0 mg) at day 0 intrarectally, and given one intravenous (i.v.) injection of DPLG-3 (6 mg/kg) at the same time. FIG. 3C shows % body weight change relative to days post TNBS with and without DPLG-3.

FIGS. 4A-B show that production of TNFa, P40, and IL12 was inhibited by DPLG-3 in a dose-dependent manner. FIG. 4C shows that the transcription of P35 and P40 was reduced by DPLG-3 in a dose-dependent manner. FIG. 4D shows DPLG-3 mitigated trinitrobenzene sulfonic acid (TNBS)-induced colitis in a dose-dependent manner.

FIG. 5A is a graph showing experimental results relating to inhibition of i-20S β5i and c-20S β5c by selected dipeptides. FIG. 5B is a graph showing inhibition of 20S inside the human Karpas lymphoma cell line assayed with cell-based Proteasome-glo™ after compound removal. FIG. 5C is an image of an SDS-page gel showing accumulation of poly-ubiquitinylated (ub) proteins. Karpas cells were treated with dipeptides, or with bortezomib as a control, at indicated concentrations for 24 hours, and the poly-ub proteins in the lysates were blotted with anti-ub antibody and visualized with a second antibody directed against the first antibody and tagged with a dye that absorbs infrared light (Odyssey® CLx imaging system, LICOR).

DETAILED DESCRIPTION OF THE INVENTION

Figures 1A, 1B:
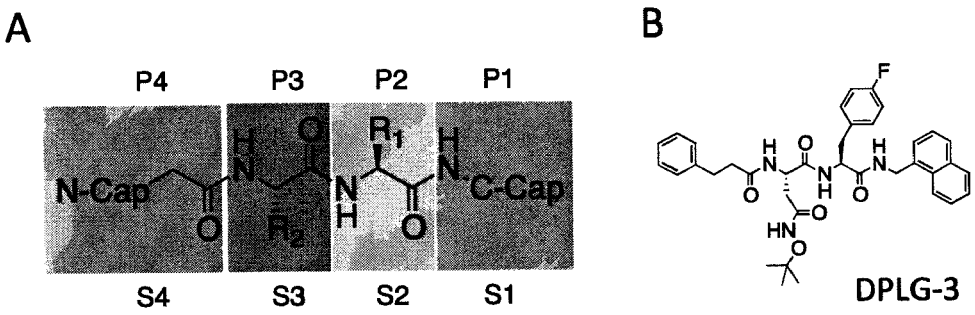
FIGS. 1A-B show N,C-capped dipeptides.

One aspect of the present invention relates to a compound of Formula (I):

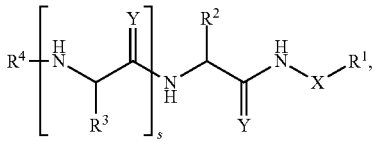

(I)

wherein $R^1$ is selected from the group consisting of monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, $—CF_3$, $C_{1-6}$ alkyl, and $C_{1-6}$ alkoxy;

$R^2$ is independently selected at each occurrence thereof from the group consisting of H, D, $C_{1-6}$ alkyl, $—CH_2OC_{1-6}$ alkyl, $—CH_2Ar$, and $—CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy; $R^3$ is independently selected at each occurrence thereof from the group consisting of H, D, $—CH_2OC_{1-6}$ alkyl, $—(CH_2)_mC(O)NHR^5$, and $—(CH_2)_mC(O)NR^6R^7$;

$R^4$ is selected from the group consisting of $—C(O)(CH_2)_1Ph$, $—C(O)CH_2NR^6R^7$, $—SO_2Ar$, $—SO_2C_{1-6}$ alkyl, $—SO_2C_{3-6}$cycloalkyl, $—C(O)(CH_2)_n$Het, —C(O)C(O)Het, $—C(O)C_{1-6}$ alkyl, $—C(O)OC_{1-6}$ alkyl, $—C(O)CF_3$, heteroaryl, $—C(O)R^{10}$, and $—(CH_2)_1NR^6R^7$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^5$ is selected from the group consisting of $C_{1-6}$ alkyl, $C_{1-6}$ alkoxy, non-aromatic heterocycle, $—NR^6R^7$, and $—CR^8R^9$;

$R^6$, $R^7$, $R^8$, and $R^9$ are each independently selected from the group consisting of H, D, $C_{1-6}$ alkyl, and $—(CH_2)_kOH$;

or $R^6$ and $R^7$ are taken together with the nitrogen to which they are attached to form a piperidine, pyrrolidine, or morpholine ring;

or $R^8$ and $R^9$ are taken together with the carbon to which they are attached to form an oxetane ring;

$R^{10}$ is monocyclic carbocycle or fused bicyclic carbocycle;

X is $—(CH_2)_q—$, —O—, or $—(CD_2)_q—$;

Y is O or S;

k is 1, 2, or 3;

m is 0, 1, 2, 3, 4, or 5;

n is 0, 1, 2, or 3;

q is 0, 1, or 2; and s is 0 or 1;

or an oxide thereof, a pharmaceutically acceptable salt thereof, a solvate thereof, or a prodrug thereof.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "cycloalkyl" means a non-aromatic mono- or multicyclic ring system of about 3 to about 7 carbon atoms, preferably of about 5 to about 7 carbon atoms. Exemplary monocyclic cycloalkyls include cyclopentyl, cyclohexyl, cycloheptyl, and the like.

The term "monocyclic carbocycle" means a monocyclic ring system of 5 to about 8 ring carbon atoms, preferably 5 or 6. The ring is nonaromatic, but may contain one or more carbon-carbon double bonds. Representative monocyclic carbocycles include cyclopentyl, cyclohexyl, cyclopentenyl, cyclohexenyl, and the like.

The term "fused bicyclic carbocycle" means a bicyclic ring system consisting of about 8 to 11 ring carbon atoms, preferably 9 or 10. One or both of the rings is/are aromatic. Representative fused bicyclic carbocycles include indenyl, indanyl, naphthyl, dihydronaphthyl, tetrahydronaphthyl, benzocycloheptenyl, dihydrobenzocycloheptenyl, tetrahydrobenzocycloheptenyl, and the like.

The term "aryl" means an aromatic monocyclic or multicyclic ring system of 6 to about 14 carbon atoms, preferably of 6 to about 10 carbon atoms. Representative aryl groups include phenyl and naphthyl.

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxopyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "biheteroaryl" or "bi-heteroaryl" refers to a heteroaryl group substituted by another heteroaryl group.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

As used herein, "biheterocyclyl" or "bi-heterocyclyl" refers to a heterocyclyl group substituted by another heterocyclyl or heterocycle group.

The term "non-aromatic heterocycle" means a non-aromatic monocyclic system containing 3 to 10 atoms, preferably to about 7 carbon atoms, in which one or more of the atoms in the ring system is/are element(s) other than carbon, for example, nitrogen, oxygen, or sulfur. Representative non-aromatic heterocycle groups include pyrrolidinyl, 2-oxopyrrolidinyl, piperidinyl, 2-oxopiperidinyl, azepanyl, 2-oxoazepanyl, 2-oxooxazolidinyl, morpholino, 3-oxomorpholino, thiomorpholino, 1,1-dioxothiomorpholino , piperazinyl, tetrohydro-2H-oxazinyl, and the like.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, Protective Groups in Organic Synthesis, John Wiley & Sons, New York (1991), which is hereby incorporated by reference in its entirety.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

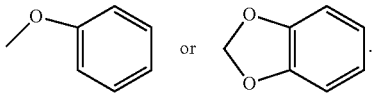

A compound with a hydroxy group drawn next to a nitrogen on a heterocycle can exist as the "keto" form. For example, 3-(2-hydroxy-[1,2,4]triazolo[1,5-a]pyridin-6-yl) propanoic acid can exist as 3-(2-oxo-2,3-dihydro-[1,2,4] triazolo[1,5-a]pyridin-6-yl)propanoic acid.

The term "halo" or "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =0), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =0), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "method of treating" means amelioration or relief from the symptoms and/or effects associated with the disorders described herein. As used herein, reference to "treatment" of a patient is intended to include prophylaxis.

The term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic, and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like (see, for example, Berge et al., "Pharmaceutical Salts," J. Pharm. Sci., 66:1-9 (1977) and Remington's Pharmaceutical Sciences, 17th ed., Mack Publishing Company, Easton, Pa., 1985, p. 1418, which are hereby incorporated by reference in their entirety). Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include, for example, sodium hydride, sodium hydroxide, potassium hydroxide, calcium hydroxide, aluminium hydroxide, lithium hydroxide, magnesium hydroxide, and zinc hydroxide. Suitable amine base addition salts are prepared from amines which have sufficient basicity to form a stable salt, and preferably include those amines which are frequently used in medicinal chemistry because of their low toxicity and acceptability for medical use, such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); Methods in Enzymology, K. Widder et al, Ed., Academic Press, 42, p. 309-396 (1985); A Textbook of Drug Design and Development, Krogsgaard-Larsen and H. Bundgaard, ed., Chapter 5; "Design and Applications of Prodrugs" p. 113-191 (1991); Advanced Drug Delivery Reviews, H. Bundgard, 8, p. 1-38 (1992); J. Pharm. Sci., 77:285 (1988); Nakeya et al, Chem. Pharm. Bull., 32:692 (1984); Higuchi et al., "Pro-drugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amounts" is meant to describe an amount of compound of the present invention effective in increasing the levels of serotonin, norepinephrine, or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history; the particular compound used, as well as the carrier in which it is formulated and the route of administration selected for it; and, the nature and severity of the condition being treated.

The term "pharmaceutical composition" means a composition comprising a compound of Formula (I) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifingal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

Compounds of Formula (I) can be produced according to known methods. For example, compounds of Formula (I) wherein s is 0 can be prepared according to Scheme 1 and Scheme 2 outlined below.

Scheme 1

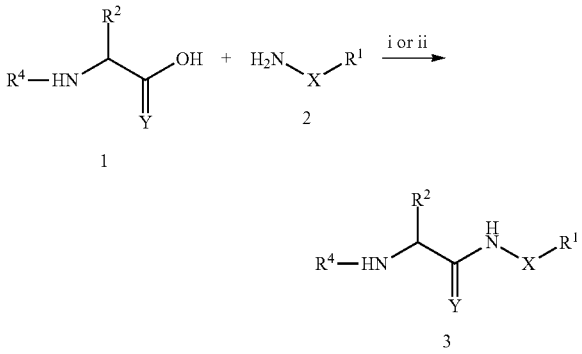

i) HATU, HOAt, DMF
ii) EDC, HOBt, DMF

Coupling of the carboxylic acid (1) with the amine (2) leads to formation of the compound (3). The coupling reaction can be carried out in a variety of solvents, for example in methylene chloride ($CH_2Cl_2$), tetrahydrofuran (THF), dimethylformamide (DMF), or other such solvents or in the mixture of such solvents. During the coupling process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Trot), t-amytoxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like.

Scheme 2

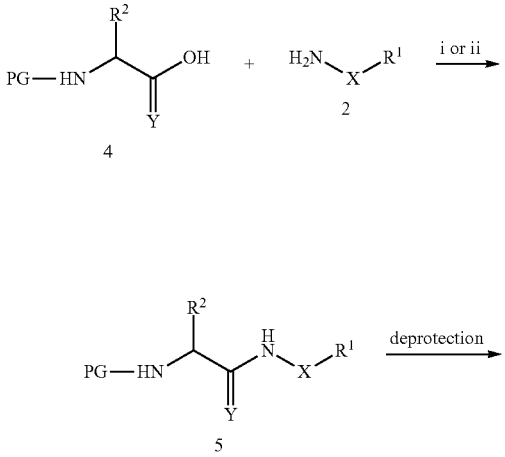

i) HATU, HOAt, DMF
ii) EDC, HOBt, DMF
PG is a protecting group

-continued

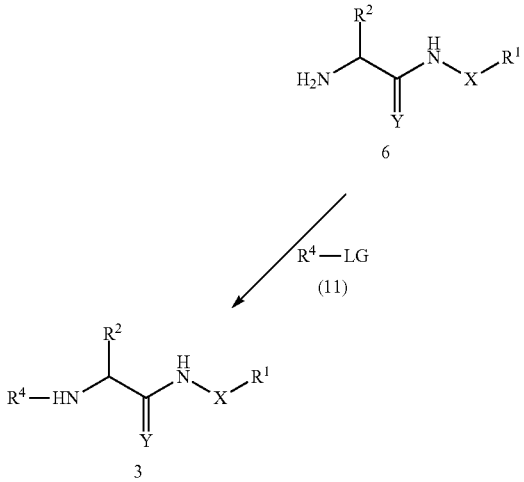

LG is a leaving group

Alternatively, carboxylic acid bearing protecting group (PG) (4) can be coupled with the amine (2) to form compound (5). Following the deprotection reaction, compound (6) can be reacted with compound (11), $R^4$-LG (wherein LG is a suitable leaving group), to form final product (3).

Compounds of Formula (I) wherein s is 1 can be prepared according to the general schemes outlined below (Scheme 3 and Scheme 4).

Scheme 3

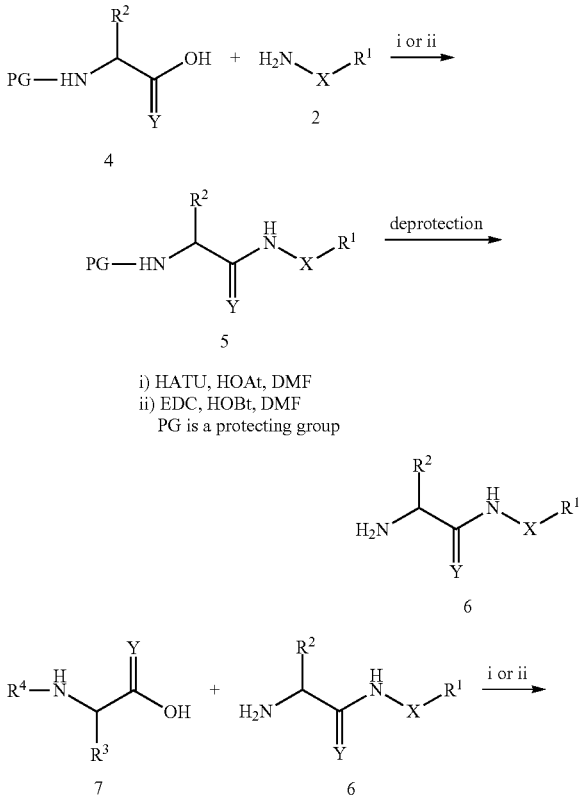

i) HATU, HOAt, DMF
ii) EDC, HOBt, DMF
PG is a protecting group

-continued

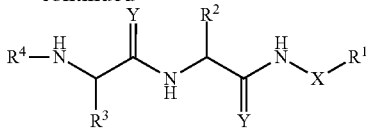

8 i) HATU, HOAt, DMF
ii) EDC, HOBt, DMF

The compounds of the present invention may be prepared by stepwise coupling of the amino acids. The coupling reactions are conducted in solvents such as methylene chloride ($CH_2Cl_2$), tetrahydrofuran (THF), dimethylformamide (DMF), or other such solvents. During the coupling process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides; Vol. 3", Gross and Meinenhofer, L ds Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, t-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Carboxylic acid bearing protecting group (PG) (4) is coupled with the amine (2) to form compound (5). Following the deprotection the reaction, compound (6) is coupled with another acid (7) to form final product (8).

Alternatively, carboxylic acid bearing protecting group (PG) (4) can be coupled with the amine (6) to form compound (9). Following the deprotection reaction, compound (10) can be reacted with compound (11), $R^4$-LG (wherein LG is a suitable leaving group), to form final product. (8).

In one embodiment, compound has the Formula (Ia):

(Ia)

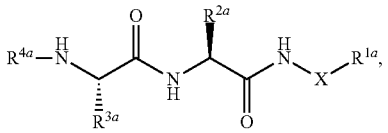

wherein $R^{1a}$ is selected from the group consisting of monocyclic and bicyclic aryl, monocyclic and bicyclic heteroaryl, and monocyclic and bicyclic non-aromatic heterocycle, wherein monocyclic and bicyclic aryl, monocyclic and bicyclic heteroaryl, and monocyclic and bicyclic non-aromatic heterocycle can be optionally substituted from 1 to 3 times with a substituent selected independently at each occurrence thereof from the group consisting of halogen, cyano, $C_{1-6}$ alkyl, and $C_{1-6}$ alkoxy;

$R^{2a}$ is selected from the group consisting of $C_{1-6}$ alkyl, —$CH_2OC_{1-6}$ alkyl, —$CH_2Ar$, and heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^{1a}$ s selected from the group consisting of —$CH_2OC_{1-6}$ alkyl, —$CH_2C(O)NHR^{5a}$, and —$CH_2C(O)R^{5a}$;

$R^{4a}$ is selected from the group consisting of —C(O)$(CH_2)_1$ Ph, —C(O)$CH_2NR^{6a}R^{7a}$, —$SO_2Ar$, —$SO_2C_{1-6}$ alkyl, —C(O)$(CH_2)_n$Het, —C(O)$C_{1-6}$ alky, —C(O)$CF_3$, het- Scheme 4

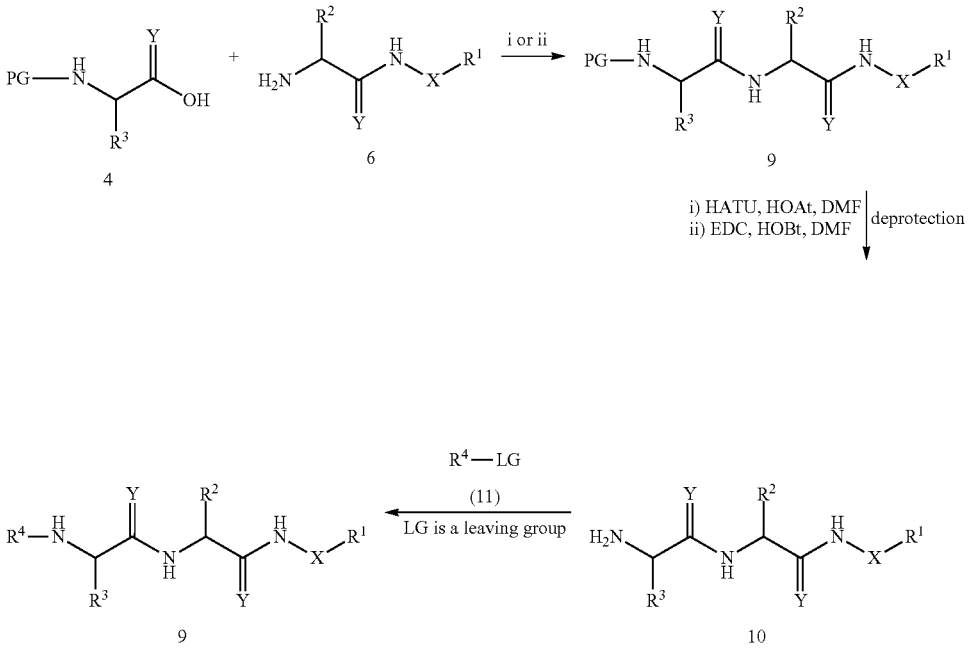

eroaryl, and —$(CH_2)_1NR^{6a}R^{7a}$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ akoxy;

$R^{5a}$ is selected from the group consisting of $C_{1-6}$ alkyl, $C_{1-6}$ alkoxy, non-aromatic heterocycle, —$NR^{6a}R^{7a}$, and —$CR^{8a}R^{9a}$;

$R^{6a}$, $R^{7a}$, $R^{8a}$, and $R^{9a}$ are each independently selected from the group consisting of H, $C_{1-6}$ alkyl, and —$(CH_2)_k$OH;

or $R^{6a}$ and $R^{7a}$ are taken together with the nitrogen to which they are attached to form a piperidine, pyrrolidine, azepane, azetidine, or morpholine ring;

or $R^{8a}$ and $R^{9a}$ are taken together with the carbon to which they are attached to form an oxetane ring;

n is 0, 1, 2, or 3; and k is 1, 2, or 3.

Another embodiment relates to the compound of Formulae (I) where $R^1$ is selected from the group consisting of

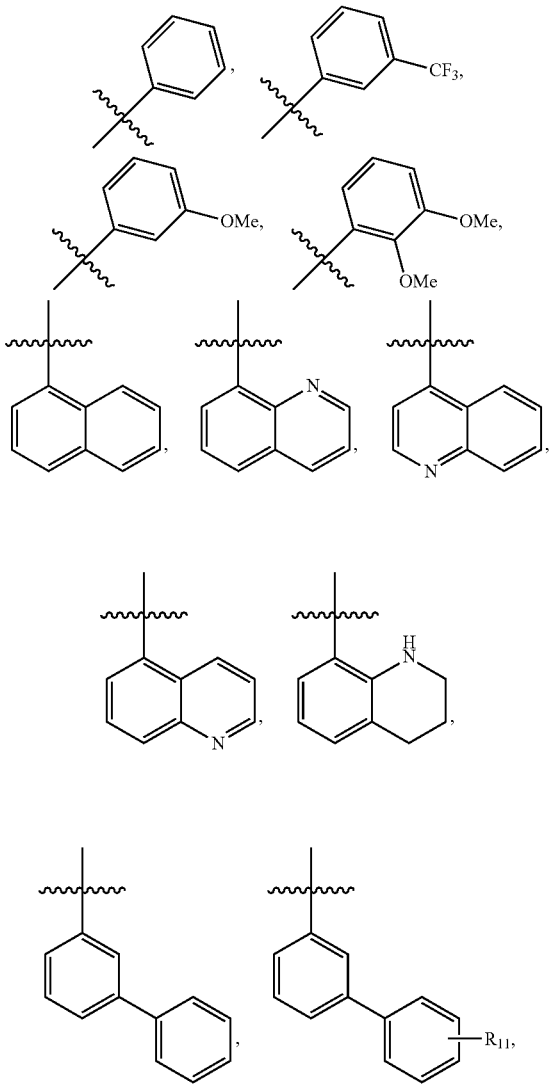

-continued

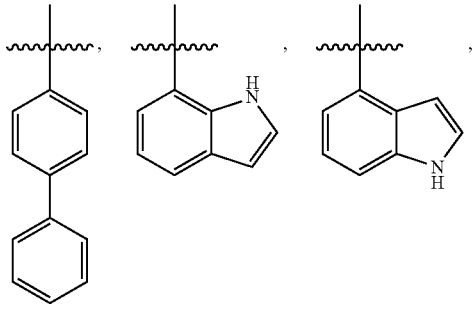

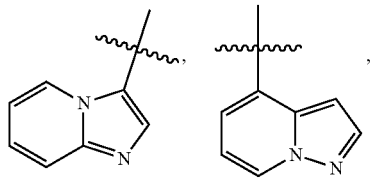

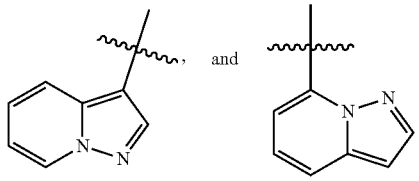

and $R^{11}$ is selected from the group consisting of halogen, cyano, —$CF_3$, $C_{1-6}$ alkyl, and $C_{1-6}$ alkoxy.

Another embodiment relates to the compound of Formuae (I) where $R^2$ is selected from the group consisting of Me, —$CH(Me)_2$, —$CH_2OMe$,

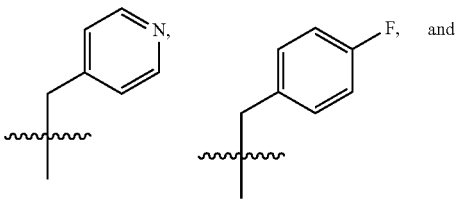

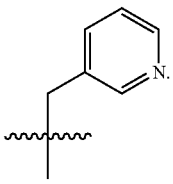

Another embodiment relates to the compound of Formulae (I) where $R^3$ is selected from the group consisting of —$CH_2OMe$,

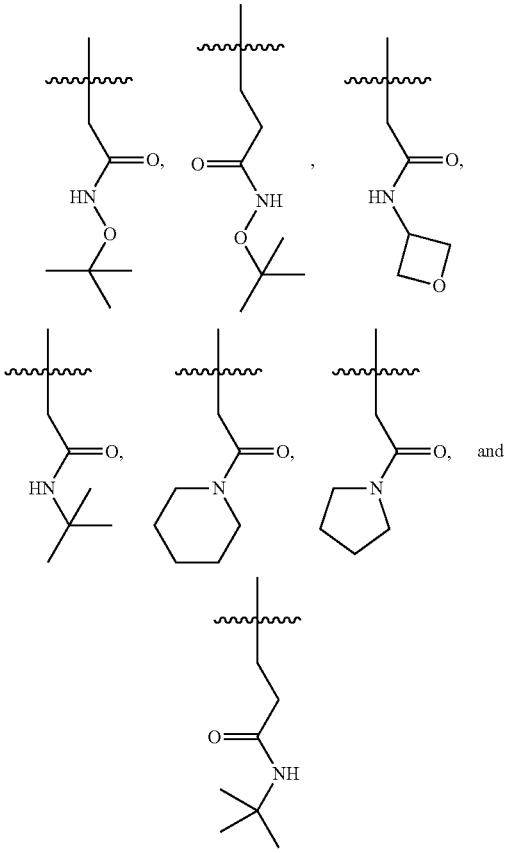

Another embodiment relates to the compound of Formulae (I) where $R^4$ is selected from the group consisting of trifluoroacetyl,

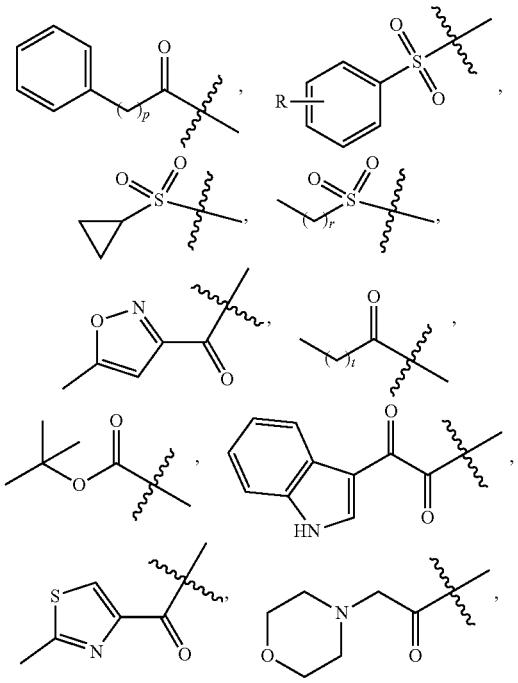

-continued

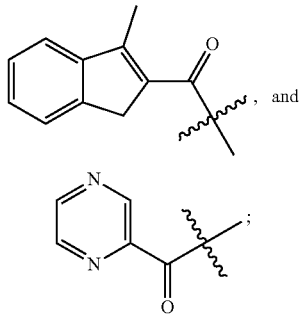

p is 0, 1, 2, or 3;

r is 0, 1, 2, 3, 4, or 5;

t is 0, 1, 2, 3, or 4; and

R is selected from the group consisting of H, halogen, cyano, $C_{1-6}$ alkyl, and $C_{1-6}$ alkoxy.

Another embodiment relates to the compound of Formulae (I) where the compound has a structure selected from the group consisting of:

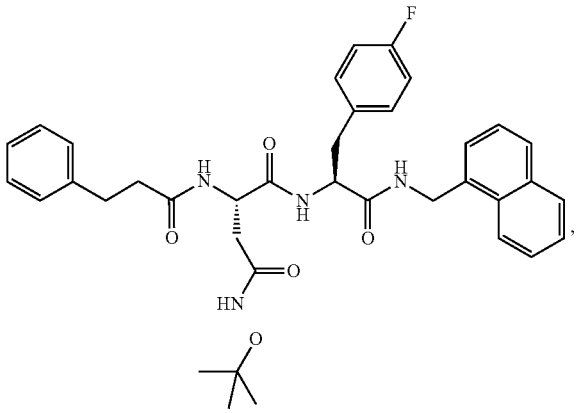

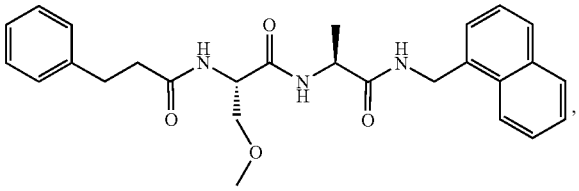

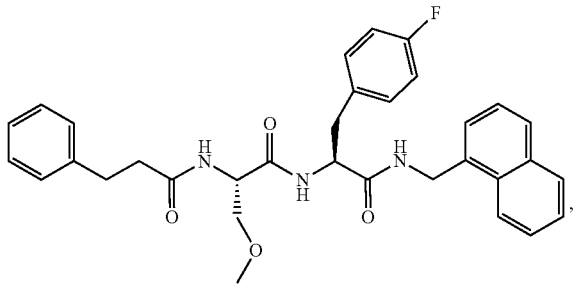

-continued
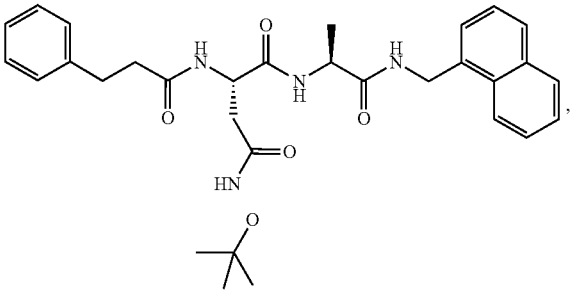
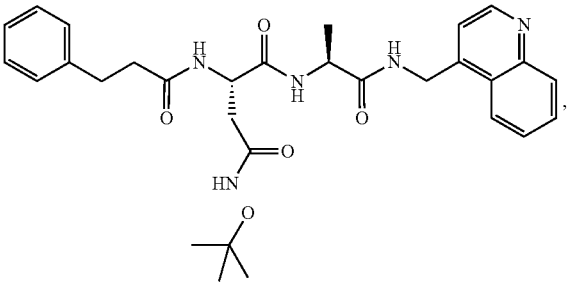
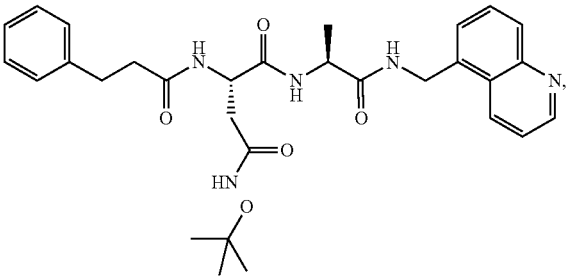
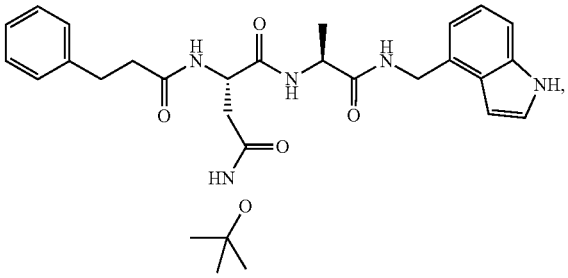
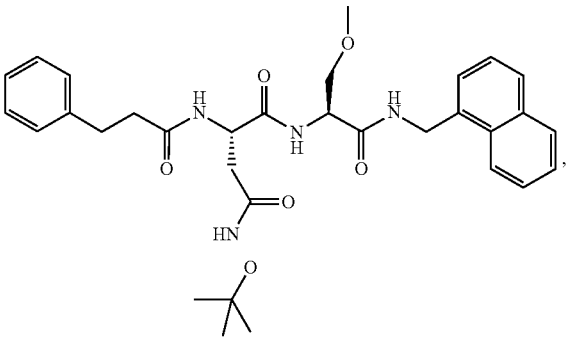
-continued
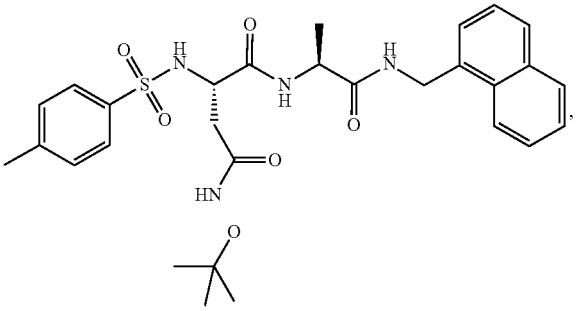
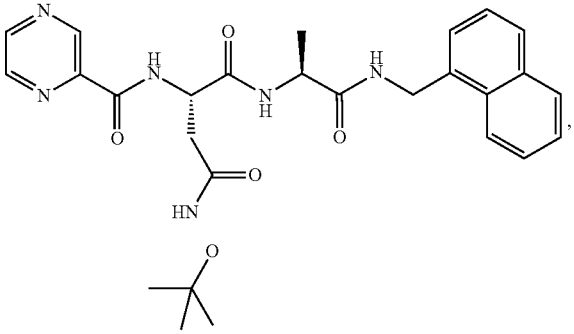
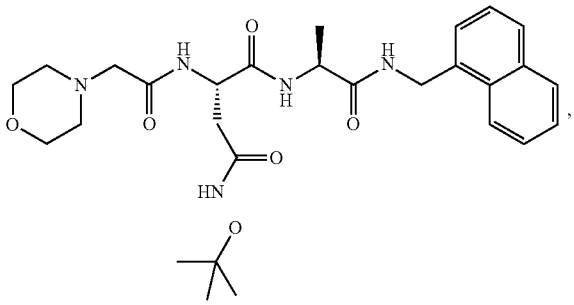
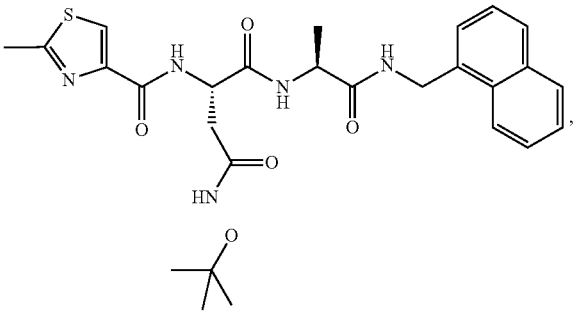
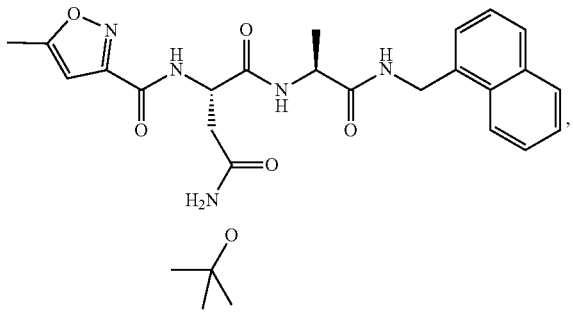

-continued
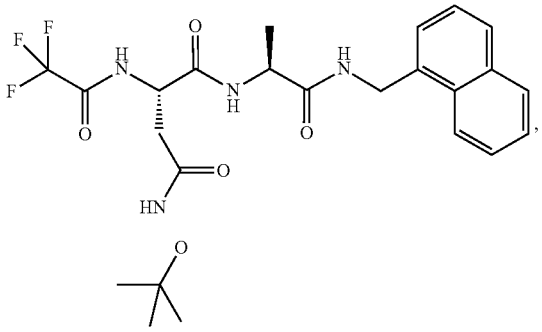
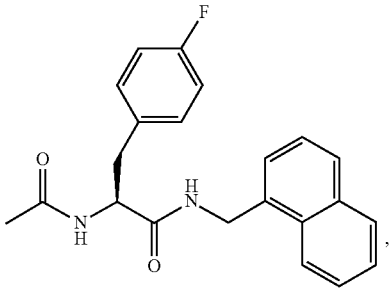
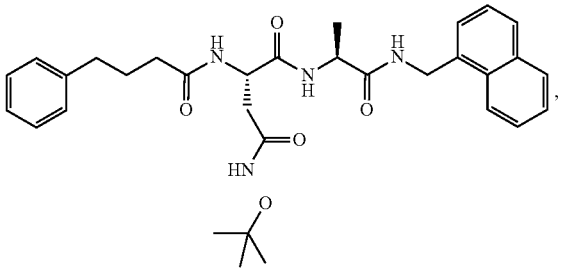
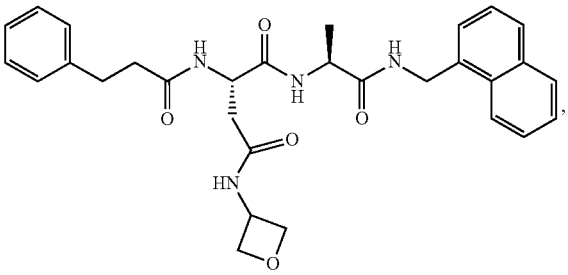
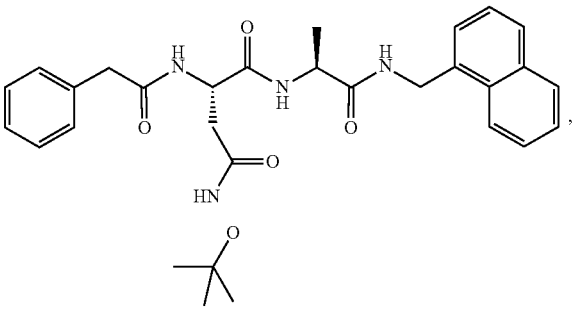
-continued
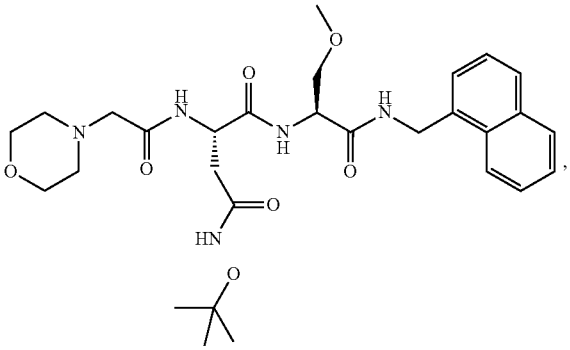
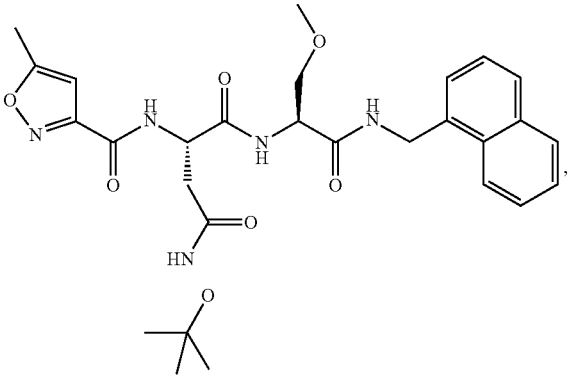
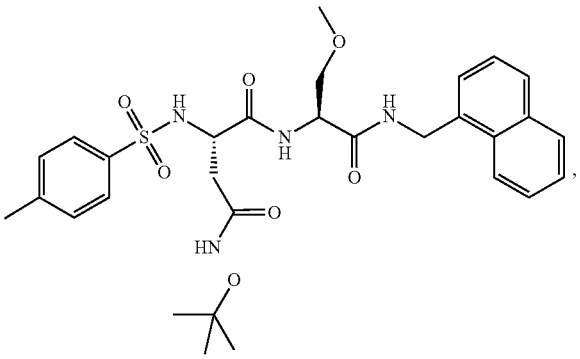
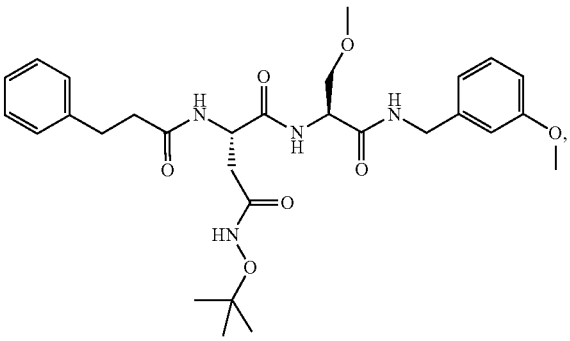

-continued
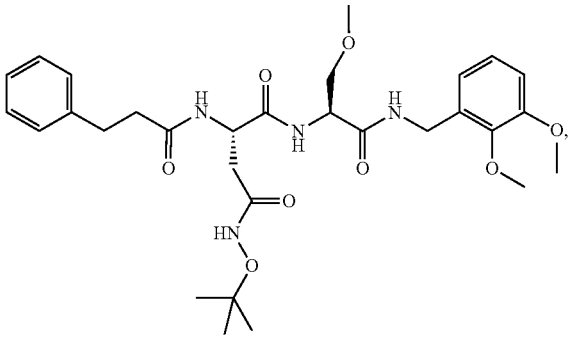
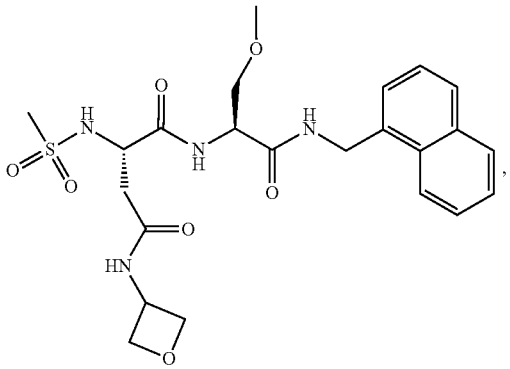
DPLG-2219
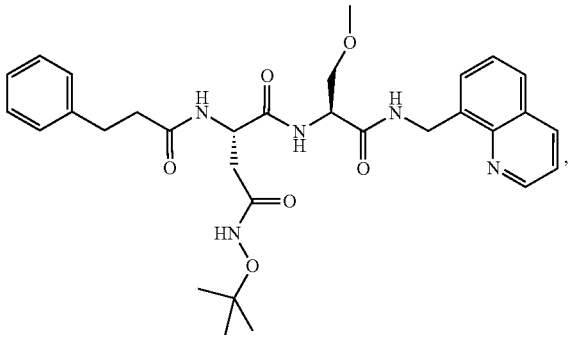
DPLG-2220
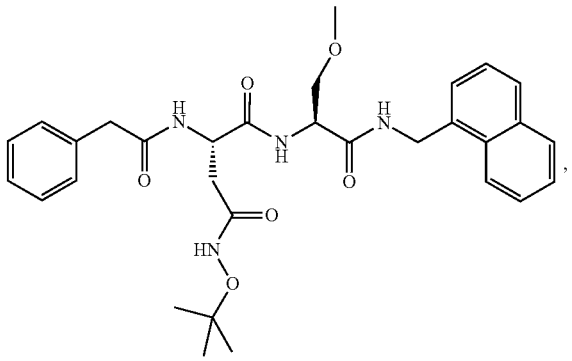
DPLG-2222
-continued
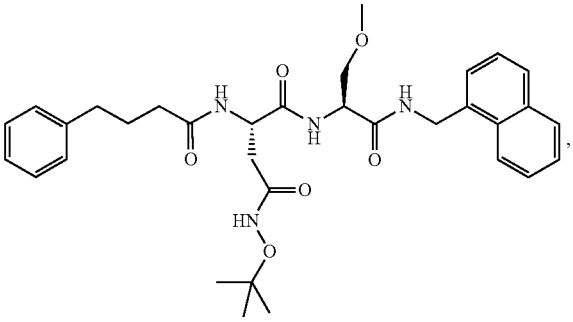
DPLG-2223
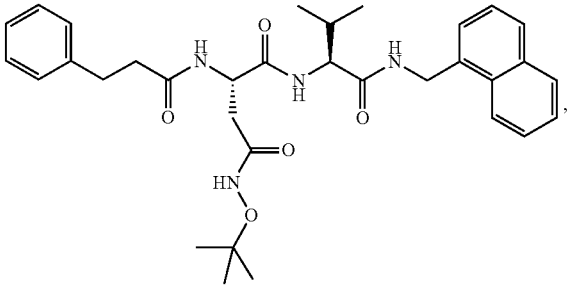
DPLG-2224
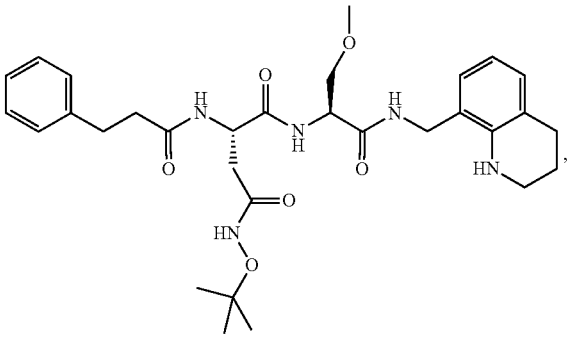
DPLG-2226
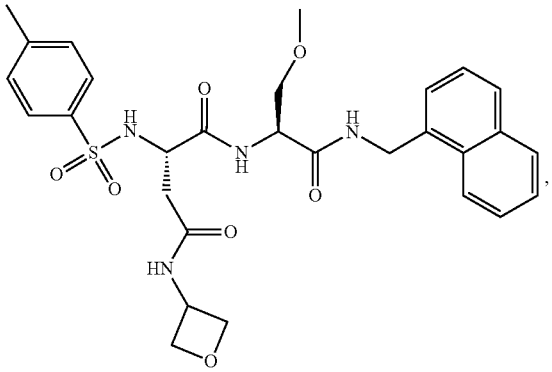
DPLG-2229

-continued
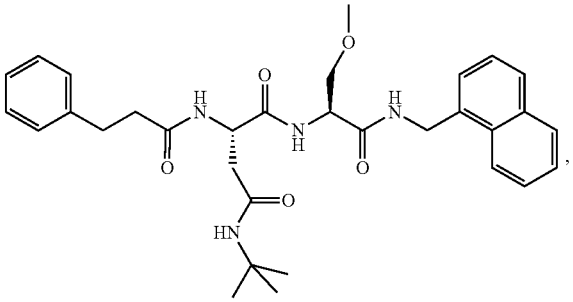
DPLG-2230
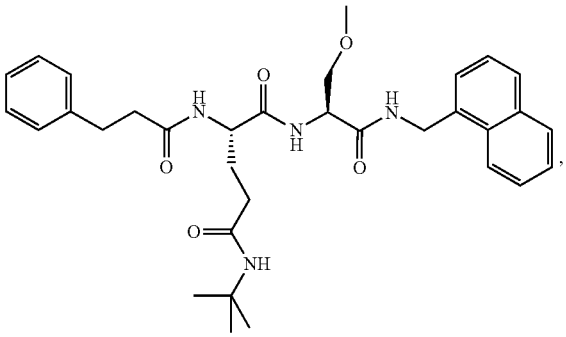
DPLG-2243
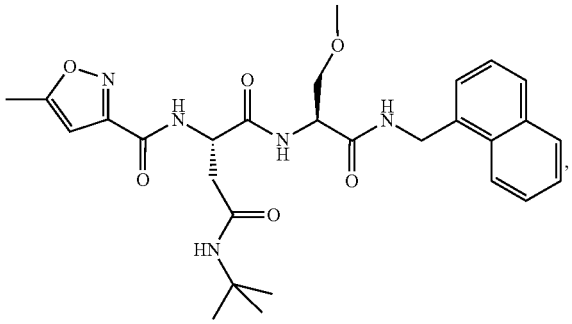
DPLG-2244
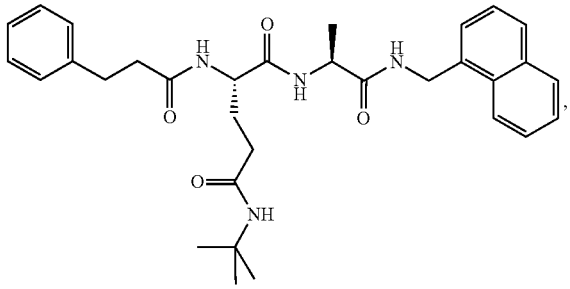
DPLG-2255
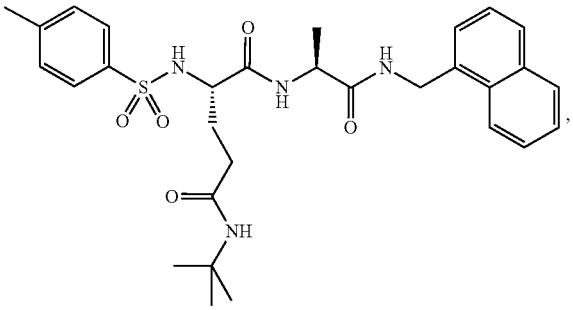
DPLG-2256
-continued
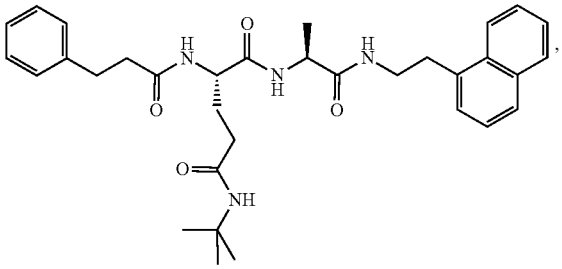
DPLG-3012
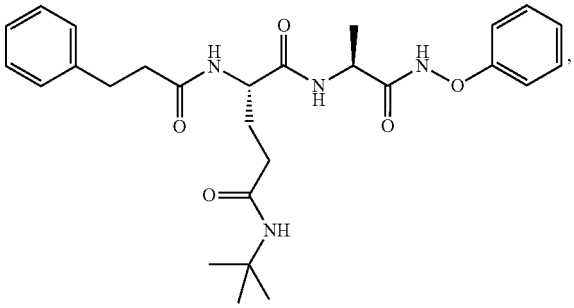
DPLG-3013
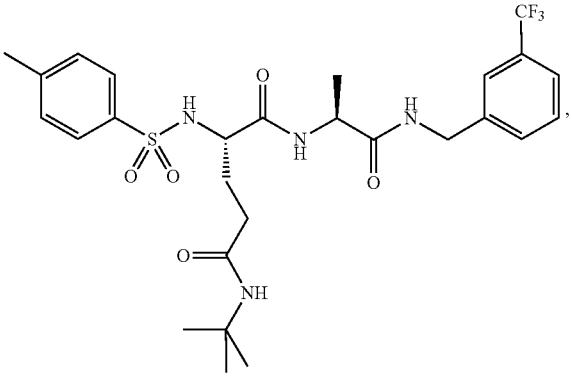
DPLG-3014
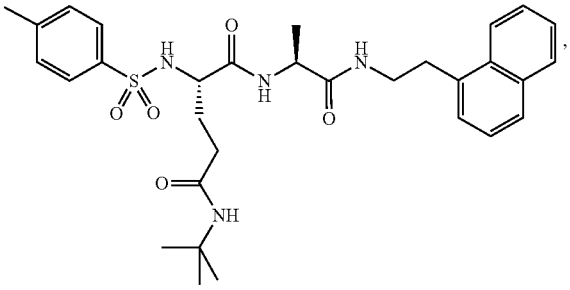
DPLG-3016

-continued

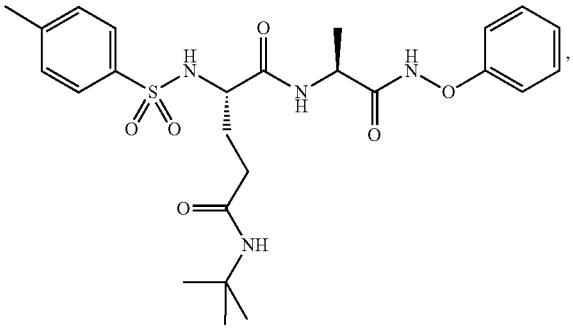

DPLG-3017

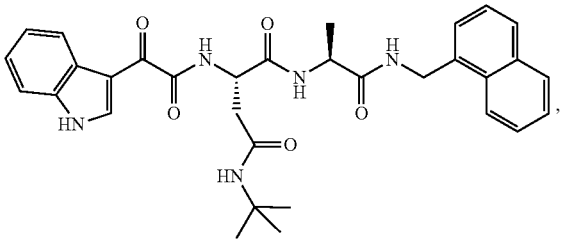

DPLG-3053

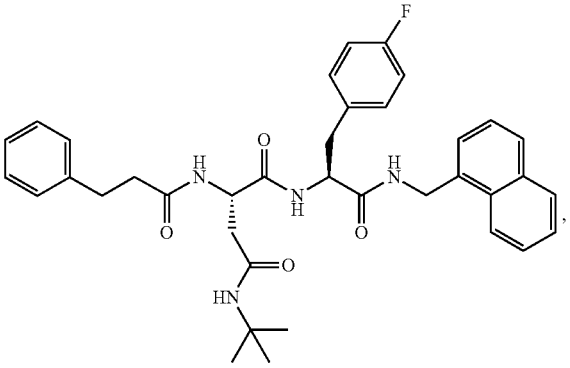

DPLG-3066

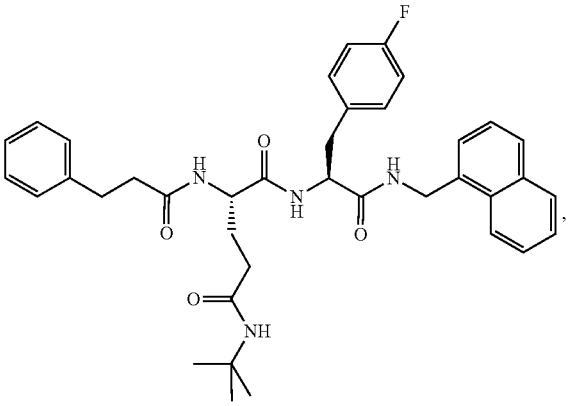

DPLG-3083

-continued

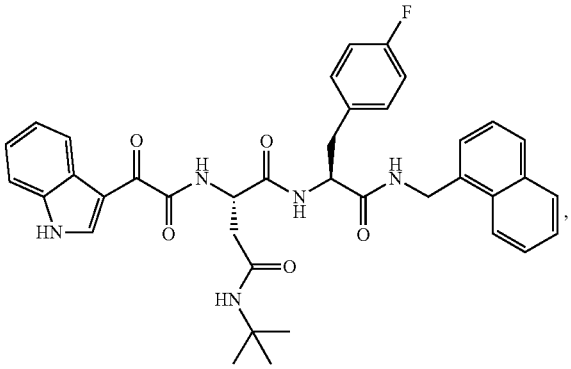

DPLG-3084

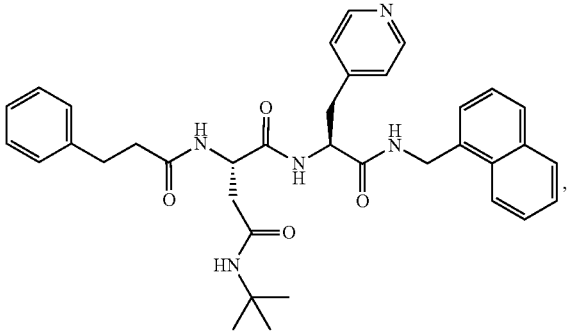

DPLG-21033

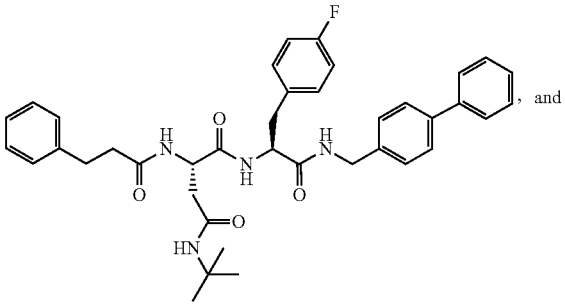

DPLG-21049

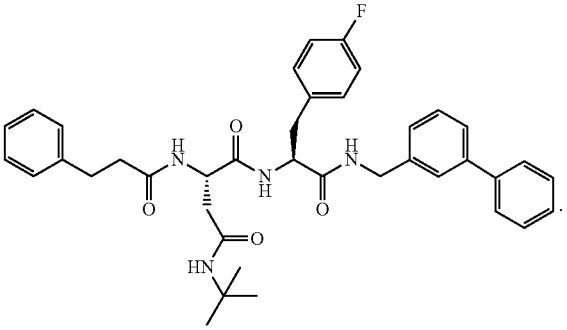

DPLG-21050

A second aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (I):

(I)

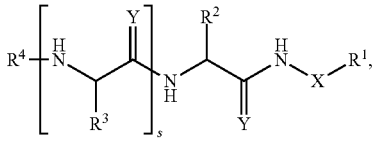

wherein $R^1$ is selected from the group consisting of monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —$CF_3$, $C_{1-6}$ alkyl, and $C_{1-6}$ alkoxy;

$R^2$ is independently selected at each occurrence thereof from the group consisting of H, D, $C_{1-6}$ alkyl, '$CH_2OC_{1-6}$ alkyl, —$CH_2$Ar, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^3$ is independently selected at each occurrence thereof from the group consisting of H, D, —$CH_2OC_{1-6}$ alkyl, —$(CH_2)_m$C(O)NHR$^5$, and —$(CH_2)_m$C(O)NR$^6$R$^7$;

$R^4$ is selected from the group consisting of —C(O)$(CH_2)_1$ Ph, —C(O)$CH_2$NR$^6$R$^7$, —$SO_2$Ar, —$SO_2C_{1-6}$ alkyl, —$SO_2C_{3-6}$cycloalkyl, —C(O)$(CH_2)_n$Het, —C(O)C(O)Het, —C(O)$C_{1-6}$ alkyl, C(O)$OC_{1-6}$ alkyl, —C(O)$CF_3$, heteroaryl, —C(O)R$^{10}$, and —$(CH_2)_1$NR$^6$R$^7$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^5$ is selected from the group consisting of $C_{1-6}$ alkyl, $C_{1-6}$ alkoxy, non-aromatic heterocycle, —NR$^6$R$^7$, and CR$^8$R$^9$;

$R^6$, $R^7$, $R^8$, and $R^9$ are each independently selected from the group consisting of H, D, $C_{1-6}$ alkyl, and —$(CH_2)_k$OH;

or $R^6$ and $^7$ are taken together with the nitrogen to which they are attached to form a piperidine, pyrrolidine, or morpholine ring;

or $R^8$ and $R^9$ are taken together with the carbon to which they are attached to form an oxetane ring;

$R^{10}$ is monocyclic carbocycle or fused bicyclic carbocycle;

X is —$(CH_2)_q$—, —O—, or —$(CD_2)_q$—;

Y is O or S;

k is 1, 2, or 3;

m is 0, 1, 2, 3, 4, or 5;

n is 0, 1, 2, or 3;

q is 0, 1, or 2; and s is 0 or 1.

In one embodiment, an autoimmune disorder is treated. The autoimmune disorder is selected from the group consisting of arthritis, colitis, multiple sclerosis, lupus, systemic sclerosis, and sjögren syndrome.

In another embodiment, immunosuppression is provided for transplanted organs or tissues. The immunosuppression is used to prevent transplant rejection and graft-verse-host disease.

In another embodiment, an inflammatory disorder is treated. The inflammatory disorder is Crohn's disease or ulcerative colitis.

In yet another embodiment, cancer is treated. The cancer is selected from the group consisting of neoplastic disorders, hematologic malignancies, and lymphocytic malignancies.

While it may be possible for compounds of Formula (I) to be administered as raw chemicals, it will often be preferable to present them as a part of a pharmaceutical composition. Accordingly, another aspect of the present invention is a pharmaceutical composition containing a therapeutically effective amount of the compound of Formula (I), or a pharmaceutically acceptable salt or solvate thereof, and a pharmaceutically acceptable carrier. The carrier must be "acceptable" in the sense of being compatible with the other ingredients of the formulation and not deleterious to the recipient thereof.

In practicing the method of the present invention, agents suitable for treating a subject can be administered using any method standard in the art. The agents, in their appropriate delivery form, can be administered orally, intradermally, intramuscularly, intraperitoneally, intravenously, subcutaneously, or intranasally. The compositions of the present invention may be administered alone or with suitable pharmaceutical carriers, and can be in solid or liquid form, such as tablets, capsules, powders, solutions, suspensions, or emulsions.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. (Abuchowski and Davis, "Soluble Polymer Enzyme Adducts," In: Enzymes as Drugs, Hocenberg and Roberts, eds., Wiley-Interscience, New York, N.Y, pp. 367-383 (1981), which are hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucrulose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agents of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The agents of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Effective doses of the compositions of the present invention, for the treatment of cancer or pathogen infection vary depending upon many different factors, including type and stage of cancer or the type of pathogen infection, means of administration, target site, physiological state of the patient, other medications or therapies administered, and physical state of the patient relative to other medical complications. Treatment dosages need to be titrated to optimize safety and efficacy.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.1 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

EXAMPLES

The following examples are provided to illustrate embodiments of the present invention but are by no means intended to limit its scope.

Example 1—General Procedure for HATU Mediated Amide Bond Formation

Carboxylic acid (1.0 eq.), O-(7-Azabenzotriazol-1-yl)-N,N,N,N'-tetramethyluronium hexafluorophosphate (HATU) (1.2 eq.) and 1-Hydroxy-7-Azabenzotriazole (HOAt) 0.6M in DMF (1.0 eq.) were dissolved in DMF under argon atmosphere. The solution was cooled to 0° C. and amine (1.1 eq.) was added. After stirring for 5 minutes at 0° C., Hünig's base (3-4 eq.) was added. The reaction mixture was stirred at 0° C. After completion of reaction (1 h; monitored by LCMS), water was added to reaction mixture and stirred 30 minutes. Product was isolated either by filtration or ethyl acetate extraction.

Example 2—General Procedure for EDC Mediated Amide Bond Formation

Carboxylic acid (1.0 eq.), N-(3-Dimethylaminopropyl)-N'-ethylcarbodiimide hydrochloride (EDC) (1.2 eq.) and 1-Hydroxybenzotriazole (HOBt) (1.3 eq.) were dissolved in DMF under argon atmosphere. The solution was cooled to 0° C. and amine (1.1 eq.) was added. After stirring for 5 minutes at 0° C., Hünig's base (2-3 eq.) was added. The reaction mixture was allowed to warm to room temperature slowly and stirred at room temperature overnight.

Example 3—General Procedure for Boc-Deprotection

The substrate was dissolved in dichloromethane and the solution was cooled to 0° C. Trifluoroacetic acid (20% v/v with respect to dichloromethane) was added to the solution drop wise at 0° C. with constant stirring. The mixture was allowed to warm to room temperature slowly (over a period of 1 hour), and stirred until the completion of reaction (monitored by LCMS). Excess trifluoroacetic acid and dichloromethane were evaporated and crude was dried under vacuum.

Example 4—General Procedure for O-Debenzylation

The substrate was dissolved in methanol. Palladium on carbon (10%) was added carefully. Residual air from the flask was removed and flushed with hydrogen. The mixture was stirred at room temperature under hydrogen atmosphere using a hydrogen balloon. After completion of reaction (3-4 hours; monitored by LCMS), the mixture was filtered through celite. Filtrate was evaporated and dried under vacuum to give product.

Example 5—Preparation of tert-butyl (S)-(3-(4-fluorophenyl)-1-((naphthalen-1-ylmethyl)amino)-1-oxopropan-2-yl)carbamate (DPLG-2122)

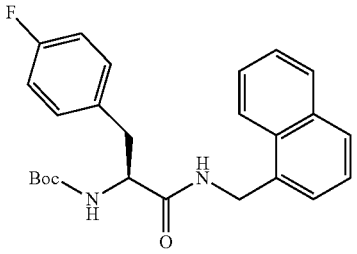

DPLG-2122 was prepared following the general procedure for HATU mediated coupling of Boc-4-F-Phe-OH (2.00 g, 7.06 mmol) and 1-naphthylmethylamine (1.17 mL, 7.77 mmol). After completion of reaction (1 h), 100 mL water was added to the reaction mixture. A precipitate was formed. The mixture was stirred for 15 minutes and filtered. The precipitate was washed with water and dried to give 2.96 g (99%) product. $^1$H NMR (500 MHz, DMSO-$d_6$) δ 8.47 (t, J=5.8 Hz, 1H), 8.03 (dd, J=6.3, 3.4 Hz, 1H), 7.94 (dd, J=6.2, 3.4 Hz, 1H), 7.84 (d, J=8.1 Hz, 1H), 7.55-7.52 (m, 2H), 7.44-7.41 (m, 1H), 7.38-7.36 (m, 1H), 7.28-7.25 (m, 2H), 7.07-7.00 (m, 3H), 4.74 (d, J=5.6 Hz, 2H), 4.25-4.15 (m, 1H), 2.93 (dd, J=13.6, 5.1 Hz, 1H), 2.77 (dd, J=13.6, 10.0 Hz, 1H), 1.30 (s, 9H).

Example 6—Preparation of (S)-2-amino-3-(4-fluorophenyl)-N-(naphthalen-1-ylmethyl)propanamide 2,2,2-trifluoroacetate (DPLG-2123)

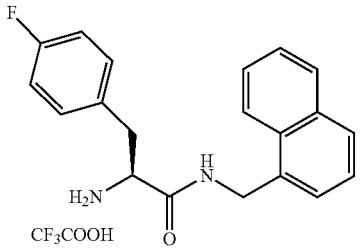

DPLG-2123 was prepared by following the general procedure for Boc-deprotection of DPLG-21046 (2.96 g, 7.00 mmol). The crude was triturated with diethyl ether and filtered to give product as a white solid (2.54 g, 83%). $^1$H NMR (500 MHz, DMSO-$d_6$) δ 8.91-8.88 (m, 1H), 8.30 (bs, 3H), 7.98-7.94 (m, 2H), 7.89 (d, J=8.2 Hz, 1H), 7.58-7.55 (m, 2H), 7.44 (dd, J=8.2, 7.0 Hz, 1H), 7.28 (d, J=7.0 Hz, 1H), 7.22-7.19 (m, 2H), 7.09-7.06 (m, 2H), 4.81 (dd, J=15.1, 5.8 Hz, 1H), 4.69 (dd, J=15.1, 5.1 Hz, 1H), 4.04-4.01 (m, 1H), 3.06-2.98 (m, 2H).

Example 7—Preparation of (S)-benzyl 3-((tert-butoxycarbonyl)amino)-4-(((S)-3-(4-fluorophenyl)-1-((naphthalen-1-ylmethyl)amino)-1-oxopropan-2-yl)amino)-4-oxobutanoate (DPLG-2134)

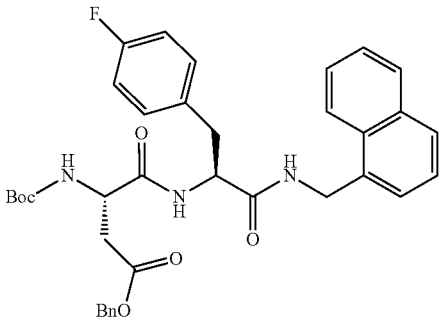

DPLG-2134 was prepared following the general procedure for HATU mediated coupling of Boc-Asp(OBn)OH (356 mg, 1.1 mmol) and (S)-2-amino-3-(4-fluorophenyl)-N-(naphthalen-1-ylmethyl)propanamide 2,2,2-trifluoroacetate (436 mg, 1.0 mmol). After completion of reaction (3 h), the mixture was precipitated by the addition of 100 mL water. The mixture was stirred for 15 minutes and filtered. The precipitate was dried to give 627 mg (quant.) product. $^1$H NMR (500 MHz, DMSO-$d_6$) δ 8.51 (t, J=5.7 Hz, 1H), 8.01-7.99 (m, 1H), 7.96-7.94 (m, 2H), 7.85 (d, J=8.2 Hz, 1H), 7.56-7.52 (m, 2H), 7.42 (t, J=7.6 Hz, 1H), 7.39-7.29 (m, 6H), 7.20-7.17 (m, 3H), 7.02-6.98 (m, 2H), 5.12-5.04 (m, 2H), 4.71 (d, J=5.6 Hz, 2H), 4.56-4.51 (m, 1H), 4.34 (td, J=8.7, 5.1 Hz, 1H), 2.99-2.95 (m, 1H), 2.87-2.80 (m, 1H), 2.69 (dd, J=16.2, 5.0 Hz, 1H), 2.57-2.52 (m, 1H), 1.36 (s, 9H).

Example 8—Preparation of (S)-benzyl 3-amino-4-(((S)-3-(4-fluorophenyl)-1-((naphthalen-1-ylmethyl)amino)-1-oxopropan-2-yl)amino)-4-oxobutanoate 2,2,2-trifluoroacetate (DPLG-2135)

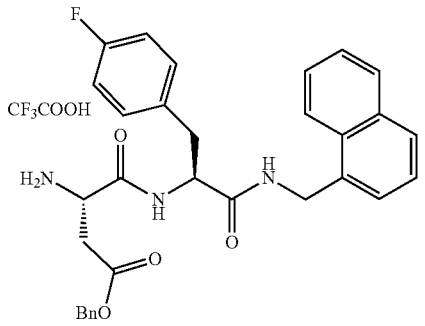

DPLG-2135 was synthesized by following the general procedure for Boc-deprotection of (S)-benzyl 3-((tert-butoxycarbonyl)amino)-4-(((S)-3-(4-fluorophenyl)-1-((naphthalen-1-ylmethyl)amino)-1-oxopropan-2-yl)amino)-4-oxobutanoate (627 mg, 1 mmol). After completion of reaction dichloromethane and excess trifluoroacetic acid were evaporated. The crude was washed with diethyl ether to give product (628 mg, 98%). $^1$H NMR (500 MHz, DMSO-$d_6$) δ 8.76 (d, J=8.2 Hz, 1H), 8.62 (t, J=5.7 Hz, 1H), 8.18 (bs, 3H), 8.02-7.99 (m, 1H), 7.96-7.93 (m, 1H), 7.85 (d, J=8.2 Hz, 1H), 7.56-7.51 (m, 2H), 7.44-7.34 (m, 6H), 7.31 (d, J=7.0 Hz, 1H), 7.26-7.23 (m, 2H), 7.08-7.04 (m, 2H), 5.18 (dd, J=12.5 Hz, 1H), 5.14 (d, J=12.5 Hz, 1H), 4.77-4.69 (m, 2H), 4.61 (td, J=8.5, 5.6 Hz, 1H), 4.10-4.18 (m, 1H), 3.04-2.97 (m, 2H), 2.87-2.80 (m, 2H).

Example 9—Preparation of (S)-benzyl 4-(((S)-3-(4-fluorophenyl)-1-((naphthalen-1-ylmethyl)amino)-1-oxopropan-2-yl)amino)-4-oxo-3-(3-phenylpropanamido)butanoate (DPLG-2138)

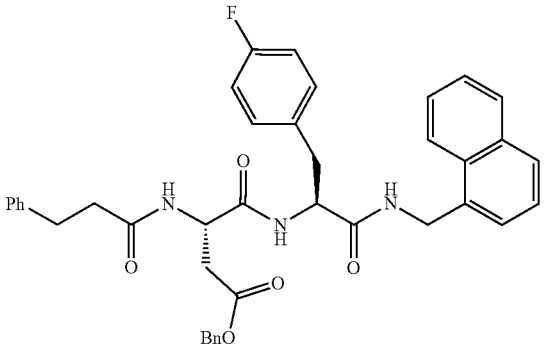

DPLG-2138 was prepared following the general procedure for HATU mediated coupling of 3-phenylpropanoic acid (162 mg, 1.08 mmol) and (S)-benzyl 3-amino-4-(((S)-3-(4-fluorophenyl)-1-((naphthalen-1-ylmethyl)amino)-1-oxopropan-2-yl)amino)-4-oxobutanoate (628 mg, 0.98 mmol). After completion of reaction (3 h), the mixture was precipitated by the addition of 100 mL water. The mixture was stirred for 15 minutes and filtered. The precipitate was dried to give 600 mg (93%) product. $^1$H NMR (500 MHz, DMSO-$d_6$) δ 8.45 (t, J=5.7 Hz, 1H), 8.20 (d, J=8.0 Hz, 1H), 8.07 (d, J=8.3 Hz, 1H), 8.03-8.01 (m, 1H), 7.95-7.93 (m, 1H), 7.84 (d, J=8.2 Hz, 1H), 7.56-7.51 (m, 2H), 7.44-7.41 (m, 1H), 7.38-7.30 (m, 6H), 7.27-7.24 (m, 2H), 7.20-7.15 (m, 5H), 7.02-6.98 (m, 2H), 5.04 (s, 2H), 4.72 (d, J=5.6 Hz, 2H), 4.67 (td, J=8.2, 5.8 Hz, 1H), 4.51 (td, J=8.5, 5.4 Hz, 1H), 2.99 (dd, J=13.8, 5.4 Hz, 1H), 2.84 (dd, J=13.8, 8.8 Hz, 1H), 2.77-2.72 (m, 3H), 2.54-2.49 (m, 1H), 2.39-2.32 (m, 2H).

Example 10—Preparation of (S)-4-(((S)-3-(4-fluorophenyl)-1-((naphthalen-1-ylmethyl)amino)-1-oxopropan-2-yl)amino)-4-oxo-3-(3-phenylpropanamido) butanoic acid (DPLG-2141)

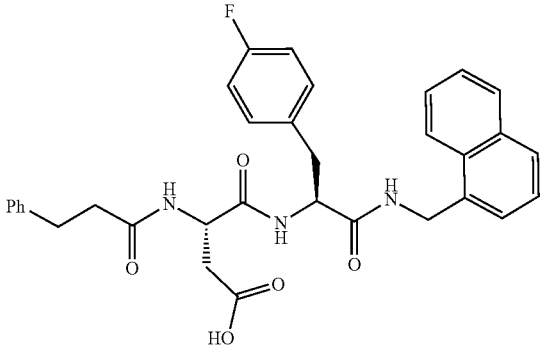

DPLG-2141 was synthesized by following the general procedure for O-debenzylation of DPLG-2138 (600 mg, 0.91 mmol). The product (518 mg, quant.) was isolated as a white solid. $^1$H NMR (500 MHz, DMSO-$d_6$) δ 12.42 (s, 1H), 8.50 (t, J=6.0 Hz, 1H), 8.15 (d, J=7.8 Hz, 1H), 8.06-8.03 (m, 2H), 7.95-7.93 (m, 1H), 7.84 (d, J=8.2 Hz, 1H), 7.57-7.52 (m, 2H), 7.44-7.41 (m, 1H), 7.34-7.32 (m, 1H), 7.27-7.24 (m, 2H), 7.20-7.15 (m, 5H), 7.01-6.97 (m, 2H), 4.72 (d, J=5.7 Hz, 2H), 4.58-4.53 (m, 1H), 4.48 (td, J=8.4, 5.1 Hz, 1H), 3.01 (dd, J=13.8, 5.3 Hz, 1H), 2.84 (dd, J=13.8, 8.9 Hz, 1H), 2.78-2.74 (m, 2H), 2.60 (dd, J=16.5, 6.2 Hz, 1H), 2.41-2.31 (m, 3H).

Example 11—Preparation of DPLG-21054

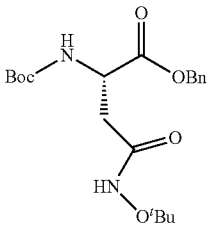

DPLG-21054 was synthesized by following the general protocol for HATU mediated coupling of Boc-Asp-OBn (2.00 g, 6.19 mmol) with O-tert-butyl hydroxylamine hydrochloride (855.2 mg, 6.81 mmol). After completion of reaction, water was added. Mixture was extracted with ethyl acetate twice. Combined organic layer was washed with saturated brine and dried over anhydrous sodium sulfate. Organic layer was evaporated to give product as colorless paste (2.40 g, 98%). The crude was used in next step without further purification. $^1$H NMR (500 MHz, DMSO-$d_6$) δ 10.33 (s, 1H), 7.43-7.27 (m, 5H), 7.21 (d, J=8.3 Hz, 1H), 5.11 (s, 2H), 4.43-4.36 (m, 1H), 2.55 (dd, J=14.8, 5.9 Hz, 1H), 2.40 (dd, J=14.8, 8.0 Hz, 1H), 1.36 (s, 9H), 1.13 (s, 9H).

Example 12—Preparation of DPLG-21055

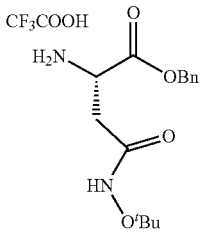

DPLG-21055 was synthesized by following the general procedure for Boc-deprotection of DPLG-21054 (2.40 g, 6.08 mmol). Crude was dried under vacuum to give colorless paste (2.48 g, quant.). Product was used in next step without further purification. $^1$H NMR (500 MHz, DMSO-$d_6$) δ 10.64 (s, 1H), 8.36 (bs, 3H), 7.44-7.34 (m, 5H), 5.23-5.19 (m, 2H), 4.47-4.39 (m, 1H), 2.71 (d, J=5.3 Hz, 2H), 1.13 (s, 9H).

Example 13—Preparation of DPLG-21056

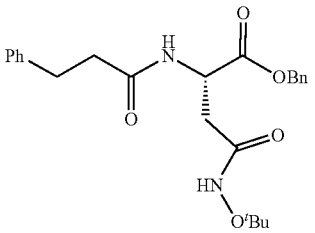

DPLG-21056 was synthesized by following the general procedure for HATU mediated coupling of 3-phenylpropanoic acid (991.1 mg, 6.60 mmol) with DPLG-21055 (2.45 g, 6.00 mmol). After completion of reaction, water was added. A white precipitate was formed. White precipitate was filtered, washed with water, and dried to give product (2.02 g, 79%). Product was used in the next step without further purification. Complex NMR due to presence of 90:10 rotamers. $^1$H NMR (500 MHz, DMSO-$d_6$) δ 10.36 (s, 1H), 10.15 (s, 0.1H), 8.37 (d, J=7.8 Hz, 0.9H), 8.30 (d, J=7.7 Hz, 0.1H), 7.38-7.31 (m, 5H), 7.27-7.24 (m, 2H), 7.20-7.14 (m, 3H), 5.10 (s, 2H), 4.74-4.71 (m, 0.1H), 4.67-4.62 (m, 0.9H), 2.77 (t, J=7.9 Hz, 2H), 2.57 (dd, J=15.0, 6.2 Hz, 1H), 2.46-2.37 (m, 3H), 1.12 (s, 9H).

Example 14—Preparation of DPLG-21059

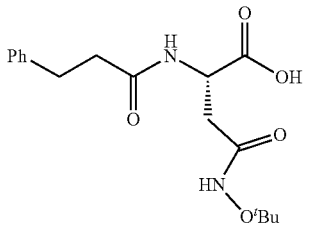

DPLG-21059 was synthesized by following the general procedure for O-debenzylation of DPLG-21056 (1.98 g, 4.64 mmol). Product (1.55 g, 99%) was isolated as a white solid. $^1$H NMR (500 MHz, DMSO-$d_6$) δ 12.61 (s, 1H), 10.33 (s, 1H), 8.16 (d, J=8.0 Hz, 1H), 7.29-7.23 (m, 2H), 7.22-7.14 (m, 3H), 4.64-4.46 (m, 1H), 2.81-2.76 (m, 2H), 2.54-2.46 (m, 1H), 2.43-2.37 (m, 2H), 2.35 (dd, J=14.8, 7.5 Hz, 1H), 1.13 (s, 9H).

Example 15—Preparation of (S)—N4-(tert-butoxy)-N1(S)-3-(4-fluorophenyl)-1-((naphthalen-1-ylmethyl)amino)-1-oxopropan-2-yl)-2-(3-phenylpropanamido)succinamide (DPLG3)

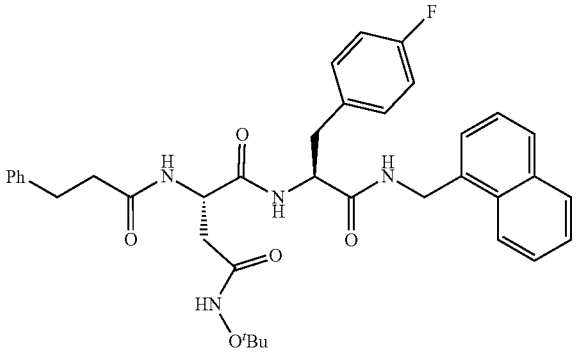

DPLG3 was prepared following the general procedure for HATU mediated coupling of $PhCH_2CH_2C(O)$-Asp(CONHOtBu)-OH (1.35 g, 4.00 mmol) and H-4F-Phe-$CH_2$-naphth TFA salt (1.92 g, 4.40 mmol). After completion of reaction, 100 mL water was added. A white precipitate was formed. Precipitate was filtered and washed with ethanol. The precipitate was triturated with methanol and filtered. Precipitate was dried to give 1.73 g (67%) pure product as a white solid. $^1$H NMR (500 MHz, DMSO-$d_6$) δ 10.33 (s, 1H), 8.53 (t, J=5.8 Hz, 1H), 8.11-8.04 (m, 3H), 7.97-7.91 (m, 1H), 7.84 (d, J=8.1 Hz, 1H), 7.59-7.50 (m, 2H), 7.43 (dd, J=8.1, 7.1 Hz, 1H), 7.36 (d, J=7.0 Hz, 1H), 7.29-7.23 (m, 2H), 7.22-7.13 (m, 5H), 7.03-6.95 (m, 2H), 4.76 (dd, J=15.3, 5.9 Hz, 1H), 4.70 (dd, J=15.3, 5.7 Hz, 1H), 4.63-4.54 (m, 1H), 4.51-4.43 (m, 1H), 3.04 (dd, J=13.8, 5.0 Hz, 1H), 2.82 (dd, J=13.8, 9.2 Hz, 1H), 2.78-2.72 (m, 2H), 2.46 (dd, J=14.9, 6.4 Hz, 1H), 2.39-2.32 (m, 2H), 2.27 (dd, J=14.9, 7.8 Hz, 1H), 1.11 (s, 9H). $^{13}$C NMR (126 MHz, DMSO-$d_6$) δ 171.38, 170.70, 170.45, 167.61, 160.93 (d, 7=242.0 Hz), 141.26, 134.21, 133.83 (d, J=3.3 Hz), 133.24, 130.98 (d, J=8.2 Hz), 130.83, 128.48, 128.32, 128.11, 127.50, 126.22, 125.88, 125.77, 125.42, 125.37, 123.45, 114.71 (d, 7=21.1 Hz) 80.58, 54.29, 49.63, 40.23, 36.80, 36.45, 34.65, 30.97, 6.26. $^{19}$F NMR (471 MHz, DMSO-$d_6$) δ −119.28 (tt, J=9.3, 5.3 Hz).

Example 16—Preparation of tert-butyl ((S)-1-(((S)-3-(4-fluorophenyl)-1-((naphthalen-1-ylmethyl) amino)-1-oxopropan-2-yl)amino)-3-methoxy-1-oxo-propan-2-yl)carbamate (Boc-Ser(OMe)-4F-Phe-naphth, DPLG-2049)

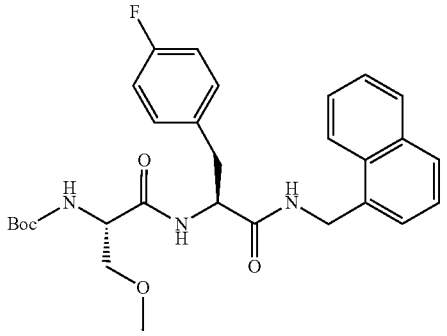

Boc-β-methoxyalanine dicyclohexylamine (80 mg, 0.2 mmol) was dissolved in DMF (4 mL). The solution was cooled to 0° C. and dipyrrolidino(N-succinimidyloxy)carbenium hexafluorophosphate (90.5 mg, 0.22 mmol) was added in one portion. 30 μL triethylamine was added and mixture was stirred at 0° C. for 15 minutes. A solution of amine (TFA.H-4F-Phe-naphth) (87.3 mg, 0.2 mmol) in 1 mL DMF and 30 μL $Et_3N$ was added to the reaction mixture. The reaction mixture was allowed to warm to room temperature and stirred overnight. The reaction mixture was diluted with chloroform and washed with 1N HCl, water, aq. $NaHCO_3$, water and brine. The organic layer was evaporated and purified by column chromatography to give product with traces of urea (dipyrrolidin-1 -ylmethanone) byproduct. The crude was used in next step without further purification. $^1$H NMR (500 MHz, DMSO-$d_6$) δ 8.46 (t, J=5.6 Hz, 1H), 8.07 (d, J=8.3 Hz, 1H), 8.02-8.00 (m, 1H), 7.96-7.94 (m, 1H), 7.85 (d, J=8.2 Hz, 1H), 7.56-7.53 (m, 2H), 7.43 (dd, J=8.2, 7.0 Hz, 1H), 7.30 (d, J=6.9 Hz, 1H), 7.22-7.19 (m, 2H), 7.04-6.99 (m, 2H), 6.88 (d, J=8.1 Hz, 1H), 4.72 (d, J=5.6 Hz, 2H), 4.61-4.54 (m, 1H), 4.14-4.10 (m, 1H), 3.35 (d, J=6.1 Hz, 2H), 3.15 (s, 3H), 3.00 (dd, J=13.8, 5.4 Hz, 1H), 2.84 (d, J=13.8, 8.8 Hz, 1H), 1.45-1.30 (m, 9H).

Example 17—Preparation of (S)-2-amino-N—((S)-3-(4-fluorophenyl)-1-((naphthalen-1-ylmethyl) amino)-1-oxopropan-2-yl)-3-methoxypropanamide (H-Ser(OMe)-4F-Phe-naphth, DPLG-2050)

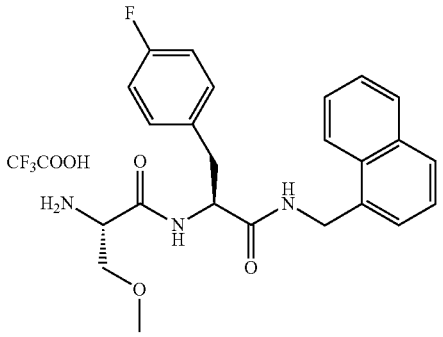

DPLG-2050 was synthesized by following the general procedure for Boc-deprotection of Boc-Ser(OMe)-4F-Phe-naphth (from previous step). After completion of reaction (3 h), excess trifluoroacetic acid and dichloromethane were evaporated. Crude product was washed with diethyl ether and dried to give product 70.0 mg (65% for 2 steps). $^1$H NMR (500 MHz, DMSO-$d_6$) 67 8.80 (d, J=8.2 Hz, 1H), 8.65 (t, J=5.6 Hz, 1H), 8.14 (bs, 3H), 8.02-7.99 (m, 1H), 7.98-7.95 (m, 1H), 7.87 (d, J=8.1 Hz, 1H), 7.58-7.53 (m, 2H), 7.43 (dd, J=8.2, 7.0 Hz, 1H), 7.30 (dd, J=7.0, 1.2 Hz, 1H), 7.26-7.23 (m, 2H), 7.10-7.05 (m, 2H), 4.74 (d, J=5.6 Hz, 2H), 4.62 (td, J=8.5, 5.7 Hz, 1H), 3.97 (m, 1H), 3.66 (dd, J=10.7, 3.6 Hz, 1H), 3.56 (dd, J=10.7, 7.0 Hz, 1H), 3.26 (s, 3H), 3.00 (dd, J=13.7, 5.7 Hz, 1H), 2.85 (dd, J=13.7, 8.8 Hz, 1H).

Example 18—Preparation of (S)-3-(4-fluorophenyl)-2-((S)-3-methoxy-2-(3-phenylpropanamido) propanamido)-N-(naphthalen-1-ylmethyl)propanamide(3-Phenylpropanoyl-Ser(OMe)-4F-Phe-naphth, DPLG-2054)

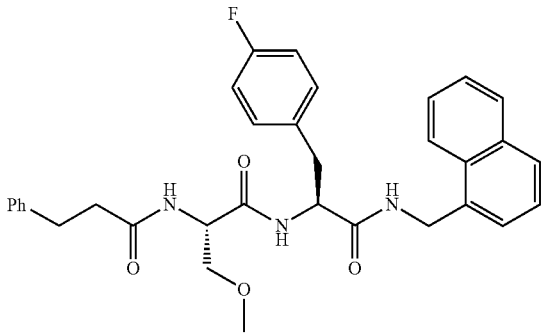

DPLG-2054 was prepared by following the general procedure for EDCI coupling of TFA.H-Ser(OMe)-4F-Phe-naphth (16 mg, 0.03 mmol) and 3-phenylpropanoic acid (5.4 mg, 0.036 mg). The product was purified by HPLC to give 5.8 mg (29%) of product. $^1$H NMR (500 MHz, Chloroform-d) δ 7.92-7.91 (m, 1H), 7.87-7.86 (m, 1H), 7.80 (d, J=8.2 Hz, 1H), 7.54-7.50 (m, 2H), 7.40 (t, J=7.6 Hz, 1H), 7.34 (d, J=6.9 Hz, 1H), 7.28-7.24 (m, 2H), 7.22-7.19 (m, 1H), 7.12-7.10 (m, 2H), 7.06-7.03 (m, 2H), 6.86-6.82 (m, 2H), 6.44 (t, J=5.7 Hz, 1H), 6.41 (d, J=8.4 Hz, 1H), 6.08 (d, J=6.3 Hz, 1H), 4.90 (dd, J=14.6, 5.7 Hz, 1H), 4.78 (dd, J=14.6, 5.2 Hz, 1H), 4.68 (dt, J=8.5, 6.5 Hz, 1H), 4.34 (td, J=6.7, 4.4 Hz, 1H), 3.50 (dd, J=9.4, 4.4 Hz, 1H), 3.14-3.08 (m, 2H), 3.05 (dd, J=14.0, 6.6 Hz, 1H), 2.99 (s, 3H), 2.86-2.79 (m, 2H), 2.43 (t, J=7.7 Hz, 2H).

Example 19—Preparation of (S)-3-(4-fluorophenyl)-2-(S)-3-methoxy-2-(4-methylphenylsulfonamido)propanamido)-N-(naphthalen-1-ylmethyl)propanamide (Ts-Ser(OMe)-4F-Phe-naphth, DPLG-2052)

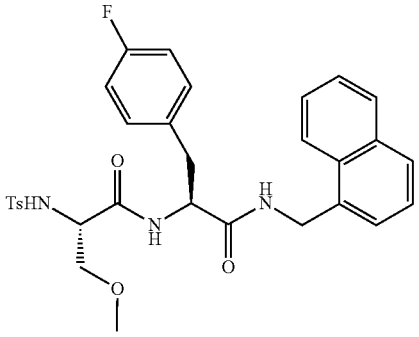

TFA.H-Ser(OMe)-4F-Phe-naphth (13.4 mg, 0.025 mmol) was dissolved in dichloromethane and the solution was cooled to 0° C. Triethylamine (28 μL) followed by TsCl (6 mg+20 mg) were added to the reaction mixture. The reaction mixture was allowed to warm to room temperature and stirred overnight. Dichloromethane was evaporated and the crude was dissolved in ethylacetate. The solution was washed with water, 1N HCl followed by brine. The product was purified by HPLC to give 7.8 mg (54%) of product. $^1$H NMR (500 MHz, DMSO-$d_6$) δ 8.39 (t, J=5.9 Hz, 1H), 8.27 (d, J=8.1 Hz, 1H), 8.00-7.93 (m, 3H), 7.84 (d, J=8.3 Hz, 1H), 7.61-7.59 (m, 2H), 7.55-7.53 (m, 2H), 7.40 (dd, J=8.2, 7.0 Hz, 1H), 7.27-7.24 (m, 3H), 7.17-7.13 (m, 2H), 7.04-7.00 (m, 2H), 4.70 (d, J=5.7 Hz, 2H), 4.38 (td, J=8.0, 6.1 Hz, 1H), 3.96-3.93 (m, 1H), 3.26-3.24 (m, 2H), 3.02 (s, 3H), 2.88 (dd, J=13.7, 6.0 Hz, 1H), 2.67 (dd, J=13.7, 8.0 Hz, 1H), 2.32 (s, 3H).

Example 20—Preparation of tert-butyl (S)-(1-((naphthalen-1-ylmethyl)amino)-1-oxopropan-2-yl) carbamate (Boc-Ala-naphth)

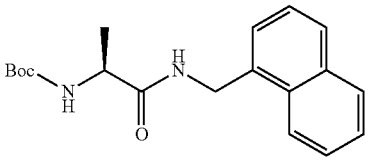

Boc-Ala-OSu (286 mg, 1.0 mmol) and 1-naphthylmethylamine (160 ↑l, 1.1 mmol) were dissolved in dichloromethane (10 mL). The solution was cooled to 0° C. and triethylamine (100 μL) was added. Reaction mixture was allowed to warm to room temperature slowly and stirred at room temperature. After completion of reaction, dichloromethane was evaporated and crude was suspended in water. Water layer was extracted twice with ethyl acetate. The combined organic layer was washed with aq. $NaHCO_3$, water, 1N HCl and brine. The organic layer was dried over anhydrous sodium sulfate and evaporated to give product (320 mg, 97%), which was used in next step without further purification. $^1$H NMR (500 MHz, Chloroform-d) δ 7.96 (d, J=8.1 Hz, 1H), 7.87 (dd, J=7.5, 1.7 Hz, 1H), 7.80 (dd, J=6.9, 2.5 Hz, 1H), 7.59-7.48 (m, 2H), 7.44-7.40 (m, 2H), 6.44 (s, 1H), 4.96-4.88 (m, 3H), 4.18-4.15 (m, 1H), 1.37 (d, J=7.1 Hz, 3H), 1.34 (s, 9H).

Example 21—Preparation of (S)-2-amino-N-(naphthalen-1-ylmethyl)propanamide 2,2,2-trifluoroacetate (H-Ala-naphth, DPLG-2026)

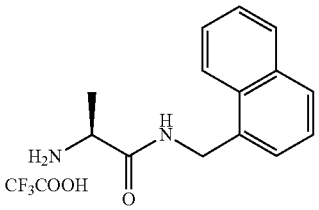

DPLG-2026 was synthesized by following the general procedure for Boc-deprotection of Boc-Ala-naphth (158 mg, 0.48 mmol). After completion of reaction (3 h), dichloromethane and excess TFA were evaporated. The crude product was dried under vacuum to give product (164 mg, quant.). $^1$H NMR (500 MHz, DMSO-$d_6$) δ 8.91 (t, J=5.7 Hz, 1H), 8.15 (bs, 3H), 8.07-8.04 (m, 1H), 7.99-7.97 (m, 1H), 7.91-7.87 (m, 1H), 7.60-7.55 (m, 2H), 7.51-7.48 (m, 2H), 4.85 (dd, J=15.2, 5.7 Hz, 1H), 4.78 (dd, J=15.2, 5.5 Hz, 1H), 3.91-3.86 (m, 1H), 1.37 (d, J=7.0 Hz, 3H).

Example 22—Preparation of tert-butyl ((S)-3-methoxy-1-(((S)-1-((naphthalen-1-ylmethyl)amino)-1-oxopropan-2-yl)amino)-1-oxopropan-2-yl)carbamate (Boc-Ser(OMe)-Ala-naphth, DPLG-2032)

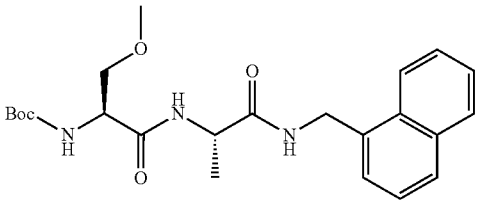

H-Ala-naphth TFA salt (0.24 mmol) was dissolved in 3 mL dimethylformamide and basified with N-methylmorpholine. Boc-Ser(OMe)-OH (96 mg, 0.24 mmol) was added to the solution. The mixture was cooled to 0° C. and dipyrrolidino(N-succinimidyloxy)carbenium hexafluorophosphate (103 mg, 0.25 mmol) were added in one portion. The reaction mixture was allowed to warm to room temperature slowly and stirred at room temperature overnight. The reaction mixture was diluted with water and extracted twice with ethyl acetate. The organic layer was dried over anhydrous $Na_2SO_4$ and evaporated. The product was purified by silica gel column chromatography (eluent ethylacetate and hexane) to give 95 mg (92%) of product. $^1$H NMR (500 MHz, DMSO-$d_6$) δ 8.29 (t, J=5.8 Hz, 1H), 8.11 (d, J=7.4 Hz, 1H), 8.03-8.01 (m, 1H), 7.96-7.94 (m, 1H), 7.85 (d, J=8.0 Hz, 1H), 7.57-7.53 (m, 2H), 7.48-7.45 (m, 1H), 7.42 (dd, J=7.0, 1.4 Hz, 1H), 6.95 (d, J=8.0 Hz, 1H), 4.75 (d, J=5.6 Hz, 2H), 4.36-4.31 (m, 1H), 4.19-4.15 (m, 1H), 3.47-3.39 (m, 2H), 3.15 (s, 3H), 1.37 (s, 9H), 1.25 (d, J=7.1 Hz, 3H).

Example 23—Preparation of (S)-2-amino-3-methoxy-N—((S)-1-((naphthalen-1-ylmethyl) amino)-1-oxopropan-2-yl)propanamide 2,2,2-trifluoroacetate (H-Ser(OMe)-Ala-naphth, DPLG-2038)

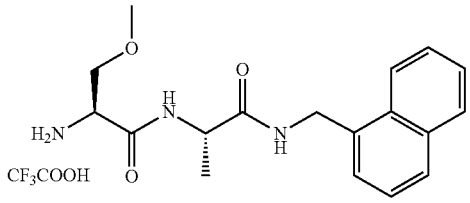

DPLG-2038 was synthesized by following the general procedure for Boc-deprotection of Boc-Ser(OMe)-Alanaphth (95 mg, 0.22 mmol). After completion of reaction, dichloromethane and excess trifluoroacetic acid were evaporated and crude was triturated with diethylether. The mixture was filtered to give corresponding amine TFA salt (60 mg, 61%) as a white powder. $^1$H NMR (500 MHz, DMSO-$d_6$) δ 8.73 (d, J=7.6 Hz, 1H), 8.51 (t, J=5.7 Hz, 1H), 8.18 (bs, 3H), 8.05-8.03 (m, 1H), 7.97-7.95 (m, 1H), 7.87 (d, J=8.0 Hz, 1H), 7.58-7.54 (m, 2H), 7.49-7.43 (m, 2H), 4.80-4.72 (m, 2H), 4.45-4.39 (m, 1H), 4.03 (m, 1H), 3.65 (dd, J=10.7, 3.8 Hz, 1H), 3.56 (dd, J=10.7, 7.2 Hz, 1H), 3.25 (s, 3H), 1.28 (d, J=7.0 Hz, 3H).

Example 24—Preparation of (S)-3-methoxy-N—((S)-1-((naphthalen-1-ylmethyl)amino)-1-oxopropan-2-yl)-2-(3-phenylpropanamido)propanamide (3-Phenylproapanamide-Ser(OMe)-Ala-naphth, DPLG-2048)

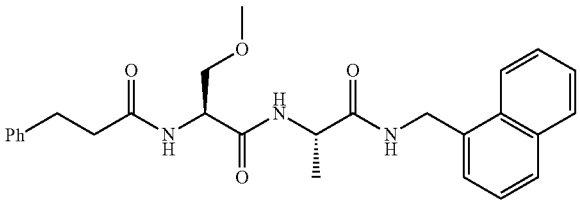

DPLG-2048 was prepared following the general procedure for EDC coupling of 3-phenylpropianic acid (16.5 mg, 0.11 mmol) with TFA.H-Ser(OMe)-Ala-naphth (44.3 mg, 0.1 mmol). The crude was purified by silica gel column chromatography to give 44.1 mg (87%) of product. $^1$H NMR (500 MHz, DMSO-$d_6$) δ 8.24-8.18 (m, 2H), 8.15 (d, J=7.8 Hz, 1H), 8.04-8.02 (m, 1H), 7.96-7.94 (m, 1H), 7.86-7.84 (m, 1H), 7.56-7.53 (m, 2H), 7.45-7.40 (m, 2H), 7.27-7.24 (m, 2H), 7.20-7.16 (m, 3H), 4.75 (d, J=5.7 Hz, 2H), 4.50 (dt, J=7.9, 6.0 Hz, 1H), 4.36-4.30 (m, 1H), 3.45-3.41 (m, 2H), 3.12 (s, 3H), 2.79 (t, J=7.9 Hz, 2H), 2.47-2.44 (m, 2H), 1.26 (d, J=7.1 Hz, 3H).

Example 25—Preparation of N—((S)-3-methoxy-1-(((S)-1-((naphthalen-1-ylmethyl)amino)-1-oxopropan-2-yl)amino)-1-oxopropan-2-yl)-5-methylisoxazole-3-carboxamide (5-methylisoxazole-3-carbamide-Ser(OMe)-Ala-naphth, DPLG-2040)

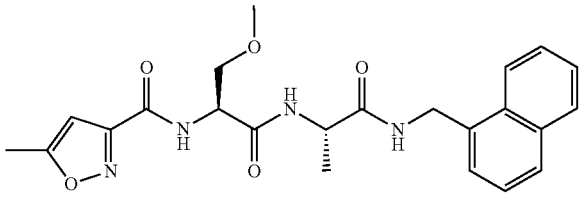

DPLG-2040 was prepared following the general procedure for EDC mediated coupling of 5-methyl-iso-oxazole-3-carboxylic acid (9.2 mg, 0.072 mmol) with TFA.H-Ser (OMe)-Ala-naphth (28.0 mg, 0.06 mmol). The product was purified by HPLC to give 16.3 mg (62%) of product. $^1$H NMR (500 MHz, DMSO-$d_6$) δ 8.50 (d, J=7.9 Hz, 1H), 8.37 (d, J=7.5 Hz, 1H), 8.32 (t, J=5.8 Hz, 1H), 8.04-8.02 (m, 1H), 7.96-7.94 (m, 1H), 7.86 (d, J=8.0 Hz, 1H), 7.57-7.53 (m, 2H), 7.48-7.42 (m, 2H), 6.56 (d, J=1.1 Hz, 1H), 4.76-4.68 (m, 3H), 4.39-4.34 (m, 1H), 3.64-3.58 (m, 2H), 3.19 (s, 3H), 2.47 (s, 3H), 1.27 (d, J=7.1 Hz, 3H). $^{13}$C NMR (126 MHz, DMSO) δ 172.19, 171.82, 168.93, 159.05, 158.95, 134.77, 133.72, 131.25, 128.96, 128.04, 126.66, 126.28, 125.85, 125.58, 123.84, 101.82, 72.05, 58.64, 53.19, 48.97, 39.57, 18.71, 12.31.

Example 26—Preparation of N—((S)-3-methoxy-1-(((S)-1-((naphthalen-1-ylmethyl)amino)-1-oxopropan-2-yl)amino)-1-oxopropan-2-yl)-2-methylthiazole-4 -carboxamide (2-methylthiazole-4-carboxamide-Ser(OMe)-Ala-naphth, DPLG-2039)

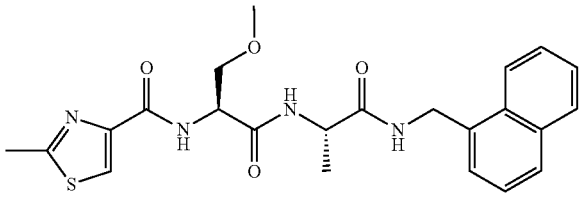

DPLG-2039 was prepared following the general procedure for EDCI coupling of 2-methylthiazole-4-carboxylic acid (10.3 mg, 0.072 mmol) and TFA.H-Ser(OMe)-Ala-naphth (28.0 mg, 0.06 mmol). The product was purified by HPLC to give 14.3 mg (52%) mg of product. $^1$H NMR (500 MHz, DMSO-$d_6$) δ 8.42 (d, J=7.6 Hz, 1H), 8.32 (t, J=5.7 Hz, 1H), 8.13 (s, 1H), 8.09 (d, J=8.1 Hz, 1H), 8.04-8.02 (m, 1H), 7.96-7.94 (m, 1H), 7.86 (d, J=8.0 Hz, 1H), 7.57-7.53 (m, 2H), 7.49-7.42 (m, 2H), 4.76 (d, J=5.7 Hz, 2H), 4.71 (dt, J=8.2, 5.5 Hz, 1H), 4.42-4.36 (m, 1H), 3.65 (dd, J=10.0, 6.1 Hz, 1H), 3.58 (dd, J=10.0, 4.9 Hz, 1H), 3.17 (s, 3H), 2.72 (s, 3H), 1.27 (d, J=7.0 Hz, 3H). $^{13}$C NMR (126 MHz, DMSO) δ 172.14, 169.22, 166.95, 160.38, 149.16, 134.76, 133.73, 131.26, 128.96, 128.06, 126.67, 126.29, 125.86, 125.62, 124.73, 123.85, 72.68, 58.74, 52.69, 48.94, 40.67, 19.22, 18.77.

Example 27—Preparation of tert-butyl (S)-(1-(((1H-indol-4-yl)methyl)amino)-1-oxopropan-2-yl)carbamate (Boc-Ala-Indole, DPLG-2022)

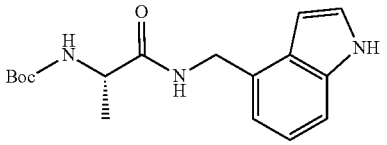

Boc-Ala-OSu (515 mg, 1.8 mmol) was dissolved in 10 mL dry dichloromethane. The solution was cooled to 0° C. and a solution of 4-(aminomethyl)indole (263 mg, 1.8 mmol) in DMF (2 mL) was added. The reaction mixture was warmed to room temperature and stirred overnight. After completion of reaction, dichloromethane was evaporated. The crude solid was dissolved in ethyl acetate and washed with water followed by brine. The organic layer was dried over anhydrous sodium sulfate and evaporated to give product (560 mg, 98%), which was pure by NMR. $^1$H NMR (500 MHz, DMSO-$d_6$) δ 11.11 (s, 1H), 8.17 (t, J=5.8 Hz, 1H), 7.32-7.29 (m, 2H), 7.01 (t, J=7.6 Hz, 1H), 6.90-6.87 (m, 2H), 6.48-6.47 (m, 1H), 4.58 (dd, J=15.2, 6.0 Hz, 1H), 4.47 (dd, J=15.2, 5.5 Hz, 1H), 4.05-3.99 (m, 1H), 1.38 (s, 9H), 1.20 (d, J=7.1 Hz, 3H).

Example 28—Preparation of (S)—N-((1H-indol-4-yl)methyl)-2-aminopropanamide (H-Ala-indole, DPLG-2025)

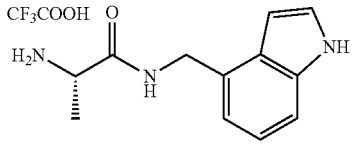

DPLG-2025 was synthesized by following the general procedure for Boc-deprotection of Boc-Ala-Indole (276 mg, 0.87 mmol). After completion of reaction (2 h) dichloromethane and excess TFA were evaporated. The crude product was dissolved in water and washed with dichloromethane. The water layer was frozen and lyophilized to give solid product (213 mg 74%). $^1$H NMR (500 MHz, DMSO-$d_6$) δ 11.19 (s, 1H), 8.76 (t, J=5.8 Hz, 1H), 8.05 (bs, 3H), 7.36-7.32 (m, 2H), 7.04 (t, J=7.6 Hz, 1H), 6.93-6.90 (m, 1H), 6.50-6.48 (m, 1H), 4.63 (dd, J=14.9, 5.8 Hz, 1H), 4.53 (dd, J=14.9, 5.4 Hz, 1H), 3.84-3.80 (m, 1H), 1.35 (d, J=6.9 Hz, 3H).

Example 29—Preparation of tert-butyl ((S)-1-(((S)-1-(((1H-indol-4 -yl)methyl)amino)-1-oxopropan-2-yl)amino)-1-oxopropan-2-yl)carbamate (Boc-Ala-Ala-Indole, DPLG-2028)

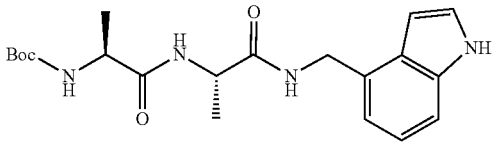

(S)—N-((1H-indol-4-yl)methyl)-2-aminopropanamide (33.1 mg, 0.1 mmol) was dissolved in dichloromethane (2 mL) and tetrahydrofuran (2 mL) and triethylamine (28 μL, 0.2 mmol) was added. The solution was cooled to 0° C. and Boc-Ala-OSu was added in one portion. A white precipitate appeared. After 30 minutes, the solvent was evaporated and the crude was dissolved in ethyl acetate. The solution was washed with water, $NaHCO_3$ solution followed by brine. The organic layer was dried over anhydrous sodium sulfate and evaporated to give product (38.0 mg, 98%). $^1$H NMR (500 MHz, DMSO-$d_6$) δ 11.12 (s, 1H), 8.34-8.31 (m, 1H), 7.86 (d, J=7.6 Hz, 1H), 7.32-7.29 (m, 2H), 7.03-7.00 (m, 2H), 6.86 (d, J=7.2 Hz, 1H), 6.47-6.45 (m, 1H), 4.55 (dd, J=15.1, 5.8 Hz, 1H), 4.50 (dd, J=15.1, 5.6 Hz, 1H), 4.37-4.29 (m, 1H), 3.99-3.93 (m, 1H), 1.37 (s, 9H), 1.23 (d, J=7.0 Hz, 3H), 1.16 (d, J=6.6 Hz, 3H).

Example 30—Preparation of (S)—N-((1H-indol-4-yl)methyl)-2-((S)-2-aminopropanamido)propanamide 2,2,2-trifluoroacetate (H-Ala-Ala-Indole, DPLG-2033)

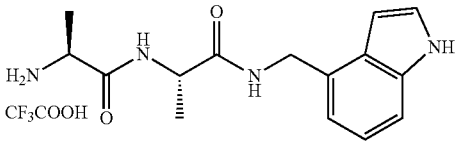

DPLG-2033 was synthesized by following the general procedure for Boc-deprotection of tert-butyl ((S)-1-4(S)-1-4(1H-indol-4-yl)methyl)amino)-1-oxopropan-2-yl)amino)-1-oxopropan-2-yl)carbamate (240 mg, 0.618 mmol). After completion of reaction (4 h), excess trifluoroacetic acid and dichloromethane were evaporated and the crude was washed twice with diethyl ether to give product (193 mg, 78%). $^1$H NMR (500 MHz, DMSO-$d_6$) δ 11.14 (s, 1H), 8.59 (d, J=7.7 Hz, 1H), 8.46 (t, J=5.7 Hz, 1H), 8.06 (bs, 3H), 7.33-7.30 (m, 2H), 7.04-7.01 (m, 1H), 6.87 (d, J=7.2 Hz, 1H), 6.48 (d, J=2.8 Hz, 1H), 4.57 (dd, J=15.1, 5.7 Hz, 1H), 4.51 (dd, J=15.1, 5.5 Hz, 1H), 4.44-4.38 (m, 1H), 3.87 (m, 1H), 1.33 (d, J=7.0 Hz, 3H), 1.27 (d, J=7.0 Hz, 3H).

Example 31—Preparation of N—((S)-1-(((S)-1-(((1H-indol-4-yl)methyl)amino)-1-oxopropan-2-yl)amino)-1-oxopropan-2-yl)-2-methylthiazole-4 -carboxamide (2-methylthiazole-4-carboxamide-Ala-Ala-Indole, DPLG-2042)

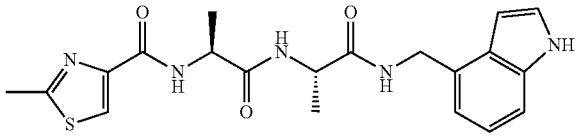

DPLG-2042 was prepared following the general procedure for EDC mediated coupling of 2-methylthiazole-4-carboxylic acid (21 mg, 0.144 mmol) and (S)—N-((1H-indol-4-yl)methyl)-2-((S)-2-aminopropanamido) propanamide 2,2,2-trifluoroacetate (50.0 mg, 0.12 mmol). The crude was purified by HPLC to give 16.0 mg (32%) of product. $^1$H NMR (500 MHz, DMSO-$d_6$) δ 11.12 (s, 1H), 8.35 (t, J=5.9 Hz, 1H), 8.28 (d, J=7.7 Hz, 1H), 8.17 (d, J=7.8 Hz, 1H), 8.11 (s, 1H), 7.32-7.29 (m, 2H), 7.04-7.01 (m, 1H), 6.87 (d, J=7.1 Hz, 1H), 6.48 (t, J=2.2 Hz, 1H), 4.59-4.48 (m, 3H), 4.41-4.35 (m, 1H), 2.72 (s, 3H), 1.32 (d, J=7.0 Hz, 3H), 1.25 (d, J=7.0 Hz, 3H). $^{13}$C NMR (126 MHz, DMSO) δ 172.14, 171.88, 166.82, 160.09, 149.42, 136.22, 130.45, 126.57, 125.37, 124.46, 121.16, 117.64, 110.86, 79.64, 48.73, 48.59, 41.07, 19.36, 19.21, 19.00.

Example 32—Preparation of N—((S)-1-(((S)-1-(((1H-indol-4-yl)methyl)amino)-1-oxopropan-2-yl)amino)-1-oxopropan-2-yl)-5-methylisoxazole-3-carboxamide (5-methylisoxazole-3-carboxamide-Ala-Ala-Indole, DPLG-2041)

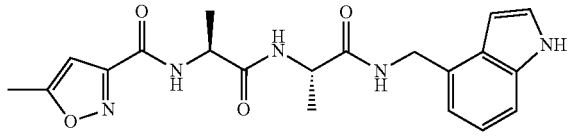

DPLG-2041 was prepared following the general procedure for EDC mediated coupling of 5-methyl-iso-oxazole-3-carboxylic acid (18.3 mg, 0.144 mmol) and (S)—N-((1H-indol-4-yl)methyl)-2-((S)-2-aminopropanamido) propanamide 2,2,2-trifluoroacetate (50.0 mg, 0.12 mmol). The product was purified by HPLC to give 6.1 mg (13%) of product. $^{1}$H NMR (500 MHz, DMSO-$d_6$) δ 11.12 (s, 1H), 8.58 (d, J=7.4 Hz, 1H), 8.32 (t, J=5.8 Hz, 1H), 8.15 (d, J=7.6 Hz, 1H), 7.32-7.29 (m, 2H), 7.02 (t, J=7.6 Hz, 1H), 6.87 (d, J=7.1 Hz, 1H), 6.54 (s, 1H), 6.48-6.47 (m, 1H), 4.58-4.45 (m, 3H), 4.38-4.33 (m, 1H), 2.47 (s, 3H), 1.32 (d, J=7.1 Hz, 3H), 1.25 (d, J=7.0 Hz, 3H). $^{13}$C NMR (126 MHz, DMSO) δ 172.21, 171.67, 171.62, 159.08, 158.75, 136.22, 130.44, 126.56, 125.37, 121.16, 117.63, 110.85, 101.80, 99.82, 49.01, 48.74, 41.06, 18.98, 18.44, 12.30.

Example 33—Preparation of N4-(tert-butoxy)-N2-(tert-butoxycarbonyl)-L-asparagine (DPLG-2076)

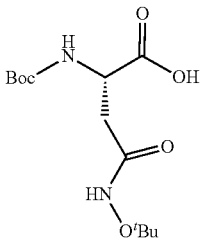

DPLG-2076 was synthesized by following the general procedure for O-debenzylation of benzyl $N^4$-(tert-butoxy)-$N^2$-(tert-butoxycarbonyl)-L-asparaginate (592 mg, 1.5 mmol). After completion of reaction (5 h), the mixture was filtered through celite and filterate was evaporated to give product (450 mg, 98%). $^{1}$H NMR (500 MHz, Chloroform-d) δ 9.28 & 8.98 (s, rotamers, 1H), 6.92 & 5.76 (bs, rotamers, 1H), 4.59-4.47 (m, 1H), 3.22-2.69 (m, 2H), 1.44 (s, 9H), 1.27 & 1.24 (s, rotamers, 9H).

Example 34—Preparation of Benzyl N4-(tert-butoxy)-N2-(tert-butoxycarbonyl)-L-asparaginyl-L-alaninate (DPLG-2081)

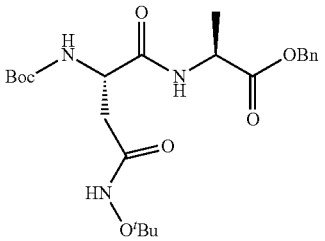

DPLG-2081 was prepared by following the general procedure for HATU mediated coupling of $N^4$-(tert-butoxy)-$N^2$-(tert-butoxycarbonyl)-L-asparagine (304 mg, 1 mmol) and O-benzylalanine hydrochloride (237 mg, 1.1 mmol). After completion of reaction (4 h), water was added to the reaction mixture and extracted twice with ethyl acetate. The combined organic layer was evaporated and the crude product was purified by recrystallization with ethanol-water to give pure product (276 mg, 59%). $^{1}$H NMR (500 MHz, Chloroform-d) δ 8.20 (s, 1H), 7.51-7.34 (m, 6H), 6.13 & 5.89 (bs, rotamers, 1H), 5.20 (d, J=12.4 Hz, 1H), 5.15 (d, J=12.4 Hz, 1H), 4.60-4.45 (m, 2H), 2.79-2.66 (m, 1H), 2.49-2.45 (m, 1H), 1.46 (s, 9H), 1.41 (d, J=7.2 Hz, 3H), 1.26 (s, 9H).

Example 35—Preparation of N4-(tert-butoxy)-N2-(tert-butoxycarbonyl)-L-asparaginyl-L-alanine (DPLG-2092)

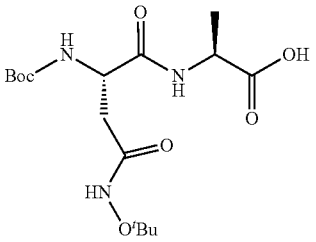

DPLG-2092 was synthesized by following the general procedure for O-debenzylation of benzyl $N^4$-(tert-butoxy)-$N^2$-(tert-butoxycarbonyl)-L-asparaginyl-L-alaninate (150 mg, 0.32 mmol). After completion of reaction, mixture was filtered through celite and evaporated to give product (120 mg, quant.). $^{1}$H NMR (500 MHz, DMSO-$d_6$) δ 12.96 (bs, 1H), 10.37 (s, 1H), 7.94 (d, J=6.7 Hz, 1H), 7.01 (d, J=6.6 Hz, 1H), 4.28-4.23 (m, 1H), 4.10-4.04 (m, 1H), 2.39 (dd, J=14.4, 4.4 Hz, 1H), 2.27 (dd, J=14.4, 9.9 Hz, 1H), 1.37 (s, 9H), 1.23 (d, J=7.2 Hz, 3H), 1.14 (s, 9H).

Example 36—Preparation of tert-butyl ((4S,7S)-4,12,12-trimethyl-1-(naphthalen-1-yl)-3,6,9-trioxo-11-oxa-2,5,10-triazatridecan-7-yl)carbamate (DPLG-2095)

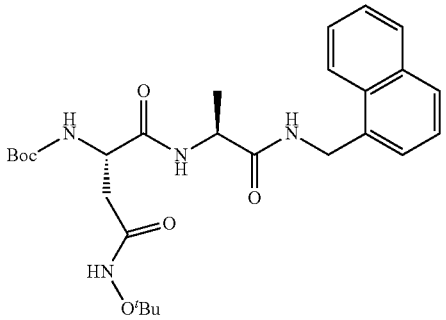

DPLG-2095 was prepared following the general procedure for HATU mediated coupling of $N^4$-(tert-butoxy)-$N^2$-(tert-butoxycarbonyl)-L-asparaginyl-L-alanine (120 mg, 0.32 mmol) and 1-naphthylmethylamine (56 μl, 0.38 mmol). After completion of reaction (6 h), the mixture was precipitated with water. The precipitate was filtered and dried to give product (153 mg, 93%). $^1$H NMR (500 MHz, DMSO-$d_6$) δ 0.26 (s, 1H), 8.47 (t, J=5.7 Hz, 1H), 8.06-8.04 (m, 1H), 8.01 (d, J=7.4 Hz, 1H), 7.96-7.94 (m, 1H), 7.86-7.84 (m, 1H), 7.57-7.52 (m, 2H), 7.48-7.43 (m, 2H), 6.94 (d, J=8.1 Hz, 1H), 4.74 (d, J=5.8 Hz, 2H), 4.32-4.26 (m, 2H), 2.46 (dd, J=14.6, 5.5 Hz, 1H), 2.29 (dd, J=14.6, 8.5 Hz, 1H), 1.37 (s, 9H), 1.24 (d, J=7.0 Hz, 3H), 1.13 (s, 9H).

Example 37—Preparation of (S)-2-amino-N4-(tert-butoxy)-N1-((S)-1-((naphthalen-1-ylmethyl)amino)-1-oxopropan-2-yl)succinamide (DPLG-2097)

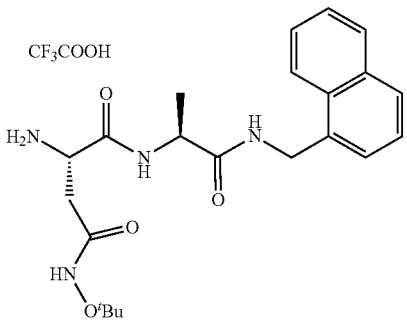

DPLG-2097 was synthesized by following the general procedure for Boc-deprotection of tert-butyl ((4S,7S)-4,12,12-trimethyl-1-(naphthalen-1-yl)-3,6,9-trioxo-11-oxa-2,5,10-triazatridecan-7-yl)carbamate (118 mg, 0.23 mmol). After completion of reaction, excess trifluoroacetic acid and dichloromethane were evaporated. The crude was triturated with diethyl ether to give product (120 mg, 98%). $^1$H NMR (500 MHz, DMSO-$d_6$) δ 10.68 (s, 1H), 8.71 (d, J=7.3 Hz, 1H), 8.58 (t, J=5.7 Hz, 1H), 8.16 (s, 3H), 8.07-8.05 (m, 1H), 7.97-7.95 (m, 1H), 7.87-7.85 (m, 1H), 7.58-7.53 (m, 2H), 7.49-7.44 (m, 2H), 4.79-4.71 (m, 2H), 4.39-4.34 (m, 1H), 4.13 (m, 1H), 2.70 (dd, J=16.4, 4.9 Hz, 1H), 2.56 (dd, J=16.4, 8.1 Hz, 1H), 1.28 (d, J=7.0 Hz, 3H), 1.15 (s, 9H).

Example 38—Preparation of (S)—N4-(tert-butoxy)-N14(S)-1-((naphthalen-1-ylmethyl)amino)-1-oxopropan-2-yl)-2-(pyrazine-2-carboxamido)succinamide (DPLG-2098)

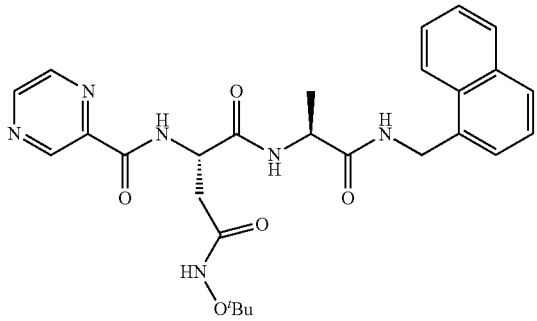

DPLG-2098 was prepared by following the general procedure for HATU mediated coupling of pyrazine-2-carboxylic acid (2.5 mg, 0.02 mmol) and (S)-2-amino-$N^4$-(tertbutoxy)-$N^1$—((S)-1-((naphthalen-1-ylmethyl)amino)-1-oxopropan-2-yl)succinamide (10.6 mg, 0.02 mmol). The crude was purified by HPLC to give 10.3 mg (99%) of product. $^1$H NMR (500 MHz, DMSO-$d_6$) δ 10.45 (s, 1H), 9.19 (d, J=1.4 Hz, 1H), 8.94 (d, J=8.1 Hz, 1H), 8.92 (d, J=2.5 Hz, 1H), 8.78 (t J=2.0 Hz, 1H), 8.50 (t J=5.8 Hz, 1H), 8.37 (d, J=7.3 Hz, 1H), 8.07-8.05 (m, 1H), 7.95-7.93 (m, 1H), 7.85-7.83 (m, 1H), 7.56-7.52 (m, 2H), 7.48-7.44 (m, 2H), 4.85-4.81 (m, 1H), 4.75 (d, J=5.8 Hz, 2H), 4.36-4.30 (m, 1H), 2.68 (dd, J=14.7, 7.2 Hz, 1H), 2.63 (dd, J=14.7, 5.2 Hz, 35 1H), 1.27 (d, J=7.1 Hz, 3H), 1.06 (s, 9H). $^{13}$C NMR (126 MHz, DMSO-$d_6$) δ 172.34, 170.17, 167.99, 162.82, 148.35, 144.51, 143.88, 134.86, 133.69, 131.25, 128.94, 127.92, 126.62, 126.21, 125.85, 125.63, 123.84, 81.09, 50.50, 49.19, 40.63, 35.39, 26.62, 18.44.

Example 39—Preparation of (S)—N4-(tert-butoxy)-2-(2-morpholinoacetamido)-N1-((S)-1-((naphthalen-1-ylmethyl)amino)-1-oxopropan-2-yl)succinamide (DPLG-2099)

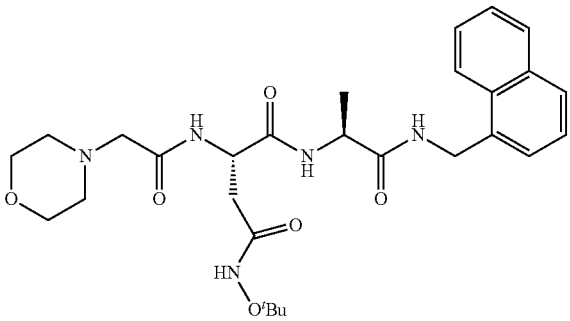

DPLG-2099 was prepared by following the general procedure for HATU mediated coupling of morpholine-4-acetic acid (3.0 mg, 0.02 mmol) and (S)-2-amino-$N^4$-(tert-butoxy)-$N^1$—((S)-1-((naphthalen-1-ylmethyl)amino)-1-oxopropan-2-yl)succinamide (10.6 mg, 0.02 mmol). The crude was purified by HPLC to give 10.6 mg (98%) of product. $^1$H NMR (500 MHz, DMSO-$d_6$) δ 10.38 (s, 1H), 8.50 (t, J=5.8

Hz, 1H), 8.20 (d, J=7.3 Hz, 1H), 8.08-8.06 (m, 1H), 7.98-8.02 (m, 1H), 7.96-7.94 (m, 1H), 7.85 (dd, J=7.0, 2.6 Hz, 1H), 7.57-7.52 (m, 2H), 7.48-7.44 (m, 2H), 4.73 (d, J=5.7 Hz, 2H), 4.62-4.57 (m, 1H), 4.31-4.27 (m, 1H), 3.61 (t, J=4.6 Hz, 4H), 2.94 (s, 2H), 2.50-2.43 (m, 6H), 1.25 (d, J=7.2 Hz, 3H), 1.11 (s, 9H).

Example 40—Preparation of S)—N4-(tert-butoxy)-2-((4-methylphenyl)sulfonamido)-N1-((S)-1-((naphthalen-1-ylmethyl)amino)-1-oxopropan-2-yl)succinamide (DPLG-2091)

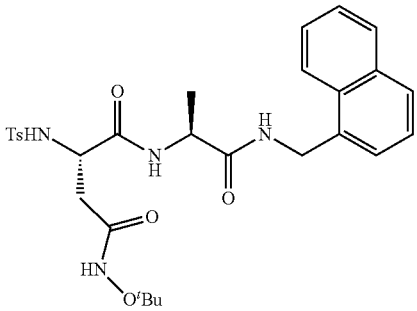

((S)-2-amino-$N^4$-(tert-butoxy)-$N^1$—((S)-1-((naphthalen-1-ylmethyl)amino)-1-oxopropan-2-yl)succinamide (10.6 mg, 0.02 mmol) was dissolved in dichloromethane and dimethylformamide (1 mL+1 mL) and the solution was cooled to 0° C. 4-(Dimethylamino)pyridine (1.2 mg, 0.01 mmol), Hunig's base (11 mL, 0.06 mmol) and 4-toluenesulphonyl chloride (0.02 mmol) were added and the solution was allowed to warm to room temperature. After completion of the reaction (5 h), mixture was diluted with dichloromethane and washed with water. The organic layer was evaporated and purified by HPLC to give product (5.1 mg, 45%). $^1$H NMR (500 MHz, DMSO-$d_6$) δ 10.40 (s, 1H), 8.33 (t, J=6.0 Hz, 1H), 8.22 (d, J=7.2 Hz, 1H), 8.08-8.06 (m, 1H), 7.94-7.92 (m, 1H), 7.83 (d, J=7.6, 1H), 7.65 (d, J=7.9 Hz, 2H), 7.55-7.51 (m, 2H), 7.45-7.41 (m, 2H), 7.32 (d, J=7.9 Hz, 2H), 4.74 (dd, J=15.3, 6.1 Hz, 1H), 4.64 (dd, J=15.3, 5.7 Hz, 1H), 4.10-4.07 (m, 1H), 3.92-3.86 (m, 1H), 2.42 (dd, J=14.8, 7.7 Hz, 1H), 2.36 (s, 3H), 2.22 (dd, J=14.8, 6.5 Hz, 1H), 1.09-1.06 (m, 12H). $^{13}$C NMR (126 MHz, DMSO-$d_6$) δ 172.14, 169.91, 167.48, 134.89, 133.67, 131.25, 129.69, 128.91, 127.86, 127.13, 126.60, 126.34, 126.22, 126.18, 125.80, 125.64, 123.85, 81.10, 53.41, 49.06, 40.58, 36.34, 26.68, 21.41, 18.08.

Example 41—Preparation of (S)—N4-(tert-butoxy)-2-(2-methylthiazole-4-carboxamido)-N1-((S)-1-((naphthalen-1-ylmethyl)amino)-1-oxopropan-2-yl) succinamide (DPLG-2102)

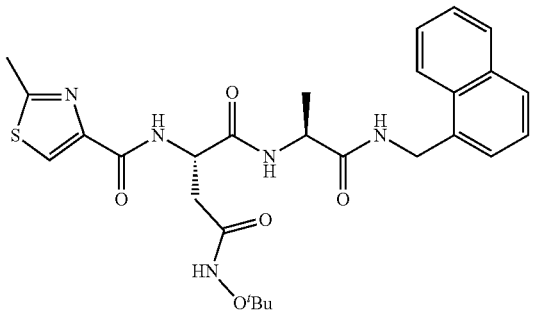

DPLG-2102 was prepared by following the general procedure for HATU mediated coupling of 2-methylthiazole-3-carboxylic acid (2.9 mg, 0.02 mmol) and (S)-2-amino-$N^4$-(tert-butoxy)-$N^1$—((S)-1-((naphthalen-1-ylmethyl)amino)-1-oxopropan-2-yl)succinamide (10.6 mg, 0.02 mmol). The crude was purified by HPLC to give 8.4 mg (77%) of product. $^1$H NMR (500 MHz, DMSO-$d_6$) δ 10.44 (s, 1H), 8.52 (t, J=5.8 Hz, 1H), 8.32 (d, J=7.3 Hz, 1H), 8.29 (d, J=8.1 Hz, 1H), 8.12 (s, 1H), 8.08-8.06 (m, 1H), 7.96-7.94 (m, 1H), 7.84 (dd, J=7.0, 2.5 Hz, 1H), 7.56-7.52 (m, 2H), 7.48-7.44 (m, 2H), 4.78-4.74 (m, 3H), 4.35-4.29 (m, 1H), 2.71 (s, 3H), 2.63 (dd, J=14.6, 7.3 Hz, 1H), 2.58 (dd, J=14.6, 5.3 Hz, 1H), 1.26 (d, J=7.1 Hz, 3H), 1.07 (s, 9H). $^{13}$C NMR (125 MHz, DMSO-$d_6$) δ 172.36, 170.42, 167.98, 166.75, 160.36, 149.21, 134.86, 133.69, 131.26, 128.94, 127.91, 126.63, 126.22, 125.87, 125.64, 124.70, 123.85, 81.11, 50.30, 49.14, 40.63, 35.60, 26.64, 19.20, 18.50.

Example 42—Preparation of (S)—N4-(tert-butoxy)-2-(5-methylisoxazole-3-carboxamido)-N1-((S)-1-((naphthalen-1-ylmethyl)amino)-1-oxopropan-2-yl) succinamide (DPLG-2105)

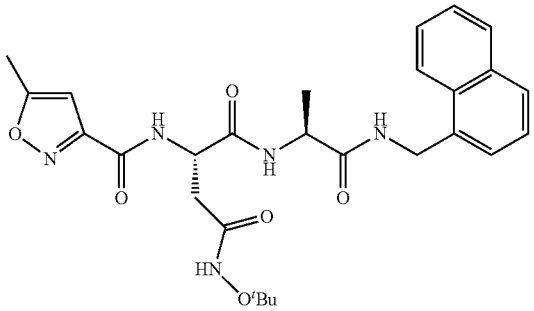

DPLG-2105 was prepared by following the general procedure for HATU mediated coupling of 5-methylisoxazole-3-carboxylic acid (2.5 mg, 0.02 mmol) and (S)-2-amino-$N^4$-(tert-butoxy)-$N^1$—((S)-1-((naphthalen-1-ylmethyl)amino)-1-oxopropan-2-yl)succinamide (10.6 mg, 0.02 mmol). The crude was purified by HPLC to give 10.2 mg (97%) of product. $^1$H NMR (500 MHz, DMSO-$d_6$) δ 10.37 (s, 1H), 8.62 (d, J=8.0 Hz, 1H), 8.48 (t, J=5.8 Hz, 1H), 8.27 (d, J=7.4 Hz, 1H), 8.06-8.04 (m, 1H), 7.96-7.94 (m, 1H), 7.85 (dd, J=7.4, 1.9 Hz, 1H), 7.56-7.52 (m, 2H), 7.48-7.43 (m, 2H), 6.54 (s, 1H), 4.79-4.76 (m, 1H), 4.74 (d, J=5.8 Hz, 2H), 4.34-4.28 (m, 1H), 2.60 (dd, J=14.7, 5.5 Hz, 1H), 2.55 (dd, J=14.7, 8.0 Hz, 1H), 2.47 (s, 3H), 1.25 (d, J=7.1 Hz, 3H), 1.09 (s, 9H). $^{13}$C NMR (125 MHz, DMSO-$d_6$) δ 171.88, 171.36, 169.73, 167.46, 158.45, 158.36, 134.38, 133.22, 130.78, 128.47, 127.47, 126.17, 125.76, 125.40, 125.16, 123.37, 101.31, 80.59, 50.03, 48.65, 40.15, 34.65, 26.20, 18.10, 11.83.

Example 43—Preparation of (S)—N4-(tert-butoxy)-N1-((S)-1-((naphthalen-1-ylmethyl)amino)-1-oxopropan-2-yl)-2-(oxirane-2-carboxamido)succinamide (DPLG-2103)

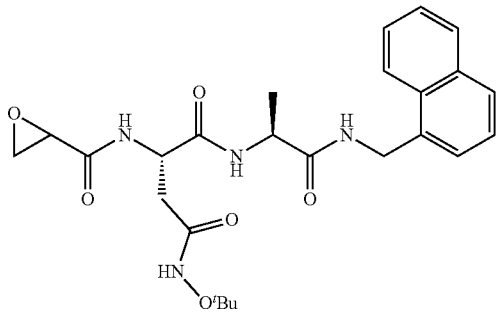

DPLG-2103 was prepared by following the general procedure for HATU mediated coupling of potassium oxirane-2-benzoate (2.5 mg, 0.02 mmol) and (S)-2-amino-N$^4$-(tert-butoxy)-N$^1$—((S)-1-((naphthalen-1-ylmethyl)amino)-1-oxopropan-2-yl)succinamide (10.6 mg, 0.02 mmol). The crude was purified by HPLC to give 8.0 mg (82%) of product. $^1$H NMR (500 MHz, DMSO-$d_6$) δ 10.38 (s, 1H), 8.48 (t, J=5.8 Hz, 1H), 8.32 (d, J=8.2 Hz, 1H), 8.20 (d, J=7.4 Hz, 1H), 8.08-8.06 (m, 1H), 7.96-7.94 (m, 1H), 7.84 (dd, J=7.3, 2.1 Hz, 1H), 7.57-7.52 (m, 2H), 7.48-7.43 (m, 2H), 4.74 (d, J=5.8 Hz, 2H), 4.62 (td, J=8.1, 5.7 Hz, 1H), 4.31-4.25 (m, 1H), 3.46 (dd, J=4.3, 2.5 Hz, 1H), 2.90 (dd, J=6.4, 4.3 Hz, 1H), 2.77 (dd, J=6.4, 2.5 Hz, 1H), 2.55-2.51 (m, 1H), 2.42 (dd, J=14.7, 8.0 Hz, 1H), 1.25 (d, J=7.1 Hz, 3H), 1.12 (s, 9H). $^{13}$C NMR (125 MHz, DMSO-$d_6$) δ 171.90, 169.94, 167.57, 167.40, 134.40, 133.23, 130.79, 128.47, 127.45, 126.17, 125.76, 125.39, 125.19, 123.38, 80.60, 49.54, 48.60, 48.23, 45.59, 40.15, 34.83, 26.23, 18.05.

Example 44—Preparation of (S)—N4-(tert-butoxy)-N1-((S)-1-((naphthalen-1-ylmethyl)amino)-1-oxopropan-2-yl)-2-(2,2,2-trifluoroacetamido)succinamide (DPLG-2106)

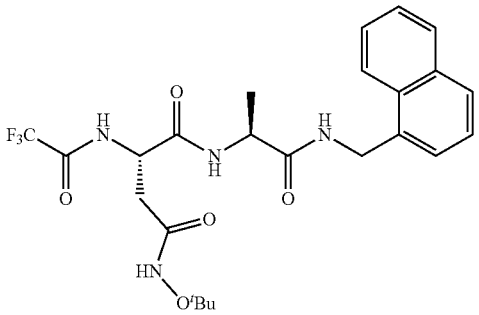

(S)-2-amino-N$^4$-(tert-butoxy)-N$^1$—((S)-1-((naphthalen-1-ylmethyl)amino)-1-oxopropan-2-yl)succinamide (10.6 mg, 0.02 mmol) was dissolved in 1 mL tetrahydrofuran and the solution was cooled to 0° C. The mixture was basified with N-methylmorpholine (4.4 mL, 0.04 mmol). Trifluoroacetic anhydride (2.8 mL, 0.02 mmol) was added, and mixture was stirred for one hour at 0° C. The crude was purified by HPLC to give pure product (8.3 mg, 81%). $^1$H NMR (500 MHz, DMSO-$d_6$) δ 10.38 (s, 1H), 9.67 (s, 1H), 8.48 (t, J=5.7 Hz, 1H), 8.41 (d, J=7.3 Hz, 1H), 8.06-8.04 (m, 1H), 7.96-7.94 (m, 1H), 7.85 (d, J=7.6 Hz, 1H), 7.57-7.53 (m, 2H), 7.48-7.43 (m, 2H), 4.74-4.70 (m, 3H), 4.33-4.27 (m, 1H), 2.63 (dd, J=15.2, 5.0 Hz, 1H), 2.54-2.49 (m, 1H), 1.26 (d, J=7.1 Hz, 3H), 1.12 (s, 9H). $^{13}$C NMR (125 MHz, DMSO-$d_6$) δ 172.37, 169.53, 167.42, 134.87, 133.70, 131.25, 128.94, 127.93, 126.63, 126.24, 125.86, 125.58, 123.84, 81.08, 50.66, 49.19, 40.62, 34.60, 26.65, 18.50. $^{19}$F NMR (471 MHz, DMSO, $C_6F6$ external reference) 6-71.81.

Example 45—Preparation of (S)—N4-(tert-butoxy)-N1-((S)-1-((naphthalen-1-ylmethyl)amino)-1-oxopropan-2-yl)-2-(4 -phenylbutanamido)succinamide (DPLG-2127)

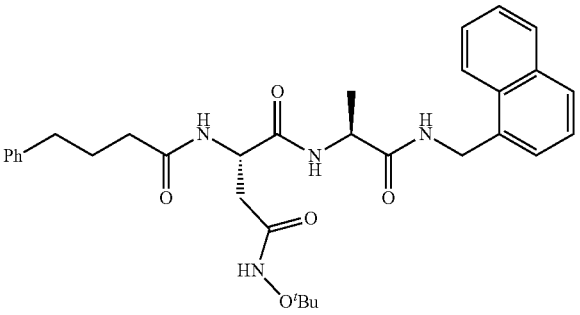

DPLG-2127 was prepared by following the general procedure for HATU mediated coupling of 4-phenylbutanoic acid (5.4 mg, 0.033 mmol) and (S)-2-amino-N$^4$-(tert-butoxy)-N$^1$—((S)-1-((naphthalen-1-ylmethyl)amino)-1-oxopropan-2-yl)succinamide (17.3 mg, 0.033 mmol). The crude was purified by HPLC to give 15.7 mg (85%) of product. $^1$H NMR (500 MHz, DMSO-$d_6$) δ 10.34 (s, 1H), 8.46 (t, J=5.9 Hz, 1H), 8.11-8.06 (m, 3H), 7.95-7.93 (m, 1H), 7.85-7.83

(m, 1H), 7.56-7.52 (m, 2H), 7.45 (d, J=5.0 Hz, 2H), 7.28-7.25 (m, 2H), 7.19-7.16 (m, 3H), 4.75 (dd, J=15.3, 5.9 Hz, 1H), 4.70 (dd, J=15.3, 5.7 Hz, 1H), 4.60-4.56 (m, 1H), 4.30-4.24 (m, 1H), 2.56-2.50 (m, 3H), 2.34 (dd, J=14.8, 7.8 Hz, 1H), 2.13 (t, J=7.4 Hz, 2H), 1.80-1.74 (m, 2H), 1.24 (d, J=7.0 Hz, 3H), 1.10 (s, 9H). $^{13}$C NMR (125 MHz, DMSO-$d_6$) δ 172.43, 172.37, 171.03, 168.12, 142.26, 134.87, 133.69, 131.26, 128.93, 128.77, 128.70, 127.90, 126.62, 126.21, 126.17, 125.84, 125.67, 123.85, 99.99, 80.99, 50.17, 49.05, 35.24, 35.10, 35.04, 27.48, 26.70, 18.55.

Example 46—Preparation of (S)—N4-(tert-butoxy)-N1-((S)-1-((naphthalen-1-ylmethyl)amino)-1-oxopropan-2-yl)-2-(2-phenylacetamido)succinamide (DPLG-2142)

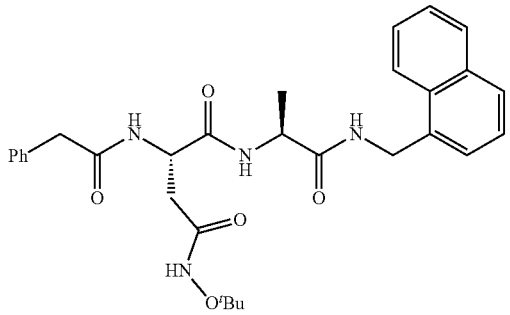

DPLG-2142 was prepared by following the general procedure for HATU mediated coupling of phenylacetic acid (4.9 mg, 0.036 mmol) and (S)-2-amino-N$^4$-(tert-butoxy)-N$^1$—((S)-1-((naphthalen-1-ylmethyl)amino)-1-oxopropan-2-yl)succinamide (17.3 mg, 0.033 mmol). The crude was purified by HPLC to give 12.1 mg (68%) of product. $^1$H NMR (500 MHz, DMSO-$d_6$) δ 10.38 (s, 1H), 8.47 (t, J=5.9 Hz, 1H), 8.36 (d, J=7.9 Hz, 1H), 8.18 (d, J=7.4 Hz, 1H), 8.09-8.07 (m, 1H), 7.95-7.93 (m, 1H), 7.85-7.83 (m, 1H), 7.56-7.52 (m, 2H), 7.45 (d, J=5.0 Hz, 2H), 7.29-7.19 (m, 5H), 4.76 (dd, J=15.3, 6.0 Hz, 1H), 4.69 (dd, J=15.3, 5.8 Hz, 1H), 4.60-4.56 (m, 1H), 4.29-4.23 (m, 1H), 3.46 (s, 2H), 2.56-2.51 (m, 1H), 2.37 (dd, J=14.9, 7.3 Hz, 1H), 1.22 (d, J=7.1 Hz, 3H), 1.10 (s, 9H). $^{13}$C NMR (126 MHz, DMSO) δ 172.37, 170.90, 170.54, 168.07, 136.60, 134.91, 133.69, 131.28, 129.51, 128.93, 128.60, 127.90, 126.77, 126.63, 126.20, 125.84, 125.72, 123.87, 81.03, 50.18, 49.12, 42.40, 40.58, 35.30, 26.71, 18.41.

Example 47—Preparation of benzyl (S)-3-((tertbutoxycarbonyl)amino)-4-(((S)-1-((naphthalen-1-ylmethyl)amino)-1-oxopropan-2-yl)amino)-4-oxobutanoate (DPLG-2074)

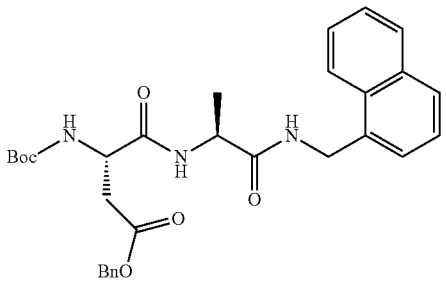

DPLG-2074 was prepared following the general procedure for HATU mediated coupling of N-(tert-butoxycarbonyl)-L-aspartic acid 4-benzyl ester (217 mg, 0.67 mmol) and (S)-2-amino-N-(naphthalen-1-ylmethyl)propanamide (230 mg, 0.67 mmol). The product was isolated by ethyl acetate extraction and purified by recrystallization with ethanol-water (yield=302 mg, 85%). $^1$H NMR (500 MHz, Chloroform-d) δ 7.95 (d, J=8.3 Hz, 1H), 7.83 (d, J=8.1 Hz, 1H), 7.76 (dd, J=7.0, 2.4 Hz, 1H), 7.53-7.46 (m, 2H), 7.41-7.37 (m, 2H), 7.34-7.28 (m, 3H), 7.26-7.24 (m, 2H), 6.76 (d, J=7.6 Hz, 1H), 6.64 (m, 1H), 5.45 (d, J=8.4 Hz, 1H), 4.96 (d, J=11.9 Hz, 1H), 4.93 (d, J=11.9 Hz, 1H), 4.86 (d, J=5.4 Hz, 2H), 4.45-4.35 (m, 2H), 2.86 (dd, J=17.1, 4.6 Hz, 1H), 2.67 (dd, J=17.1, 6.7 Hz, 1H), 1.39-1.38 (m, 12H).

Example 48—Preparation of benzyl (S)-3-amino-4-(((S)-1-((naphthalen-1-ylmethyl)amino)-1-oxopropan-2-yl)amino)-4-oxobutanoate 2,2,2-trifluoroacetate (DPLG-2114)

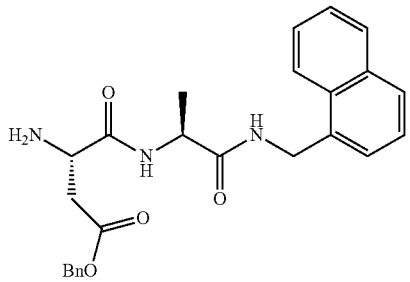

DPLG-2114 was synthesized by following the general procedure for Boc-deprotection of benzyl (S)-3-((tert-butoxycarbonyl)amino)-4-(((S)-1-((naphthalen-1-ylmethyl)amino)-1-oxopropan-2-yl)amino)-4-oxobutanoate (50 mg, 0.094 mmol). After completion of reaction (3 h), excess trifluoroacetic acid and dichloromethane were evaporated and the crude was dried under vacuum. The crude product (51 mg, quant.) was used in next step without further purification. $^1$H NMR (500 MHz, DMSO-$d_6$) δ 8.75 (d, J=7.4 Hz, 1H), 8.50 (t, J=5.8 Hz, 1H), 8.26 (d, J=5.1 Hz, 3H), 8.04-8.02 (m, 1H), 7.96-7.94 (m, 1H), 7.85 (d, J=7.9 Hz, 1H), 7.56-7.51 (m, 2H), 7.48-7.42 (m, 2H), 7.39-7.34 (m, 5H), 5.16 (d, J=12.3 Hz, 1H), 5.12 (d, J=12.3 Hz, 1H), 4.79-4.70 (m, 2H), 4.41-4.35 (m, 1H), 4.21-4.18 (m, 1H), 3.00 (dd, J=17.5, 4.0 Hz, 1H), 2.81 (dd, J=17.5, 8.7 Hz, 1H), 1.28 (d, J=7.0 Hz, 3H).

Example 49—Preparation of benzyl (S)-4-(((S)-1-((naphthalen-1-ylmethyl)amino)-1-oxopropan-2-yl)amino)-4-oxo-3-(3-phenylpropanamido)butanoate (DPLG-2115)

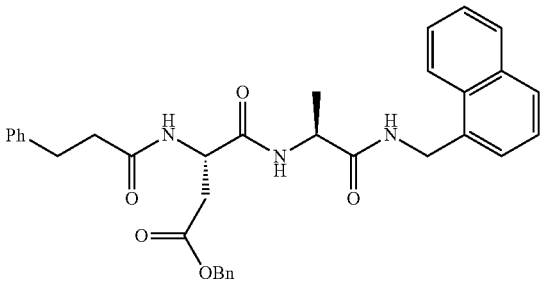

DPLG-2115 was prepared following the general procedure for HATU mediated coupling of 3-phenylproapanoic acid (15.5 mg, 0.103 mmol) and benzyl (S)-3-amino-4-(((S)-1-((naphthalen-1-ylmethyl)amino)-1-oxopropan-2-yl)amino)-4-oxobutanoate 2,2,2-trifluoroacetate (51 mg, 0.094 mmol). After completion of reaction (4 h), the mixture was precipitated by the addition of 50 mL water. The white precipitate was filtered and dried to give product (50 mg, 94%). $^1$H NMR (500 MHz, DMSO-$d_6$) δ 8.34 (t, J=5.8 Hz, 1H), 8.27 (d, J=8.0 Hz, 1H), 8.11 (d, J=7.4 Hz, 1H), 8.05-8.03 (m, 1H), 7.95-7.93 (m, 1H), 7.84 (dd, J=7.6, 1.7 Hz, 1H), 7.56-7.51 (m, 2H), 7.47-7.42 (m, 2H), 7.37-7.30 (m, 5H), 7.27-7.24 (m, 2H), 7.20-7.15 (m, 3H), 5.04 (s, 2H), 4.74 (d, J=5.7 Hz, 2H), 4.69 (td, J=8.1, 5.7 Hz, 1H), 4.32-4.26 (m, 1H), 2.82-2.77 (m, 3H), 2.57 (dd, J=16.2, 8.3 Hz, 1H), 2.40 (t, J=7.9 Hz, 2H), 1.23 (d, J=7.1 Hz, 3H).

Example 50—Preparation of (S)-4-(((S)-1-((naphthalen-1-ylmethyl)amino)-1-oxopropan-2-yl)amino)-4-oxo-3-(3-phenylpropanamido)butanoic acid (DPLG-2124)

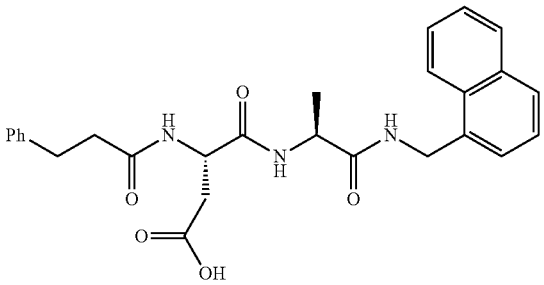

Benzyl (S)-4-(((S)-1-((naphthalen-1-ylmethyl)amino)-1-oxopropan-2-yl)amino)-4-oxo -3-(3 -phenylpropanamido) butanoate (50 mg, 0.088 mmol) was dissolved in 5 mL ethanol and 1 mL dimethylformamide. 20 mg palladium on carbon (10%) was added carefully and the mixture was stirred under hydrogen atmosphere. The reaction was not complete after 24 hours. The mixture was filtered through celite, evaporated, and purified by HPLC to give product (22.5 mg, 54%). $^1$H NMR (500 MHz, DMSO-$d_6$) δ 12.34 (s, 1H), 8.37 (m, 1H), 8.23 (d, J=7.7 Hz, 1H), 8.07-8.04 (m, 2H), 7.96-7.94 (m, 1H), 7.84 (d, J=7.9 Hz, 1H), 7.57-7.52 (m, 2H), 7.48-7.42 (m, 2H), 7.28-7.25 (m, 2H), 7.21-7.15 (m, 3H), 4.74 (d, J=5.8 Hz, 2H), 4.61-4.56 (m, 1H), 4.31-4.25 (m, 1H), 2.80 (t, J=7.9 Hz, 2H), 2.67 (dd, J=16.6, 6.1 Hz, 1H), 2.48-2.39 (m, 3H), 1.23 (d, J=7.1 Hz, 3H).

Example 51—Preparation of (S)—N1-((S)-1-((naphthalen-1-ylmethyl)amino)-1-oxopropan-2-yl)-N4-(oxetan-3-yl)-2-(3 -phenylpropanamido)succinamide (DPLG-2130)

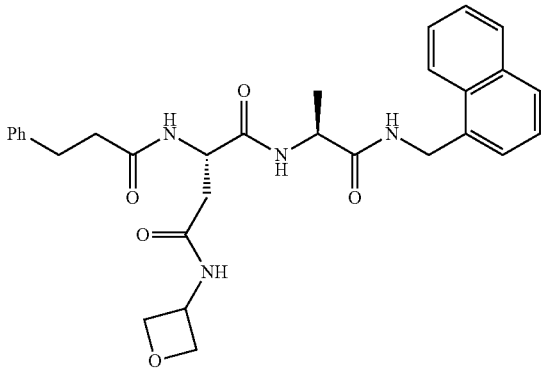

DPLG-2130 was prepared following the general procedure for HATU mediated coupling of (S)-4-(((S)-1-((naphthalen-1-ylmethyl)amino)-1-oxopropan-2-yl)amino)-4 -oxo-3-(3-phenylpropanamido)butanoic acid (12.4 mg, 0.026 mmol) and 3-aminoxetane (2.2 μL, 0.031 mmol). The mixture was purified by HPLC to give product (12.0 mg, 87%). $^1$H NMR (500 MHz, DMSO-$d_6$) δ 8.71 (d, J=6.4 Hz, 1H), 8.44 (t, J=5.8 Hz, 1H), 8.21 (d, J=7.3 Hz, 1H), 8.15 (d, J=7.9 Hz, 1H), 8.07-8.05 (m, 1H), 7.95-7.94 (m, 1H), 7.84 (d, J=7.8 Hz, 1H), 7.57-7.52 (m, 2H), 7.47-7.42 (m, 2H), 7.27-7.24 (m, 2H), 7.19-7.15 (m, 3H), 4.76 (dd, J=15.4, 5.9 Hz, 1H), 4.70 (dd, J=15.4, 5.8 Hz, 1H), 4.64-4.51 (m, 4H), 4.34-4.22 (m, 3H), 2.78 (t, J=7.8 Hz, 2H), 2.58 (dd, J=15.2, 7.5 Hz, 1H), 2.44-2.40 (m, 3H), 1.25 (d, J=7.2 Hz, 3H). $^{13}$C NMR (126 MHz, DMSO) δ 172.43, 171.96, 171.01, 169.79, 141.67, 134.83, 133.68, 131.25, 128.94, 128.72, 128.61, 127.90, 126.63, 126.32, 126.23, 125.81, 125.56, 123.81, 77.44, 77.28, 50.01, 49.15, 44.28, 40.63, 37.82, 37.12, 31.42, 18.31.

Example 52—Preparation of benzyl (S)-3-((4-methylphenyl)sulfonamido)-4-(((S)-1-((naphthalen-1-ylmethyl)amino)-1-oxopropan-2-yl)amino)-4-oxobutanoate (DPLG-2079)

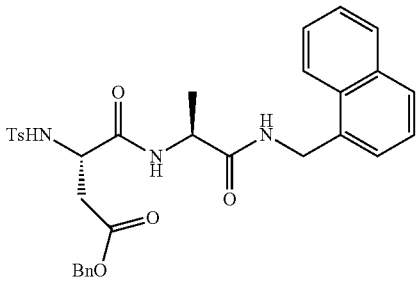

Benzyl (S)-3-amino-4-(((S)-1-((naphthalen-1-ylmethyl)amino)-1-oxopropan-2-yl)amino)-4-oxobutanoate 2,2,2-trifluoroacetate (55 mg, 0.01 mmol) was dissolved in 5 mL dichloromethane, and triethylamine (42 μl, 0.3 mmol) was added. The solution was cooled to 0° C. and 4-toluenesulfonylchloride (23 mg, 0.12 mmol) was added. After completion of reaction, the mixture was diluted in dichloromethane and washed with 1N HCl followed by brine. The organic layer was evaporated to give product (22 mg, 37%). $^1$H NMR (500 MHz, DMSO-$d_6$) δ 8.25-8.17 (m, 3H), 8.02-8.00 (m, 1H), 7.94-7.92 (m, 1H), 7.83 (d, J=8.1 Hz, 1H), 7.65 (d, J=8.0 Hz, 2H), 7.55-7.51 (m, 2H), 7.45-7.29 (m, 9H), 4.98 (d, J=12.6 Hz, 1H), 4.91 (d, J=12.6 Hz, 1H), 4.70 (d, J=5.8 Hz, 2H), 4.18 (m, 1H), 4.03-3.97 (m, 1H), 2.68-2.64 (m, 1H), 2.46-2.41 (m, 1H), 2.35 (s, 3H), 1.10 (d, J=7.0 Hz, 3H).

Example 53—Preparation of (S)-3-((4-methylphenyl)sulfonamido)-4-(((S)-1-((naphthalen-1-ylmethyl) amino)-1-oxopropan-2-yl)amino)-4-oxobutanoic acid (DPLG-2088)

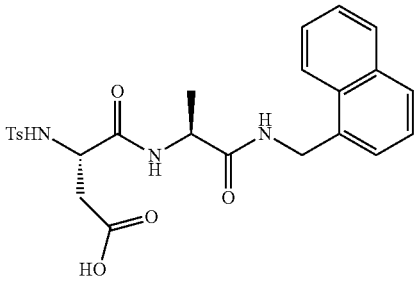

DPLG-2088 was synthesized by following the general procedure for O-debenzylation of benzyl (S)-3-((4-methylphenyl)sulfonamido)-4-(((S)-1-((naphthalen-1-ylmethyl) amino)-1-oxopropan-2-yl)amino)-4-oxobutanoate (21 g, 0.0357 mmol). The isolated crude was purified by HPLC to give product (12.1 mg, 68%). $^1$H NMR (500 MHz, DMSO-$d_6$) δ 12.41 (bs, 1H), 8.32 (bs, 1H), 8.20 (d, J=7.3 Hz, 1H), 8.04-8.02 (m, 1H), 7.95-7.93 (m, 1H), 7.83 (d, J=8.1 Hz, 1H), 7.66 (d, J=8.0 Hz, 2H), 7.56-7.52 (m, 2H), 7.44 (t, J=7.6 Hz, 1H), 7.39 (d, J=7.0 Hz, 1H), 7.33 (d, J=8.0 Hz, 2H), 4.70 (d, J=5.8 Hz, 2H), 4.08-4.06 (m, 1H), 4.01-3.96 (m, 1H), 2.54-2.50 (m, 1H), 2.36 (s, 3H), 2.28 (dd, J=16.3, 7.3 Hz, 1H), 1.11 (d, J=7.1 Hz, 3H).

Example 54—Preparation of (S)—N4,N4-diethyl-2-((4-methylphenyl)sulfonamido)-N1-((S)-1-((naphthalen-1-ylmethyl)amino)-1-oxopropan-2-yl)succinamide (DPLG-2090)

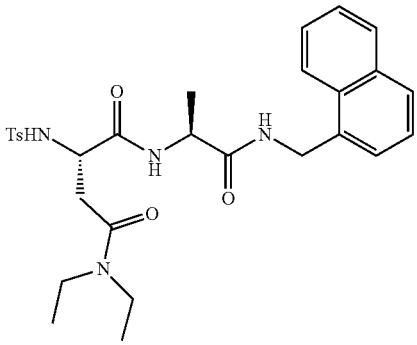

DPLG-2090 was prepared following the general procedure for HATU mediated coupling of (S)-3-((4-methylphenyl)sulfonamido)-4-((((S)-1-((naphthalen-1-ylmethyl) amino)-1-oxopropan-2-yl)amino)-4-oxobutanoic acid (5.0 mg, 0.01 mmol) and diethyl amine hydrochloride (1.6 mg, 0.015 mmol). The mixture was purified by HPLC to give the product (4.0 mg, 73%). $^1$H NMR (500 MHz, DMSO-$d_6$) δ 8.36 (d, J=7.4 Hz, 1H), 8.26 (t, J=6.0 Hz, 1H), 8.09-8.03 (m, 2H), 7.94-7.92 (m, 1H), 7.81 (d, J=8.1 Hz, 1H), 7.70-7.67 (m, 2H), 7.54-7.51 (m, 2H), 7.42-7.34 (m, 4H), 4.77 (dd, J=15.5, 6.2 Hz, 1H), 4.60 (dd, J=15.5, 5.7 Hz, 1H), 4.09-4.06 (m, 1H), 3.96-3.90 (m, 1H), 3.15-2.98 (m, 3H), 2.94-2.87 (m, 1H), 2.70 (dd, J=16.2, 9.4 Hz, 1H), 2.43 (dd, J=16.2, 4.7 Hz, 1H), 2.36 (s, 3H), 1.11 (d, J=7.2 Hz, 3H), 0.95 (t, J=7.1 Hz, 3H), 0.77 (t, J=7.0 Hz, 3H). $^{13}$C NMR (126 MHz, DMSO) δ 172.30, 170.23, 168.80, 142.95, 139.00, 134.85, 133.64, 131.21, 129.75, 128.91, 127.78, 127.05, 126.57, 126.16, 125.75, 125.30, 123.74, 53.43, 49.20, 41.75, 36.18, 21.39, 17.74, 14.19, 13.15.

Example 55—Preparation of (S)—N4-(tert-butoxy)-2-((4-methylphenyl)sulfonamido)-N1-((S)-1-((naphthalen-1-ylmethyl)amino)-1-oxopropan-2-yl)succinamide (DPLG-2091)

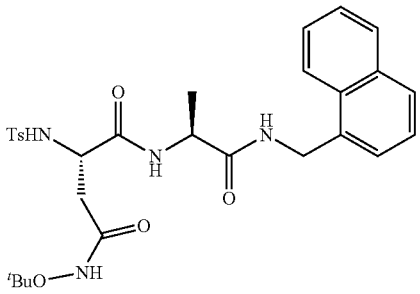

DPLG-2091 was prepared following the general procedure for HATU mediated coupling of (S)-3-((4-methylphenyl)sulfonamido)-4-((((S)-1-((naphthalen-1-ylmethyl) amino)-1-oxopropan-2-yl)amino)-4-oxobutanoic acid (5.0 mg, 0.01 mmol) and O-tert-butyl hydroxylamine hydrochloride (2 mg, 0.015 mmol). The mixture was purified by HPLC to give the product (3.3 mg, 56%). $^1$H NMR (500 MHz, DMSO-$d_6$) δ 10.40 (s, 1H), 8.33 (t, J=6.0 Hz, 1H), 8.22 (d, J=7.2 Hz, 1H), 8.08-8.06 (m, 1H), 8.01 (bs, 1H), 7.94-7.92 (m, 1H), 7.83 (d, J=7.6 Hz, 1H), 7.65 (d, J=7.9 Hz, 2H), 7.55-7.51 (m, 2H), 7.45-7.40 (m, 2H), 7.32 (d, J=8.0 Hz, 2H), 4.73 (dd, J=15.4, 6.0 Hz, 1H), 4.64 (dd, J=15.4, 5.7 Hz, 1H), 4.10-4.07 (m, 1H), 3.92-3.86 (m, 1H), 2.42 (dd, J=14.9, 7.7 Hz, 1H), 2.36 (s, 3H), 2.22 (dd, J=14.9, 6.6 Hz, 1H), 1.08-1.06 (m, 12H). $^{13}$C NMR (126 MHz, DMSO) δ 172.14, 169.91, 167.48, 134.89, 133.67, 131.25, 129.69, 128.91, 127.86, 127.13, 126.60, 126.34, 126.22, 126.18, 125.80, 125.64, 123.85, 81.10, 53.41, 49.06, 40.58, 36.34, 26.68, 21.41, 18.08. HRMS calc. for C29H36N4O6S [M+H]': 591.2253. Found: 591.2271.

Example 56—Preparation of (S)-benzyl 2-((S)-4-(tert-butoxyamino)-4-oxo-2-(3-phenylpropanamido)butanamido)propanoate ( PhCH2CH2 CO-Asp (CONHOtBu)-Ala-OBn, DPLG-2063)

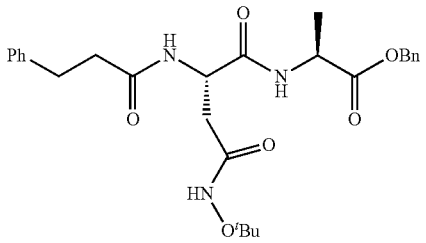

DPLG-2063 was prepared by following the general procedure for HATU mediated coupling of (S)-4-(tert-butoxyamino)-4-oxo-2-(3-phenylpropanamido)butanoic acid (33.6 mg, 0.1 mmol) and H-Ala-OBn.HCl (21.5 mg, 0.1 mmol). After completion of the reaction, the mixture was precipitated by the addition of cold water. The precipitate was filtered and dried to give the product (27 mg, 54%). $^1$H NMR (500 MHz, DMSO-$d_6$) δ 10.20 (s, 1H), 8.31 (d, J=7.0 Hz, 1H), 8.07 (d, J=8.2 Hz, 1H), 7.40-7.32 (m, 5H), 7.28-7.25 (m, 2H), 7.20-7.15 (m, 3H), 5.11 (s, 2H), 4.66 (td, J=9.0, 4.9 Hz, 1H), 4.33-4.27 (m, 1H), 2.80-2.76 (m, 2H), 2.41-2.37 (m, 3H), 2.26 (dd, J=14.8, 9.5 Hz, 1H), 1.29 (d, J=7.2 Hz, 3H), 1.14 (s, 9H).

Example 57—Preparation of (S)-2-((S)-4-(tert-butoxyamino)-4-oxo-2-(3-phenylpropanamido)butanamido)propanoic acid (PhCH$_2$CH$_2$CO-Asp(CONHO'Bu)-Ala-OH, DPLG-2067)

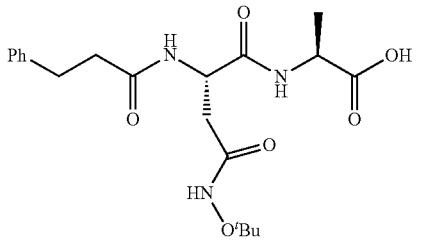

DPLG-2067 was synthesized by following the general procedure for O-debenzylation of (S)-benzyl 2-((S)-4-(tert-butoxylamino)-4-oxo-2-(3-phenylpropanamido)butanamido)propanoate (25.0 mg, 0.05 mmol). After completion of the reaction (5 h), the mixture was filtered through celite. The filtrate was evaporated and dried under vacuum to give the product (20 mg, quant.). $^1$H NMR (500 MHz, DMSO-$d_6$)δ 12.35 (s, 1H), 9.75 (s, 1H), 7.80 (s, 1H), 7.20-7.17 (m, 2H), 7.12-7.09 (m, 1H), 7.01 (d, J=7.4 Hz, 2H), 4.32-4.28 (m, 1H), 3.67-3.61 (m, 1H), 2.67-2.58 (m, 2H), 2.43-2.37 (m, 1H), 2.34-2.28 (m, 1H), 2.23-2.21 (m, 2H), 1.15 (d, J=6.8 Hz, 3H), 1.12 (s, 9H).

Example 58—Preparation of (S)—N$^4$-(tert-butoxy)-N$^1$—((S)-1-oxo-1-((quinolin-4 -ylmethyl)amino) propan-2-yl)-2-(3-phenylpropanami-do)succinamide (DPLG-20681

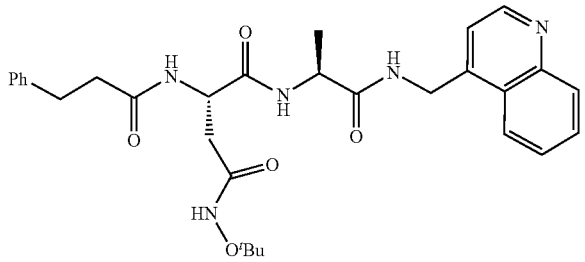

DPLG-2068 was prepared by following the general procedure for HATU mediated coupling of N$^4$-(tert-butoxy)-N$^2$-(3-phenylpropanoyl)-L-asparaginyl-L-alanine (5.0 mg, 0.0123 mmol) and quinolin-4-ylmethylamine dihydrochloride (2.8 mg, 0.0123 mmol). The crude was purified by HPLC to give 2.0 mg (30%) of product. $^1$H NMR (500 MHz, DMSO-$d_6$) δ 10.39 (s, 1H), 8.84 (d, J=4.5 Hz, 1H), 8.60 (t, J=6.0 Hz, 1H), 8.29 (d, J=7.1 Hz, 1H), 8.19-8.15 (m, 2H), 8.05 (dd, J=8.5, 1.3 Hz, 1H), 7.80-7.76 (m, 1H), 7.66-7.63 (m, 1H), 7.40 (d, J=4.4 Hz, 1H), 7.27-7.24 (m, 2H), 7.20-7.15 (m, 3H), 4.80-4.78 (m, 2H), 4.64-4.59 (m, 1H), 4.30-4.27 (m, 1H), 2.80-2.77 (m, 2H), 2.56-2.51 (m, 1H), 2.44-2.40 (m, 2H), 2.35 (dd, J=14.9, 7.1 Hz, 1H), 1.29 (d, J=7.1 Hz, 3H), 1.06 (s, 9H). $^{13}$C NMR (126 MHz, DMSO) δ 172.37, 171.41, 170.72, 167.72, 150.12, 147.30, 144.63, 141.24, 129.42, 129.30, 128.27, 128.13, 126.65, 125.94, 125.85, 123.50, 118.92, 80.55, 64.91, 49.62, 48.81, 36.73, 34.82, 30.95, 26.19, 17.72. HRMS calc. for C30H37N5O5 [M+H]$^+$: 548.2873. Found: 548.2857.

Example 59—Preparation of (S)—N$^4$-(tert-butoxpropan-2-yl)-2-(3-phenylpropanami-do)succinamide (DPLG-2073)

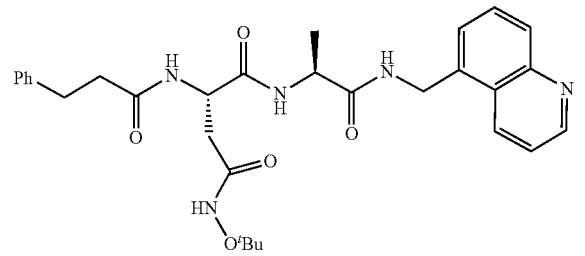

DPLG-2073 was prepared by following the general procedure for HATU mediated coupling of N$^4$-(tert-butoxy)-N$^2$-(3-phenylpropanoyl)-L-asparaginyl-L-alanine (5.0 mg, 0.0123 mmol) and quinolin-5-ylmethylamine (2.0 mg, 0.0123 mmol). The crude was purified by HPLC to give 4.7 mg (70%) of product. $^1$H NMR (500 MHz, DMSO-$d_6$)δ 10.39 (s, 1H), 8.92-8.91 (m, 1H), 8.55 (d, J=8.6 Hz, 1H), 8.51 (t, J=6.0 Hz, 1H), 8.18-8.15 (m, 2H), 7.94 (d, J=8.4 Hz, 1H), 7.70 (dd, J=8.5, 7.0 Hz, 1H), 7.57-7.54 (m, 2H), 7.27-7.24 (m, 2H), 7.19-7.15 (m, 3H), 4.79 (dd, J=15.4, 6.1 Hz, 1H), 4.70 (dd, J=15.4, 5.7 Hz, 1H), 4.61-4.56 (m, 1H), 4.27-4.21 (m, 1H), 2.80-2.76 (m, 2H), 2.53-2.48 (m, 1H), 2.43-2.39 (m, 2H), 2.33 (dd, J=14.8, 7.2 Hz, 1H), 1.23 (d, J=7.1 Hz, 3H), 1.10 (s, 9H). $^{3}$C NMR (126 MHz, DMSO) δ 172.42, 171.86, 170.99, 168.15, 150.64, 148.44, 141.70, 135.99, 132.49, 129.36, 128.90, 128.74, 128.60, 126.39, 126.31, 126.22, 121.75, 81.04, 70.24, 50.08, 49.12, 37.19, 35.28, 31.41, 26.70, 18.32. HRMS calc. for C30H37N5O5 [M+H]': 548.2873. Found: 548.2879.

Example 60—Preparation of (S)—N$^{1}$—((S)-1-(((1H-indol-4-yl)methyl)amino)-1-oxopropan-2-yl)-N$^{4}$-(tert-butoxy)-2-(3-phenylpropanam-ido)succinamide (DPLG-2083)

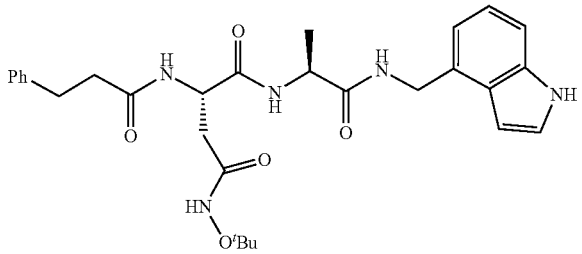

DPLG-2083 was prepared by following the general procedure for HATU mediated coupling of N$^{4}$-(tert-butoxy)-N$^{2}$-(3-phenylpropanoyl)-L-asparaginyl-L-alanine (5.0 mg, 0.0123 mmol) and 4-(aminomethyl)indole (1.8 mg, 0.0123 mmol). The crude was purified by HPLC to give 5.8 mg (88%) of product. $^{1}$H NMR (500 MHz, DMSO-d$_{6}$) δ 11.10 (s, 1H), 10.35 (s, 1H), 8.36 (t, J=5.9 Hz, 1H), 8.16 (d, J=8.0 Hz, 1H), 8.05 (d, J=7.4 Hz, 1H), 7.32-7.25 (m, 4H), 7.20-7.16 (m, 3H), 7.01 (t, J=7.6 Hz, 1H), 6.89 (d, J=7.1 Hz, 1H), 6.52-6.51 (m, 1H), 4.61-4.48 (m, 3H), 4.28-4.24 (m, 1H), 2.81-2.77 (m, 2H), 2.53-2.49 (m, 1H), 2.46-2.38 (m, 2H), 2.33 (dd, J=14.8, 7.6 Hz, 1H), 1.23 (d, J=7.1 Hz, 3H), 1.13 (s, 9H). $^{13}$C NMR (126 MHz, DMSO) δ 172.15, 171.85, 170.85, 168.06, 141.73, 136.20, 130.54, 128.75, 128.63, 128.60, 126.61, 126.31, 125.31, 121.14, 117.76, 110.77, 81.01, 50.13, 49.00, 41.04, 37.24, 35.31, 31.43, 26.72, 18.68. HRMS calc. for C29H37N5O5 [M+H]': 558.2692. Found: 558.2698.

Example 61—Preparation of tert-butyl (S)-(3-methoxy-1-((naphthalen-1-ylmethyl)amino)-1-oxopropan-2-yl)carbamate (Boc-Ser(OMe)-naphth, DPLG-2078)

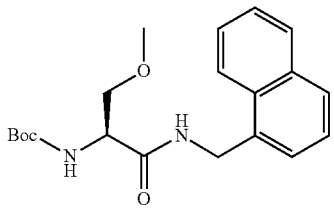

DPLG-2078 was prepared following the general procedure for HATU coupling. Reaction was carried using Boc-β-methoxyalanine dicyclohexylamine (1.202 g, 3.0 mmol) and 1-naphthylmethylamine (484 mL, 3.3 mmol). After completion of the reaction 150 mL water was added to the reaction mixture and extracted twice with ethyl acetate (2×150 mL). The combined organic layer was washed with brine, dried over anhydrous sodium sulfate, and evaporated. The crude product was purified by silica gel column chromatography using a gradient of 20%-40% ethyl acetate-hexane to give 1.05 g (98%) of pure product. $^{1}$H NMR (500 MHz, Chloroform-d) δ 7.96 (d, J=8.4 Hz, 1H), 7.87-7.85 (m, 1H), 7.79 (dd, J=7.2, 2.4 Hz, 1H), 7.54-7.48 (m, 2H), 7.44-7.39 (m, 2H), 6.73 (m, 1H), 5.40 (m, 1H), 4.91 (m, 2H), 4.27 (m, 1H), 3.82 (dd, J=9.0, 4.1 Hz, 1H), 3.47 (dd, J=9.0, 6.2 Hz, 1H), 3.28 (s, 3H), 1.37 (s, 9H).

Example 62—Preparation of (S)-2-amino-3-methoxy-N-(naphthalen-1-ylmethyl)propanamide 2,2,2-trifluoroacetate (H-Ser(OMe)-naphth, DPLG-2082)

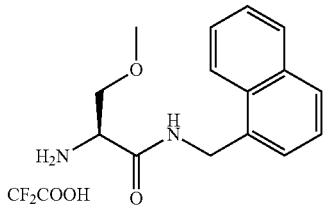

DPLG-2082 was synthesized by following the general procedure for Boc deprotection of DPLG-2120 (72 mg, 0.02 mmol). After completion of the reaction (4 h), dichloromethane and excess TFA were evaporated and dried under high vacuum. The paste was soluble in diethyl ether. Diethyl ether solution was extracted with water. The water layer was frozen and lyophilized to give product (67 mg, 90%). $^{1}$H NMR (500 MHz, DMSO-d$_{6}$) δ 8.94 (t, J=5.5 Hz, 1H), 8.20 (bs, 3H), 8.04-8.02 (m, 1H), 7.98-7.95 (m, 1H), 7.89-7.87 (m, 1H), 7.59-7.54 (m, 2H), 7.51-7.48 (m, 2H), 4.85 (dd, J=15.2, 5.7 Hz, 1H), 4.77 (dd, J=15.2, 5.4 Hz, 1H), 4.05-4.03 (m, 1H), 3.70-3.63 (m, 2H), 3.28 (s, 3H).

Example 63—Preparation of Benzyl (S)-3-((tertbutoxycarbonyl)amino)-4-(((S)-3-methoxy-1-((naphthalen-1-ylmethyl)amino)-1-oxopropan-2-yl)amino)-4-oxobutanoate (DPLG-2126)

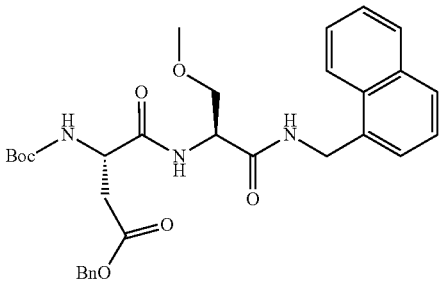

DPLG-2126 was prepared following the general procedure of HATU mediated coupling of N-(tert-butoxycarbonyl)-L-aspartic acid 4-benzyl ester (378 mg, 1.17 mmol) and (S)-2-amino-3-methoxy-N-(naphthalen-1-ylmethyl)propanamide (435.6 mg, 1.17 mmol). After completion of the reaction (2 h), the mixture was diluted with water and extracted twice with ethyl acetate. The organic layer was evaporated and the crude was recrystallized from ethanol-water mixture to give 576 mg (88%) pure product. $^1$H NMR (500 MHz, DMSO-$d_6$) δ 8.50 (t, J=5.7 Hz, 1H), 8.04-8.02 (m, 1H), 7.95-7.91 (m, 2H), 7.84 (dd, J=7.0, 2.4 Hz, 1H), 7.56-7.51 (m, 2H), 7.47-7.43 (m, 2H), 7.38-7.28 (m, 6H), 5.09 (d, J=12.6 Hz, 1H), 5.05 (d, J=12.6 Hz, 1H), 4.75 (d, J=5.7 Hz, 2H), 4.49-4.45 (m, 1H), 4.43-4.39 (m, 1H), 3.58 (dd, J=9.7, 5.5 Hz, 1H), 3.48 (dd, J=9.7, 5.1 Hz, 1H), 3.24 (s, 3H), 2.81 (dd, J=16.4, 5.1 Hz, 1H), 2.61 (dd, J=16.4, 9.0 Hz, 1H), 1.38 (s, 9H).

Example 64—Preparation of (S)-3-((tert-butoxycarbonyl)amino)-4-(((S)-3-methoxy-1-((naphthalen-1-ylmethyl)amino)-1-oxopropan-2-yl)amino)-4-oxobutanoic acid (DPLG-2131)

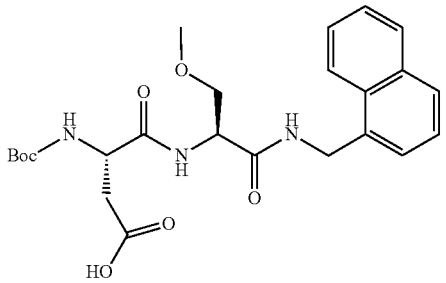

DPLG-2131 was synthesized by following the general procedure for O-debenzylation of benzyl (S)-3-((tert-butoxycarbonyl)amino)-4-(((S)-3-methoxy-1-((naphthalen-1-ylmethyl)amino)-1-oxopropan-2-yl)amino)-4-oxobutanoate (113 mg, 0.2 mmol). After completion of the reaction (4 h), the mixture was filtered through celite. The filtrate was evaporated and dried under vacuum to give the product (94 mg, 99%). $^1$H NMR (500 MHz, DMSO-$d_6$) δ 8.54 (t, J=5.7 Hz, 1H), 8.05-8.03 (m, 1H), 7.96-7.94 (m, 1H), 7.88 (d, J=7.9 Hz, 1H), 7.84 (dd, J=7.2, 2.0 Hz, 1H), 7.57-7.52 (m, 2H), 7.48-7.43 (m, 2H), 7.19 (d, J=7.9 Hz, 1H), 4.75 (d, J=5.7 Hz, 2H), 4.48-4.44 (m, 1H), 4.32-4.28 (m, 1H), 3.59 (dd, J=9.7, 5.5 Hz, 1H), 3.49 (dd, J=9.7, 5.1 Hz, 1H), 3.24 (s, 3H), 2.64 (dd, J=16.4, 5.5 Hz, 1H), 2.46 (dd, J=16.4, 8.3 Hz, 1H), 1.38 (s, 9H).

Example 65—Preparation of tert-butyl ((4S,7S)-4-(methoxymethyl)-12,12-dimethyl-1-(naphthalen-1-yl)-3,6,9-trioxo-11-oxa-2,5,10-triazatridecan-7 -yl) carbamate (DPLG-2133)

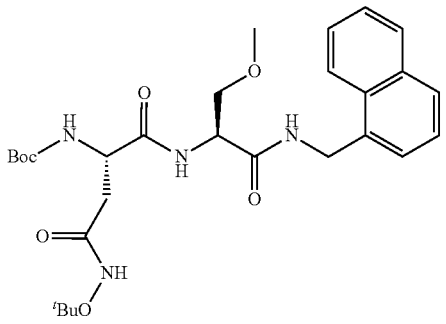

DPLG-2133 was prepared following the general procedure of HATU mediated coupling of (S)-3-((tert-butoxycarbonyl)amino)-4-(((S)-3-methoxy-1-((naphthalen-1-ylmethyl)amino)-1-oxopropan-2-yl)amino)-4-oxobutanoic acid (710 mg, 1.5 mmol) and 0-tert-butyl hydroxylamine hydrochloride (226 mg, 1.8 mmol). After completion of the reaction the mixture was precipitated by the addition of 100 mL water. The precipitate was filtered and dried to give 692 mg (85%) pure product. $^1$H NMR (500 MHz, DMSO-$d_6$)δ 10.27 (s, 1H), 8.57-8.55 (m, 1H), 8.06-8.04 (m, 1H), 7.96-7.94 (m, 2H), 7.85-7.83 (m, 1H), 7.56-7.53 (m, 2H), 7.48-7.43 (m, 2H), 7.01 (d, J=7.8 Hz, 1H), 4.75 (d, J=5.8 Hz, 2H), 4.48-4.44 (m, 1H), 4.35-4.30 (m, 1H), 3.59 (dd, J=9.8, 5.6 Hz, 1H), 3.51-3.48 (m, 1H), 3.24 (s, 3H), 2.47 (dd, J=14.8, 5.5 Hz, 1H), 2.33-2.28 (m, 1H), 1.37 (s, 9H), 1.13 (s, 9H).

Example 66—Preparation of (S)-2-amino-$N^4$-(tert-butoxy)-$N^1$—((S)-3 -methoxy-1-((naphthalen-1-ylmethyl)amino)-1-oxopropan-2-yl)succinamide (DPLG-2137)

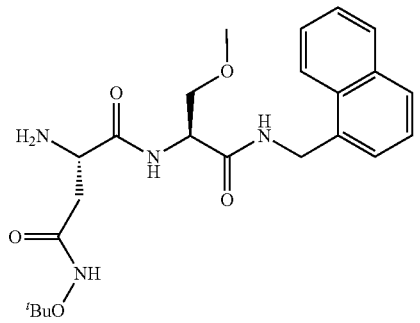

DPLG-2137 was synthesized by following the general procedure for Boc deprotection of tert-butyl ((4S,7S)-4-(methoxymethyl)-12,12-dimethyl-1-(naphthalen-1-yl)-3,6,9-trioxo-11-oxa-2,5,10-triazatridecan-7-yl)carbamate (692 mg, 1.27 mmol). The isolated crude was triturated with diethyl ether to give pure product (691 mg, 97%). $^1$H NMR (500 MHz, DMSO-$d_6$) δ 10.70 (s, 1H), 8.81 (d, J=7.5 Hz, 1H), 8.67 (t, J=5.8 Hz, 1H), 8.20 (bs, 3H), 8.07-8.05 (m, 1H), 7.96-7.95 (m, 1H), 7.86-7.84 (m, 1H), 7.57-7.53 (m, 2H), 7.47-7.45 (m, 2H), 4.80-4.72 (m, 2H), 4.56-4.53 (m, 1H), 4.22-4.19 (m, 1H), 3.63 (dd, J=9.9, 6.0 Hz, 1H), 3.53 (dd, J=9.9, 4.5 Hz, 1H), 3.26 (s, 3H), 2.72 (dd, J=16.3, 5.1 Hz, 1H), 2.58 (dd, J=16.3, 7.6 Hz, 1H), 1.15 (s, 9H).

Example 67—Preparation of (S)—$N^4$-(tert-butoxy)-$N^1$—((S)-3 -methoxy-1-((naphthalen-1-ylmethyl) amino)-1-oxopropan-2-yl)-2-(3-phenylpropanamido) succinamide (DPLG-2086)

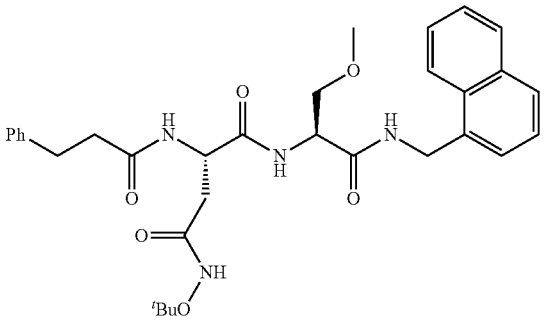

DPLG-2086 was prepared following the general procedure for HATU mediated coupling of (S)-4-(tert-butoxyamino)-4-oxo-2-(3-phenylpropanamido)butanoic acid (11.0 mg, 0.033 mmol) and [(S)-2-amino-3-methoxy-N-(naphthalen-1-ylmethyl)propanamide] (H-Ser(OMe)-naphth) (11.0 mg, 0.03 mmol). The product was purified by HPLC (yield 15.3 mg, 88%). $^1$H NMR (500 MHz, DMSO-$d_6$) δ 10.39 (s, 1H), 8.58 (t, J=5.8 Hz, 1H), 8.21 (d, J=8.0 Hz, 1H), 8.11 (d, J=7.7 Hz, 1H), 8.09-8.07 (m, 1H), 7.95-7.93 (m, 1H), 7.84-7.82 (m, 1H), 7.56-7.52 (m, 2H), 7.48-7.43 (m, 2H), 7.28-7.25 (m, 2H), 7.20-7.16 (m, 3H), 4.78 (dd, J=15.4, 5.9 Hz, 1H), 4.71 (J=15.4, 5.7 Hz, 1H), 4.68-4.64 (m, 1H), 4.45-4.42 (m, 1H), 3.60 (dd, J=9.7, 5.9 Hz, 1H), 3.51 (dd, J=9.7, 4.7 Hz, 1H), 3.24 (s, 3H), 2.80-2.77 (m, 2H), 2.53-2.49 (m, 1H), 2.43-2.39 (m, 2H), 2.34 (dd, J=14.8, 7.6 Hz, 1H), 1.11 (s, 9H). $^{13}$ C NMR (126 MHz, DMSO) δ 171.94, 171.38, 169.66, 168.05, 141.70, 134.69, 133.65, 131.22, 128.89, 128.76, 128.58, 127.85, 126.59, 126.32, 126.18, 125.83, 125.54, 123.87, 81.02, 72.27, 58.74, 53.69, 50.11, 40.72, 37.24, 35.30, 31.45, 26.71. HRMS calc. for C32H40N4O6 [M+H]$^+$: 577.3026. Found: 577.3005.

Example 68—Preparation of (S)—$N^4$-(tert-butoxy)-$N^1$—((S)-3-methoxy-1-((naphthalen-1-ylmethyl) amino)-1-oxopropan-2-yl)-2-(2-morpholinoacetamido)succinamide (DPLG-2143)

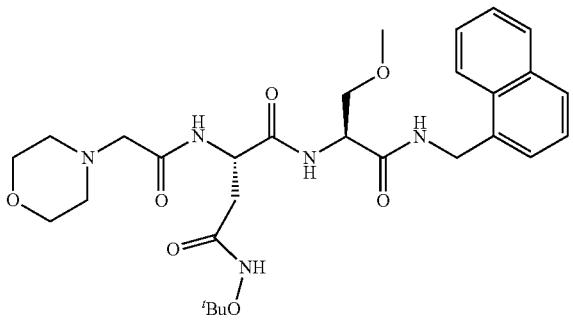

DPLG-2143 was prepared following the general procedure for HATU mediated coupling of morpholin 4-yl-acetic acid (3.2 mg, 0.022 mmol) and (S)-2-amino-$N^4$-(tert-butoxy)-$N^1$—((S)-3 -methoxy-1-((naphthalen-1-ylmethyl) amino)-1-oxopropan-2-yl)succinamide (11.2 mg, 0.02 mmol). The product was purified by HPLC (yield 9.5 mg, 83%). $^1$H NMR (500 MHz, DMSO-$d_6$) δ 10.37 (s, 1H), 8.60 (t, J=5.8 Hz, 1H), 8.19 (d, J=7.7 Hz, 1H), 8.07-8.05 (m, 1H), 8.03 (d, J=8.1 Hz, 1H), 7.95-7.93 (m, 1H), 7.83 (t, J=4.8, 1H), 7.56-7.52 (m, 2H), 7.45-7.44 (m, 2H), 4.74 (d, J=5.8 Hz, 2H), 4.67-4.63 (m, 1H), 4.47-4.43 (m, 1H), 3.62-3.58 (m, 5H), 3.51 (dd, J=9.8, 4.7 Hz, 1H), 3.23 (s, 3H), 2.92 (s, 2H), 2.54-2.36 (m, 6H), 1.11 (s, 9H). $^{13}$C NMR (126 MHz, DMSO) δ 170.54, 169.22, 168.97, 167.59, 134.20, 133.20, 130.75, 128.45, 127.41, 126.14, 125.74, 125.38, 125.07, 123.40, 99.52, 80.60, 71.80, 66.13, 61.34, 58.27, 53.18, 49.23, 40.29, 34.89, 26.24.

Example 69—Preparation of (S)—$N^4$-(tert-butoxy)-$N^1$—((S)-3-methoxy-1-((napthalen-1-ylmethyl) amino)-1-oxopropan-2-yl)-2-(5-methylisoxazole-3-carboxamido)succinamide (DPLG-2144)

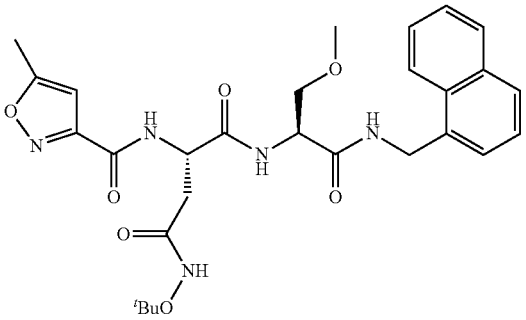

DPLG-2144 was prepared following the general procedure for HATU mediated coupling of 5-methylisoxazole-3-carboxylic acid (2.8 mg, 0.022 mmol) and (S)-2-amino-$N^4$-(tert-butoxy)-$N^1$—((S)-3-methoxy-1-((naphthalen-1-ylmethyl)amino)-1-oxopropan-2-yl)succinamide (11.2 mg, 0.02 mmol). The product was purified by HPLC (yield 10.2 mg, 92%). $^1$H NMR (500 MHz, DMSO-$d_6$) δ 10.38 (s, 1H), 8.65 (d, J=8.1 Hz, 1H), 8.60 (t, J=5.8 Hz, 1H), 8.26 (d, J=7.8 Hz, 1H), 8.05-8.03 (m, 1H), 7.95-7.93 (m, 1H), 7.85-7.83 (m, 1H), 7.54-7.52 (m, 2H), 7.46-7.43 (m, 2H), 6.54 (s, 1H), 4.84-4.80 (m, 1H), 4.74 (d, J=5.8 Hz, 2H), 4.50-4.47 (m, 1H), 3.59 (dd, J=9.7, 5.9 Hz, 1H), 3.51 (dd, J=9.7, 5.0 Hz, 1H), 3.23 (s, 3H), 2.62-2.54 (m, 2H), 2.47 (s, 3H), 1.09 (s, 9H). $^{13}$C NMR (126 MHz, DMSO) δ 171.40, 170.13, 169.17, 167.41, 158.43, 158.35, 134.17, 133.20, 130.74, 128.44, 127.41, 126.13, 125.74, 125.38, 125.03, 123.38, 101.31, 80.60, 71.83, 58.27, 53.11, 50.03, 40.28, 34.66, 26.21, 11.83.

Example 70—Preparation of (S)—$N^4$-(tert-butoxy)-$N^1$—((S)-3-methoxy-1-((naphthalen-1-ylmethyl)amino)-1-oxopropan-2-yl)-2-((4-methylphenyl)sulfonamido)succinamide (DPLG-2150)

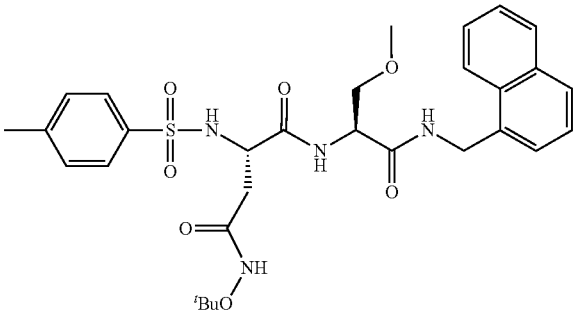

(S)-2-amino-$N^4$-(tert-butoxy)-$N^1$—((S)-3-methoxy-1-((naphthalen-1-ylmethyl)amino)-1-oxopropan-2-yl)succinamide (22.4 mg, 0.04 mmol) was dissolved in 2 mL dichloromethane and the solution was cooled to 0° C. 4-(Dimethylamino)pyridine (1.2 mg, 0.01 mmol), Hunig's base (17 mL, 0.12 mmol), and 4-toluenesulphonyl chloride were added and the solution was allowed to warm to room temperature. After completion of the reaction (4 h), the mixture was diluted with dichloromethane and washed with water. Organic layer was evaporated and purified by HPLC to give product (15.1 mg, 63%). $^1$H NMR (500 MHz, DMSO-$d_6$) δ 10.36 (s, 1H), 8.48 (t, J=5.9 Hz, 1H), 8.23 (d, J=7.7 Hz, 1H), 8.07-8.05 (m, 1H), 7.99 (bs, 1H), 7.94-7.92 (m, 1H), 7.83-7.81 (m, 1H), 7.66 (d, J=7.9 Hz, 2H), 7.55-7.51 (m, 2H), 7.44-7.42 (m, 2H), 7.32 (d, J=7.9 Hz, 2H), 4.75 (dd, J=15.5, 6.0 Hz, 1H), 4.68 (dd, J=15.5, 5.8 Hz, 1H), 4.24-4.20 (m, 1H), 4.15-4.12 (m, 1H), 3.46 (dd, J=9.6, 5.1 Hz, 1H), 3.31 (dd, J=9.6, 5.0 Hz, 1H), 3.22 (s, 3H), 2.40 (dd, J=14.8, 7.4 Hz, 1H), 2.36 (s, 3H), 2.19 (dd, J=14.8, 6.7 Hz, 1H), 1.08 (s, 9H). $^{13}$C NMR (126 MHz, DMSO) δ 170.45, 169.48, 167.37, 142.90, 138.58, 134.66, 133.64, 131.20, 129.75, 128.87, 127.81, 127.13, 126.56, 126.16, 125.80, 125.51, 123.88, 81.09, 72.05, 58.78, 53.62, 53.30, 40.68, 36.45, 26.69, 21.44.

Example 71—Preparation of (S)—$N^4$-(tert-butoxy)-$N^1$—((S)-3-methoxy-1-((naphthalen-1-ylmethyl)amino)-1-oxopropan-2-yl)-2-(2 -phenylacetamido)succinamide (DPLG-2222)

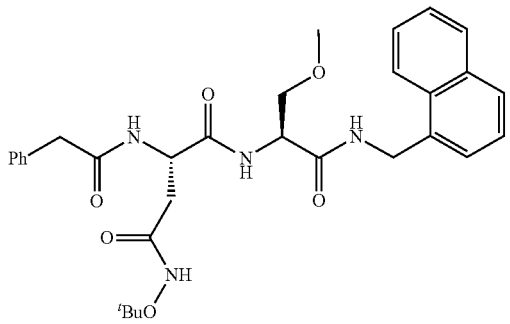

DPLG-2222 was prepared following the general procedure for HATU mediated coupling of phenylacetic acid (4.5 mg, 0.033 mmol) and (S)-2-amino-$N^4$-(tert-butoxy)-$N^1$—((S)-3-methoxy-1-((naphthalen-1-ylmethyl)amino)-1-oxopropan-2-yl)succinamide (16.8 mg, 0.03 mmol). The product was purified by HPLC (yield 9.8 mg, %). $^1$H NMR (500 MHz, DMSO-$d_6$) δ 10.39 (s, 1H), 8.58 (t, J=6.0 Hz, 1H), 8.39 (d, J=7.9 Hz, 1H), 8.15 (d, J=7.7 Hz, 1H), 8.08-8.06 (m, 1H), 7.95-7.93 (m, 1H), 7.83 (dd, J=6.9, 2.5 Hz, 1H), 7.55-7.53 (m, 2H), 7.46-7.44 (m, 2H), 7.29-7.19 (m, 5H), 4.77 (dd, J=15.5, 6.0 Hz, 1H), 4.70 (dd, J=15.5, 5.7 Hz, 1H), 4.67-4.63 (m, 1H), 4.45-4.41 (m, 1H), 3.58 (dd, J=9.7, 5.9 Hz, 1H), 3.50-3.47 (m, 3H), 3.22 (s, 3H), 2.56-2.50 (m, 1H), 2.38 (dd, J=14.9, 7.5 Hz, 1H), 1.10 (s, 9H). $^{13}$C NMR (126 MHz, DMSO) δ 171.33, 170.56, 169.64, 167.99, 136.59, 134.70, 133.64, 131.21, 129.51, 128.89, 128.60, 127.83, 126.76, 126.59, 126.18, 125.83, 125.54, 123.88, 81.02, 72.22, 58.71, 53.71, 50.14, 42.37, 40.71, 35.31, 26.71.

Example 72—Preparation of (S) $N^4$-(tert-butoxy)-$N^{1—((S)-}$3methoxy-1-((naphthalen-1-ylmethyl)amino)-1-oxopropan-2-yl)-2-(4-phenylbutanamido)succinamide (DPLG-2223)

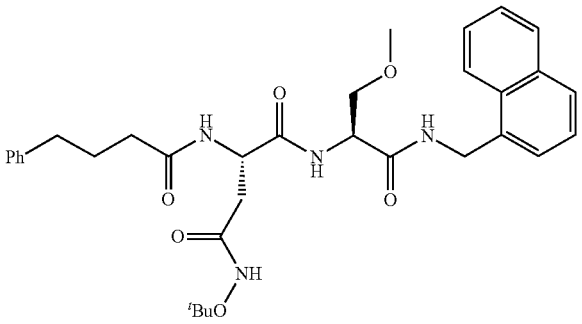

DPLG-2223 was prepared following the general procedure for HATU mediated coupling of 4-phenylbutyric acid (5.4 mg, 0.033 mmol) and (S)-2-amino-1V4-(tert-butoxy)-$N^1$-((S)-3-methoxy-1-((naphthalen-1-ylmethyl)amino)-1-oxopropan-2-yl)succinamide (16.8 mg, 0.03 mmol). The product was purified by HPLC (yield 10.5 mg, 59%). $^1$H NMR (500 MHz, DMSO-$d_6$) δ 10.35 (s, 1H), 8.56 (t, J=5.7 Hz, 1H), 8.15 (d, J=8.0 Hz, 1H), 8.06-8.03 (m, 2H), 7.94-7.93 (m, 1H), 7.84-7.82 (m, 1H), 7.55-7.51 (m, 2H), 7.45-7.42 (m, 2H), 7.28-7.22 (m, 2H), 7.19-7.15 (m, 3H), 4.78-4.69 (m, 2H), 4.66-4.61 (m, 1H), 4.45-4.42 (m, 1H), 3.59 (dd, J=9.8, 5.9 Hz, 1H), 3.50 (dd, J=9.8, 4.8 Hz, 1H), 3.20 (s, 3H), 2.56-2.50 (m, 3H), 2.35 (dd, J=14.8, 8.1 Hz, 1H), 2.13 (t, J=7.5 Hz, 2H), 1.76 (p, J=7.5 Hz, 2H), 1.10 (s, 9H). $^{13}$C NMR (126 MHz, DMSO) δ 172.05, 170.96, 169.18, 167.59, 141.79, 134.19, 133.18, 130.74, 128.42, 128.30, 128.22, 127.38, 126.12, 125.70, 125.36, 125.03, 123.38, 80.51, 71.84, 58.24, 53.11, 49.70, 40.25, 34.72, 34.63, 34.57, 27.04, 26.24.

Example 73—Preparation of benzyl (S)-3-amino-4-(((S)-3-methoxy-1-((naphthalen-1-ylmethyl)amino)-1-oxopropan-2-yl)amino)-4-oxobutanoate 2,2,2-trifluoroacetate (DPLG-2192)

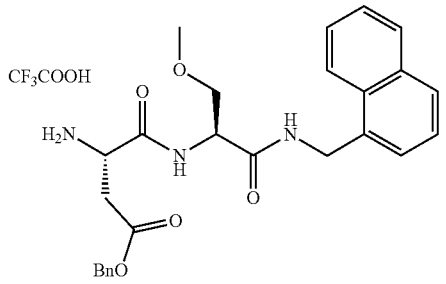

DPLG-2192 was synthesized by following the general procedure for Boc deprotection of benzyl (S)-3-((tert-butoxycarbonyl)amino)-4-(((S)-3-methoxy-1-((naphthalen-1-ylmethyl)amino)-1-oxopropan-2-yl)amino)-4-oxobutanoate (225 mg, 0.4 mmol). Yield=230 mg, quant. $^1$H NMR (500 MHz, DMSO-$d_6$) δ 8.85 (d, J=7.8 Hz, 1H), 8.57 (t, J=5.8 Hz, 1H), 8.27 (bs, 3H), 8.03-8.01 (m, 1H), 7.95-7.93 (m, 1H), 7.84 (dd, J=7.1, 2.4 Hz, 1H), 7.56-7.50 (m, 2H), 7.47-7.43 (m, 2H), 7.40-7.33 (m, 5H), 5.14 (d, J=12.4 Hz, 1H), 5.11 (d, J=12.4 Hz, 1H), 4.79-4.71 (m, 2H), 4.56 (ddd, J=7.8, 6.0, 4.8 Hz, 1H), 4.26 (m, 1H), 3.60 (dd, J=9.8, 6.0 Hz, 1H), 3.53 (dd, J=9.8, 4.8 Hz, 1H), 3.26 (s, 3H), 3.01 (dd, J=17.5, 4.0 Hz, 1H), 2.81 (dd, J=17.5, 8.7 Hz, 1H).

Example 74—Preparation of benzyl (S)-4-(((S)-3-methoxy-1-((naphthalen-1-ylmethyl)amino)-1-oxopropan-2-yl)amino)-3-(methylsulfonamido)-4-oxobutanoate (DPLG-2196)

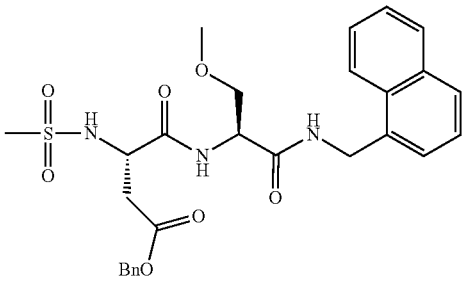

Benzyl (S)-3-amino-4-(((S)-3-methoxy-1-((naphthalen-1-ylmethyl)amino)-1-oxopropan-2-yl)amino)-4-oxobutanoate 2,2,2-trifluoroacetate (29 mg, 0.05 mmol) and N,N-dimethylaminopyridine (1 mg) were suspended in dichloromethane (1 mL). Triethylamine was added (21 μL, 0.15 mmol). The resulting transparent solution was cooled to 0° C. and methanesulphonyl chloride (6 μl, 0.075 mmol) was added. After completion of reaction (1 h), the product was isolated by ethyl acetate extraction and purified by HPLC to give product (16.5 mg, 61%). $^1$H NMR (500 MHz, DMSO-$d_6$) δ 8.45 (t, J=5.8 Hz, 1H), 8.38 (d, J=7.9 Hz, 1H), 8.03-8.01 (m, 1H), 7.95-7.93 (m, 1H), 7.85-7.82 (m, 1H), 7.70 (bs, 1H), 7.57-7.50 (m, 2H), 7.46-7.43 (m, 2H), 7.36-7.31 (m, 5H), 5.09-5.04 (m, 2H), 4.74 (d, J=5.8 Hz, 2H), 4.54-4.48 (m, 1H), 4.34-4.31 (m, 1H), 3.59 (dd, J=9.8, 6.0 Hz, 1H), 3.52 (dd, J=9.8, 5.0 Hz, 1H), 3.24 (s, 3H), 2.87 (s, 3H), 2.83 (dd, J=16.4, 5.3 Hz, 1H), 2.63 (dd, J=16.4, 8.7 Hz, 1H).

Example 75—Preparation of (S)-4-(((S)-3-methoxy-1-((naphthalen-1-ylmethyl)amino)-1-oxopropan-2-yl)amino)-3-(methylsulfonamido)-4-oxobutanoic acid (DPLG-2203)

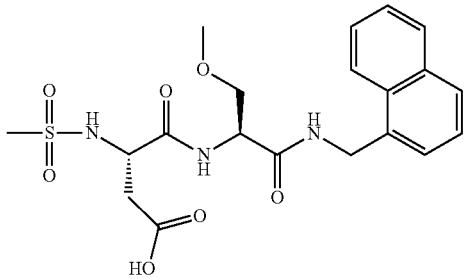

DPLG-2203 was synthesized by following the general procedure for O-debenzylation of benzyl (S)-4-(((S)-3-methoxy-1-((naphthalen-1-ylmethyl)amino)-1-oxopropan-2-yl)amino)-3-(methyl sulfonamido)-4 -oxobutanoate (16.5 mg, 0.03 mmol). The reaction mixture was filtered through celite and evaporated to give the product (11.0 mg, 80%). $^1$H NMR (500 MHz, DMSO-$d_6$) δ 8.53 (t, J=5.8 Hz, 1H), 8.34 (d, J=8.0 Hz, 1H), 8.05-8.03 (m, 1H), 7.95-7.93 (m, 1H), 7.83 (dd, J=7.2, 2.2 Hz, 1H), 7.57-7.52 (m, 2H), 7.47-7.43 (m, 2H), 4.78-4.71 (m, 2H), 4.52-4.48 (m, 1H), 4.23 (dd, J=7.9, 5.7 Hz, 1H), 3.60 (dd, J=9.8, 6.1 Hz, 1H), 3.54 (dd, J=9.8, 4.9 Hz, 1H), 3.24 (s, 3H), 2.91 (s, 3H), 2.68 (dd, J=16.4, 5.7 Hz, 1H), 2.49-2.45 (m, 1H).

Example 76—Preparation of (S)—N$^1$—((S)-3-methoxy-1-((naphthalen-1-ylmethyl)amino)-1-oxopropan-2-yl)-2-(methylsulfonamido)-N$^4$-(oxetan-3-yl)succinamide (DPLG-2219)

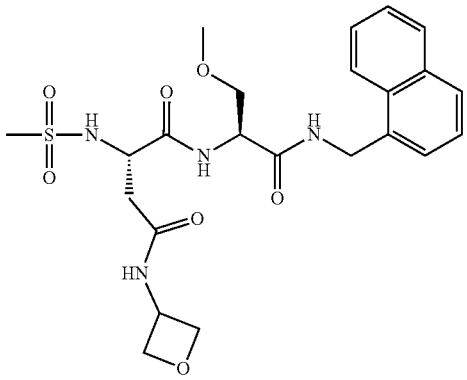

DPLG-2219 was prepared following the general procedure for HATU mediated coupling of (S)-4-(((S)-3-methoxy-1-((naphthalen-1-ylmethyl)amino)-1-oxopropan-2-yl)amino)-3-(methylsulfonamido)-4-oxobutanoic acid (6.8 g, 0.015 mmol) and 3-aminoxetane (1.2 μL, 0.0165 mmol). The crude was purified by HPLC to give product (5.2 mg, 68%). $^1$H NMR (500 MHz, DMSO-$d_6$) δ 8.78 (d, J=6.3 Hz, 1H), 8.50 (t, J=5.8 Hz, 1H), 8.42 (d, J=7.9 Hz, 1H), 8.06-8.04 (m, 1H), 7.95-7.93 (m, 1H), 7.84 (dd, J=7.8, 1.7 Hz, 1H), 7.57-7.52 (m, 3H), 7.47-7.42 (m, 2H), 4.78 (dd, J=15.5, 6.0 Hz, 1H), 4.70 (dd, J=15.5, 5.7 Hz, 1H), 4.65-4.57 (m, 2H), 4.54-4.47 (m, 2H), 4.36-4.30 (m, 2H), 4.25-4.22 (m, 1H), 3.63 (dd, J=9.8, 6.3 Hz, 1H), 3.57 (dd, J=9.8, 4.5 Hz, 1H), 3.24 (s, 3H), 2.89 (s, 3H), 2.63 (dd, J=15.4, 7.3 Hz, 1H), 2.49-2.45 (m, 1H). $^{13}$C NMR (126 MHz, DMSO) δ 171.25, 169.48, 169.44, 134.62, 133.66, 131.22, 128.91, 127.90, 126.62, 126.22, 125.80, 125.47, 123.85, 77.43, 77.24, 72.19, 58.69, 53.56, 53.38, 44.31, 41.07, 40.76, 38.81.

Example 77—Preparation of benzyl (S)-4-(((S)-3-methoxy-1-((naphthalen-1-ylmethyl)amino)-1-oxopropan-2-yl)amino)-344-methylphenyl)sulfonamido)-4-oxobutanoate (DPLG-2199)

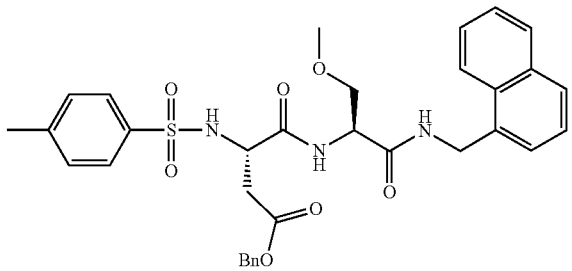

Benzyl (S)-3-amino-4-(((S)-3-methoxy-1-((naphthalen-1-ylmethyl)amino)-1-oxopropan-2-yl)amino)-4 -oxobutanoate 2,2,2-trifluoroacetate (48 mg, 0.083 mmol) was dissolved in dichloromethane (1 mL), and triethylamine (35 μl, 0.25 mmol) was added. The resulting solution was cooled to 0° C., and 4-toluenesulphonyl chloride (23.8 mg, 0.125 mmol) was added. After completion of reaction (2 h), the crude was isolated by ethyl acetate extraction and purified by HPLC to give product (11.0 mg, 22%). $^{1}$H NMR (500 MHz, DMSO-$d_6$) δ 8.36 (t, J=5.8 Hz, 1H), 8.24 (d, J=7.7 Hz, 1H), 8.19 (d, J=8.9 Hz, 1H), 8.02-8.00 (m, 1H), 7.94-7.92 (m, 1H), 7.83 (dd, J=7.2, 2.3 Hz, 1H), 7.65 (d, J=8.2 Hz, 2H), 7.55-7.50 (m, 2H), 7.45-7.41 (m, 2H), 7.38-7.29 (m, 7H), 4.97 (d, J=12.6 Hz, 1H), 4.91 (d, J=12.6 Hz, 1H), 4.72 (d, J=5.8 Hz, 2H), 4.28 (dt, J=8.5, 5.6 Hz, 1), 4.23 (td, J=7.7, 5.3 Hz, 1H), 3.42 (dd, J=9.6, 5.2 Hz, 1H), 3.35-3.32 (m, 1H), 3.23 (s, 3H), 2.65 (dd, J=16.0, 5.6 Hz, 1H), 2.41 (dd, J=16.0, 8.2 Hz, 1H), 2.35 (s, 3H).

Example 78—Preparation of (S)-4-(((S)-3-methoxy-1-((naphthalen-1-ylmethyl)amino)-1-oxopropan-2-yl)amino)-3-((4-methylphenyl)sulfonamido)-4-oxobutanoic acid (DPLG-2227)

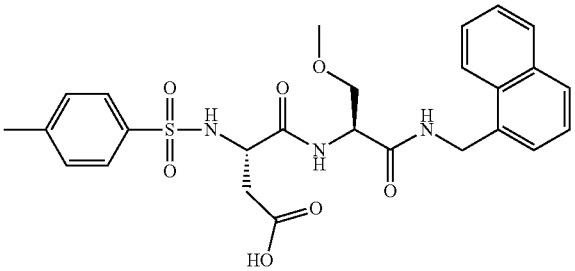

DPLG-2227 was synthesized by following the general procedure for O-debenzylation of benzyl (S)-4-(((S)-3-methoxy-1-((naphthalen-1-ylmethyl)amino)-1-oxopropan-2-yl)amino)-3-((4 -methylphenyl) sulfonamido)-4 -oxobutanoate (11.0 mg, 0.0178 mmol). Yield=7.5 mg, 80%. $^{1}$H NMR (500 MHz, DMSO-$d_6$) δ 12.37 (s, 1H), 8.39 (t, J=5.7 Hz, 1H), 8.20 (d, J=7.7 Hz, 1H), 8.13-8.10 (m, 1H), 8.03-8.01 (m, 1H), 7.95-7.93 (m, 1H), 7.83 (d, J=7.8 Hz, 1H), 7.65 (d, J=8.0 Hz, 2H), 7.55-7.51 (m, 2H), 7.45-7.40 (m, 2H), 7.33 (d, J=8.0 Hz, 2H), 4.72 (d, J=5.7 Hz, 2H), 4.23-4.16 (m, 2H), 3.44 (dd, J=9.6, 5.1 Hz, 1H), 3.36-3.33 (m, 1H), 3.23 (s, 3H), 2.54-2.49 (m, 1H), 2.36 (s, 3H), 2.27 (dd, J=16.3, 7.5 Hz, 1H).

Example 79—Preparation of (S)—N$^{1}$—((S)-3-methoxy-1-((naphthalen-1-ylmethyl)amino)-1-oxopropan-2-yl)-24(4 -methylphenyl) sulfonamido)-N$^{4}$-(oxetan-3 -yl)succinamide (DPLG-2229)

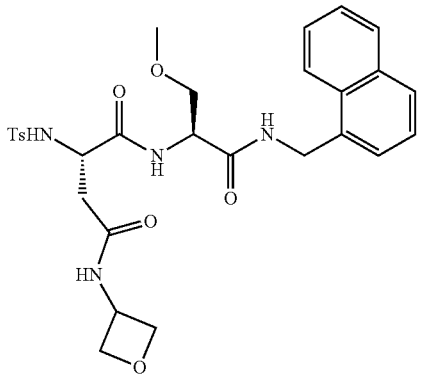

DPLG-2229 was prepared following the general procedure for HATU mediated coupling of (S)-4-(((S)-3-methoxy-1-((naphthalen-1-ylmethyl)amino)-1-oxopropan-2 -yl)amino)-3-((4 -methylphenyl) sulfonamido)-4-oxobutanoic acid (7.5 mg, 0.014 mmol) and 3-aminoxetane (1.1 mL, 0.0154 mmol). The product was purified by HPLC (yield=6.4 mg, 78%). $^{1}$H NMR (500 MHz, DMSO-$d_6$) δ 8.67 (d, J=5.7 Hz, 1H), 8.45 (t, J=6.0 Hz, 1H), 8.23 (d, J=7.6 Hz, 1H), 8.05-8.03 (m, 2H), 7.94-7.92 (m, 1H), 7.83 (d, J=8.0 Hz, 1H), 7.64 (d, J=8.0 Hz, 2H), 7.55-7.51 (m, 2H), 7.45-7.39 (m, 2H), 7.32 (d, J=8.0 Hz, 2H), 4.73 (dd, J=15.6, 5.9 Hz, 1H), 4.68 (dd, J=15.6, 5.8 Hz, 1H), 4.54-4.44 (m, 3H), 4.30-4.12 (m, 4H), 3.52 (dd, J=9.6, 5.2 Hz, 1H), 3.32-3.29 (m, 1H), 3.22 (s, 3H), 2.51-2.46 (m, 1H), 2.36 (s, 3H), 2.27 (dd, J=15.0, 6.1 Hz, 1H). $^{13}$C NMR (126 MHz, DMSO) δ 170.12, 169.03, 168.59, 142.44, 138.28, 134.18, 133.18, 130.74, 129.30, 128.44, 127.38, 126.61, 126.13, 125.75, 125.32, 124.90, 123.41, 76.94, 76.74, 71.56, 58.34, 53.25, 52.75, 43.75, 40.27, 38.45, 21.00.

Example 80—Preparation of tert-butyl (S)-(1-(((1H-indol-4-yl)methyl)amino)-3-methoxy-1-oxopropan-2-yl)carbamate (Boc-Ser(OMe)-indole, DPLG-2153)

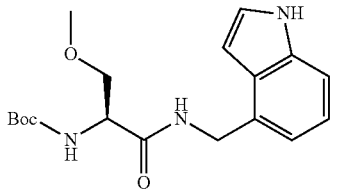

DPLG-2153 was prepared following the general procedure of HATU mediated coupling of Boc-β-methoxyalanine dicyclohexylamine (50 mg, 0.125 mmol) and 4-(aminomethyl)indole (20 mL, 0.138 mmol). The product was isolated by ethyl acetate extraction and purified by silica-gel column chromatography (yield 40 mg, 93%). $^1$H NMR (500 MHz, Chloroform-d) δ 8.57 (bs, 1H), 7.35 (dd, J=8.1, 2.0 Hz, 1H), 7.22-7.20 (m, 1H), 7.16-7.12 (m, 1H), 7.02-7.00 (m, 1H), 6.74 (bs, 1H), 6.58-6.56 (m, 1H), 5.42 (m, 1H), 4.76 (m, 2H), 4.28 (m, 1H), 3.85-3.82 (m, 1H), 3.49 (dd, J=9.3, 6.3 Hz, 1H), 3.32 (s, 3H), 1.41 (s, 9H).

Example 81—Preparation of (S)—N$^1$—((S)-1-(((1H-indol-4-yl)methyl)amino)-3-methoxy-1-oxopropan-2-yl)-N$^4$-(tert-butoxy)-2-(3-phenylpropanamido)succinamide (DPLG-2161)

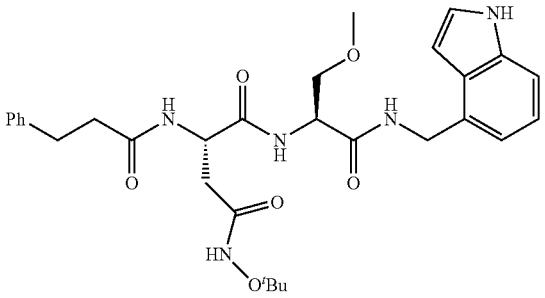

Tert-butyl (S)-(1-(((1H-indol-4-yl)methyl)amino)-3-methoxy-1-oxopropan-2-yl)carbamate (40 mg, 0.115 mmol) was added to 2 mL 4N HCl in dioxane at 20° C. Within 30 minutes the reaction mixture turned red. LCMS showed completion of the reaction. Dioxane and HCl were evaporated. The crude was coupled with (S)-4-(tert-butoxyamino)-4-oxo-2-(3-phenylpropanamido)butanoic acid (16.8 mg, 0.05 mmol) following the general procedure for HATU mediated coupling. The product was purified by HPLC to give pure product (8.2 mg, 29%). $^1$H NMR (500 MHz, DMSO-d$_6$) δ 11.09 (s, 1H), 10.36 (s, 1H), 8.46 (t, J=5.9 Hz, 1H), 8.20 (d, J=8.0 Hz, 1H), 8.02 (d, J=7.9 Hz, 1H), 7.30 (t, J=2.8 Hz, 1H), 7.29-7.25 (m, 3H), 7.20-7.15 (m, 3H), 7.02-6.99 (m, 1H), 6.89 (d, J=7.2 Hz, 1H), 6.51 (t, J=2.4 Hz, 1H), 4.67-4.63 (m, 1H), 4.55 (dd, J=15.2, 5.9 Hz, 1H), 4.49 (dd, J=15.2, 5.9 Hz, 1H), 4.44-4.41 (m, 1H), 3.57 (dd, J=9.8, 6.0 Hz, 1H), 3.50 (dd, J=9.8, 4.7 Hz, 1H), 3.23 (s, 3H), 2.81-2.75 (m, 2H), 2.53-2.47 (m, 1H), 2.44-2.38 (m, 2H), 2.33 (dd, J=14.9, 8.0 Hz, 1H), 1.12 (s, 9H).

Example 82—Preparation of tert-butyl (S)-(3-methoxy-1-((3-methoxybenzyl)amino)-1-oxopropan-2-yl)carbamate (DPLG-2154)

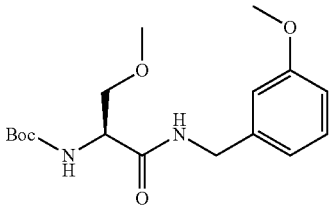

DPLG-2154 was prepared following the general procedure of HATU mediated coupling of Boc-β-methoxyalanine dicyclohexylamine (100 mg, 0.25 mmol) and 3-methoxybenzyl amine (36 mL, 0.275 mmol). The product was isolated by ethyl acetate extraction and purified by silica-gel column chromatography (yield 74 mg, 87%). $^1$H NMR (500 MHz, Chloroform-d) δ 7.26-7.22 (m, 1H), 6.86-6.84 (m, 1H), 6.82-6.80 (m, 2H), 6.75 (t, J=6.2 Hz, 1H), 5.42 (bs, 1H), 4.47-4.46 (m, 2H), 4.28 (m, 1H), 3.85 (dd, J=9.2, 3.8 Hz, 1H), 3.80 (s, 3H), 3.51 (dd, J=9.2, 6.2 Hz, 1H), 3.38 (s, 3H), 1.44 (s, 9H).

Example 83—Preparation of (S)-2-amino-3-methoxy-N-(3-methoxybenzyl)propanamide 2,2,2 trifluoroacetate (DPLG-2158)

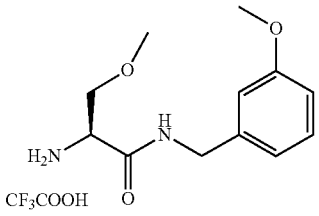

DPLG-2158 was synthesized by following the general procedure for Boc-deprotection of tert-butyl (S)-(3-methoxy-1-((3-methoxybenzyl)amino)-1-oxopropan-2-yl) carbamate (74 mg, 0.219 mmol). After 2 h, dichloromethane and excess TFA were evaporated and crude was dried under vacuum to give product (70 mg, 91%). $^1$H NMR (500 MHz, Chloroform-d) δ 9.13 (bs, 1H), 8.01 (bs, 2H), 7.56 (t, J=5.8 Hz, 1H), 7.22 (t, J=7.9 Hz, 1H), 6.80 (dd, J=8.3, 2.5 Hz, 1H), 6.75 (d, J=7.6 Hz, 1H), 6.73-6.72 (m, 1H), 4.41-4.35 (m, 2H), 4.29 (dd, J=15.0, 5.5 Hz, 1H), 3.75 (s, 3H), 3.73 (dd, J=10.4, 4.7 Hz, 1H), 3.67 (dd, J=10.4, 5.3 Hz, 1H), 3.32 (s, 3H).

Example 84—Preparation of (S)—$N^4$-(tert-butoxy)-$N^1$—-((S)-3-methoxy-1-((3 -methoxybenzyl)amino)-1-oxopropan-2-yl)-2-(3 -phenylpropanamido)succinamide (DPLG-2160)

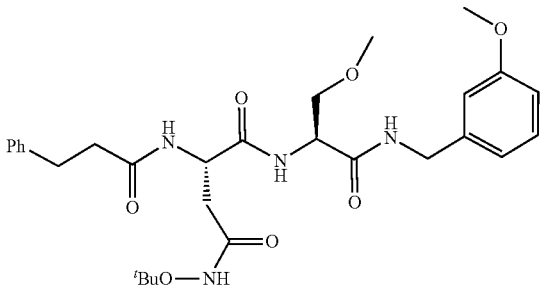

DPLG-2160 was prepared following the general procedure for HATU mediated coupling of (S)-4-(tert-butoxyamino)-4-oxo-2-(3-phenylpropanamido)butanoic acid (15.8 mg, 0.047 mmol) and (S)-2-amino-3-methoxy-N-(3-methoxybenzyl)propanamide 2,2,2 trifluoroacetate (18.4 mg, 0.052 mmol). The product was purified by HPLC (yield 16.2 mg, 62%). $^1$H NMR (500 MHz, DMSO-$d_6$) δ 10.39 (s, 1H), 8.51 (t, J=6.1 Hz, 1H), 8.20 (d, J=7.9 Hz, 1H), 8.09 (d, J=7.7 Hz, 1H), 7.27-7.25 (m, 2H), 7.21-7.15 (m, 4H), 6.82-6.81 (m, 2H), 6.77 (dd, J=8.1, 2.4 Hz, 1H), 4.67-4.63 (m, 1H), 4.40-4.37 (m, 1H), 4.30-4.21 (m, 2H), 3.72 (s, 3H), 3.61 (dd, J=9.8, 5.9 Hz, 1H), 3.50 (dd, J=9.8, 4.6 Hz, 1H), 3.25 (s, 3H), 2.80-2.76 (m, 2H), 2.53-2.48 (m, 1H), 2.43-2.39 (m, 2H), 2.34 (dd, J=14.8, 7.6 Hz, 1H), 1.11 (s, 9H).

Example 85—Preparation of tert-butyl (S)-(1-((2,3-dimethoxybenzyl)amino)-3-methoxy-1-oxopropan-2-yl)carbamate (DPLG-2184)

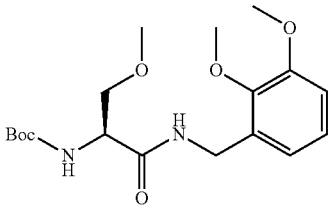

DPLG-2184 was prepared following the general procedure of HATU mediated coupling of Boc-β-methoxyalanine dicyclohexylamine (200 mg, 0.5 mmol) and 2,3-dimethoxybenzyl amine (83 μl, 0.55 mmol). The product was isolated by ethyl acetate extraction and purified by silica-gel column chromatography (yield=184 mg, quant.). $^1$H NMR (500 MHz, DMSO-$d_6$) δ 8.24 (t, J=5.9 Hz, 1H), 7.00-6.97 (m, 1H), 6.93 (dd, J=8.3, 1.7 Hz, 1H), 6.86 (d, J=8.3 Hz, 1H), 6.81 (dd, J=7.6, 1.7 Hz, 1H), 4.31-4.23 (m, 2H), 4.20-4.15 (m, 1H), 3.79 (s, 3H), 3.72 (s, 3H), 3.48-3.46 (m, 2H), 3.24 (s, 3H), 1.38 (s, 9H).

Example 86—Preparation of (S)-2-amino-N-(2,3-dimethoxybenzyl)-3-methoxypropanamide 2, 2, 2-trifluoroacetate (DPLG-2190)

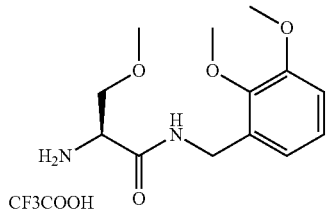

DPLG-2190 was synthesized by following the general procedure for Boc-deprotection of tert-butyl (S)-(1-((2, 3-dimethoxybenzyl)amino)-3-methoxy-1-oxopropan-2-yl)carbamate (180 mg, 0.49 mmol). Crude product was dried under vacuum to give viscous paste, which upon standing turned solid. $^1$H NMR (500 MHz, DMSO-$d_6$) δ 8.78 (t, J=5.7 Hz, 1H), 8.21 (bs, 3H), 7.05-7.02 (m, 1H), 6.97 (dd, J=8.2, 1.6 Hz, 1H), 6.83 (dd, J=7.6, 1.6 Hz, 1H), 4.36 (dd, J=15.1, 5.7 Hz, 1H), 4.31 (dd, J=15.1, 5.6 Hz, 1H), 4.04-4.01 (m, 1H), 3.80 (s, 3H), 3.75 (s, 3H), 3.66 (d, J=5.1 Hz, 2H), 3.30 (s, 3H).

Example 87—Preparation of benzyl (S)-3-((tertbutoxycarbonyl)amino)-4-(((S)-1-(2,3-dimethoxybenzyl)amino)-3-methoxy-1-oxopropan-2-yl)amino)-4-oxobutanoate (DPLG-2191)

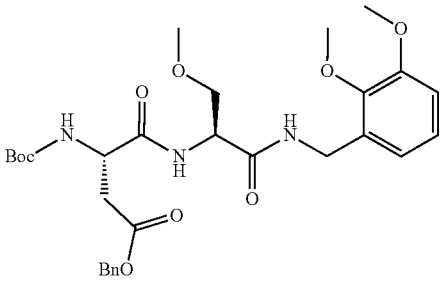

DPLG-2191 was prepared following the general procedure of HATU mediated coupling of N-(tert-butoxycarbonyl)-L-aspartic acid 4-benzyl ester (159 mg, 0.49 mmol) and (S)-2-amino-N-(2,3-dimethoxybenzyl)-3-methoxypropanamide 2,2,2-trifluoroacetate (0.49 mmol, from previous step). The product was isolated by ethyl acetate extraction and recrystallized with ethanol-water (yield=245 mg, 87% for 2 steps). $^1$H NMR (500 MHz, DMSO-$d_6$) δ 8.29 (t, J=5.8 Hz, 1H), 7.86 (d, J=7.9 Hz, 1H), 7.38-7.31 (m, 5H), 7.28 (d, J=8.0 Hz, 1H), 7.00-6.97 (m, 1H), 6.92 (dd, J=8.2, 1.6 Hz, 1H), 6.78 (dd, J=7.7, 1.6 Hz, 1H), 5.08 (d, J=12.6 Hz, 1H), 5.05 (d, J=12.6 Hz, 1H), 4.45-4.37 (m, 2H), 4.31-4.23 (m, 2H), 3.78 (s, 3H), 3.71 (s, 3H), 3.56 (dd, J=9.7, 5.6 Hz, 1H), 3.46 (dd, J=9.7, 5.1 Hz, 1H), 3.24 (s, 3H), 2.82-2.78 (m, 1H), 2.61 (dd, J=16.3, 8.9 Hz, 1H), 1.37 (s, 9H).

Example 88—Preparation of benzyl (S)-3-amino-4-(((S)-1-(2,3-dimethoxybenzyl)amino)-3-methoxy-1-oxopropan-2-yl)amino)-4-oxobutanoate 2,2,2-trifluoroacetate (DPLG-2197)

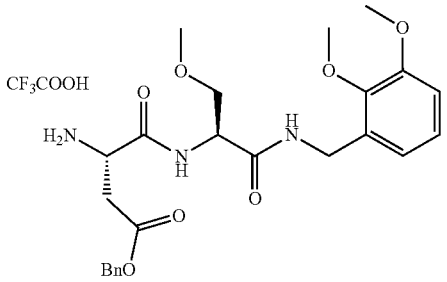

DPLG-2197 was synthesized by following the general procedure for Boc-deprotection of benzyl (S)-3-((tert-butoxycarbonyl)amino)-4-(((S)-1-((2,3-dimethoxybenzyl) amino)-3-methoxy-1-oxopropan-2-yl)amino)-4-oxobutanoate (115 mg, 0.2 mmol). The crude was used in next step without further purification. $^1$H NMR (500 MHz, DMSO-$d_6$) δ 8.81 (d, J=7.8 Hz, 1H), 8.37 (t J=5.9 Hz, 1H), 8.26 (bs, 3H), 7.39-7.34 (m, 5H), 6.99 (t, J=7.9 Hz, 1H), 6.93 (dd, J=8.3, 1.6 Hz, 1H), 6.78 (dd, J=7.7, 1.6 Hz, 1H), 5.14 (d, J=12.4 Hz, 1H), 5.11 (d, J=12.4 Hz, 1H), 4.55-4.51 (m, 1H), 4.33-4.23 (m, 3H), 3.78 (s, 3H), 3.71 (s, 3H), 3.59 (dd, J=9.9, 6.2 Hz, 1H), 3.52 (dd, J=9.9, 4.8 Hz, 1H), 3.27 (s, 3H), 3.02 (dd, J=17.5, 4.1 Hz, 1H), 2.82 (dd, J=17.5, 8.8 Hz, 1H).

Example 89—Preparation of benzyl (S)-4-(((S)-1-((2,3-dimethoxybenzyl)amino)-3-methoxy-1-oxopropan-2-yl)amino)-4-oxo-3-(3-phenylpropanamido) butanoate (DPLG-2200)

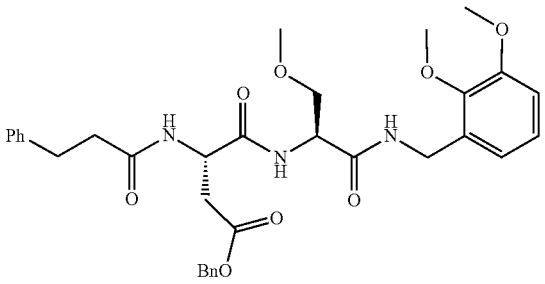

DPLG-2200 was prepared following the general procedure of HATU mediated coupling of 3-phenylpropanoic acid (33 mg, 0.22 mmol) and benzyl (S)-3-amino-4-(((S)-1-((2,3-dimethoxybenzyl)amino)-3-methoxy-1-oxopropan-2-yl) amino)-4-oxobutanoate 2,2,2-trifluoroacetate (0.2 mmol, from previous step). The reaction mixture was precipitated with water and the precipitate was filtered and dried to give product (110 mg, 91% for 2 steps). 1H NMR (500 MHz, DMSO-$d_6$) δ 8.30 (d, J=7.9 Hz, 1H), 8.24 (t, J=5.9 Hz, 1H), 8.04 (d, J=7.9 Hz, 1H), 7.38-7.32 (m, 5H), 7.28-7.25 (m, 2H), 7.18-7.15 (m, 3H), 6.99 (t, J=7.9 Hz, 1H), 6.92 (dd, J=8.0, 1.6 Hz, 1H), 6.79 (dd, J=7.5, 1.6 Hz, 1H), 5.04 (s, 2H), 4.74 (td, J=8.1, 5.7 Hz, 1H), 4.42 (dt, J=7.8, 5.4 Hz, 1H), 4.31-4.24 (m, 2H), 3.78 (s, 3H), 3.72 (s, 3H), 3.56 (dd, J=9.8, 5.8 Hz, 1H), 3.47 (dd, J=9.8, 5.0 Hz, 1H), 3.24 (s, 3H), 2.85-2.77 (m, 3H), 2.59 (dd, J=16.2, 8.3 Hz, 1H), 2.41-2.38 (m, 2H).

Example 90—Preparation of (S)-4-(((S)-1-((2,3-dimethoxybenzyl)amino)-3-methoxy-1-oxopropan-2-yl)amino)-4-oxo-3-(3-phenylpropanamido)butanoic acid (DPLG-2204)

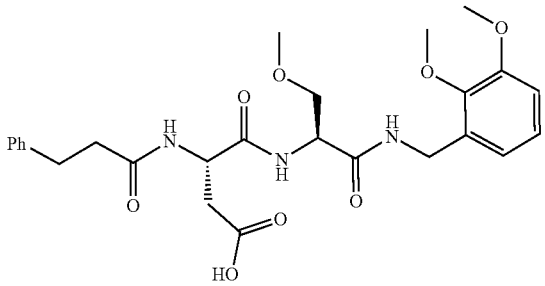

Benzyl (S)-4-(((S)-1-((2,3-dimethoxybenzyl)amino)-3-methoxy-1-oxopropan-2-yl)amino)-4-oxo-3-(3-phenylpropanamido)butanoate (110 mg, 0.18 mmol) was dissolved in 30 mL methanol, and 35 mg palladium on carbon (10%) was added carefully. The air of flask was replaced by hydrogen and the mixture was stirred at room temperature under hydrogen atmosphere for 2 days. The reaction was not complete. Mixture was filtered through celite. The filterate was evaporated and purified by HPLC to give 40 mg product (50% bsrm; 16.0 mg starting material was recovered). $^1$H NMR (500 MHz, DMSO-$d_6$) δ 12.34 (s, 1H), 8.27-8.24 (m, 2H), 7.95 (d, J=7.9 Hz, 1H), 7.28-7.25 (m, 2H), 7.20-7.15 (m, 3H), 6.99 (t, J=7.9 Hz, 1H), 6.93 (dd, J=8.2, 1.5 Hz, 1H), 6.80 (dd, J=7.7, 1.5 Hz, 1H), 4.66-4.60 (m, 1H), 4.43-4.38 (m, 1H), 4.28 (d, J=5.9 Hz, 2H), 3.78 (s, 3H), 3.72 (s, 3H), 3.56 (dd, J=9.7, 5.8 Hz, 1H), 3.47 (dd, J=9.7, 5.0 Hz, 1H), 3.24 (s, 3H), 2.79 (t, J=7.9 Hz, 2H), 2.68 (dd, J=16.6, 5.9 Hz, 1H), 2.48-2.39 (m, 3H).

Example 91—Preparation of (S)—$N^4$-(tert-butoxy)-$N^1$—((S)-1-((2,3-dimethoxybenzyl)amino-3-methoxy-1-oxopropan-2-yl)-2-(3-phenylpropanmido)succinamide (DPLG-2211)

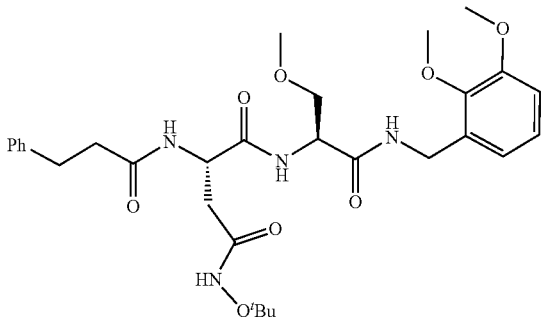

DPLG-2211 was prepared following the general procedure for HATU mediated coupling of 0-tert-butyl hydroxylamine hydrochloride (6.6 mg, 0.0525 mmol) and (S)-4-(((S)-1-((2,3 -dimethoxybenzyl)amino)-3 -methoxy-1-oxopropan-2-yl)amino)-4-oxo -3-(3 -phenylpropanamido) butanoic acid (18.0 mg, 0.035 mmol). After completion of reaction (1 h), the mixture was diluted with water and extracted with ethyl acetate. The organic layer was evaporated and purified by HPLC to give the product (11.0 mg, 54%). $^1$H NMR (500 MHz, DMSO-$d_6$) δ 10.37 (s, 1H), 8.37 (t, J=6.0 Hz, 1H), 8.20 (d, J=7.9 Hz, 1H), 8.05 (d, J=7.7 Hz, 1H), 7.28-7.25 (m, 2H), 7.19-7.15 (m, 3H), 6.98 (t, J=7.9 Hz, 1H), 6.92 (dd, J=8.1, 1.6 Hz, 1H), 6.82 (d, J=7.7 Hz, 1H), 4.67-4.63 (m, 1H), 4.40 (dt, J=7.6, 5.3 Hz, 1H), 4.31-4.24 (m, 2H), 3.78 (s, 3H), 3.72 (s, 3H), 3.59 (dd, J=9.8, 6.0 Hz, 1H), 3.49 (dd, J=9.8, 4.6 Hz, 1H), 3.24 (s, 3H), 2.80-2.76 (m, 2H), 2.52-2.48 (m, 1H), 2.43-2.39 (m, 2H), 2.33 (dd, J=14.9, 7.8 Hz, 1H), 1.11 (s, 9H). $^{13}$C NMR (126 MHz, DMSO) δ 171.97, 171.35, 169.68, 168.02, 152.58, 146.48, 141.70, 132.79, 128.76, 128.58, 126.32, 124.13, 120.29, 111.99, 81.02, 72.26, 60.39, 58.73, 56.12, 53.56, 50.10, 37.38, 37.24, 35.27, 31.44, 26.70.

Example 92—Preparation of tert-butyl (S)-(3-methoxy-1-oxo -1-((quinolin-8-ylmethyl)amino) propan-2-yl)carbamate (DPLG-2175)

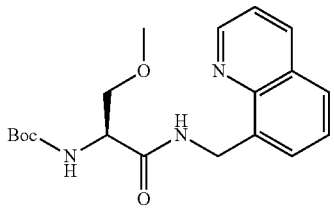

DPLG-2175 was prepared following the general procedure for HATU coupling of Boc-β-methoxyalanine dicyclohexylamine (80 mg, 0.02 mmol) and quinolin-8-ylmethylamine dihydrochloride (46 mg, 0.2 mmol) in 2 mL dimethylformamide. (Note: reaction mixture was not soluble in dimethylformamide) After completion of the reaction (3 h), water was added to the reaction mixture (the reaction mixture turned transparent) and extracted twice with chloroform. The combined organic layer was washed with water followed by brine, dried over anhydrous sodium sulfate, and evaporated. The crude product was purified by HPLC to give 68.5 mg (95%) of pure product. $^1$H NMR (500 MHz, DMSO-$d_6$) δ 8.96-8.94 (m, 1H), 8.46 (t, J=6.2 Hz, 1H), 8.39 (dd, J=8.1, 1.6 Hz, 1H), 7.88 (d, J=8.1 Hz, 1H), 7.64 (d, J=7.1 Hz, 1H), 7.58 (dd, J=8.3, 4.2 Hz, 1H), 7.54 (t, J=7.6 Hz, 1H), 6.96 (d, J=8.1 Hz, 1H), 4.96-4.87 (m, 2H), 4.26-4.22 (m, 1H), 3.54-3.53 (m, 2H), 3.27 (s, 3H), 1.39 (s, 9H).

Example 93—Preparation of (S)-2-amino-3-methoxy-N-(quinolin-8-ylmethyl)propanamide bis (2,2,2-trifluoroacetate) (DPLG-2181)

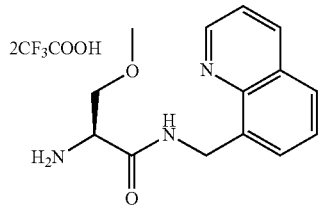

DPLG-2181 was synthesized by following the general procedure for Boc-deprotection of tert-butyl (S)-(3-methoxy-1-oxo -1-((quinolin-8-ylmethyl)amino)propan-2-yl)carbamate (68.5 mg, 0.19 mmol). The crude was used in next step. $^1$H NMR (500 MHz, DMSO-$d_6$) δ 8.98 (dd, J=4.2, 1.8 Hz, 1H), 8.95 (t, J=5.9 Hz, 1H), 8.42 (dd, J=8.2, 1.8 Hz, 1H), 8.22 (bs, 3H), 7.93 (dd, J=8.1, 1.5 Hz, 1H), 7.67 (dd, J=7.1, 1.5 Hz, 1H), 7.62-7.58 (m, 2H), 5.02 (dd, J=15.9, 5.9 Hz, 1H), 4.96 (dd, J=15.9, 5.7 Hz, 1H), 4.13-4.10 (m, 1H), 3.75-3.69 (m, 2H), 3.32 (s, 3H).

Example 94—Preparation of benzyl (S)-3-((tertbutoxycarbonyl)amino)-4-(((S)-3-methoxy-1-oxo-1-((quinolin-8-ylmethyl)amino)propan-2-yl)amino)-4-oxobutanoate (DPLG-2188)

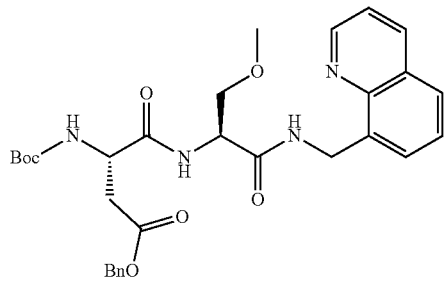

DPLG-2188 was prepared following the general procedure for HATU mediated coupling of N-(tert-butoxycarbonyl)-L-aspartic acid 4-benzyl ester (61.4 mg, 0.19 mmol) and (S)-2-amino-3-methoxy-N-(quinolin-8-ylmethyl)propanamide bis(2,2,2-trifluoroacetate) (0.19 mmol, from previous step). After completion of reaction (1 h), reaction mixture was diluted with water and extracted twice with ethyl acetate. Ethyl acetate layer was dried over anhydrous $Na_2SO_4$ and evaporated. The crude was dried under high $^1$H NMR (500 MHz, DMSO-$d_6$) δ 8.96 (dd, J=4.3, 1.8 Hz, 1H), 8.49 (t, J=5.9 Hz, 1H), 8.43 (dd, J=8.3, 1.8 Hz, 1H), 7.95 (d, J=7.8 Hz, 1H), 7.90 (dd, J=8.0, 1.5 Hz, 1H), 7.63 (dd, J=7.1, 1.5 Hz, 1H), 7.61-7.55 (m, 2H), 7.37-7.30 (m, 6H), 5.09 (d, J=12.7 Hz, 1H), 5.05 (d, J=12.7 Hz, 1H), 4.96 (dd, J=16.4, 6.0 Hz, 1H), 4.89 (dd, J=16.4, 5.9 Hz, 1H), 4.51-4.48 (m, 1H), 4.43 (td, J=8.5, 5.0 Hz, 1H), 3.63 (dd, J=9.7, 5.5 Hz, 1H), 3.52 (dd, J=9.7, 5.1 Hz, 1H), 3.28 (s, 3H), 2.85-2.81 (m, 1H), 2.62 (dd, J=16.2, 8.9 Hz, 1H), 1.38 (s, 9H).

Example 95—Preparation of benzyl (S)-3-amino-4-(((S)-3-methoxy-1-oxo-1-((quinolin-8-ylmethyl) amino)propan-2-yl)amino)-4-oxobutanoate bis(2,2, 2-trifluoroacetate) (DPLG-2194)

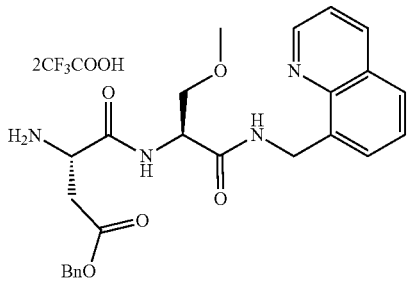

DPLG-2194 was synthesized by following the general procedure for Boc-deprotection of benzyl (S)-3-((tert-butoxycarbonyl)amino)-4-(((S)-3-methoxy-1-oxo -1-((quinolin-8-ylmethyl)amino)propan-2-yl)amino)-4 -oxobutanoate (0.19 mmol, from previous step). After completion of the reaction (3 h), excess trifluoroacetic acid and dichloromethane were evaporated. Crude paste was washed twice with diethyl ether to give product as off white solid (yield=111 mg, 84% for 3 steps). $^1$H NMR (500 MHz, DMSO-$d_6$)8 8.94 (dd, J=4.2, 1.8 Hz, 1H), 8.87 (d, J=7.8 Hz, 1H), 67 J=6.0 Hz, 1H), 8.39 (dd, J=8.4, 1.8 Hz, 1H), 8.27 (bs, 3H), 7.88 (dd, J=8.1, 1.5 Hz, 1H), 7.61 (dd, J=7.2, 1.5 Hz, 1H), 7.58-7.54 (m, 2H), 7.40-7.31 (m, 5H), 5.13 (J=12.5 Hz, 1H), 5.10 (d, J=12.5 Hz, 1H), 4.97 (dd, J=16.4, 6.1 Hz, 1H), 4.90 (dd, J=16.4, 5.9 Hz, 1H), 4.62-4.58 (m, 1H), 4.27 (m, 1H), 3.66 (dd, J=9.8, 6.0 Hz, 1H), 3.57 (dd, J=9.8, 4.8 Hz, 1H), 3.30 (s, 3H), 3.04 (dd, J=17.5, 3.9 Hz, 1H), 2.85-2.80 (m, 1H).

Example 96—Preparation of benzyl (S)-4-(((S)-3-methoxy-1-oxo-1-((quinolin-8-ylmethyl)amino)propan-2-yl)amino)-4-oxo-3-(3-phenylpropanamido) butanoate (DPLG-2198)

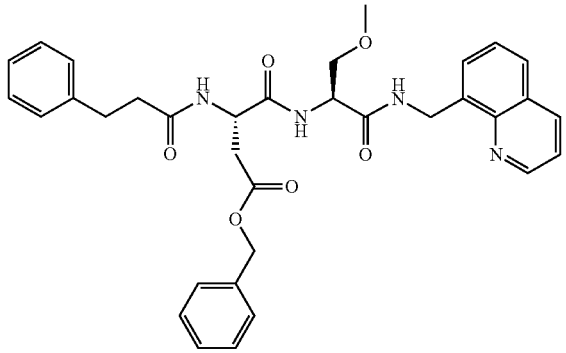

DPLG-2198 was prepared following the general procedure for HATU mediated coupling of 3-phenylpropanoic acid (26.4 mg, 0.176 mmol) and benzyl (S)-3-amino-4-(((S)-3-methoxy-1-oxo-1-((quinolin-8-ylmethyl)amino)propan-2-yl)amino)-4-oxobutanoate bis(2,2,2-trifluoroacetate) (111 mg, 0.16 mmol). After completion of the reaction (3 h), the mixture was precipitated with water. The precipitate was filtered and dried to give the product (77 mg, 81%). $^1$H NMR (500 MHz, DMSO-$d_6$) δ 8.94 (dd, J=4.2, 1.8 Hz, 1H), 8.43 (t, J=6.1 Hz, 1H), 8.38 (dd, J=8.3, 1.8 Hz, 1H), 8.32 (d, J=8.0 Hz, 1H), 8.12 (d, J=7.8 Hz, 1H), 7.87 (dd, J=8.1, 1.5 Hz, 1H), 7.61 (dd, J=7.2, 1.5 Hz, 1H), 7.57-7.53 (m, 2H), 7.35-7.30 (m, 5H), 7.27-7.24 (m, 2H), 7.19-7.15 (m, 3H), 5.03 (s, 2H), 4.95 (dd, J=16.4, 6.1 Hz, 1H), 4.90 (dd, J=16.4, 5.9 Hz, 1H), 4.77 (td, J=8.2, 5.7 Hz, 1H), 4.49 (dt, J=7.8, 5.3 Hz, 1H), 3.62 (dd, J=9.7, 5.8 Hz, 1H), 3.52 (dd, J=9.7, 5.0 Hz, 1H), 3.28 (s, 3H), 2.85-2.77 (m, 3H), 2.59 (dd, J=16.2, 8.4 Hz, 1H), 2.42-2.38 (m, 2H).

Example 97—Preparation of (S)-4-(((S)-3-methoxy-1-oxo-1-(((1,2,3,4-tetrahydroquinolin-8-yl)methyl) amino)propan-2-yl)amino)-4-oxo-3-(3-phenylpropanamido)butanoic acid (DPLG-2202)

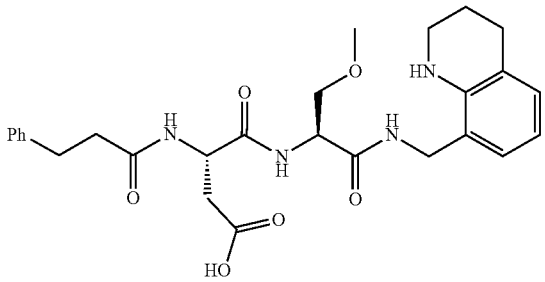

Benzyl (S)-4-(((S)-3-methoxy-1-oxo-1-((quinolin-8-ylmethyl)amino)propan-2-yl)amino)-4-oxo-3-(3-phenylpropanamido)butanoate (73 mg, 0.122 mmol) was dissolved in 3 mL methanol and 25 mg 10 palladium on carbon (10%) was added. The mixture was stirred overnight under hydrogen atmosphere. The mixture was filtered through celite, evaporated, and purified by HPLC to give the product (19 mg, 30%). $^1$H NMR (500 MHz, DMSO-$d_6$) δ 12.34 (s, 1H), 8.26-8.23 (m, 2H), 7.99 (d, J=7.8 Hz, 1H), 7.28-7.25 (m, 2H), 7.21-7.15 (m, 3H), 6.81 (dd, J=7.5, 1.5 Hz, 1H), 6.76 (dd, J=7.5, 1.5 Hz, 1H), 6.40 (t, J=7.4 Hz, 1H), 4.63 (td, J=7.8, 5.8 Hz, 1H), 4.40 (dt, J=7.7, 5.4 Hz, 1H), 4.08 (dd, J=15.3, 6.1 Hz, 1H), 4.03 (dd, J=15.3, 5.9 Hz, 1H), 3.56 (dd, J=9.8, 5.8 Hz, 1H), 3.47 (dd, J=9.8, 5.0 Hz, 1H), 3.24 (s, 3H), 3.22 (t, J=5.5 Hz, 2H), 2.80 (t, J=7.9 Hz, 2H), 2.70-2.65 (m, 3H), 2.48-2.39 (m, 3H), 1.79-1.74 (m, 2H).

Example 98—Preparation of (S)—$N^4$-(tert-butoxy)-$N^{-1}$—((S)-3-methoxy-1-oxo-1-(((1,2,3,4-tetrahydroquinolin-8-yl)methyl)amino)propan-2-yl)-2-(3 -phenylpropanamido)succinamide (DPLG-2226)

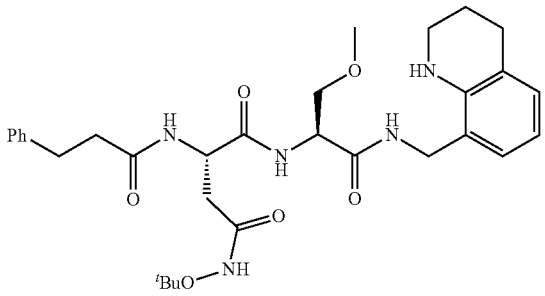

DPLG-2226 was prepared following the general procedure for HATU mediated coupling of (S)-4-(((S)-3-methoxy-1-oxo-1-(((1,2,3,4 -tetrahydroquinolin-8-yl) methyl)amino)propan-2-yl)amino)-4-oxo-3-(3-phenylpropanamido)butanoic acid (19.0 mg, 0.037 mmol) and O-tert-butylhydroxylamine hydrochloride (5.1 mg, 0.041 mmol). The product was purified by HPLC (17.9 mg, 83%). $^1$H NMR (500 MHz, DMSO-$d_6$) δ 10.40 (s, 1H), 8.41 (t, J=6.1 Hz, 1H), 8.18 (d, J=7.9 Hz, 1H), 8.10 (d, J=7.8 Hz, 1H), 7.28-7.25 (m, 2H), 7.20-7.15 (m, 3H), 6.84 (d, J=7.5 Hz, 1H), 6.75 (d, J=7.5 Hz, 1H), 6.38 (t, J=7.4 Hz, 1H), 5.24-5.20 (m, 1H), 4.67-4.62 (m, 1H), 4.40-4.37 (m, 1H), 4.10 (dd, J=15.1, 6.3 Hz, 1H), 4.00 (dd, J=15.1, 5.8 Hz, 1H), 3.60 (dd, J=9.8, 5.9 Hz, 1H), 3.49 (dd, J=9.8, 4.5 Hz, 1H), 3.24 (s, 3H), 3.22-3.21 (m, 2H), 2.80-2.76 (m, 2H), 2.66 (t, J=6.4 Hz, 2H), 2.52-2.48 (m, 1H), 2.42-2.39 (m, 2H), 2.35 (dd, J=14.8, 7.5 Hz, 1H), 1.79-1.74 (m, 2H), 1.14 (s, 9H). $^{13}$C NMR (126 MHz, DMSO) δ 171.45, 170.86, 169.46, 167.61, 142.51, 141.23, 128.29, 128.11, 128.00, 126.47, 125.85, 121.30, 120.04, 114.64, 80.59, 71.75, 58.29, 53.09, 49.63, 41.33, 36.77, 34.84, 30.99, 27.16, 26.26, 21.33.

Example 99—Preparation of (S)—N$^4$-(tert-butoxy)-N$^1$—(S)-3-methoxy-1-oxo 1-((quinolin-8-ylmethyl) amino)propan-2-yl)-2-(3-phenylpropanamido)succinamide (DPLG-2220)

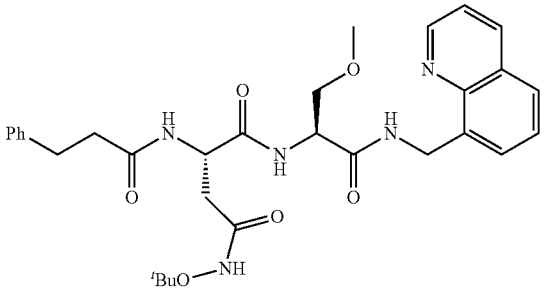

DPLG-2220 was prepared following the general procedure for HATU mediated coupling of (S)-4-(tert-butoxyamino)-4-oxo-2-(3-phenylpropanamido)butanoic acid (20.2 mg, 0.06 mmol) and (S)-2-amino-3-methoxy-N-(quinolin-8-ylmethyl)propanamide bis(2,2,2-trifluoroacetate) (32.2 mg, 0.066 mmol). The product was purified by HPLC (yield=21.6 mg, 62%). $^1$H NMR (500 MHz, DMSO-d$_6$) δ 10.36 (s, 1H), 8.95 (dd, J=4.2, 1.8 Hz, 1H), 8.57 (t, J=6.1 Hz, 1H), 8.38 (dd, J=8.3, 1.8 Hz, 1H), 8.22 (d, J=8.0 Hz, 1H), 8.15 (d, J=7.8 Hz, 1H), 7.87 (dd, J=8.3, 1.5 Hz 1H), 7.63 (dd, J=7.4, 1.5 Hz, 1H), 7.59-7.54 (m, 2H), 7.28-7.25 (m, 2H), 7.20-7.17 (m, 3H), 4.98-4.89 (m, 2H), 4.71-4.67 (m, 1H), 4.50-4.46 (m, 1H), 3.66 (dd, J=9.7, 5.8 Hz, 1H), 3.55 (dd, J=9.7, 4.7 Hz, 1H), 3.29 (s, 3H), 2.80-2.77 (m, 2H), 2.55-2.51 (m, 1H), 2.42 (td, J=7.6, 3.6 Hz, 2H), 2.35 (dd, J=14.7, 7.7 Hz, 1H), 1.06 (s, 9H). $^{13}$C NMR (126 MHz, DMSO) δ 171.95, 171.47, 169.97, 168.04, 150.09, 145.84, 141.70, 136.89, 136.79, 128.76, 128.58, 128.10, 127.15, 126.89, 126.67, 126.32, 121.86, 80.98, 72.30, 58.78, 53.74, 50.11, 39.16, 37.25, 35.29, 31.45, 26.66.

Example 100—Preparation of tert-butyl (S)-(3-methyl-1-((naphthalen-1-ylmethyl)amino)-1-oxobutan-2-yl)carbamate (DPLG-2218)

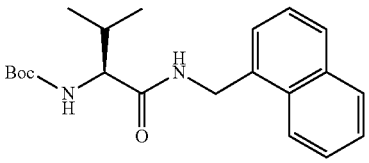

DPLG-2218 was prepared following the general procedure for HATU mediated coupling of Boc-Val-OH (217 mg, 1 mmol) and 1-naphthylmethylamine (161 μL, 1.1 mmol). The product was isolated by ethyl acetate extraction and purified by recrystallization with ethanol/water (322 mg, 90%). $^1$H NMR (500 MHz, DMSO-d$_6$) δ 8.37 (t, J=5.7 Hz, 1H), 8.07-8.05 (m, 1H), 7.95-7.93 (m, 1H), 7.84 (d, J=7.9 Hz, 1H), 7.55-7.52 (m, 2H), 7.49-7.42 (m, 2H), 6.71 (d, J=8.9 Hz, 1H), 4.75 (d, J=5.6 Hz, 2H), 3.84-3.81 (m, 1H), 1.96-1.89 (m, 1H), 1.38 (s, 9H), 0.83 (d, J=6.5 Hz, 6H).

Example 101—Preparation of (S)-2-amino-3methyl-N-(naphthalen-1-ylmethyl)butanamide 2,2,2-trifluoroacetate (DPLG-2221)

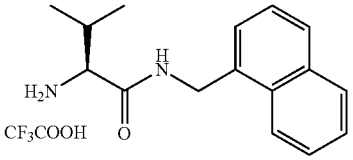

DPLG-2221 was synthesized by following the general procedure for Boc-deprotection of tert-butyl (S)-(3-methyl-1-((naphthalen-1-ylmethyl)amino)-1-oxobutan-2-yl)carbamate (107 mg, 0.3 mmol). After completion of reaction (3 h), excess trifluoroacetic acid and dichloromethane were evaporated to give a paste. The paste was treated with hexane and left overnight. A white solid appeared, which was isolated by decantation of hexane. The solid was dried under vacuum to give pure product (97 mg, 87%). $^1$H NMR (500 MHz, DMSO-d$_6$) δ 8.94 (t, J=5.7 Hz, 1H), 8.19 (d, J=5.2 Hz, 3H), 8.08-8.07 (m, 1H), 7.98-7.96 (m, 1H), 7.89 (d, J=7.9 Hz, 1H), 7.58-7.47 (m, 4H), 4.90 (dd, J=14.9, 5.8 Hz, 1H), 4.73 (dd, J=14.9, 5.1 Hz, 1H), 3.63-3.61 (m, 1H), 2.10-2.03 (m, 1H), 0.91-0.88 (m, 6H).

Example 102—Preparation of (S)—N$^4$-(tert-butoxy)-N$^1$—((S)-3-methyl-1-((naphthalen-1-ylmethyl) amino)-1-oxobutan-2-yl)-2-(3 -phenylpropanamido) succinamide (DPLG-2224)

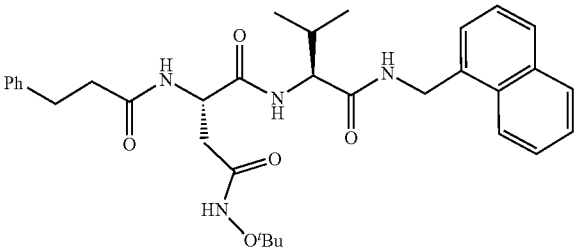

DPLG-2224 was prepared following the general procedure for HATU mediated coupling of (S)-4-(tert-butoxyamino)-4-oxo-2-(3-phenylpropanamido)butanoic acid (20.2 mg, 0.06 mmol) and (S)-2-amino-3-methyl-N-(naphthalen-1-ylmethyl)butanamide 2,2,2-trifluoroacetate (24.4 mg, 0.066 mmol). The product was purified by HPLC (yield=12.2 mg, 35%). $^1$H NMR (500 MHz, DMSO-d$_6$) δ 10.33 (s, 1H), 8.52 (t, J=5.8 Hz, 1H), 8.23 (d, J=8.0 Hz, 1H), 8.09-8.06 (m, 1H), 7.95-7.93 (m, 1H), 7.86-7.83 (m, 1H), 7.74 (d, J=8.8 Hz, 1H), 7.56-7.51 (m, 2H), 7.48-7.45 (m, 2H), 7.27-7.24 (m, 2H), 7.20-7.15 (m, 3H), 4.79-4.65 (m, 3H), 4.20-4.17 (m, 1H), 2.81-2.77 (m, 2H), 2.50-2.47 (m, 1H), 2.42-2.39 (m, 2H), 2.31 (dd, J=14.8, 8.0 Hz, 1H), 2.04-1.99 (m, 1H), 1.12 (s, 9H), 0.81 (d, J=6.8 Hz, 3H), 0.78 (d, J=6.7 Hz, 3H). $^{13}$C NMR (126 MHz, DMSO) δ 171.97, 171.27, 170.98, 168.00, 141.67, 134.92, 133.72, 131.31, 128.92, 128.76, 128.58, 128.01, 126.59, 126.33, 126.24, 126.10, 125.84, 124.02, 80.99, 58.24, 50.18, 37.27, 35.05, 31.48, 30.93, 26.72, 19.67, 18.13.

Example 103—Preparation of benzyl (S)-4-(((S)-3-methoxy-1-((naphthalen-1-ylmethyl)amino)-1-oxopropan-2-yl)amino)-4 -oxo -3-(3 -phenylpropanamido)butanoate (DPLG-2195)

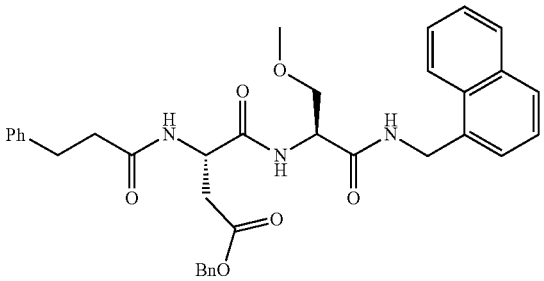

DPLG-2195 was prepared following the general procedure for HATU mediated coupling of 3-phenylpropanoic acid (50 mg, 0.33 mmol) and DPLG-2192 (173 mg, 0.3 mmol). Reaction mixture was precipitated by the addition of 5 water. The precipitate was filtered and dried to give pure product (149 mg, 83%). $^{1}$H NMR (500 MHz, DMSO-$d_6$) δ 8.44 (t, J=5.8 Hz, 1H), 8.30 (d, J=8.0 Hz, 1H), 8.08 (d, J=7.9 Hz, 1H), 8.04-8.02 (m, 1H), 7.94-7.93 (m, 1H), 7.84-7.81 (m, 1H), 7.56-7.50 (m, 2H), 7.46-7.43 (m, 2H), 7.37-7.25 (m, 7H), 7.19-7.15 (m, 3H), 5.03 (s, 2H), 4.76-4.72 (m, 3H), 4.46 (dt, J=7.9, 5.4 Hz, 1H), 3.57 (dd, J=9.7, 5.8 Hz, 1H), 3.48 (dd, J=9.7, 5.1 Hz, 1H), 3.23 (s, 3H), 2.82-2.76 (m, 3H), 2.58 (dd, J=16.2, 8.4 Hz, 1H), 2.41-2.38 (m, 2H).

Example 104—Preparation of (S)-4-(((S)-3-methoxy-1-((naphthalen-1-ylmethyl)amino)-1-oxopropan-2-yl)amino)-4-oxo-3-(3-phenylpropanamido) butanoic acid (DPLG-2201)

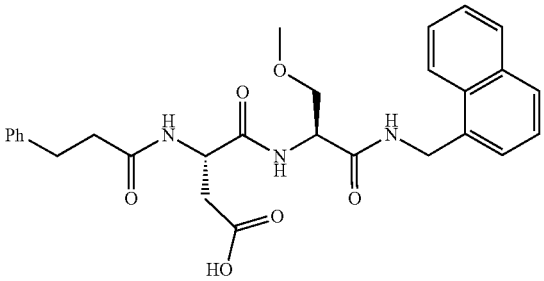

DPLG-2201 was synthesized by following the general procedure for O-debenzylation of benzyl (S)-4-(((S)-3-methoxy-1-((naphthalen-1-ylmethyl)amino)-1-oxopropan-2-yl)amino)-4 -oxo-3-(3-phenylpropanamido)butanoate (145 mg, 0.24 mmol). Yield=120 mg, 99%. $^{1}$H NMR (500 MHz, DMSO-$d_6$) δ 12.48 (s, 1H), 8.52 (t, J=5.8 Hz, 1H), 8.25 (d, J=7.8 Hz, 1H), 8.06-8.03 (m, 2H), 7.95-7.93 (m, 1H), 7.84-7.82 (m, 1H), 7.57-7.51 (m, 2H), 7.47-7.43 (m, 2H), 7.28-7.25 (m, 2H), 7.20-7.15 (m, 3H), 4.74 (d, J=5.8 Hz, 2H), 4.63 (td, J=7.6, 6.1 Hz, 1H), 4.44 (dt, J=7.8, 5.4 Hz, 1H), 3.58 (dd, J=9.7, 5.8 Hz, 1H), 3.49 (dd, J=9.7, 5.0 Hz, 1H), 3.23 (s, 3H), 2.79 (t, J=7.9 Hz, 2H), 2.66 (dd, J=16.5, 6.2 Hz, 1H), 2.46-2.38 (m, 3H).

Example 105—Preparation of (S)—N$^{4}$-(tert-butyl)-N$^{1}$—((S)-3-methoxy-1-((naphthalen-1-ylmethyl) amino)-1-oxopropan-2-yl)-2-(3-phenylpropanamido) succinamide (DPLG-2230)

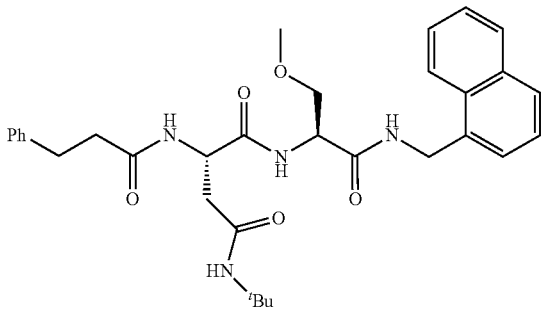

DPLG-2230 was prepared following the general procedure for HATU mediated coupling of (S)-4-(((S)-3-methoxy-1-((naphthalen-1-ylmethyl)amino)-1-oxopropan-2-yl)amino)-4 -oxo-3-(3-phenylpropanamido)butanoic acid (15.2 mg, 0.03 mmol) and tert-butylamine (9.5 μL, 0.09 mmol). The product was purified by HPLC to give pure product (8.7 mg, 52%). $^{1}$H NMR (500 MHz, DMSO-$d_6$) δ 8.66 (t, J=5.9 Hz, 1H), 8.19 (d, J=7.7 Hz, 1H), 8.12 (d, J=8.0 Hz, 1H), 8.07-8.05 (m, 1H), 7.94-7.92 (m, 1H), 7.83-7.81 (m, 1H), 7.55-7.50 (m, 3H), 7.46-7.15 (m, 2H), 7.28-7.25 (m, 2H), 7.20-7.15 (m, 3H), 4.79 (dd, J=15.6, 6.0 Hz, 1H), 4.70 (dd, J=15.6, 5.8 Hz, 1H), 4.63-4.59 (m, 1H), 4.45-4.41 (m, 1H), 3.63 (dd, J=9.8, 6.1 Hz, 1H), 3.54 (dd, J=9.8, 4.4 Hz, 1H), 3.24 (s, 3H), 2.78 (t, J=7.9 Hz, 2H), 2.55-2.51 (m, 1H), 2.43-2.34 (m, 3H), 1.14 (s, 9H). $^{13}$C NMR (126 MHz, DMSO) δ 171.34, 171.21, 169.26, 169.15, 141.26, 134.21, 133.16, 130.71, 128.43, 128.27, 128.12, 127.32, 126.08, 125.84, 125.68, 125.33, 124.87, 123.32, 71.76, 58.24, 53.32, 50.09, 49.74, 40.25, 38.46, 36.75, 31.05, 28.36.

Example 106—Preparation of tert-butyl ((S)-4-(tert-butylamino)-1-(((S)-3 -methoxy-1-((naphthalen-1-ylmethyl)amino)-1-oxopropan-2-yl)amino)-1,4-di-oxobutan-2-yl)carbamate (DPLG-2237)

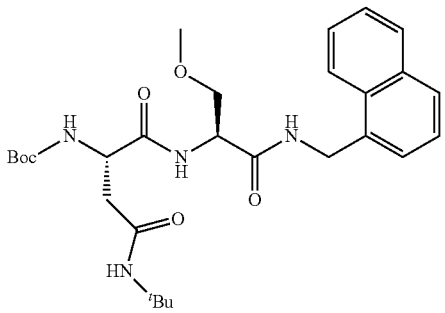

DPLG-2237 was prepared following the general procedure for HATU mediated coupling of (S)-3-((tert-butoxycarbonyl)amino)-4-(((S)-3-methoxy-1-((naphthalen-1-ylmethyl)amino)-1-oxopropan-2-yl)amino)-4-oxobutanoic acid (DPLG-2131, DPLG-2215, DPLG-2236) (118 mg, 0.25 mmol) and tert-butylamine (32 mL, 0.3 mmol). The product was isolated by ethylacetate extraction and purified by HPLC (yield=37.0 mg). $^1$H NMR (500 MHz, DMSO-$d_6$) δ 8.59 (t, J=5.8 Hz, 1H), 8.05-8.03 (m, 1H), 7.98-7.93 (m, 2H), 7.84-7.82 (m, 1H), 7.55-7.51 (m, 2H), 7.46-7.43 (m, 3H), 6.93 (d, J=8.1 Hz, 1H), 4.79-4.70 (m, 2H), 4.47-4.43 (m, 1H), 4.31-4.26 (m, 1H), 3.61 (dd, J=9.7, 5.7 Hz, 1H), 3.51 (dd, J=9.7, 4.8 Hz, 1H), 3.24 (s, 3H), 2.50-2.45 (m, 1H), 2.33 (dd, J=14.9, 7.8 Hz, 1H), 1.36 (s, 9H), 1.18 (s, 9H).

Example 107—Preparation of (S)-2-amino-N$^4$-(tert-butyl)-N$^1$—((S)-3 -methoxy-1-((naphthalen-1-ylmethyl)amino)-1-oxopropan-2-yl)succinamide 2,2,2-trifluoroacetate (DPLG-2242)

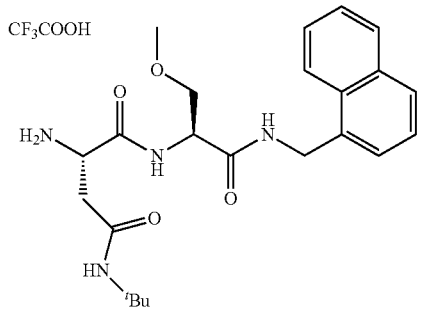

DPLG-2242 was synthesized by following the general procedure for Boc-deprotection of tert-butyl ((S)-4-(tert-butylamino)-1-(((S)-3-methoxy-1-((naphthalen-1-ylmethyl)amino)-1-oxopropan-2-yl)amino)-1,4 -dioxobutan-2-yl)carbamate (34.4 mg, 0.065 mmol). Yield=32 mg, 91%. $^1$H NMR (500 MHz, DMSO-$d_6$) δ 8.76 (d, J=7.7 Hz, 1H), 8.67 (t, J=5.8 Hz, 1H), 8.14 (bs, 3H), 8.04-8.02 (m, 1H), 7.95-7.93 (m, 1H), 7.88 (s, 1H), 7.85-7.83 (m, 1H), 7.56-7.52 (m, 2H), 7.47-7.43 (m, 2H), 4.80-4.72 (m, 2H), 4.53 (ddd, J=7.7, 5.9, 4.6 Hz, 1H), 4.16-4.13 (m, 1H), 3.63 (dd, J=9.8, 5.9 Hz, 1H), 3.53 (dd, J=9.8, 4.6 Hz, 1H), 3.26 (s, 3H), 2.73 (dd, J=16.7, 5.2 Hz, 1H), 2.60-2.55 (m, 1H), 1.21 (s, 9H).

Example 108—Preparation of (S)—N$^4$-(tert-butyl)-N$^1$((S)-3-methoxy-1-((naphthalen-1-ylmethyl)amino)-1-oxopropan-2-yl)-2-(5-methylisoxazole-3-carboxamido)succinamide (DPLG-2244)

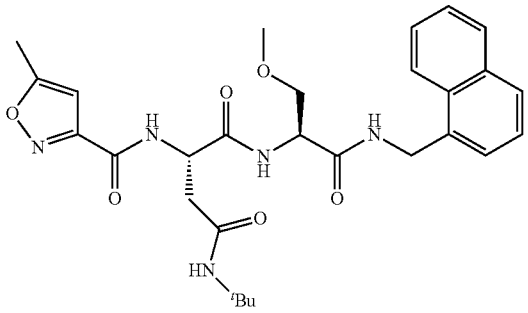

DPLG-2244 was synthesized following the general procedure for HATU mediated coupling of (S)-2-amino-N$^4$-(tert-butyl)-N$^1$—((S)-3-methoxy-1-((naphthalen-1-ylmethyl)amino)-1-oxopropan-2-yl)succinamide 2,2,2-trifluoroacetate (21.7 mg, 0.04 mmol) and 5-methylisoxazole-3-carboxylic acid (5.6 mg, 0.044 mmol). The product was purified by HPLC to give pure product (18.6 mg, 87%). $^1$H NMR (500 MHz, DMSO-$d_6$) δ 8.62 (t, J=5.8 Hz, 1H), 8.56 (d, J=8.0 Hz, 1H), 8.25 (d, J=7.8 Hz, 1H), 8.05-8.03 (m, 1H), 7.95-7.93 (m, 1H), 7.85-7.82 (m, 1H), 7.54-7.51 (m, 3H), 7.45-7.43 (m, 2H), 6.54 (s, 1H), 4.80-4.74 (m, 3H), 4.50-4.46 (m, 1H), 3.60 (dd, J=9.8, 5.9 Hz, 1H), 3.53 (dd, J=9.8, 4.9 Hz, 1H), 3.23 (s, 3H), 2.58 (d, J=6.7 Hz, 2H), 2.47 (s, 3H), 1.16 (s, 9H). $^{13}$C NMR (126 MHz, DMSO) δ 171.38, 170.37, 169.19, 168.90, 158.48, 158.27, 134.17, 133.19, 130.72, 128.44, 127.40, 126.11, 125.72, 125.36, 124.97, 123.35, 101.30, 71.81, 58.25, 53.14, 50.21, 50.14, 40.29, 38.09, 28.33, 11.84.

Example 109—Preparation of DPLG-2231

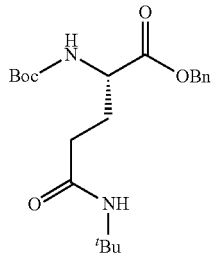

DPLG-2231 was synthesized by following the general procedure of EDC mediated coupling of Boc-Glu-OBn (5.06 g, 15.0 mmol) with tert-butylamine (2.37 mL, 22.5 mmol). After completion of the reaction, water was added to the mixture. The mixture was extracted twice with ethyl acetate. The combined organic layer was washed with aq. $NaHCO_3$, water, 1N HCl, water followed by saturated brine solution. Ethyl acetate layer was dried over anhydrous $Na_2SO_4$ and evaporated to give product (5.78 g, 98%) as white solid. The product was used in next step without further purification. $^1$H NMR (500 MHz, Chloroform-d) δ 7.43-7.29 (m, 5H), 5.58 (s, 1H), 5.27 (d, J=8.3 Hz, 1H), 5.20 (d, J=12.3 Hz, 1H), 5.13 (d, J=12.3 Hz, 1H), 4.36-4.23 (m, 1H), 2.22-2.06 (m, 3H), 2.02-1.87 (m, 1H), 1.42 (s, 9H), 1.32 (s, 9H).

Example 110—Preparation of DPLG-2233

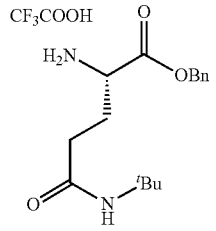

DPLG-2233 was synthesized by following the general procedure for Boc-deprotection of DPLG-21002 (3.68 g, 9.38 mmol). After completion of the reaction (5 h), excess trifluoroacetic acid and dichloromethane were evaporated.

Crude was dried under high vacuum to give product (3.81 g, quant.) as a colorless paste. Product was used in the next step without further purification. $^1$H NMR (500 MHz, Chloroform-d) δ 8.44 (s, 3H), 7.42-7.29 (m, 5H), 6.07 (bs, 1H), 5.27 (d, J=11.9 Hz, 1H), 5.20 (d, J=11.9 Hz, 1H), 4.24-4.16 (m, 1H), 2.53-2.44 (m, 1H), 2.43-2.34 (m, 1H), 2.34-2.24 (m, 1H), 2.24-2.13 (m, 1H), 1.30 (d, J=2.1 Hz, 9H).

Example 111—Preparation of DPLG-2234

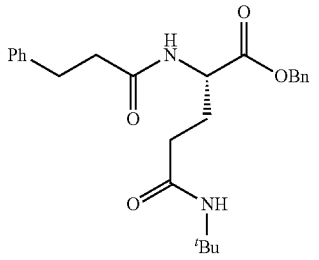

DPLG-2234 was synthesized by following the general procedure for HATU mediated coupling of 3-phenylpropanoic acid (82.6 mg, 0.55 mmol) and DPLG-21008 (203.2 mg, 0.5 mmol). After completion of the reaction, the mixture was diluted with water and extracted twice with ethyl acetate. Combined organic layer was washed with aq. $NaHCO_3$, water, 1N HCl, water followed by saturated brine solution. Ethyl acetate layer was dried over anhydrous $Na_2SO_4$ and evaporated. Crude was purified by column chromatography to give product (193 mg, 91%) as a white solid. $^1$H NMR (500 MHz, DMSO-$d_6$) δ 8.28 (d, J=7.4 Hz, 1H), 7.41-7.30 (m, 5H), 7.30-7.21 (m, 3H), 7.21-7.13 (m, 3H), 5.13 (d, J=12.6 Hz, 1H), 5.10 (d, J=12.6 Hz, 1H), 4.31-4.20 (m, 1H), 2.80-2.76 (m, 2H), 2.45-2.38 (m, 2H), 2.07 (t, J=7.7 Hz, 2H), 1.97-1.84 (m, 1H), 1.79-1.67 (m, 1H), 1.22 (s, 9H).

Example 112—Preparation of DPLG-2239

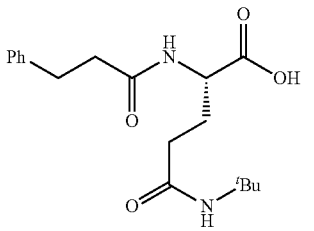

DPLG-2239 was synthesized by following the general procedure for O-debenzylation of DPLG-2234 (180 mg, 0.34 mmol). The product was isolated as a white solid (140 mg, 99%). $^1$H NMR (500 MHz, DMSO-$d_6$) δ 8 12.58 (s, 1H), 8.10 (d, J=7.7 Hz, 1H), 7.37 (s, 1H), 7.27-7.13 (m, 5H), 4.19-4.11 (m, 1H), 2.81 (t, J=7.9 Hz, 2H), 2.49-2.36 (m, 2H), 2.10-1.98 (m, 2H), 1.96-1.85 (m, 1H), 1.76-1.63 (m, 1H), 1.23 (s, 9H).

Example 113—Preparation of DPLG-2243

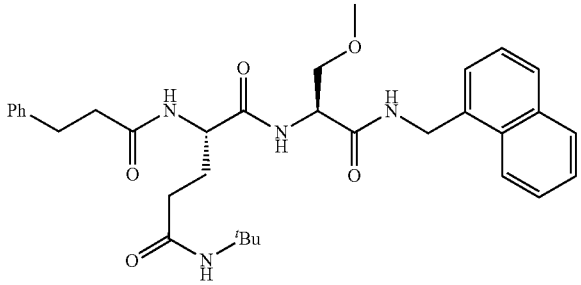

DPLG-2243 was synthesized by following the general procedure for HATU mediated coupling of DPLG-2239 (20.1 mg, 0.06 mmol) and H-Ser(OMe)-$CH_2$-naphth TFA salt (22.3 mg, 0.06 mmol). The crude was purified by HPLC to give product (18.8 mg, 54%) as a white solid. $^1$H NMR (500 MHz, DMSO-$d_6$) δ 8.55 (t, J=5.8 Hz, 1H), 8.10-8.00 (m, 3H), 7.96-7.92 (m, 1H), 7.83 (dd, J=6.1, 3.4 Hz, 1H), 7.56-7.50 (m, 2H), 7.47-7.43 (m, 2H), 7.35 (s, 1H), 7.28-7.23 (m, 2H), 7.21-7.13 (m, 3H), 4.75 (d, J=5.7 Hz, 2H), 4.51 (dt, J=7.7, 5.6 Hz, 1H), 4.27 (td, J=8.3, 5.3 Hz, 1H), 3.55 (dd, J=9.7, 6.0 Hz, 1H), 3.50 (dd, J=9.7, 5.4 Hz, 1H), 3.24 (s, 3H), 2.79 (t, J=7.9 Hz, 2H), 2.48-2.37 (m, 2H), 2.03 (t, J=8.0 Hz, 2H), 1.92-1.78 (m, 1H), 1.77-1.60 (m, 1H), 1.22 (s, 9H). $^{13}$C NMR (126 MHz, DMSO) δ 171.59, 171.54, 171.19, 169.39, 141.27, 134.15, 133.21, 130.74, 128.44, 128.25, 128.14, 127.44, 126.15, 125.83, 125.75, 125.36, 124.94, 123.37, 71.94, 58.24, 52.65, 52.28, 49.83, 40.30, 36.76, 32.64, 31.03, 28.50, 28.26.

Example 114—Preparation of DPLG-2255

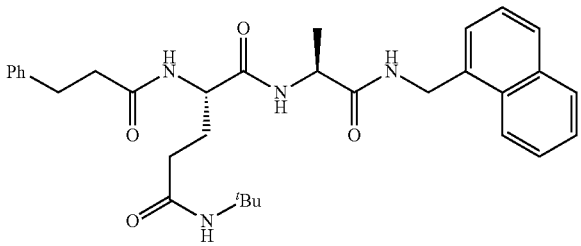

DPLG-2255 was synthesized by following the general procedure for HATU mediated coupling of DPLG-2239 (18.4 mg, 0.055 mmol) and H-Ala-CH2-naphth TFA salt (17.1 mg, 0.05 mmol). The crude was purified by HPLC to give product (20.2 mg, 74%) as a white solid. $^1$H NMR (500 MHz, DMSO-$d_6$) δ 8.45 (t, J=5.7 Hz, 1H), 8.10-8.01 (m, 3H), 7.98-7.90 (m, 1H), 7.84 (dd, J=7.5, 1.9 Hz, 1H), 7.58-7.50 (m, 2H), 7.50-7.41 (m, 2H), 7.35 (s, 1H), 7.29-7.22 (m, 2H), 7.22-7.11 (m, 3H), 4.76 (dd, J=14.2, 4.6 Hz, 1H), 4.73 (dd, J=14.2, 4.5 Hz, 1H), 4.37-4.27 (m, 1H), 4.27-4.18 (m, 1H), 2.79 (t, J=7.9 Hz, 2H), 2.47-2.36 (m, 2H), 2.09-2.00 (m, 2H), 1.90-1.79 (m, 1H), 1.75-1.63 (m, 1H), 1.24 (d, J=7.1 Hz, 3H), 1.22 (s, 9H). $^{13}$C NMR (126 MHz, DMSO) δ 172.13, 171.56, 171.22, 171.16, 141.29, 134.36, 133.24, 130.78, 128.47, 128.24, 128.15, 127.48, 126.17, 125.82, 125.77, 125.38, 125.07, 123.37, 52.28, 49.83, 48.28, 40.18, 36.74, 32.64, 31.01, 28.50, 28.29, 18.24.

Example 115—Preparation of DPLG-2238

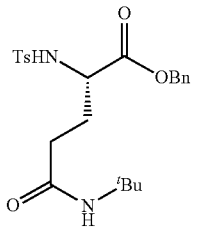

TFA.H-Glu(CONHtBu)-OH (203.0 mg, 0.5 mmol) was dissolved in dichloromethane (6 mL) and triethylamine (140 μL, 1.0 mmol) was added. After stirring the mixture for 10 minutes at room temperature, TsCl (143.0 mg, 0.75 mmol) was added. The reaction mixture was stirred for 2 hours at room temperature. Dichloromethane was evaporated, and the crude was dissolved in ethyl acetate. The solution was washed with water, 1N HCl followed by brine. The product was purified by column chromatography to give product (177.0 mg, 79%) as white solid. $^1$H NMR (500 MHz, Chloroform-d) δ 7.66 (d, J=8.5 Hz, 2H), 7.35-7.29 (m, 3H), 7.20 (d, J=8.0 Hz, 2H), 7.18-7.13 (m, 2H), 5.52 (s, 1H), 5.47 (d, J=9.1 Hz, 1H), 4.91 (d, J=12.2 Hz, 1H), 4.87 (d, J=12.2 Hz, 1H), 3.93-3.84 (m, 1H), 2.38 (s, 3H), 2.33-2.11 (m, 3H), 1.88-1.77 (m, 1H), 1.35 (s, 9H).

Example 116—Preparation of DPLG-2254

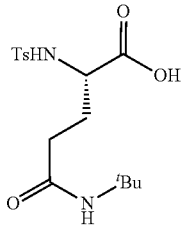

DPLG-2254 was prepared by following the general procedure for O-debenzylation of DPLG-2238 (170 mg, 0.38 mmol). The product (135 mf, quant.) was isolated as a white solid. $^1$H NMR (500 MHz, Chloroform-d) δ 7.69 (d, J=7.9 Hz, 2H), 7.26 (d, J=7.9 Hz, 2H), 6.15-5.91 (m, 2H), 3.82-3.69 (m, 1H), 2.39 (s, 3H), 2.35-2.27 (m, 1H), 2.21-2.12 (m, 1H), 2.11-2.02 (m, 1H), 1.99-1.88 (m, 1H), 1.31 (s, 9H).

Example 117—Preparation of DPLG-2256

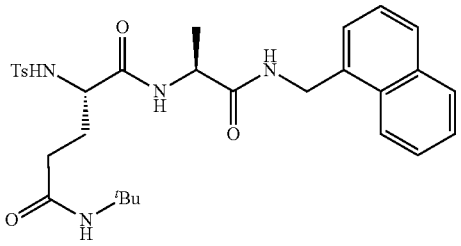

DPLG-2256 was synthesized by following the general procedure for HATU mediated coupling of DPLG-2254 (29.0 mg, 0.08 mmol) and H-Ala-CH2-naphth TFA salt (27.4 mg, 0.08 mmol). The crude was purified by HPLC to give product (32.8 mg, 74%) as a white solid. $^1$H NMR (500 MHz, DMSO-$d_6$) δ 8.43 (t, J=5.7 Hz, 1H), 8.09 (d, J=7.3 Hz, 1H), 8.04-7.98 (m, 1H), 7.97-7.90 (m, 1H), 7.86 (bs, 1H), 7.84 (d, J=8.1 Hz, 1H), 7.63 (d, J=8.3 Hz, 2H), 7.58-7.49 (m, 2H), 7.49-7.42 (m, 1H), 7.42-7.39 (m, 1H), 7.38 (s, 1H), 7.30 (d, J=7.9 Hz, 2H), 4.75 (dd, J=15.4, 5.8 Hz, 1H), 4.69 (dd, J=15.4, 5.6 Hz, 1H), 4.11-4.01 (m, 1H), 3.74-3.67 (m, 1H), 2.34 (s, 3H), 2.11-1.93 (m, 2H), 1.77-1.66 (m, 1H), 1.66-1.56 (m, 1H), 1.21 (s, 9H), 1.07 (d, J=7.0 Hz, 3H). $^{13}$C NMR (126 MHz, DMSO) δ 171.85, 171.05, 169.95, 142.40, 137.98, 134.29, 133.24, 130.77, 129.23, 128.46, 127.51, 126.66, 126.17, 125.78, 125.37, 125.11, 123.37, 55.78, 49.84, 48.11, 40.14, 32.34, 29.23, 28.46, 20.94, 18.15.

Example 118—Preparation of DPLG-3010

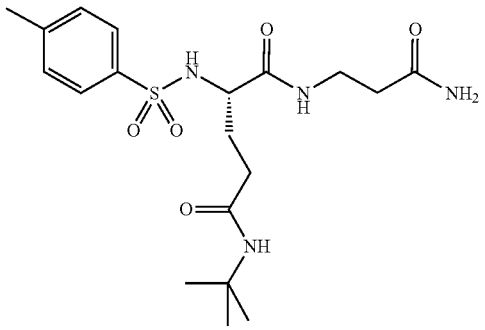

DPLG-3010 was synthesized by following the general procedure for HATU mediated coupling of DPLG-2254 (42.8 mg, 0.12 mmol) with 3-aminopropanamide hydrochloride (22.4 mg, 0.18 mmol). After completion of the reaction, the mixture was diluted with water and extracted twice with dichloromethane. The combined organic layer was evaporated and purified by HPLC to give product (21.9 mg, 43%) as a white solid. $^1$H NMR (500 MHz, DMSO-$d_6$) δ 7.88-7.74 (m, 2H), 7.61 (d, J=8.0 Hz, 2H), 7.40-7.25 (m, 4H), 6.82 (s, 1H), 3.58-3.42 (m, 1H), 3.12-2.89 (m, 2H), 2.36 (s, 3H), 2.07 (t, J=7.1 Hz, 2H), 2.02-1.85 (m, 2H), 1.69-1.50 (m, 2H), 1.19 (s, 9H). $^{13}$C NMR (126 MHz, DMSO) δ 172.77, 171.16, 170.43, 142.78, 138.02, 129.51, 126.75, 56.32, 50.08, 35.21, 34.74, 32.31, 29.10, 28.62, 21.12.

Example 119—Preparation of DPLG-3023

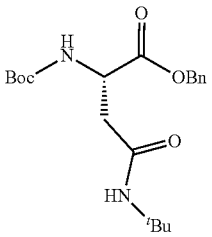

DPLG-3023 was synthesized by following the general procedure for EDC mediated coupling of Boc-Asp(OH)-

OBn (5.01 g, 15.49 mmol) with tert-butyl amine (2.44 mL, 23.24 mmol). After completion of the reaction, the mixture was diluted with water and extracted twice with ethyl acetate. The combined organic layer was washed with aq. $NaHCO_3$, water, 1N HCl, water followed by saturated brine solution. Ethyl acetate layer was dried over anhydrous $Na_2SO_4$ and evaporated to give product (5.80 g, 99%) as a white solid. The product was used in next step without further purification. $^1$H NMR (500 MHz, Chloroform-d) δ 7.33 (s, 2H), 7.36-7.26 (m, 2H), 5.84 (d, J=8.7 Hz, 1H), 5.40 (bs, 1H), 5.21 (d, J=12.4 Hz, 1H), 5.14 (d, J=12.4 Hz, 1H), 4.54-4.47 (m, 1H), 2.79 (dd, J=15.8, 5.0 Hz, 1H), 2.62 (dd, J=15.8, 4.2 Hz, 1H), 1.42 (s, 9H), 1.29 (s, 9H).

Example 120—Preparation of DPLG-3047

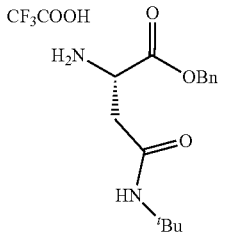

DPLG-3047 was synthesized by following the general procedure for Boc-deprotection of DPLG-21009 (3.84 g, 10.15 mmol). After completion of the reaction (3 h), excess trifluoroacetic acid and dichloromethane were evaporated. Crude was dried under high vacuum to give a colorless paste. The compound was used in next step without further purification. $^1$H NMR (500 MHz, DMSO-$d_6$) δ 8.36 (bs, 3H), 7.85 (s, 1H), 7.46-7.29 (m, 5H), 5.24 (d, J=12.6 Hz, 1H), 5.18 (d, J=12.6 Hz, 1H), 4.39-4.29 (m, 1H), 2.83-2.66 (m, 2H), 1.22 (s, 9H).

Example 121—Preparation of DPLG-21012

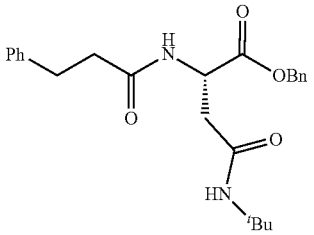

DPLG-21012 was synthesized by following the general procedure for the HATU mediated coupling of 3-phenylpropanoic acid (1.68 g, 11.17 mmol) with DPLG-21011 (3.98 g, 10.15 mmol). After completion of the reaction, water was added. A white precipitate was formed. The precipitate was filtered and washed with water. The precipitate was dried in air to give product (3.92 g, 94%) as a white solid. $^1$H NMR (500 MHz, Chloroform-d) δ 7.39-7.29 (m, 5H), 7.29-7.23 (m, 2H), 7.21-7.14 (m, 3H), 6.88 (d, J=8.0 Hz, 1H), 5.32 (s, 1H), 5.20 (d, J=12.3 Hz, 1H), 5.14 (d, J=12.3 Hz, 1H), 4.84-4.77 (m, 1H), 2.95 (t, J=7.9 Hz, 2H), 2.81 (dd, J=15.7, 4.4 Hz, 1H), 2.61-2.47 (m, 3H), 1.28 (s, 9H).

Example 122—Preparation of DPLG-21013

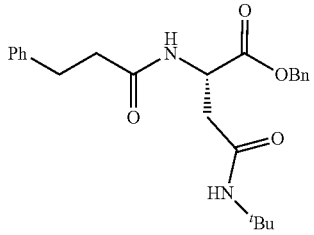

DPLG-21013 was synthesized by following the procedure for O-debenzylation of DPLG-21012 (1.44 g, 3.50 mmol). The product (1.11 g, 99%) was isolated as a white solid. $^1$H NMR (500 MHz, DMSO-$d_6$) δ 12.54 (s, 1H), 8.04 (d, J=8.0 Hz, 1H), 7.45 (s, 1H), 7.29-7.23 (m, 2H), 7.23-7.13 (m, 3H), 4.52-4.44 (m, 1H), 2.83-2.76 (m, 2H), 2.49-2.44 (m, 1H), 2.44-2.34 (m, 3H), 1.22 (s, 9H).

Example 123—Preparation of DPLG-2294

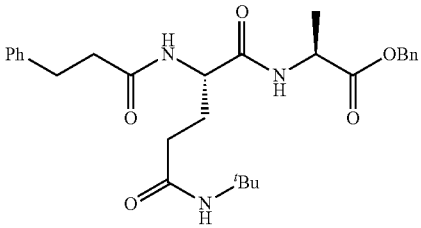

DPLG-2294 was synthesized by following the general procedure for HATU mediated coupling of 3-phenylpropanoyl-Glu(CONHtBu)-OH (46.8 mg, 0.14 mmol) and H-Ala-OBn HCl salt (33.0 mg, 0.154 mmol). After completion of the reaction, water was added to the reaction mixture and extracted twice ethyl acetate. The combined organic layer was washed 1N HCl followed by brine and dried over anhydrous sodium sulfate. Ethyl acetate was evaporated, and the crude was recrystallized from ethanol-water to give product (37.3 mg, 54%) as white solid. $^1$H NMR (500 MHz, Chloroform-d) δ 7.58 (d, J=7.2 Hz, 1H), 7.40-7.29 (m, 5H), 7.29-7.23 (m, 3H), 7.22-7.15 (m, 2H), 6.89 (d, J=6.7 Hz, 1H), 5.58 (s, 1H), 5.19 (d, J=12.3 Hz, 1H), 5.13 (d, J=12.3 Hz, 1H), 4.59-4.49 (m, 1H), 4.43-4.35 (m, 1H), 2.95 (t, J=8.2 Hz, 2H), 2.57-2.46 (m, 2H), 2.26-2.19 (m, 2H), 1.96-1.88 (m, 2H), 1.42 (d, J=7.3 Hz, 3H), 1.36 (s, 9H).

Example 124—Preparation of DPLG-2297

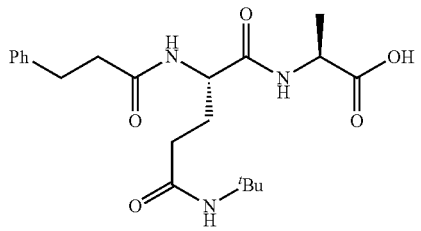

DPLG-2297 was synthesized by following the general procedure for O-debenzylation of DPLG-2294 (37.3 mg, 0.075 mmol). The product (30.0 mg, quant.) was isolated as white solid. $^1$H NMR (500 MHz, DMSO-$d_6$) δ 12.51 (bs, 1H), 8.10 (bs, 1H), 7.97 (d, J=8.2 Hz, 1H), 7.32 (s, 1H), 7.32-7.24 (m, 2H), 7.23-7.13 (m, 3H), 4.29-4.20 (m, 1H), 4.20-4.10 (m, 1H), 2.80 (t, J=7.9 Hz, 2H), 2.45-2.41 (m, 2H), 2.02 (t, J=8.2 Hz, 2H), 1.89-1.78 (m, 1H), 1.70-1.57 (m, 1H), 1.30-1.16 (m, 12H).

Example 125—Preparation of DPLG-3012

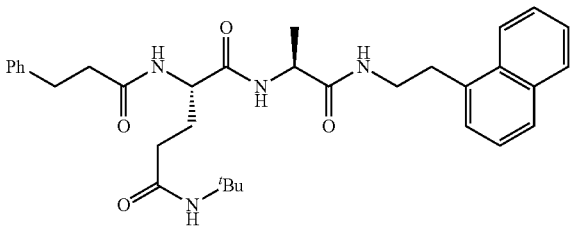

DPLG-3012 was synthesized by following the general procedure for HATU mediated coupling of DPLG-2297 (14.2 mg, 0.035 mmol) with 2-(1-naphthyl)ethylamine hydrochloride (8.0 mg, 0.0385 mmol). The crude was purified by HPLC to give product (15.6 mg, 80%) as a white solid. $^1$H NMR (500 MHz, DMSO-$d_6$) δ 8.18 (d, J=8.2 Hz, 1H), 8.09-8.01 (m, 2H), 7.96 (d, J=7.5 Hz, 1H), 7.92 (dd, J=8.1, 1.6 Hz, 1H), 7.79 (d, J=8.2 Hz, 1H), 7.58-7.49 (m, 2H), 7.42 (dd, J=8.3, 6.9 Hz, 1H), 7.40-7.33 (m, 2H), 7.30-7.23 (m, 2H), 7.23-7.19 (m, 2H), 7.19-7.13 (m, 1H), 4.26-4.16 (m, 2H), 3.48-3.33 (m, 2H), 3.22-3.14 (m, 2H), 2.82 (t, J=8.0 Hz, 2H), 2.49-2.40 (m, 2H), 2.10-1.99 (m, 2H), 1.89-1.79 (m, 1H), 1.75-1.63 (m, 1H), 1.23 (s, 9H), 1.18 (d, J=7.1 Hz, 3H).

Example 126—Preparation of DPLG-3013

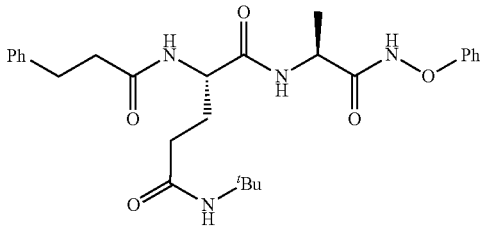

DPLG-3013 was synthesized by following the general procedure for HATU mediated coupling of DPLG-2297 (14.2 mg, 0.035 mmol) with O-phenylhydroxylamine hydrochloride (5.6 mg, 0.0385 mmol). The crude was purified by HPLC to give product (7.6 mg, 44%) as a white solid. Complex NMR due to presence of 71:29 rotamers. $^1$H NMR (500 MHz, DMSO-$d_6$) δ 11.97 (s, 0.71H), 11.86 (s, 0.29H), 8.37 (d, J=7.3 Hz, 0.29H), 8.28 (d, J=6.8 Hz, 0.71H), 8.10 (d, J=7.4 Hz, 0.29H), 8.03 (d, J=7.9 Hz, 0.71H), 7.40-7.11 (m, 8H), 7.07-6.94 (m, 3H), 4.34-4.19 (m, 2H), 2.80 (t, J=8.0 Hz, 1.42H), 2.76-2.70 (m, 0.58H), 2.48-2.35 (m, 2H), 2.02 (t, J=8.1 Hz, 2H), 1.88-1.75 (m, 1H), 1.75-1.60 (m, 1H), 1.37-1.28 (m, 3H), 1.26-1.16 (m, 9H).

Example 127—Preparation of DPLG-2293

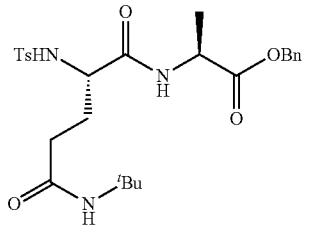

DPLG-2293 was synthesized by following the general procedure for HATU mediated coupling of Ts-Glu (CONHtBu)-OH (64.0 mg, 0.18 mmol) and H-Ala-OBn HCl salt (43.0 mg, 0.20 mmol). After completion of the reaction, water was added to the reaction mixture to give a white precipitate. The precipitate was filtered, washed with water, and dried to give product (76.0 mg, 82%). $^1$H NMR (500 MHz, Chloroform-d) δ 7.70 (d, J=8.4 Hz, 2H), 7.45 (d, J=7.4 Hz, 1H), 7.40-7.29 (m, 5H), 7.29-7.20 (m, 2H), 6.70 (d, J=7.1 Hz, 1H), 5.47 (s, 1H), 5.17 (d, J=12.3 Hz, 1H), 5.11 (d, J=12.3 Hz, 1H), 4.42-4.34 (m, 1H), 3.75-3.66 (m, 1H), 2.39 (s, 3H), 2.29-2.19 (m, 1H), 2.18-2.07 (m, 1H), 1.92-1.80 (m, 2H), 1.36 (s, 9H), 1.26 (d, J=7.2 Hz, 3H).

Example 128—Preparation of DPLG-2296

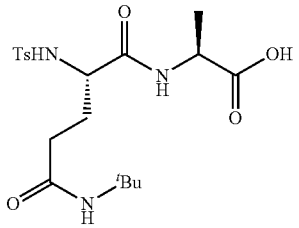

DPLG-2296 was synthesized by following the general procedure for O-debenzylation of DPLG-2293 (76.0 mg, 0.147 mmol). The product (63.0 mg, quant.) was isolated as white solid. $^1$H NMR (500 MHz, DMSO-$d_6$) δ 7.96 (d, J=6.9 Hz, 1H), 7.82 (d, J=8.7 Hz, 1H), 7.63 (d, J=8.2 Hz, 2H), 7.37 (s, 1H), 7.31 (d, J=8.0 Hz, 2H), 3.85-3.76 (m, 1H), 3.71-3.63 (m, 1H), 2.36 (s, 3H), 2.11-2.02 (m, 1H), 2.02-1.93 (m, 1H), 1.75-1.63 (m, 1H), 1.63-1.52 (m, 1H), 1.21 (s, 9H), 1.06 (d, J=7.1 Hz, 3H).

Example 129—Preparation of DPLG-3014

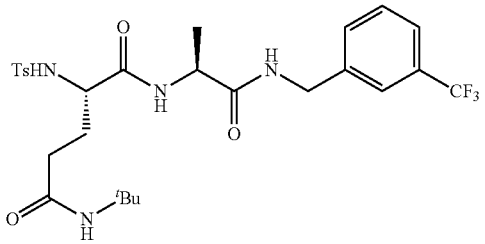

DPLG-3014 was synthesized by following the general procedure for HATU mediated coupling of DPLG-2296 (15.0 mg, 0.035 mmol) with 3-(trifluoromethyl)benzylamine (5.5 μL, 0.0385 mmol). The crude was purified by HPLC to give product (13.5 mg, 66%) as a white solid. $^1$H NMR (500 MHz, DMSO-$d_6$) δ 8.47 (t, J=6.1 Hz, 1H), 8.08 (d, J=7.2 Hz, 1H), 7.84 (d, J=8.6 Hz, 1H), 7.63 (d, J=8.3 Hz, 2H), 7.60-7.48 (m, 4H), 7.36-7.29 (m, 3H), 4.37 (dd, J=15.7, 6.0 Hz, 1H), 4.32 (dd, J=15.7, 6.0 Hz, 1H), 4.07-3.97 (m, 1H), 3.73-3.64 (m, 1H), 2.35 (s, 3H), 2.07-1.92 (m, 2H), 1.75-1.65 (m, 1H), 1.65-1.55 (m, 1H), 1.19 (s, 9H), 1.07 (d, J=7.1 Hz, 3H).

Example 130—Preparation of DPLG-3015

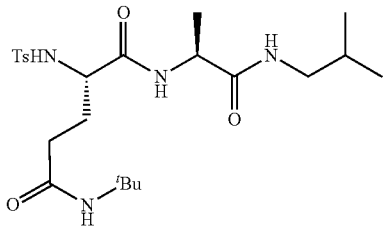

DPLG-3015 was synthesized by following the general procedure for HATU mediated coupling of DPLG-2296 (15.0 mg, 0.035 mmol) with iso-butylamine (4 μl, 0.0385 mmol). The crude was purified by HPLC to give product (11.2 mg, 66%) as a white solid. $^1$H NMR (500 MHz, DMSO-$d_6$) δ 7.96 (d, J=7.4 Hz, 1H), 7.84 (d, J=8.5 Hz, 1H), 7.78 (t, J=6.0 Hz, 1H), 7.66-7.60 (m, 2H), 7.37 (s, 1H), 7.32 (d, J=7.9 Hz, 2H), 4.04-3.94 (m, 1H), 3.72-3.63 (m, 1H), 2.96-2.86 (m, 1H), 2.84-2.75 (m, 1H), 2.36 (s, 3H), 2.06-1.92 (m, 2H), 1.72-1.53 (m, 3H), 1.21 (s, 9H), 1.03 (d, J=7.0 Hz, 3H), 0.80 (d, J=6.7 Hz, 6H). $^{13}$C NMR (126 MHz, DMSO) δ 171.74, 171.03, 169.86, 142.44, 137.93, 129.26, 126.65, 55.80, 49.84, 48.01, 45.90, 32.26, 29.16, 28.46, 28.01, 20.96, 19.98, 18.31.

Example 131—Preparation of DPLG-3016

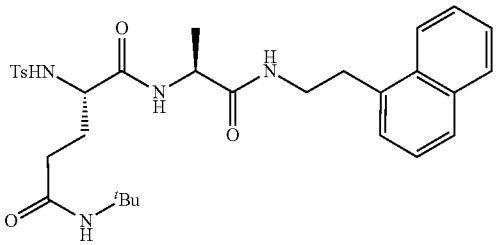

DPLG-3016 was synthesized by following the general procedure for HATU mediated coupling of DPLG-2296 (15.0 mg, 0.035 mmol) with 2-(1-naphthyl)ethylamine hydrochloride (8.0 mg, 0.0385 mmol). The crude was purified by HPLC to give product (16.0 mg, 78%) as white solid. $^1$H NMR (500 MHz, DMSO-$d_6$) δ 8.17 (d, J=8.2 Hz, 1H), 8.04 (t, J=5.7 Hz, 1H), 7.99 (d, J=7.4 Hz, 1H), 7.91 (dd, J=8.0, 1.6 Hz, 1H), 7.85 (d, J=8.6 Hz, 1H), 7.78 (d, J=8.2 Hz, 1H), 7.64 (d, J=8.3 Hz, 2H), 7.59-7.46 (m, 2H), 7.45-7.38 (m, 2H), 7.36-7.30 (m, 3H), 4.02-3.92 (m, 1H), 3.74-3.66 (m, 1H), 3.47-3.36 (m, 1H), 3.35-3.31 (m, 1H), 3.16 (t, J=7.6 Hz, 2H), 2.36 (s, 3H), 2.09-1.95 (m, 2H), 1.77-1.66 (m, 1H), 1.66-1.56 (m, 1H), 1.21 (s, 9H), 0.99 (d, J=7.0 Hz, 3H). $^{13}$C NMR (126 MHz, DMSO) δ 171.82, 171.06, 169.85, 142.43, 137.95, 135.23, 133.43, 131.52, 129.26, 128.56, 126.80, 126.66, 126.03, 125.59, 125.55, 123.66 55.81, 49.86, 47.99, 39.69, 32.34, 32.29, 29.17, 28.48, 20.95, 18.22.

Example 132—Preparation of DPLG-3017

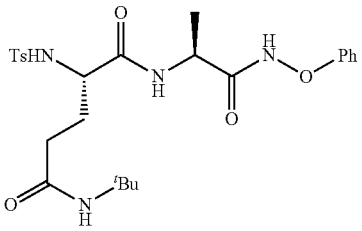

DPLG-3017 was synthesized by following the general procedure for HATU mediated coupling of DPLG-2296 (15.0 mg, 0.035 mmol) with O-phenylhydroxylamine hydrochloride (5.6 mg, 0.0385 mmol). The crude was purified by HPLC to give product (12.0 mg, 66%) as white solid. Complex NMR due to 86:14 rotamers. $^1$H NMR (500 MHz, DMSO-$d_6$) δ 11.95 (s, 0.86H), 11.92 (s, 0.14), 8.25 (d, J=6.9 Hz, 0.86H), 8.12 (d, J=7.4 Hz, 0.14H), 7.86 (d, J=8.9 Hz, 1H), 7.68-7.59 (m, 2H), 7.40-7.24 (m, 5H), 7.06-6.90 (m, 3H), 4.16-4.06 (m, 0.14H), 4.02-3.89 (m, 0.86H), 3.78-3.68 (m, 1H), 2.37 (s, 2.58H), 2.32 (s, 0.42H), 2.13-2.01 (m, 1H), 2.01-1.90 (m, 1H), 1.79-1.65 (m, 1H), 1.65-1.52 (m, 1H), 1.28-1.16 (m, 9H), 1.13 (d, J=7.1 Hz, 3H). $^{13}$C NMR (126 MHz, DMSO) δ 170.97, 170.27, 169.42, 159.32, 142.39, 138.12, 129.40, 129.20, 126.66, 122.28, 112.66, 55.50, 49.83, 46.04, 32.30, 29.16, 28.45, 20.96, 17.37.

Example 133—Preparation of DPLG-3066

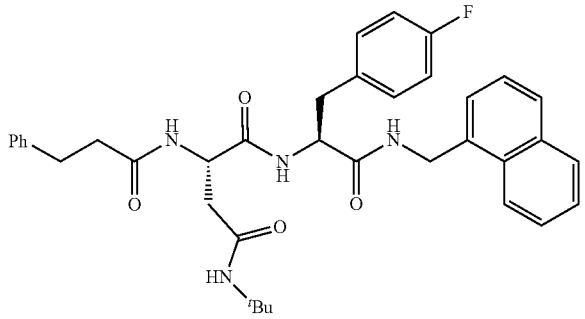

DPLG-3066 was prepared by following the general procedure for HATU mediated coupling of 3-phenylpropanoyl-Asp(CONHtBu)-OH (16.0 mg, 0.05 mmol) and H-4F-Phe-$CH_2$-naphth TFA salt (21.8 mg, 0.05 mmol). The mixture was purified by HPLC to give product (26.0 mg, 83%) as a white solid. $^1$H NMR (500 MHz, DMSO-$d_6$) δ 8.62 (t, J=5.9 Hz, 1H), 8.20 (d, J=8.3 Hz, 1H), 8.10-8.04 (m, 1H), 8.01 (d, J=8.2 Hz, 1H), 7.96-7.91 (m, 1H), 7.83 (d, J=8.2 Hz, 1H), 7.57-7.50 (m, 2H), 7.48 (s, 1H), 7.43 (t, J=7.6 Hz, 1H), 7.37 (d, J=7.0 Hz, 1H), 7.29-7.23 (m, 2H), 7.23-7.12 (m, 5H), 7.02-6.95 (m, 2H), 4.80 (dd, J=15.4, 6.0 Hz, 1H), 4.69 (dd, J=15.4, 5.6 Hz, 1H), 4.57-4.50 (m, 1H), 4.50-4.41 (m, 1H), 3.10 (dd, J=13.8, 4.5 Hz, 1H), 2.82 (dd, J=13.8, 9.6 Hz, 1H), 2.79-2.68 (m, 2H), 2.52-2.48 (m, 1H), 2.41-2.32 (m, 2H), 2.29 (dd, J=15.0, 6.6 Hz, 1H), 1.15 (s, 9H). $^{13}$C NMR (126 MHz, DMSO) δ 171.14, 170.98, 170.50, 169.13, 160.88 (d, J=241.8 Hz), 141.26, 134.21, 134.03, 133.20, 130.92 (d, J=8.0 Hz), 130.77, 128.46, 128.28, 128.08, 127.41, 126.15, 125.84, 125.71, 125.31, 125.17, 123.35, 114.66 (d, J=21.6 Hz), 54.30, 50.09, 49.67, 40.22, 38.23, 36.76, 36.18, 31.07, 28.37.

Example 134—Preparation of DPLG-3083

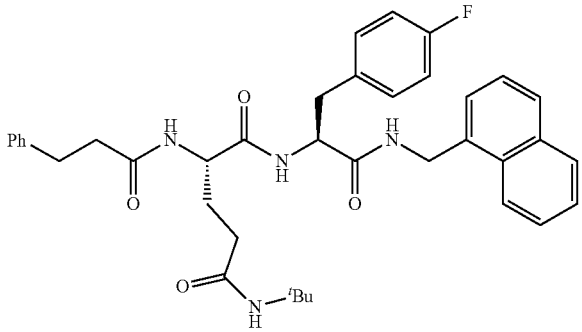

DPLG-3083 was prepared by following the general procedure for HATU mediated coupling of 3-phenylpropanoyl-Glu(CONHtBu)-OH (23.4 mg, 0.07 mmol) and H-4F-Phe-$CH_2$-naphth TFA salt (36.7 mg, 0.084 mmol). The mixture was purified by HPLC to give product (32.6 mg, 73%) as a white solid. $^1$H NMR (500 MHz, DMSO-$d_6$) δ 8.54 (t, J=5.7 Hz, 1H), 8.08 (d, J=8.2 Hz, 1H), 8.05-8.00 (m, 1H), 7.98 (d, J=7.6 Hz, 1H), 7.96-7.91 (m, 1H), 7.84 (d, J=8.2 Hz, 1H), 7.58-7.50 (m, 2H), 7.46-7.39 (m, 1H), 7.34-7.29 (m, 2H), 7.28-7.12 (m, 7H), 7.05-6.96 (m, 2H), 4.73 (d, J=5.7 Hz, 2H), 4.61-4.49 (m, 1H), 4.25-4.14 (m, 1H), 3.00 (dd, J=13.7, 5.5 Hz, 1H), 2.85 (dd, J=13.7, 9.0 Hz, 1H), 2.81-2.69 (m, 2H), 2.48-2.33 (m, 2H), 1.98 (t, J=8.0 Hz, 2H), 1.86-1.73 (m, 1H), 1.71-1.58 (m, 1H), 1.23 (s, 9H). $^{13}$C NMR (126 MHz, DMSO-$d_6$) δ 171.56, 171.35, 171.18, 170.64, 160.94 (d, J=241.4 Hz), 141.27, 134.14, 133.72, 133.23, 130.98 (d, J=7.6 Hz), 130.79, 128.46, 128.25, 128.13, 127.51, 126.19, 125.82, 125.76, 125.33, 125.20, 123.40, 114.70 (d, J=21.2 Hz), 53.99, 52.39, 49.84, 40.23, 36.76, 32.64, 31.01, 28.51, 28.28.

Example 135—Preparation of DPLG-3084

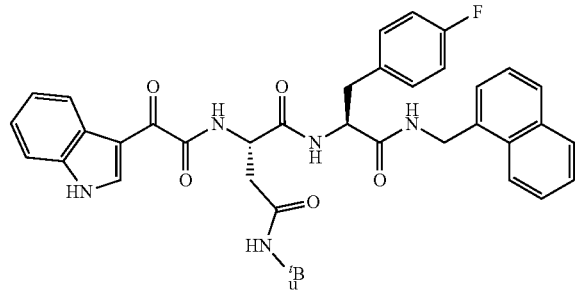

DPLG-3084 was prepared by following the general procedure for HATU mediated coupling of Ind-oxal-Asp (CONHtBu)-OH (18 mg, 0.05 mmol) and H-4F-Phe-$CH_2$-naphth TFA salt (24 mg, 0.055 mmol). The mixture was purified by HPLC to give product (18.0 mg, 55%) as a white solid. $^1$H NMR (500 MHz, DMSO-$d_6$) δ 12.27 (s, 1H), 8.76 (s, 1H), 8.66 (d, J=8.4 Hz, 1H), 8.61 (t, J=5.8 Hz, 1H), 8.28-8.21 (m, 2H), 8.07-8.00 (m, 1H), 7.97-7.91 (m, 1H), 7.83 (d, J=8.2 Hz, 1H), 7.59-7.49 (m, 4H), 7.46-7.38 (m, 1H), 7.33 (d, J=7.1 Hz, 1H), 7.31-7.25 (m, 2H), 7.24-7.17 (m, 2H), 7.01-6.91 (m, 2H), 4.74 (d, J=5.6 Hz, 2H), 4.70-4.62 (m, 1H), 4.58-4.48 (m, 1H), 3.04 (dd, J=13.7, 5.1 Hz, 1H), 2.85 (dd, J=13.7, 9.1 Hz, 1H), 2.58-2.52 (m, 2H), 1.17 (s, 9H). $^{13}$C NMR (126 MHz, DMSO) δ 181.01, 170.44, 170.17, 168.91, 162.72, 160.91 (d, J=241.6 Hz), 138.59, 136.25, 134.15, 133.76, 133.22, 130.99 (d, J=8.5 Hz), 130.80, 128.47, 127.52, 126.20, 125.77, 125.33, 123.52, 123.40, 122.65, 121.29, 114.70 (d, J=20.3 Hz), 112.60, 112.11, 54.33, 50.15, 50.09, 40.27, 38.00, 36.59, 28.37.

Example 136—Preparation of DPLG-3040

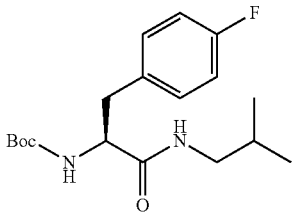

DPLG-3040 was synthesized by following the general procedure for HATU mediated coupling of Boc-4F-Phe-OH (283 mg, 1.0 mmol) with iso-butylamine (100 μL, 1.0 mmol). After completion of the reaction, water was added to precipitate the product. The precipitate was filtered, washed with water, and dried to give product (230 mg, 68%). $^1$H NMR (500 MHz, Chloroform-d) δ 7.21-7.11 (m, 2H), 7.01-6.92 (m, 2H), 5.90 (s, 1H), 5.06 (s, 1H), 4.29-4.19 (m, 1H), 3.08-2.92 (m, 4H), 1.69-1.58 (m, 1H), 1.41 (s, 9H), 0.86-0.74 (m, 6H). $^1$H NMR (500 MHz, DMSO-$d_6$) δ 7.83 (d, J=5.9 Hz, 1H), 7.30-7.23 (m, 2H), 7.12-7.04 (m, 2H), 6.89 (d, J=8.7 Hz, 1H), 4.10 (td, J=9.4, 5.0 Hz, 1H), 2.95-2.78 (m, 3H), 2.72 (dd, J=13.7, 9.9 Hz, 1H), 1.70-1.59 (m, 1H), 1.30 (s, 8H), 1.24 (s, 1H), 0.82-0.76 (m, 6H).

Example 137—Preparation of DPLG-3043

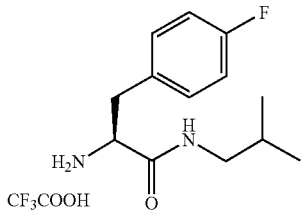

DPLG-3043 was synthesized by following the general procedure for Boc-deprotection of Boc-4F-Phe-Ibu (220 mg, 0.65 mmol). The crude product (230 mg, quant.) was used in next step without further purification. $^1$H NMR (500 MHz, Chloroform-d) δ 7.61 (s, 3H), 7.23-7.11 (m, 2H), 7.07-6.95 (m, 2H), 6.73 (t, J=5.9 Hz, 1H), 4.42-4.30 (m, 1H), 3.18 (dd, J=13.9, 6.4 Hz, 1H), 3.08 (dd, J=13.9, 8.7 Hz, 1H), 3.03-2.93 (m, 1H), 2.91-2.79 (m, 1H), 1.64-1.49 (m, 1H), 0.76 (d, J=6.7 Hz, 3H), 0.73 (d, J=6.7 Hz, 3H).

Example 138—Preparation of DPLG-3046

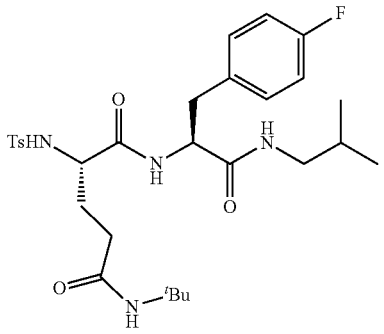

DPLG-3046 was synthesized by following the general procedure for HATU mediated coupling of Ts-Glu (COHtBu)-OH (35.6 mg, 0.1 mmol) with H-4F-Phe-Ibu TFA salt (38.8 mg, 0.11 mmol). The mixture was purified by HPLC to give product (27.4 mg) as white solid. $^{1}$H NMR (500 MHz, DMSO-$d_6$) δ 8.08 (d, J=8.2 Hz, 1H), 7.92-7.82 (m, 2H), 7.56 (d, J=7.9 Hz, 2H), 7.32 (s, 1H), 7.24 (d, J=7.9 Hz, 2H), 7.21-7.13 (m, 2H), 7.10-7.01 (m, 2H), 4.33-4.21 (m, 1H), 3.60 (td, J=8.1, 5.5 Hz, 1H), 2.89 (dt, J=12.9, 6.4 Hz, 1H), 2.85-2.71 (m, 2H), 2.63 (dd, J=13.6, 8.4 Hz, 1H), 2.32 (s, 3H), 2.00-1.80 (m, 2H), 1.67-1.46 (m, 3H), 1.21 (s, 9H), 0.81-0.68 (m, 6H).

Example 139—Preparation of DPLG-3049

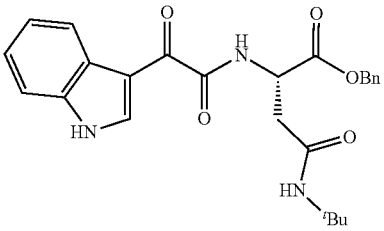

DPLG-3049 was synthesized by following the general protocol for HATU mediated coupling of Indole-3-glyoxylic acid (189 mg, 1.0 mmol) and H-Asp(CONHtBu)-OBn TFA salt (432 mg, 1.1 mmol). After completion of the reaction, water was added to the reaction mixture. A white precipitated appeared which was filtered, washed with water, and dried to give product (270 mg, 60%). $^{1}$H NMR (500 MHz, Chloroform-d) δ 10.14 (s, 1H), 9.13 (d, J=3.3 Hz, 1H), 8.42-8.34 (m, 2H), 7.47 (dd, J=6.6, 2.3 Hz, 1H), 7.34-7.23 (m, 7H), 5.54 (s, 1H), 5.23 (d, J=12.4 Hz, 1H), 5.19-5.12 (m, 1H), 5.11-5.03 (m, 1H), 2.80 (dd, J=15.2, 5.8 Hz, 1H), 2.74 (dd, J=15.2, 5.3 Hz, 1H), 1.29 (s, 9H). $^{13}$C NMR (126 MHz, $CDCl_3$) δ 179.61, 170.76, 168.78, 162.60, 139.33, 136.24, 135.30, 128.72, 128.56, 128.41, 126.86, 124.09, 123.31, 122.44, 113.14, 112.12, 67.73, 51.99, 49.58, 39.23, 28.78.

Example 140—Preparation of DPLG-3052

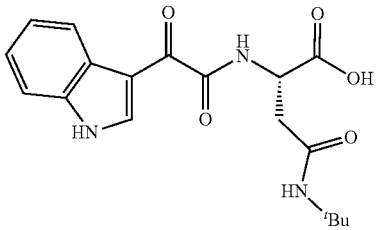

DPLG-3052 was prepared by following the general procedure for O-debenzylation of Ind-oxal-Asp(CONHtBu) OBn (265 mg, 0.59 mmol). Crude was purified by HPLC to give product (112 mg, 53%) as a white solid. $^{1}$H NMR (500 MHz, DMSO-$d_6$) δ 12.81 (s, 1H), 12.27 (d, J=3.3 Hz, 1H), 8.82-8.75 (m, 2H), 8.26-8.20 (m, 1H), 7.57 (s, 1H), 7.56-7.52 (m, 1H), 7.32-7.23 (m, 2H), 4.69-4.60 (m, 1H), 2.67 (dd, J=15.1, 7.2 Hz, 1H), 2.59 (dd, J=15.1, 5.0 Hz, 1H), 1.22 (s, 9H). $^{13}$C NMR (126 MHz, DMSO) δ 181.25, 172.26, 168.78, 162.78, 138.64, 136.25, 126.14, 123.53, 122.66, 121.28, 112.60, 112.11, 50.16, 48.97, 37.16, 28.44.

Example 141—Preparation of DPLG-3053

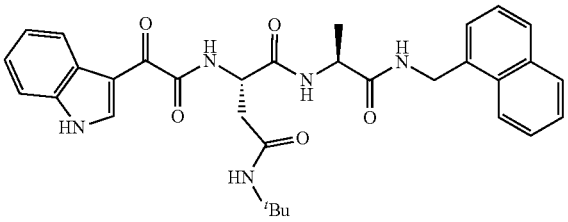

DPLG-3053 was prepared by following the general procedure for HATU mediated coupling of Ind-oxal-Asp (CONHtBu)-OH (7.2 mg, 0.02 mmol) and H-Ala-CH2-naphth TFA salt (7.5 mg, 0.022 mmol). The mixture was purified by HPLC to give product (6.4 mg, 56%) as a white solid. $^{1}$H NMR (500 MHz, DMSO-$d_6$) δ 12.26 (d, J=3.4 Hz, 1H), 8.77 (d, J=3.2 Hz, 1H), 8.71 (d, J=8.1 Hz, 1H), 8.52 (t, J=5.8 Hz, 1H), 8.30-8.21 (m, 2H), 8.08-8.02 (m, 1H), 7.97-7.91 (m, 1H), 7.86-7.80 (m, 1H), 7.57 (s, 1H), 7.56-7.49 (m, 3H), 7.47-7.41 (m, 2H), 7.31-7.24 (m, 2H), 4.75 (d, J=5.8 Hz, 2H), 4.70-4.60 (m, 1H), 4.38-4.25 (m, 1H), 2.66-2.54 (m, 2H), 1.27 (d, J=7.1 Hz, 3H), 1.17 (s, 9H). $^{13}$C NMR (126 MHz, DMSO) δ 181.15, 171.92, 170.01, 168.98, 162.84, 138.58, 136.24, 134.38, 133.22, 130.78, 128.47, 127.46, 126.15, 125.74, 125.38, 125.14, 123.51, 123.35, 122.64, 121.28, 112.59, 112.12, 50.18, 50.07, 48.68, 40.20, 40.02, 39.85, 39.69, 39.52, 39.35, 39.19, 39.02, 38.10, 28.36, 18.07.

Example 142—Preparation of DPLG-21001

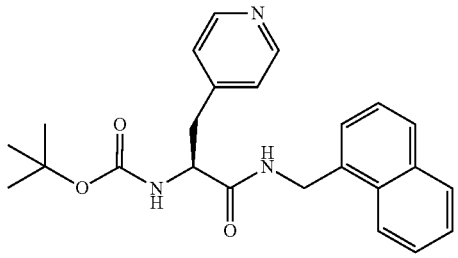

DPLG-21001 was synthesized by following the general procedure for HATU mediated coupling of Boc-β-(4-pyridyl)-L-alanine (55.48 mg, 0.2 mmol) and 1-naphthylmethylamine (32 mL, 0.22 mmol). After completion of the reaction, water was added. A white precipitate was formed. Mixture was extracted with ethyl acetate twice. The combined organic layer was washed with saturated brine and dried over anhydrous sodium sulfate. The organic layer was evaporated and dried to give a colorless paste. Crude was purified by HPLC to give pure product as a white solid (57 mg, 70%). $^1$H NMR (500 MHz, DMSO-$d_6$) δ 8.51 (t, J=5.7 Hz, 1H), 8.49-8.37 (m, 2H), 8.10-8.01 (m, 1H), 7.99-7.91 (m, 1H), 7.85 (d, J=8.1 Hz, 1H), 7.61-7.50 (m, 2H), 7.49-7.36 (m, 2H), 7.34-7.22 (m, 2H), 7.11 (d, J=8.7 Hz, 1H), 4.83-4.67 (m, 2H), 4.35-4.13 (m, 1H), 2.98 (dd, J=13.6, 4.7 Hz, 1H), 2.81 (dd, J=13.6, 10.3 Hz, 1H), 1.30 & 1.16 (s, rotamers, 9H).

Example 143—Preparation of DPLG-21023

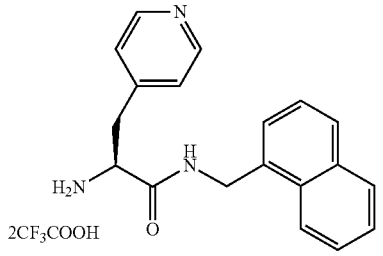

DPLG-21023 was synthesized by following the procedure for Boc-deprotection of DPLG-21001 (50 mg, 0.123 mmol). After completion of the reaction, excess trifluoroacetic acid and dichloromethane were evaporated. Crude was dried under high vacuum to give colorless paste. The paste was triturated with diethyl ether to give a white solid. Diethyl ether was decanted, and white solid was dried under vacuum to give product (65 mg, 99%). The product was used in the next step without further purification. $^1$H NMR (500 MHz, DMSO-$d_6$) δ 9.01 (t, J=5.5 Hz, 1H), 8.74-8.58 (m, 2H), 8.43 (s, 3H), 8.00-7.93 (m, 2H), 7.89 (d, J=8.2 Hz, 1H), 7.60-7.52 (m, 4H), 7.45 (dd, J=8.2, 7.0 Hz, 1H), 7.36 (d, J=7.0 Hz, 1H), 4.80 (dd, J=15.0, 5.6 Hz, 1H), 4.73 (dd, J=15.0, 5.3 Hz, 1H), 4.33-4.05 (m, 1H), 3.24 (dd, J=13.7, 6.6 Hz, 1H), 3.18 (dd, J=13.7, 7.6 Hz, 1H).

Example 144—Preparation of DPLG-21033

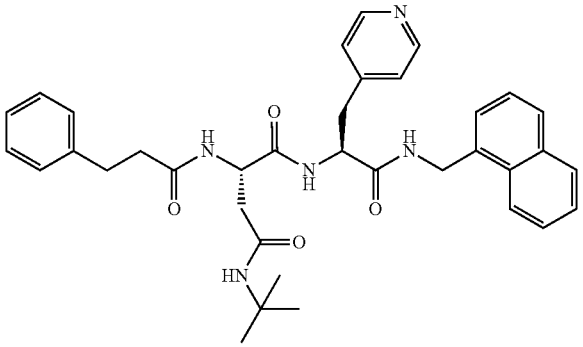

DPLG-21033 was synthesized by following the general procedure for HATU mediated coupling of DPLG-21013 (12.8 mg, 0.04 mmol) and DPLG-21023 (25.6 mg, 0.048 mmol). After completion of the reaction, the mixture was purified by HPLC to give product (20.1 mg, 83%) as a white solid. $^1$H NMR (500 MHz, DMSO-$d_6$) δ 8.66 (t, J=5.9 Hz, 1H), 8.47-8.36 (m, 2H), 8.33 (d, J=8.4 Hz, 1H), 8.11-8.05 (m, 1H), 8.03 (d, J=8.0 Hz, 1H), 7.96-7.92 (m, 1H), 7.84 (d, J=7.9 Hz, 1H), 7.58-7.51 (m, 2H), 7.50 (s, 1H), 7.46-7.38 (m, 2H), 7.29-7.14 (m, 7H), 4.82 (dd, J=15.4, 6.0 Hz, 1H), 4.70 (dd, J=15.4, 5.6 Hz, 1H), 4.60-4.48 (m, 2H), 3.18 (dd, J=14.0, 4.3 Hz, 1H), 2.87 (dd, J=14.0, 10.1 Hz, 1H), 2.81-2.70 (m, 2H), 2.52-2.48 (m, 1H), 2.38-2.26 (m, 3H), 1.14 (s, 9H). $^{13}$C NMR (126 MHz, DMSO) δ 171.19, 171.12, 170.26, 169.18, 148.96, 147.25, 141.26, 134.17, 133.22, 130.78, 128.49, 128.29, 128.11, 127.46, 126.20, 125.85, 125.75, 125.35, 125.19, 124.66, 123.34, 53.21, 50.11, 49.71, 40.31, 38.15, 36.76, 36.18, 31.05, 28.37.

Example 145—Preparation of DPLG-21035

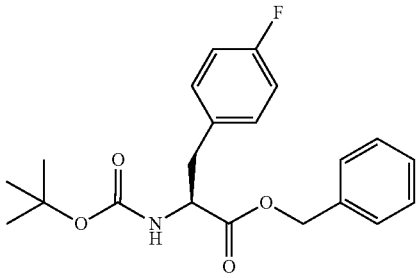

Boc-4F-Phe-OH (849.87 mg, 3.00 mmol) and 1-ethyl-3-(3-dimethylaminopropyl)carbodiimide hydrochloride (EDC) (690.12 mg, 3.60 mmol) were dissolved in dichloromethane (15.00 mL) under argon atmosphere. Benzyl alcohol (389.30 mg, 3.60 mmol) was added to the mixture at 23° C. The solution was cooled to 0° C. and triethylamine (0.5 mL, 3.60 mmol) was added. Reaction mixture was allowed to warm to room temperature (23° C.) slowly and stirred at room temperature overnight. Dichloromethane was evaporated, and crude solid was extracted using ethyl acetate and water. Organic layer was washed with aq. $NaHCO_3$, 1N HCl, water followed by saturated brine solution. Ethyl acetate layer was dried over anhydrous $Na_2SO_4$ and evaporated to give crude product. Crude was purified by combiflash to give pure product (909 mg, 81%) as white solid. $^1$H NMR (500 MHz, Chloroform-d) δ 7.39-7.33 (m, 3H), 7.33-7.28 (m, 2H), 7.02-6.94 (m, 2H), 6.93-6.85 (m, 2H), 5.18 (d, J=12.2 Hz, 1H), 5.09 (d, J=12.2 Hz, 1H), 4.98 (d, J=8.2 Hz, 1H), 4.64-4.56 (m, 1H), 3.08 (dd, J=14.0, 6.0 Hz, 1H), 3.02 (dd, J=14.0, 5.9 Hz, 1H), 1.42 (s, 9H).

Example 146—Preparation of DPLG-21037

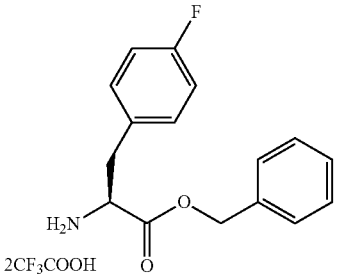

DPLG-21037 was synthesized by following the general procedure for Boc-deprotection of DPLG-21035 (485.5 mg, 1.3 mmol). After completion of the reaction, excess trifluoroacetic acid and dichloromethane were evaporated. Crude was dried under vacuum to give colorless paste. Crude was dissolved in diethyl ether to give a clear solution. The solution was kept at −20° C. overnight to crystallize the product. Product was filtered and dried (yield 467 mg, 93%). $^1$H NMR (500 MHz, DMSO-$d_6$) δ 8.66-8.36 (m, 3H), 7.40-7.34 (m, 3H), 7.32-7.24 (m, 2H), 7.24-7.18 (m, 2H), 7.15-7.07 (m, 2H), 5.19-5.13 (m, 2H), 4.40-4.34 (m, 1H), 3.17-3.10 (m, 1H), 3.07 (dd, J=14.1, 7.5 Hz, 1H).

Example 147—Preparation of DPLG-21040

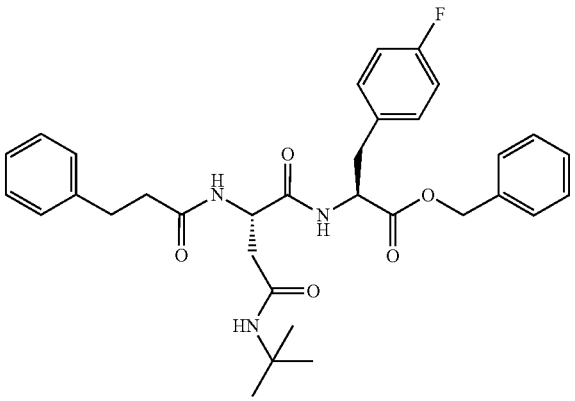

DPLG-21040 was synthesized by following the general procedure for HATU mediated coupling of DPLG-21013 (193 mg, 0.06 mmol) with DPLG-21037 (233 mg, 0.06 mmol). After completion of the reaction, water was added. A white precipitate was formed. Precipitate was filtered and dried in air to give product (310 mg, 89%) as white solid. The product was used in next step without further purification. $^1$H NMR (500 MHz, DMSO-$d_6$) δ 8.27-8.22 (m, 1H), 7.98-7.92 (m, 1H), 7.39-7.14 (m, 13H), 7.08-7.01 (m, 2H), 5.11-5.04 (m, 2H), 4.65-4.56 (m, 1H), 4.55-4.44 (m, 1H), 3.06-2.91 (m, 2H), 2.78-2.75 (m, 2H), 2.41-2.33 (m, 3H), 2.30-2.15 (m, 1H), 1.21 (s, 9H).

Example 148—Preparation of DPLG-21042

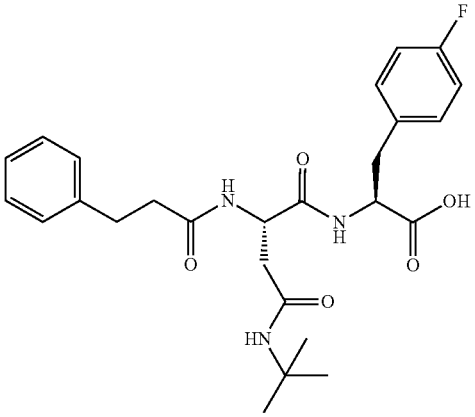

DPLG-21042 was synthesized by following the general procedure for O-debenzylation of DPLG-21040 (300 mg, 0.52 mmol). The product (248 mg, 98%) was isolated as an off-white solid. $^1$H NMR (500 MHz, DMSO-$d_6$) δ 12.93 (s, 1H), 7.99 (d, J=8.3 Hz, 1H), 7.95-7.87 (m, 1H), 7.34 (s, 1H), 7.29-7.14 (m, 7H), 7.09-7.03 (m, 2H), 4.62-4.54 (m, 1H), 4.40-4.31 (m, 1H), 3.07-3.00 (m, 1H), 2.93-2.84 (m, 1H), 2.80-2.74 (m, 2H), 2.45-2.14 (m, 4H), 1.21 (s, 9H).

Example 149—Preparation of DPLG-21049

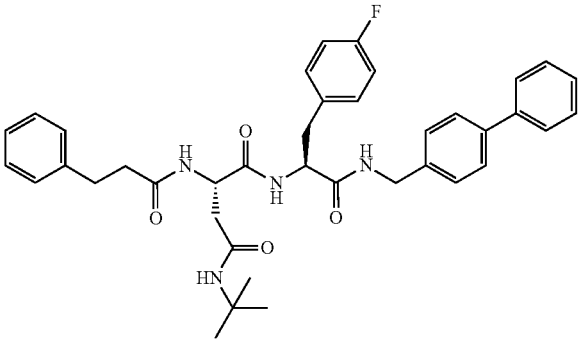

DPLG-21049 was synthesized by following the general procedure for HATU mediated coupling of DPLG-21042 (19.4 mg, 0.04 mmol) with 4-phenylbenzylamine (8.1 mg, 0.044 mmol). After completion of the reaction, the mixture was purified by HPLC to give pure product (14.0 mg, 54%) as a white solid. $^1$H NMR (500 MHz, DMSO-$d_6$) δ 8.64 (t, J=6.0 Hz, 1H), 8.23 (d, J=8.3 Hz, 1H), 8.05 (d, J=8.1 Hz, 1H), 7.68-7.61 (m, 2H), 7.60-7.55 (m, 2H), 7.53 (s, 1H), 7.50-7.42 (m, 2H), 7.39-7.33 (m, 1H), 7.32-7.21 (m, 6H), 7.21-7.13 (m, 3H), 7.09-6.99 (m, 2H), 4.58-4.23 (m, 4H), 3.14 (dd, J=13.9, 4.6 Hz, 1H), 2.89-2.80 (m, 1H), 2.80-2.70 (m, 2H), 2.53-2.50 (m, 1H), 2.43-2.25 (m, 3H), 1.19 (s, 9H).

Example 150—Preparation of DPLG-21050

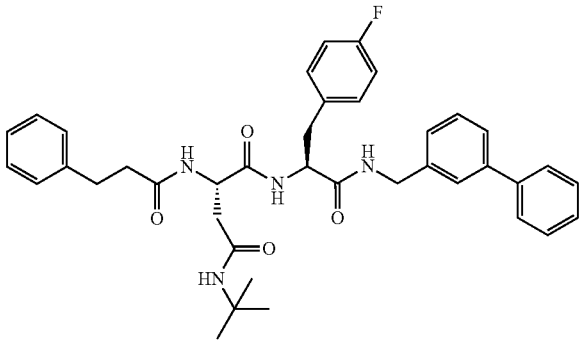

DPLG-21050 was synthesized by following the general procedure for HATU mediated coupling of DPLG-21042 (19.4 mg, 0.04 mmol) with 3-phenylbenzylamine (8.1 mg, 0.044 mmol). After completion of the reaction, the mixture was purified by HPLC to give pure product (13.2 mg, 51%) as a white solid. $^1$H NMR (599 MHz, DMSO-$d_6$) δ 8.66 (t, J=6.1 Hz, 1H), 8.21 (d, J=8.2 Hz, 1H), 8.01 (d, J=8.0 Hz, 1H), 7.68-7.61 (m, 2H), 7.57-7.44 (m, 5H), 7.42-7.34 (m, 2H), 7.30-7.12 (m, 7H), 7.06-6.96 (m, 2H), 4.57-4.29 (m, 4H), 3.14 (dd, J=13.9, 4.5 Hz, 1H), 2.89-2.80 (m, 1H), 2.80-2.69 (m, 2H), 2.54-2.50 (m, 1H), 2.42-2.26 (m, 3H), 1.17 (s, 9H).

Example 151—Proteasome Inhibitory Studies of Various N,C Capped Dipeptides

Measurement of $IC_{50}$s

All inhibitory assays for N,C capped dipeptides were performed in a black solid-bottom 96-well plate. In general, compound plates were prepared starting from 10 mM in 3× series dilution to 15 μM. 1 μl of DMSO stock was transferred to a black 96-well plate and 100 μL of reaction mixture were added 15 μM N-acetyl-Alanine-Asparagine-Tryptophan-7-amino-4-methylcourmarin (Ac-ANW-AMC) or 25 μM succinyl-Leucine-Leucine-Valine-Tyrosine-7-amino-4-methylcourmarin (succ-LLVY-AMC), 0.4 nM hu i-20S β5i-subunit or 0.2 nM hu c-20S β5c-subunit, 0.02% SDS, 1% BSA, 0.5 mM EDTA in 20 mM HEPES buffer at pH7.5. The plates were then spun at 1000 rpm for 1 minute, and the fluorescence units of each well were recorded at λex=360 nm, λem=460 nm for 2 hours. The slopes of the initial linear range of the time course were used to calculate the velocity, and relative activities were normalized to the velocities of the DMSO control. The data were fit dose-response equation with restriction of 0% activity and 100% activity in PRISM to avoid the possible miscalculation of $IC_{50}$s when complete inhibition was not achieved. For compounds with $IC_{50}$s lower than 5 nM, further dilutions were used. For beta 2c, beta 2i (N-acetyl-Leucine-Leucine-Arginine-7-amino-4-methylcourmarin [Ac-LLR-AMC], beta 1c (N-acetyl-Leucine-Leucine-glutamate-7-amino-4-methylcourmarin [Ac-LLE-AMC]) and betali (N-acetyl-Proline-Alanine-Leucine-7-amino-4-methylcourmarin [Ac-PAL-AMC]) inhibition, only one concentration of compounds at 100 μM was tested.

Example 152—Proteasome Inhibitory Studies of Various N,C Capped Dipeptides

Structure—Activity Relationship (SAR) Studies

Compounds were incubated in an 11-point series of dilutions with the Karpas lymphoma cell line, which expresses i-20S constitutively (Blackburn et al., "Characerization of a New Series of Non-Covalent Proteasome Inhibitors with Exquisite Potency and Selectivity for the 20S BetaS-Subunit," Biochem. J. 430:461-476 (2010), which is hereby incorporated by reference in its entirety), for 4 hours, and the IC50s of the inhibitors were determined using a cell-based Proteasome-Glo™ assay (Promega, Cat. No. G8660) to measure the proteasome activity inside the cells after removal of compound from the medium (Table 4 and FIG. 5B).

Example 153—DPLG-3 Induces Autophagy

Figures 7A, 7B, 7C:
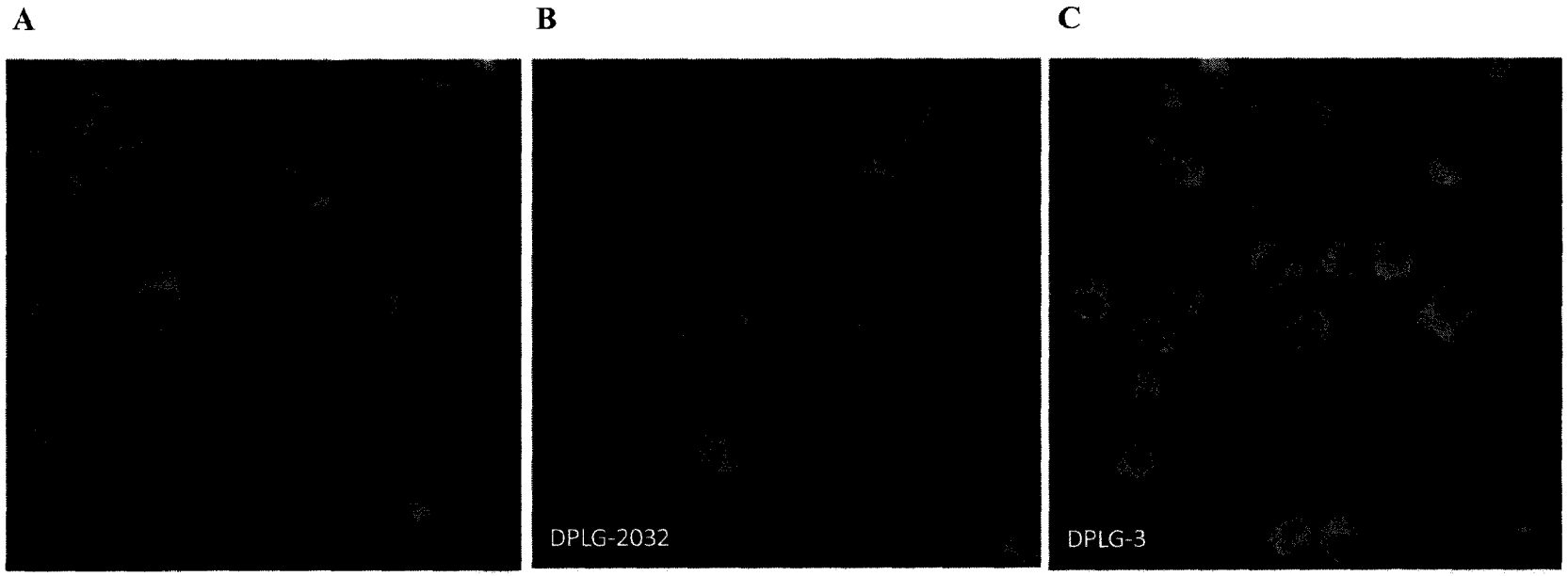
FIGS. 7A-C are fluorescent images showing results which demonstrate that N,C-capped dipeptides induce autophagy in RAW264 GFP-LC3 cells. Cells of the mouse macrophage-like cell line RAW264 transformed with light chain 3 (LC3) fused to green fluorescent protein (GFP) (RAW264 GFP-LC3 cells) were incubated with vehicle control (dimethylsulfoxide (DMSO)), DPLG-3 (10 nM), or an inactive congener of DPLG-3 called DPLG-2032 (1 μM) at 37° C. overnight. Prior to fixation with 4% paraformaldehyde, the cells were treated with bafilomycin A (20 nM), an inhibitor of the late phase of autophagy, for 4 hours. Fluorescent images were recorded digitally with a multiphoton microscope.

RAW264 GFP-LC3 cells were incubated with vehicle DMSO control, DPLG-3 (10 nM), or the inactive congener DPLG-2032 (1 μM) at 37° C. overnight. Prior to fixation with 4% paraformaldehyde, the cells were treated with bafilomycin A (20 nM), an inhibitor of the late phase of autophagy, for 4 hours. The fluorescent images taken of these different sample treatments (FIGS. 7A-C) indicated that the DPLG-3 induces autophagy.

Autophagy is a highly conserved process in eukaryotic cells that degrades a large proportion of cytosolic proteins and organelles. It involves the formation of double membrane complexes that fuse with lysosomes to form autolysosomes, where engulfed proteins or organelles are degraded by lysosomal proteases (Fleming et al., "Chemical Modulators of Autophagy as Biological Probes and Potential Therapeutics," Nature Chemical Biology 7:9-17 (2011), which is hereby incorporated by reference in its entirety). Stresses such as nutrient starvation, hypoxia, protein aggregates, ER stress, pathogens, and DNA damage induce autophagy (Kroemer et al., "Autophagy and the Integrated Stress Response," Mol. Cell 40:280-293 (2010), which is hereby incorporated by reference in its entirety).

Autophagy plays critical roles in many physiological and patho-physiological processes. It has been shown that pharmacological induction of autophagy in mice with rapamycin increases the lifespan of the mice (Harrison et al., "Rapamycin Fel Latee in Life Extends Lifespan in Genetically Heterogeneous Mice," Nature 460:392-395 (2009), which is hereby incorporated by reference in its entirety). Autophagy has also been demonstrated to protect against infectious diseases, such as infections caused by the bacteria Mycobacterium tuberculosis, Salmonella enterica, Shigella flexneri, Listeria monocytogenes, etc. and parasites such as Toxoplasma gondii, or by certain viruses (Levine et al., "Autophagy in Immunity and Inflammation," Nature 469: 323-335 (2011), which is hereby incorporated by reference in its entirety). Autophagy also protects against neurodegeneration, as it is the main clearance route for aggregation-prone proteins and unfolded proteins that are not polyubiquitinated (Rubinsztein, D., "The Roles of Intracellular Protein-Degradation Pathways in Neurodegeneration," Nature 443:780-786 (2006), which is hereby incorporated by reference in its entirety). Up-regulation of autophagy is hence considered to have potential therapeutic value in a variety of diseases.

Example 154—DPLG-3 Mitigated TNBS-Induced Colitis in Mice

Trinitrobenzene sulfonic acid (TNBS)-induced colitis exhibits a heightened Th1-Th17 response (increased IL-12 and IL-17) as the disease becomes chronic, similarly to human Crohn's disease (CD). In this model, administration of a neutralizing monoclonal antibody against the p40 subunit shared by IL-12/IL-23 fully rescued mice from the disease-associated body weight loss. This is consistent with the degree of systemic neutralization of the cytokine, as measured by serum levels of IL-12/IL-23 p40 induced in TNBS-treated mice (not shown). Moreover, treatment of TNBS-injected mice with DPLG-3 via I.P. injection at day −1, 1 and 3 relative to the time of TNBS challenge strongly inhibited colitis-induced weight loss (FIG. 4D) in a dose-dependent manner (3 mg/kg, 6 mg/kg and 12 mg/kg). DPLG-3 did not cause detectable adverse effects.

Example 155—DPLG-3 Strongly Restricts the Growth of Established Mammary Tumor In Vivo 4T1 is a tumor cell line isolated from a single spontaneously arising mammary tumor from a BALB/BfC3H mouse (mouse mammary tumor virus-positive) (Miller et al., "Characterization of Metastatic Heterogeneity among Subpopulations of a Single Mouse Mammary Tumor: Heterogeneity in Phenotypic Stability," Invasion Metastasis 33:22 (1983), which is hereby incorporated by reference in its entirety). It is an excellent model system for breast cancer research, because its tumor development is well characterized both oncologically and immunologically. The 4T1 mammary tumor, which is triple-negative (TN) for the expression of estrogen receptor alpha, progesterone receptor, and Her2, closely mimics human breast cancer in its anatomical site, immunogenicity, growth characteristics, and metastatic properties (Pulaski et al., "Reduction of Established Spontaneous Mammary Carcinoma Metastases ollowing Immunotherapy with Major Histocompatibility Complex Class II and B7.1 Cell-Based Tumor Vaccines," Cancer Res 58:1486 (1998), which is hereby incorporated by reference in its entirety). The tumor growth and metastatic spread of 4T1 cells closely resembles stage IV breast cancer (Mi et al., "Differential Osteopontin Expression in Phenotypically Distinct Subclones of Murine Breast Cancer Cells Mediates Metastatic Behavior," J. Biol. Chem. 279: 46659-46667 (2004), which is hereby incorporated by reference in its entirety).

Figure 8A:
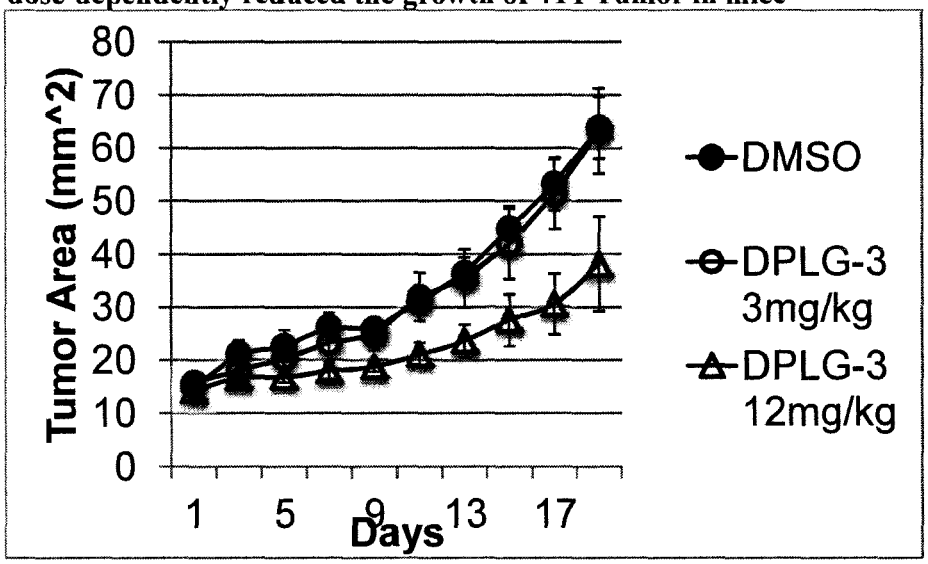
FIGS. 8A-B are graphs showing results that demonstrate that DPLG-3 strongly restricts the growth of established 4T1 mammary tumor in mice. BALB/c mice bearing established 4T1 mammary carcinoma were treated daily with i.p. injection of DPLG-3 at 3 mg/kg, 12 mg/kg in 30 μl of DMSO or DMSO alone. Primary tumors were measured every other day by their surface areas. On Day 19, mice were sacrificed and tumors excised, and measured by weight (mg). The tumor areas were shown as average±SD (FIG. 8A) and average tumor weights±SD (FIG. 8B) and $P<0.05$ at the end of experiment.
Figure 8B:
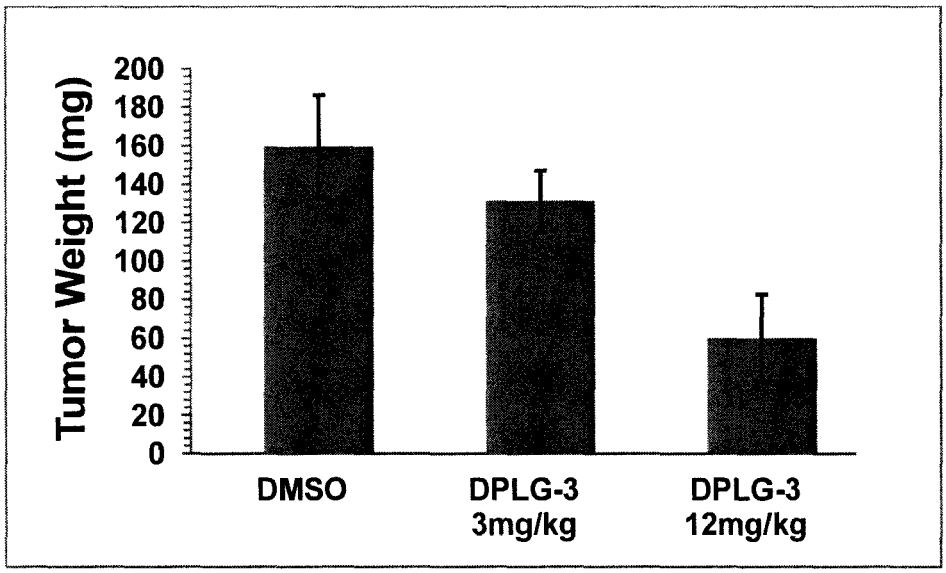

In this experiment, 4T1 mammary carcinoma cells ($1\times10^5$) were injected subcutaneously into the abdominal mammary gland area of recipient mice in 0.1 ml of a single-cell suspension in PBS on day 0 as described previously (Zhang et al., "A Novel Role of Hematopoietic CCL5 in Promoting Triple-Negative Mammary Tumor Progression by Regulating Generation of Myeloid-Derived Suppressor Cells," Cell Res. 23(3):394-408 (2013), which is hereby incorporated by reference in its entirety). Primary tumors were measured by their surface areas every other day. On Day 10, DPLG-3 in 30 ml of DMSO or DMSO alone was injected into mice by i.p. daily at 6 mg/kg. On Day 20, mice were sacrificed and tumors excised, measured by volume (ml) or by weight (mg). The results, shown in FIGS. 8A-B (4 mice per group), demonstrate the efficacy of DPLG-3 in reducing the size and weight of this tumor. The difference between the control group and the DPLG-3 treatment group is highly significant (*, $p<0.05$ by Student T test). This study indicates that these inhibitors will likely be useful in reducing inflammation-induced cancers.

Example 156—Discussion of Examples 1-155

In comparing proteasomes across species, certain similarities between the Mycobacterium tuberculosis (Mtb) proteasome and hu i-20S were found. Both preferred certain P1 aromatic amino acids in N-acetyl-tripeptide-AMC substrates and small hydrophobic amino acids in P3 (Blackburn et al., "Characterization of a New Series of Non-Covalent Proteasome Inhibitors with Exquisite Potency and Selectivity for the 20S BetaS-Subunit," Biochem. J. 430:461-476 (2010); Lin et al., "Distinct Specificities of Mycobacterium Tuberculosis and Mammalian Proteasomes for N-acetyl Tripeptide Substrates," J. Biol. Chem. 283:34423-34431 (2008); Fan et al, "Oxathiazolones Selectively Inhibit the Human Immunoproteasome over the Constitutive Proteasome". ACS Med Chem Lett. 5(4):405-10 (2014), which are hereby incorporated by reference in their entirety). The data are shown in FIGS. 1A-B. Moreover, the Mtb proteasome and hu β5i share a spacious 51 pocket that is larger than that in constitutive proteasomes (Lin et al., "N,C-Capped Dipeptides with Selectivity for Mycobacterial Proteasome Over Human Proteasomes: Role of S3 and 51 Binding Pockets," J. Am. Chem. Soc. 135:9968-9971 (2013), which is hereby incorporated by reference in its entirety). A high throughput screen against the Mtb proteasome led to discovery of a novel class of 1,3,4-oxathiazol-2-ones (Table 1) that inhibit the Mtb proteasome selectively over hu c-20S (Lin et al., "Inhibitors Selective for Mycobacterial Versus Human Proteasomes," Nature 461:621-626 (2009), which is hereby incorporated by reference in its entirety).

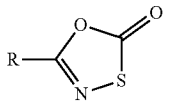

1,3,4-oxathiazol-2-ones

TABLE 1

Kinetic parameters of selected oxathiazolones vs i-20S β5i and hu c-20S β5c.

| | | Hu20S (β5i | | | Hu20S (β5c* | |
|---|---|---|---|---|---|---|
| | | $k_{inact}$ × | $K_I$ | $k_{inact}/K_I$ | $k_{inact}/K_I$ | |
| ID | R | $10^3$ ($s^{-1}$) | (μM) | ($M^{-1}$ $s^{-1}$) | ($M^{-1}$ $s^{-1}$) | Ratio |
| HT1043 | 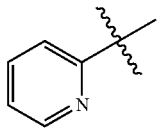 | 0.25 | 2.0 | 128.9 | 0.2 | 645 |

TABLE 1-continued

Kinetic parameters of selected oxathiazolones vs i-20S β5i and hu c-20S β5c.

| | | Hu20S (β5i | | | Hu20S (β5c* | |
|---|---|---|---|---|---|---|
| | | $k_{inact}$ × | $K_I$ | $k_{inact}/K_I$ | $k_{inact}/K_I$ | |
| ID | R | $10^3$ ($s^{-1}$) | (μM) | ($M^{-1}$ $s^{-1}$) | ($M^{-1}$ $s^{-1}$) | Ratio |
| HT1171 | $O_2N$ | 0.77 | 0.76 | 1012.2 | 10.1 | 100 |
| HT2004 | | 1.54 | 1.4 | 1093 | 0.23 | 4750 |

*The plots of $k_{obs}$ vs [I] for hu c-20S were linear. Individual kinact and $K_I$ cannot be derived; instead, $k_{inact}/K_I$ values were derived from the slopes of the plots.

Oxathiazolones inhibit the Mtb proteasome via a competitive, irreversible mechanism that results in cyclocarbonylation of the β-OH and α-$NH_2$ of the active site $Thr^{1N}$ of the Mtb proteasome. This is accompanied by a marked conformational change in the loop around the active site that was implicated in favoring suicide-substrate inhibition vs. hydrolysis of the reaction intermediate. Of the 6 pairs of amino acids that are critical for species selectivity, only two pairs are conserved in human β2c, one pair in hu β1c, β1i, and β2i, and none in hu β5c or β5i. Thus, it was predicted that oxathiazolones active against the Mtb proteasome might inhibit hu β5i. Indeed, some exhibited extremely high selectivity for hu β5i over hu β5c. Table 1, shows 3 such compounds tested; see (Fan et al., "Oxathiazolones Selectively Inhibit the Human Immunoproteasome over the Constitutive Proteasome," ACS Med. Chem. Lett. 5(4):405-410 (2014), which is hereby incorporated by reference in its entirety). However, the half-lives of oxathiazolones range from 7 minutes to 3 hours in culture medium and even less in plasma, a drawback for drug development. Further evidence for structural similarity between the Mtb20S and hu i-20S β5i comes from a series of dipeptide boronates with P1 naphthylAlaB$(OH)_2$ (Table 2), which were designed and synthesized to selectively inhibit Mtb20S over hu c-20S β5c. Although there was little selectivity between Mtb20s and hu c-20S β5c, these dipeptide boronates inhibited hu i-2S β5i over hu c-20S β5c with a selectivity index (SI) up to 17-fold.

TABLE 2

Kinetic parameters of selected dipeptide boronates vs hu i-20S β5i and c-20S β5c.

| | IC50 (μM) | | | |
|---|---|---|---|---|
| | Mtb20S | i-20S β5i | c-20S β5i | Ratio |
| BA1 | 0.07 | 0.0088 | 0.106 | 12.0 |
| BA2 | 0.10 | 0.0084 | 0.143 | 17.1 |

TABLE 2-continued

BA1, R = Naphthyl
BA2, R = Phenyl

Substrate preferences for proteasomes from bacteria, yeast, and cows were profiled, using a library of 6000 N-acetyl-P3-P2-P1-AMCs (Lin et al., "Distinct Specificities of Mycobacterium Tuberculosis and Mammalian Proteasomes for N-acetyl Tripeptide Substrates," J. Biol. Chem. 283:34423-34431 (2008), which is hereby incorporated by reference in its entirety), and a library of 1,600 N,C-capped dipeptides for screening (FIG. 1A) (Lin et al., "N,C-Capped Dipeptides with Selectivity for Mycobacterial Proteasome Over Human Proteasomes: Role of S3 and 51 Binding Pockets," J. Am. Chem. Soc. 135:9968-9971 (2013), which is hereby incorporated by reference in its entirety).

These results indicated that the combination of 51 and S3 determines substrate selectivity between hu c-20S and hu i-20S. Hu i-20S prefers P1-Trp/Tyr and P3-Gly/Thr/Pro, whereas hu c-20S prefers P1-AlaNal/Leu and P3-Trp/Tyr. Focusing on developing proteasome inhibitors that are reversible and selective N,C-capped dipeptides for the bacterial proteasome over the human proteasome, it was required to find inhibitors of the same class that are reversible and selective for hu i-20S β5i over hu c-20S β5c (FIG. 1A), based on both substrate profiling and structural analysis. X-ray crystal structures of mouse c-20S and i-20S reinforced the finding that the 51 pocket in i-20S is significantly bigger than that in c-20S, while the S3 pockets look similar between the c-20S and the i-20S (Huber et al., "Immuno- and Constitutive Proteasome Crystal Structures Reveal Differences in Substrate and Inhibitor Specificity,"

Cell 148:727-738 (2012), which is hereby incorporated by reference in its entirety). In vitro evaluations of several N,C-capped dipeptides indicated that most of the compounds tested had aqueous solubilities of 200-300 μM and $t_{1/2}$>2 hours in human plasma and dog plasma. In vitro intrinsic clearance by liver microsomes was relatively high: 1.5-14.3 L/h/kg by human and 3.1-28.2 L/h/kg by rat microsomes. A dipeptide, DPLG-2, that was designed for Mtb20S, was stable with $t_{1/2}$>24 hours in human plasma (Lin et al., "N,C-Capped Dipeptides with Selectivity for Mycobacterial Proteasome Over Human Proteasomes: Role of S3 and 51 Binding Pockets," J. Am. Chem. Soc. 135: 9968-9971 (2013), which is hereby incorporated by reference in its entirety). In vitro metabolism studies revealed that the most vulnerable site for microsomal CYP-induced hydroxylation was the α-C of the neo-pentyl Asn, with lesser reactivity at the P1 benzyl position (Blackburn et al., "Optimization of a Series of Dipeptides with a P3 [small beta]-Neopentyl Asparagine Residue as Non-Covalent Inhibitors of the Chymotrypsin-Like Activity of Human 20S Proteasome," Med Chem Comm 3:710-719 (2012), which is hereby incorporated by reference in its entirety). DPLG-3 was designed by introducing a naphthyl group in the P1 position and N-($^t$BuO)—As in the P3 position (FIG. 1B). The structure of DPLG-3 (purity>95%) was confirmed by nuclear magnetic resonance (NMR) and mass spectrometry (MS). Its competitive inhibition and selectivity for hu i-20S β5i versus hu c-20S β5c (Table 3) and its selectivity for β5i over β2i and β1i were also confirmed. Since the sequence identities between human c-20S and mouse c-20S and between human i-20S β5i and mouse i-20S β5i are 97% and 92.6%, respectively, it was predicted that DPLG-3 will potently and selectively inhibit mouse i-20S β5i over mouse c-20S β5c in a comparable manner to its selective inhibition of human i-20S β5i. In support of this expectation for preserved selectivity across the human-mouse comparison, ONX 0914 potently and relatively selectively inhibited human and mouse i-20S over human and mouse c-20S, respectively (Huber et al., "Immuno- and Constitutive Proteasome Crystal Structures Reveal Differences in Substrate and Inhibitor Specificity," Cell 148:727-738 (2012), which is hereby incorporated by reference in its entirety). At concentrations up to 50 μM, DPLG-3 was not cytotoxic against HepG2 human hepatoma cells, mouse bone marrow derived macrophages (BMDMs), human peripheral blood mononuclear cells (purchased from New York Blood Bank), or a human B-lymphoma cell line.

Because the i-20S plays important physiological roles in modulating innate and adaptive immune responses, DPLG-3's biological properties in experimental colitis and in inflammatory macrophages were investigated. Crohn's disease (CD) is a major form of inflammatory bowel disease (IBD) that may arise from the interplay of commensal and pathogenic bacteria, genetic mutations, and immunoregulatory defects (Packey et al., "Interplay of Commensal and Pathogenic Bacteria, Genetic Mutations, and Immunoregulatory Defects in the Pathogenesis of Inflammatory Bowel Diseases," J. Intern. Med. 263:597-606 (2008); Mumy et al., "The Role of Neutrophils in the Event of Intestinal Inflammation," Curr. Opin. Pharmacol. 9:697-701 (2009), which are hereby incorporated by reference in their entirety) in both innate and adaptive immune systems (Arseneau et al., "Innate and Adaptive Immune Responses Related to IBD Pathogenesis," Curr. Gastroenterol. Rep. 9:508-512 (2007), which is hereby incorporated by reference in its entirety). In CD, there is a sustained activation of mucosal immune responses of the Th1 and Th17 types, perhaps reflecting constitutive activation, failure of down-regulatory mechanisms, or continued stimulation resulting from changes in the epithelial mucosal barrier (Mashimo et al., "Impaired Defense of Intestinal Mucosa in Mice Lacking Intestinal Trefoil Factor," Science 274:262-265 (1996); Al-Sadi et al., "Mechanism of Cytokine Modulation of Epithelial Tight Junction Barrier," Front Biosci. 14:2765-2778 (2009), which are hereby incorporated by reference in their entirety).

CD has a strong genetic basis (Ogura et al., "A Frameshift Mutation in NOD2 Associated with Susceptibility to Crohn's Disease," Nature 411:603-606 (2001); Hugot et al., "Association of NOD2 Leucine-Rich Repeat Variants with Susceptibility to Crohn's Disease," Nature 411:599-603 (2001), which are hereby incorporated by reference in their entirety). Nucleotide-binding oligomerization domain 2 (NOD2) is an intracellular bacterial sensor and an important regulator of host resistance to microbial challenge as well as tissue homeostasis. The gene encoding NOD2, CARD15, was the first CD susceptibility gene identified (Ogura et al., "A Frameshift Mutation in NOD2 Associated with Susceptibility to Crohn's Disease," Nature 411:603-606 (2001); Hugot et al., "Association of NOD2 Leucine-Rich Repeat Variants with Susceptibility to Crohn's Disease," Nature 411:599-603 (2001), which are hereby incorporated by reference in their entirety). Three main variants of NOD2, R702W, G908R, and 1007fs, together account for ~80% of NOD2 mutations independently associated with susceptibility to CD (Lesage et al., "CARD15/NOD2 Mutational Analysis and Genotype-Phenotype Correlation in 612 Patients with Inflammatory Bowel Disease," Am. J. Hum. Genet. 70:845-857 (2002); Hugot et al., "Prevalence of CARD15/NOD2 Mutations in Caucasian Healthy People," Am. J. Gastroenterol. 102:1259-1267 (2007), which are hereby incorporated by reference in their entirety). All three mutations are located near or within the leucine rich repeat domain (LRR) of NOD2 that is involved in ligand binding. How these human NOD2 mutants contribute to the development and pathogenesis of CD is controversial (Girardin et al., "Nod2 is a General Sensor of Peptidoglycan through Muramyl Dipeptide (MDP) Detection," J. Biol. Chem. 278: 8869-8872 (2003); Watanabe et al., "NOD2 is a Negative Regulator of Toll-like Receptor 2-Mediated T Helper Type 1 Responses," Nat. Immunol. 5:800-808 (2004); Kobayashi et al., "Nod2-Dependent Regulation of Innate and Adaptive Immunity in the Intestinal Tract," Science 307:731-734 (2005); Maeda et al., "Nod2 Mutation in Crohn's Disease Potentiates NF-kappaB Activity and IL-1beta Processing," Science 307:734-738 (2005); Noguchi et al., "A Crohn's Disease-Associated NOD2 Mutation Suppresses Transcription of Human IL10 by Inhibiting Activity of the Nuclear Ribonucleoprotein hnRNP-A1," Nat. Immunol. 10:471-479 (2009), which are hereby incorporated by reference in their entirety). A gain-of-function property of these mutants was identified, which is to inhibit IL-10 gene transcription by interfering with the p38 MAPK-mediated phosphorylation of a novel transcription factor, heterogeneous nuclear ribonucleoprotein A1 (Noguchi et al., "A Crohn's Disease-Associated NOD2 Mutation Suppresses Transcription of Human IL10 by Inhibiting Activity of the Nuclear Ribonucleoprotein hnRNP-A1, " Nat. Immunol. 10:471-479 (2009), which is hereby incorporated by reference in its entirety), providing a plausible mechanistic explanation for the lack of adequate control of chronic intestinal mucosal inflammation associated with CD.

Genetic studies have identified mutations in the IL-12// IL-23 pathway associated with the pathogenesis of CD (Duerr et al., "A Genome-Wide Association Study Identifies IL23R as an Inflammatory Bowel Disease Gene," Science 314:1461-1463 (2006), which is hereby incorporated by reference in its entirety), including JAK2, TYK2, IL12RB1 and IL12B (Wang et al., "An IFN-Gamma-Inducible Transcription Factor, IFN Consensus Sequence Binding Protein (ICSBP), Stimulates IL-12 p40 Expression in Macrophages," J. Immunol. 165:271-279 (2000), which is hereby incorporated by reference in its entirety). IL-12 and IL-23 are crucial cytokines with respect to IBD that are involved in the development and effector functions of Th1 and Th17 cells, respectively (Shih et al., "Recent Advances in IBD Pathogenesis: Genetics and Immunobiology," Curr. Gastroenterol. Rep. 10:568-575 (2008), which is hereby incorporated by reference in its entirety). Clinical studies have strongly implicated the importance of high levels of IL-12 and IL-23 in CD pathogenesis (Monteleone et al., "Interco leukin 12 is Expressed and Actively Released by Crohn's Disease Intestinal Lamina Propria Mononuclear Cells," Gastroenterology 112:1169-1178 (1997); Schmidt et al., "Expression of Interleukin-12-Related Cytokine Transcripts in Inflammatory Bowel Disease: Elevated Interleukin-23p19 and Interleukin-27p28 in Crohn's Disease but not in Ulcerative Colitis," Inflamm. Bowel Dis. 11:16-23 (2005); Penack et al., "NOD2 Regulates Hematopoietic Cell Function During Graft-versus-Host Disease," J. Exp. Med. 206:2101-2110 (2009), which are hereby incorporated by reference in their entirety). Consistent with that, monoclonal antibody blockade of p40 (IL12B), the shared subunit of both IL-12 and IL-23, is therapeutically beneficial (Mannon et al., "Anti-Interleukin-12 Antibody for Active Crohn's Disease," N. Engl. J. Med. 351:2069-2079 (2004); Fuss et al., "Both IL-12p70 and IL-23 are Synthesized During Active Crohn's Disease and are Down-Regulated by Treatment with Anti-IL-12 p40 Monoclonal Antibody," Inflamm. Bowel Dis. 12:9-15 (2006); Melmed et al., "Future Biologic Targets for IBD: Potentials and Pitfalls," Nat. Rev. Gastroenterol. Hepatol. 7:110-117 (2010), which are hereby incorporated by reference in their entirety).

TNBS-induced experimental colitis studies showed that hematopoietic NOD2 is required to control experimental colitis and that the pathogenesis of this model is dependent on IL-12/IL-23 and is rescued by DPLG-3. In the trinitrobenzene sulfonic acid (TNBS)-induced experimental colitis mouse model, it is shown by bone marrow chimeras that NOD2 deficiency in the hematopoietic compartment critically regulates experimental colitis (FIGS. 2A-D).

Figure 3A:
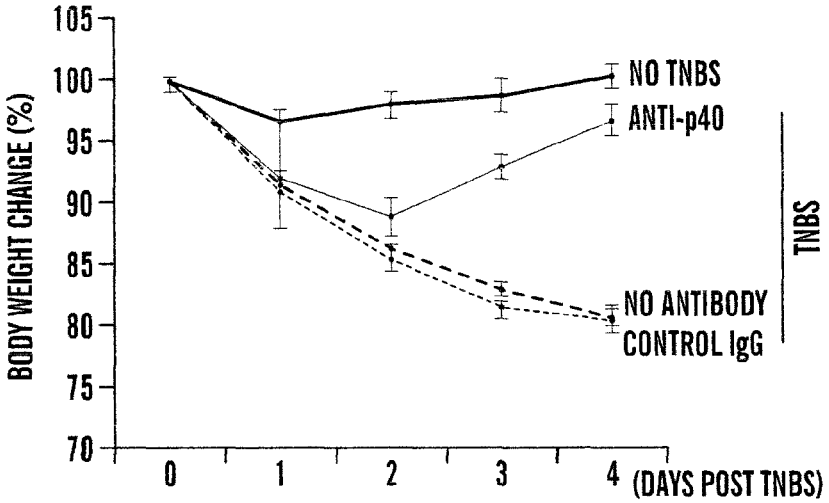
FIGS. 3A-C are graphs showing results that relate to the essential role of interleukin (IL)-12/IL-23 in TNBS-induced colitis and the effectiveness of DPLG-3 in improving the outcome in this colitis model. C57BL/6 mice (4/group) were injected with TNBS (or 50% ethanol) intrarectally (3.5 mg/mouse) on day 0. Body weight was monitored daily for four days.
Figure 3B:
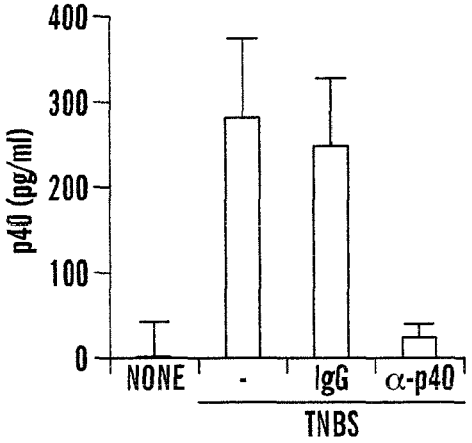
Figure 3C:
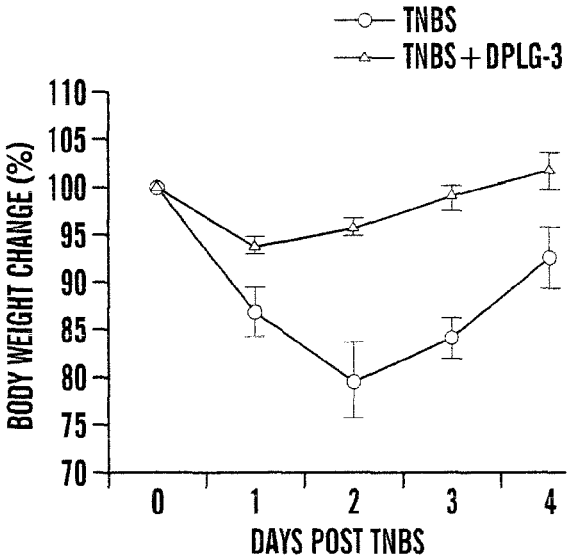

TNBS-induced colitis exhibited heightened Th1-Th17 response (increased IL-12 and IL-17) as the disease becomes chronic, similar to this progression in human CD (Mashimo et al., "Impaired Defense of Intestinal Mucosa in Mice Lacking Intestinal Trefoil Factor," Science 274:262-265 (1996); Al-Sadi et al., "Mechanism of Cytokine Modulation of Epithelial Tight Junction Barrier," Front Biosci. 14:2765-2778 (2009); Ogura et al., "A Frameshift Mutation in NOD2 Associated with Susceptibility to Crohn's Disease," Nature 411:603-606 (2001), which are hereby incorporated by reference in their entirety). In this model, Watanabe et al. also showed that administration of muramyl dipeptide (MDP), the natural ligand of NOD2, protected mice from colitis by downregulating multiple Toll-like receptor (TLR)-mediated innate responses (TLR2, 4, and 9), including the production of IL-12 and IFN-γ (Hugot et al., "Association of NOD2 Leucine-Rich Repeat Variants with Susceptibility to Crohn's Disease," Nature 411:599-603 (2001), which is hereby incorporated by reference in its entirety). Recent work in this area has further established that MDP, through activation of the NOD2 signaling pathway, induces a transcriptional regulator called CCAAT/enhancer-binding protein a (C/EBPa) to control IL-12 production and reduce colitis pathogenesis. Thus, C/EBPa KO mice, like NOD2-deficient mice, are more susceptible to colitis-associated weight loss than WT mice (FIG. 3A). Further, C/EBPa KO mice completely lose responsiveness to MDP-mediated rescue of colitis pathogenesis. Use of a neutralizing monoclonal antibody against the p40 subunit shared by IL-12/IL-23 fully rescued WT and C/EBPa KO mice from the disease (FIG. 3A), consistently with the degree of systemic neutralization of the cytokine, as measured by serum levels of IL-12 induced in TNBS-treated mice (FIG. 3B). Moreover, administration of the immune proteasome inhibitor DPLG-3 to TNBS-treated WT mice via i.v. injection strongly inhibited colitis-associated pathogenesis (FIG. 3C).

Figure 2A:
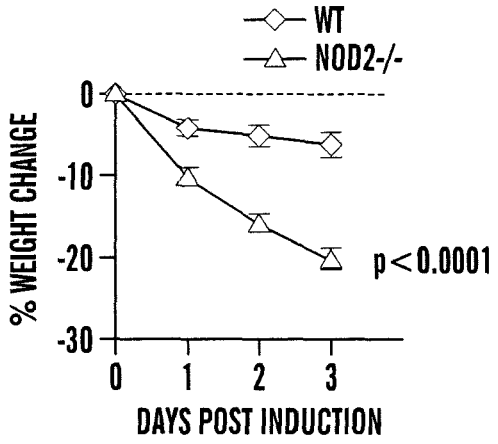
FIGS. 2A-D reports results demonstrating that NOD2 deficiency in the hematopoietic system regulates experimental colitis. Trinitrobenzene sulfonic acid (TNBS) colitis (5 mg TNBS in 50% ethanol) was induced in C57BL/6 (B6) wild type (WT) or B6 nucleotide oligomerization domain 2 (NOD2)-deficient mice ($NOD2^{-/-}$ mice). More weight loss was observed during colitis in $NOD2^{-/-}$ mice than in WT mice. Combined data from three independent experiments are shown; n=12/group.
Figure 2B:
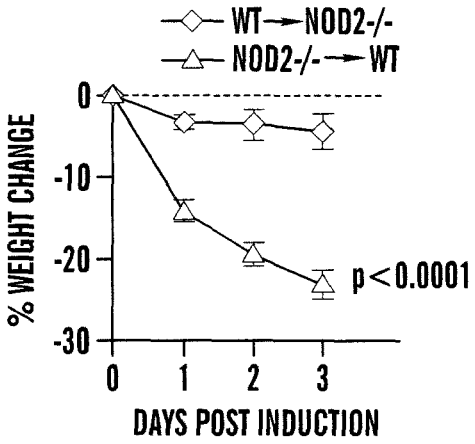
Figure 2C:
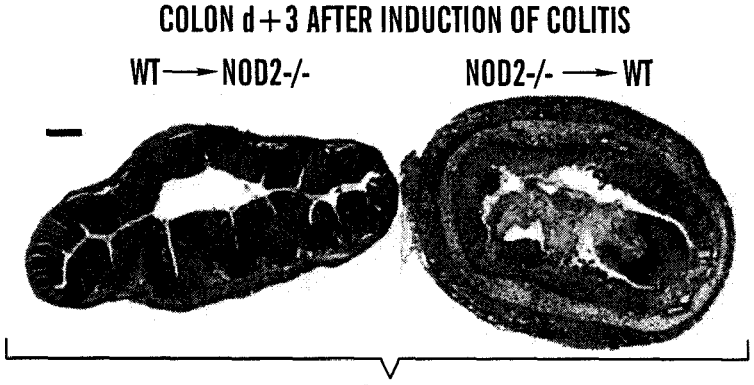
Figure 2D:
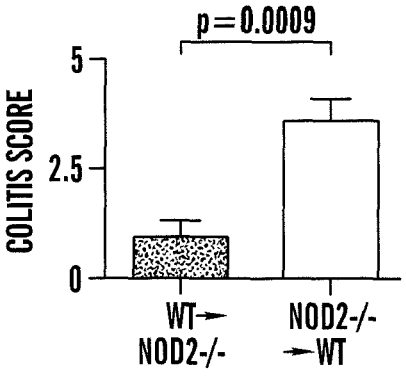

Pathogenesis of TNBS-induced experimental colitis is dependent on IL-12/IL-23 and is rescued by DPLG-3. Trinitrobenzene sulfonic acid (TNBS)-induced colitis in mice exhibits a heightened Th1-Th17 response (increased IL-12 and IL-17) as the disease becomes chronic, similarly to human CD (Noguchi et al., "A Crohn's Disease-Associated NOD2 Mutation Suppresses Transcription of Human IL10 by Inhibiting Activity of the Nuclear Ribonucleoprotein hnRNP-A1," Nat. Immunol. 10:471-479 (2009); Alex et al., "Distinct Cytokine Patterns Identified from Multiplex Profiles of Murine DSS and TNBS-Induced Colitis," Inflamm. Bowel Dis. 15:341-352 (2009); Sarra et al., "IL-23/IL-17 Axis in IBD," Inflamm. Bowel Dis. 16:1808-1813 (2010); Holler et al., "Prognostic Significance of NOD2/CARD15 Variants in HLA-Identical Sibling Hematopoietic Stem Cell Transplantation: Effect on Long-Term Outcome is Confirmed in 2 Independent Cohorts and may be Modulated by the Type of Gastrointestinal Decontamination," Blood 107: 4189-4193 (2006), which are hereby incorporated by reference in their entirety). In this model, administration of a neutralizing monoclonal antibody against the p40 subunit shared by IL-12/IL-23 fully rescued mice from the disease-associated body weight loss (FIG. 2A), consistent with the degree of systemic neutralization of the cytokine, as measured by serum levels of IL-12/IL-23 p40 induced in TNBS-treated mice (FIG. 2B). Moreover, treatment of TNBS-injected mice with DPLG-3 via one-time i.v. injection at the time of TNBS challenge strongly inhibited colitis-induced weight loss (FIG. 2C).

Figure 4A:
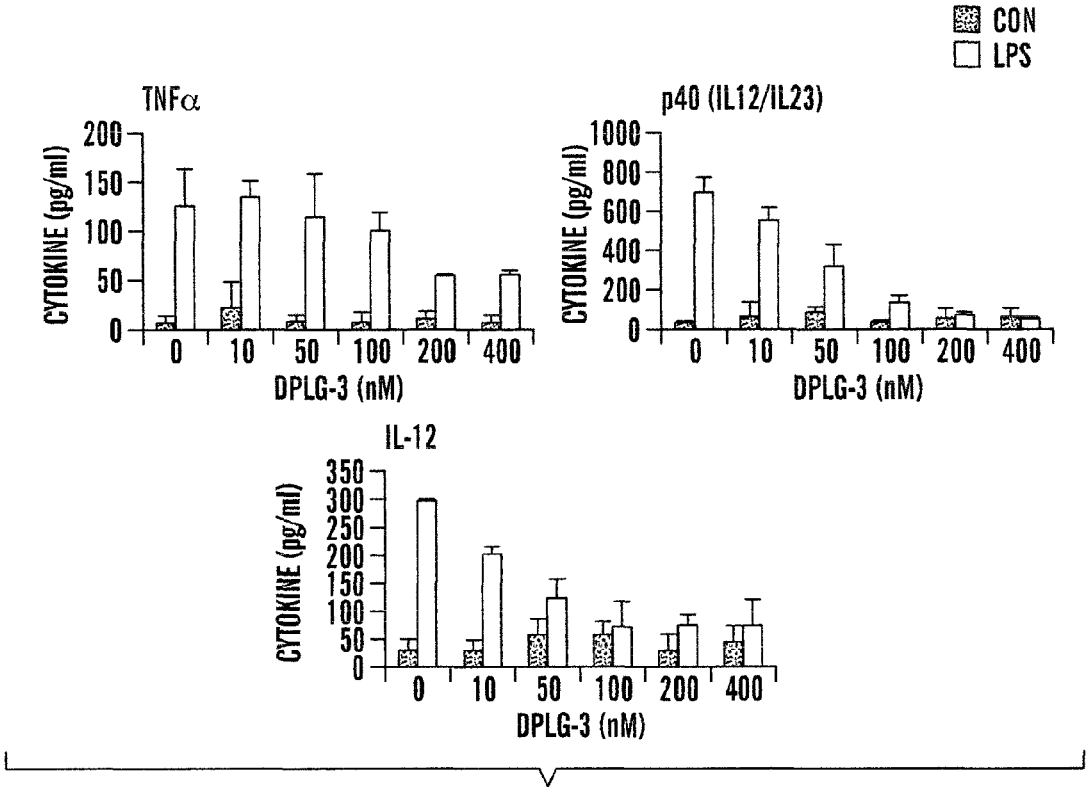
FIGS. 4A-D are bar graphs showing results demonstrating that DPLG-3 differentially regulates cytokine production. Mouse bone marrow derived macrophages (BMDMs) were stimulated or not with bacterial lipopolysaccharide (LPS) (1 μg/ml) in the presence or absence of DPLG-3 at the indicated concentrations. Culture supernatants were harvested 24 hours (h) after LPS stimulation and analyzed for cytokine production by enzyme-linked immunosorbent assay (ELISA). Total RNA was isolated 4 h after LPS stimulation and analyzed by real time quantitative polymerase chain reaction (PCR) for IL-12p35 and IL-12/IL-23p40 genes. Data are expressed relative to levels of glyceraldehyde 3-phosphate dehydrogenase (GAPDH) levels and represent three independent experiments.
Figure 4B:
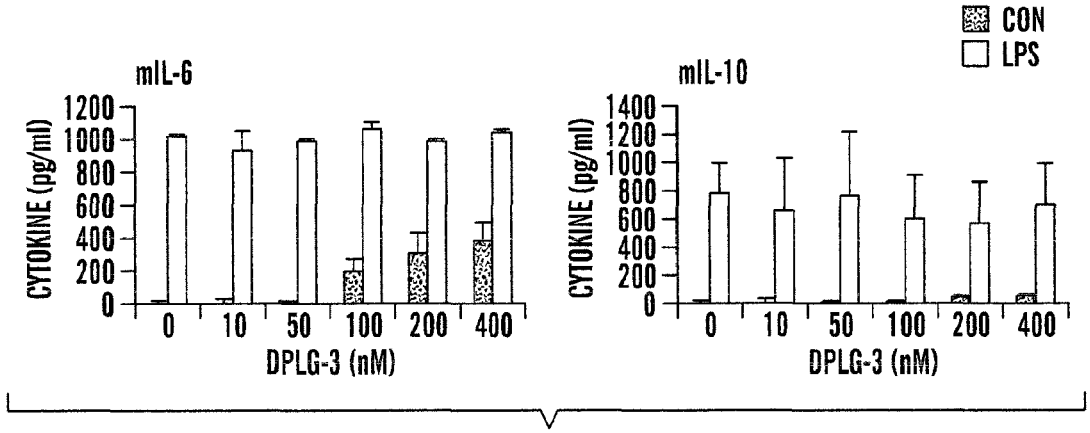
Figure 4C:
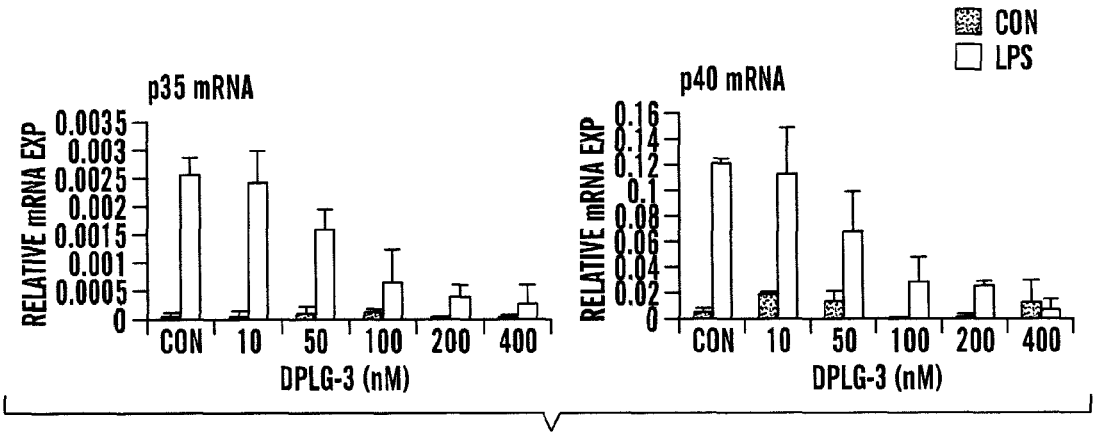
Figure 4D:
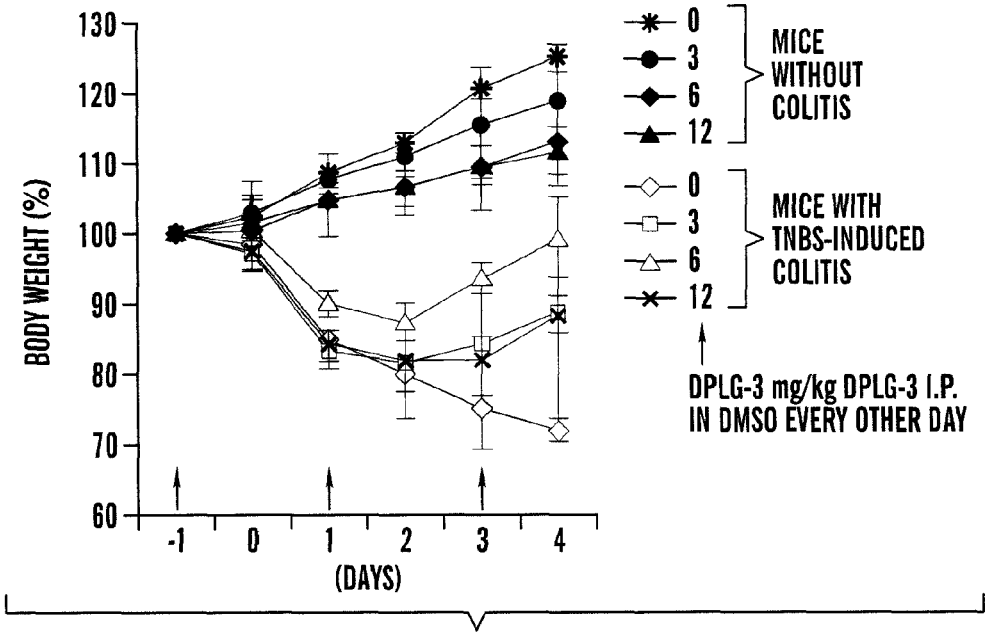

DPLG-3 differentially regulates cytokine production in macrophages. To further explore the mechanisms underlying the treatment effects of DPLG-3 on TNBS-induced colitis, the cytokine expression at both the protein and mRNA levels in macrophages was analyzed. FIG. 4A shows that in LPS-activated macrophages, DPLG-3 dose-dependently inhibited the production of TNF-α, IL-12/IL-23p40 and IL-12. Noticeably, production of IL-12 and IL-23 was more sensitive to the inhibitory effects of DPLG-3 than that of TNF-α by a factor of 10-20. In contrast, DPLG-3 dose-dependently induced IL-6 production on its own, while having no significant effects on IL-10 production (FIG. 4B). Similar degrees of the inhibitory effects of DPLG-3 on IL-12 and IL-23 production were observed at the level of mRNA expression of the IL-12p35 and p40 genes (FIG. 4C), suggestive of transcriptional regulation. The differentially cytokine-regulating property of DPLG-3 is in contrast to that of ONX 0914, which is inhibitory for all cytokines analyzed (Muchamuel et al., "A Selective Inhibitor of the Immunoproteasome Subunit LMP7 Blocks Cytokine Production and Attenuates Progression of Experimental Arthritis," Nat. Med. 15:781-787 (2009), which is hereby incorporated by reference in its entirety). The positive effects in vitro and in vivo of DPLG-3 led to performance of SAR studies to develop and test similar compounds that inhibit the enzymes of the immunoproteasomes more specifically than their counterparts in the constitutive human proteasome. The dipeptide compounds and their relative inhibitory results on the βcomponent of the human immunoproteasome (β5i) and constitutive proteasome (β5c) are described in Examples 151 and 152. The inhibitory effect of DPLG-3 in vivo tests in addition to the colitis model described above can be found in Examples 153 and 155.

Figure 5A:
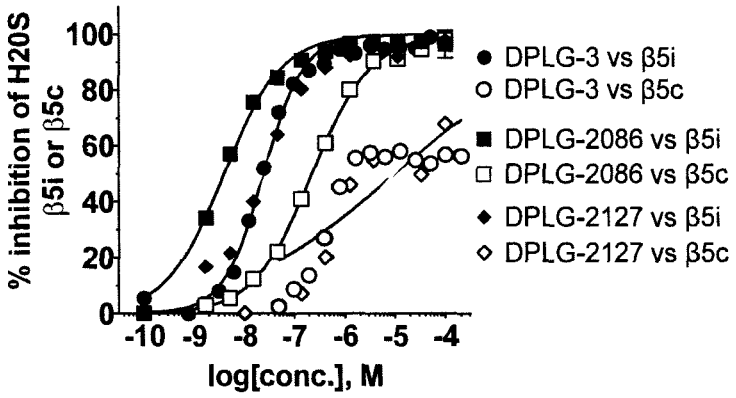
FIGS. 5A-C show experimental results relating to SAR studies and target engagement inside the cells.
Figure 5B:
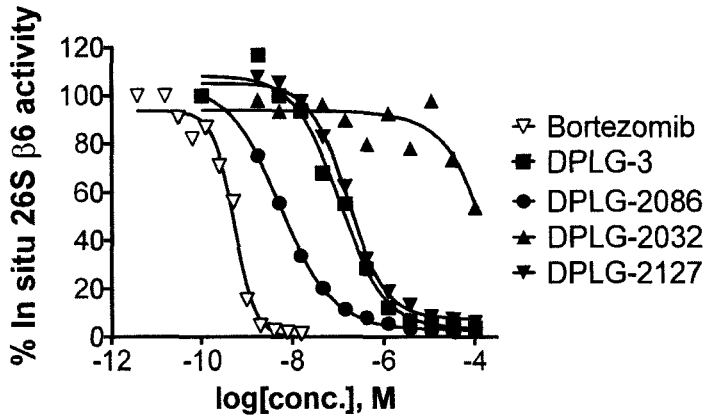
Figure 5C:
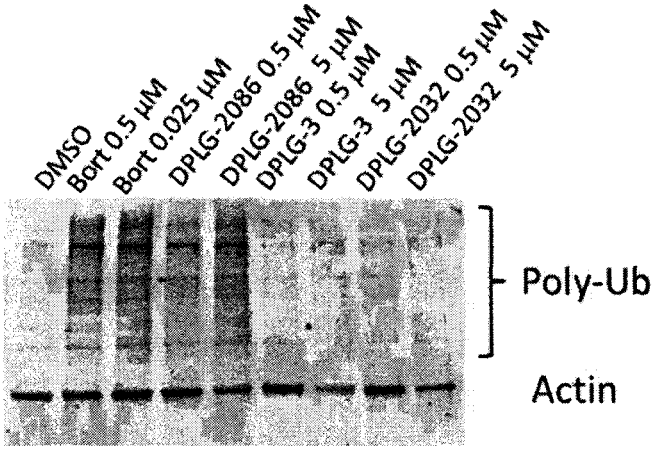
Figure 6:
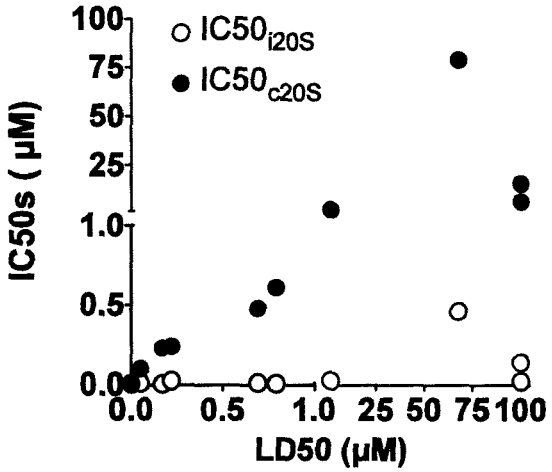
FIG. 6 is a graph showing results which demonstrate that cytotoxicities of the N,C-capped dipeptides correlate with the IC50s of the inhibitors against human constitutive proteasome other than with their IC50s against human immunoproteasome.

Encouraged by DPLG-3's positive effects in vitro and in vivo, in an effort to expand the hit library with the objectives to improve the potency, selectivity, solubility, and lipophilic ligand efficiency, applicants designed, synthesized, and enzymatically evaluated >30 dipeptides (all compounds' purity >95%). Table 3 lists the inhibition kinetic parameters, selectivity index, and calculated log Ps of selected dipeptides. Hill slopes of all compounds were <1.0 (FIG. 5A). The log P was reduced from 4.66 to <3. To determine if they were able to penetrate cell membranes, the compounds were incubated in an 11-point series of dilutions with the Karpas lymphoma cell line, which expresses i-20S constitutively (Blackburn et al., "Characterization of a New Series of Non-Covalent Proteasome Inhibitors with Exquisite Potency and Selectivity for the 20S BetaS-Subunit," Biochem. J. 430:461-476 (2010), which is hereby incorporated by reference in its entirety), for 4 hours, and the IC50s of the inhibitors were determined using a cell-based Proteasome-Glo™ assay (Promega, Cat. No. G8660) to measure the proteasome activity inside the cells after removal of the compound from the medium (Table 4 and FIG. 5B). Contra to the effect of Bortezomib, inhibition of immunoproteasome by DPLG-3 and DPLG-2086 in Karpas cells did not result in the accumulation of poly-ubiquitinated proteins (FIG. 5C). Their cytotoxicity against the Karpas lymphoma cells was determined (Table 4). The LD50s (Table 4) correlated with the IC50s for c-20S inhibition, as the LD50s were equal to or slightly higher than the IC50s for c-20S inhibition (FIG. 6). However, the IC50s for the inhibition of i-20S appeared to be irrelevant for their cytotoxicity, as seen with DPLG-3, DPLG-2106 and DPLG-2127. Moreover, DPLG-3 did not cause accumulation of poly-ubiquitinylated (poly-Ub proteins, in contrast to Bortezomib and DPLG-2086). This is further evidence for the i-20S selectivity of DPLG-3, because the i-20S's activator, PA28 (Preckel et al., "Impaired Immunoproteasome Assembly and Immune Responses in PA28−/− mice," Science 286:2162-2165 (1999), which is hereby incorporated by reference in its entirety), does not specifically recruit poly-Ub proteins for degradation (Rechsteiner et al., "Mobilizing the Proteolytic Machine: Cell Biological Roles of Proteasome Activators and Inhibitors," Trends in Cell Biology 15:27-33 (2005), which is hereby incorporated by reference in its entirety). Although DPLG-2086 is partly selective for i-20S over c-20S, it is still a relatively potent inhibitor of c-20S; thus the accumulation of poly-Ub proteins during treatment with DPLG-2086 is likely due to its inhibition of c-20S.

TABLE 3

Kinetic parameters and calculated logP for N,C-capped dipeptides

| ID | Structures | IC50 (μM) Hu i-20S | IC50 (μM) Hu c-20S | SI[a] | LD50 (μM) |
|---|---|---|---|---|---|
| DPLG-3 | 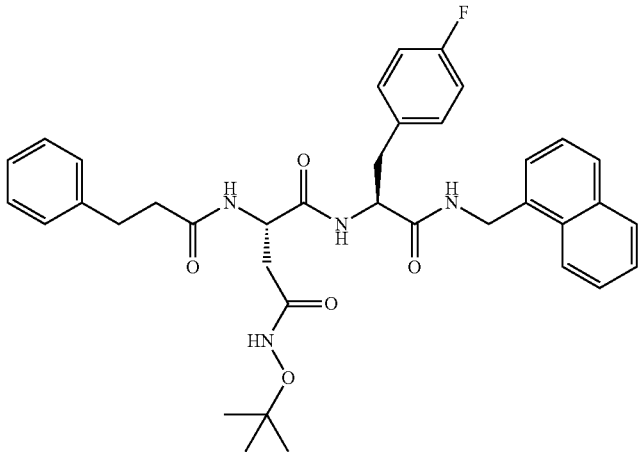 | 0.0036 | 42.1 | >11,000 | 2.04 |
| DPLG-2032 | 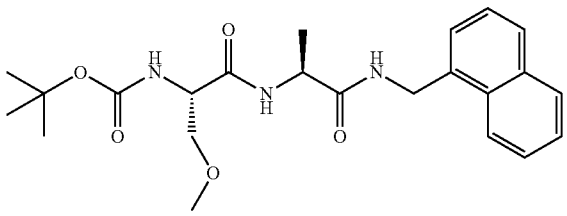 | 77.8 | >100 | — | 37 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2048 | 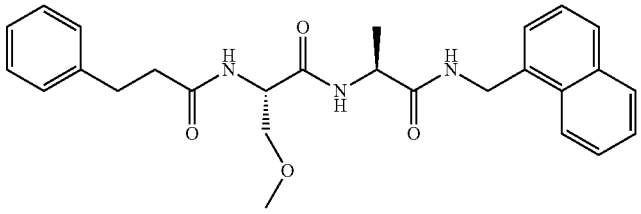 | 34.9 | 59.8 | 1.7 | >100 |
| DPLG-2054 | 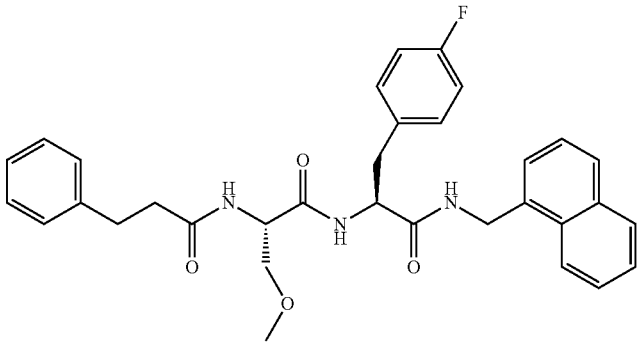 | >100 | 75.8 | <0.8 | >100 |
| DPLG-2058 | 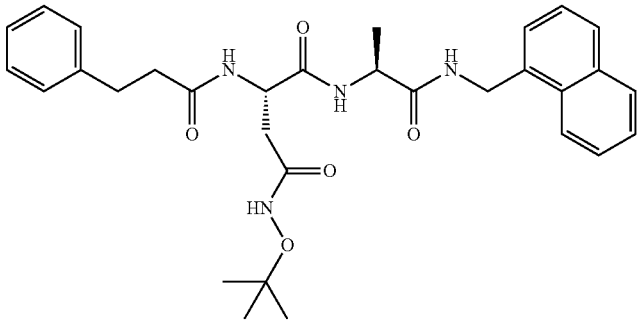 | 0.011 | 0.48 | 44 | 34.4 |
| DPLG-2068 | 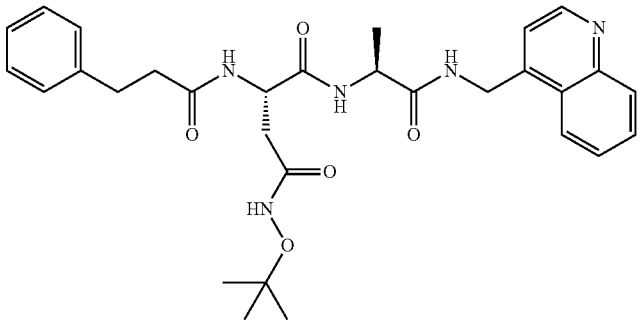 | 3.06 | 28.4 | 9.3 | >100 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2073 | 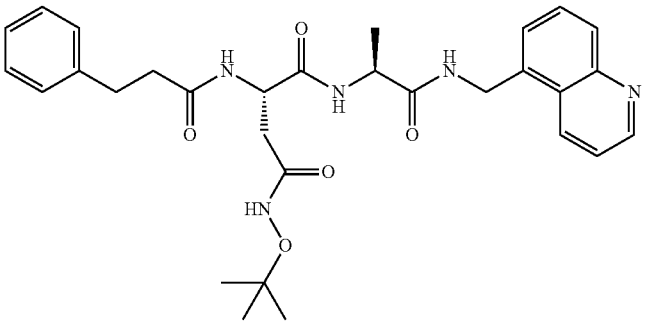 | 1.37 | 13.3 | 10 | >100 |
| DPLG-2083 | 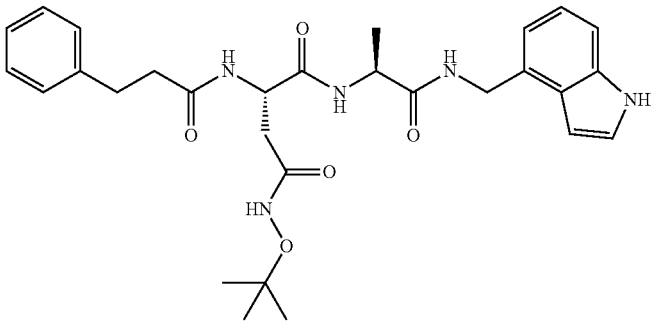 | 0.025 | 0.24 | 10 | 0.254 |
| DPLG-2086 | 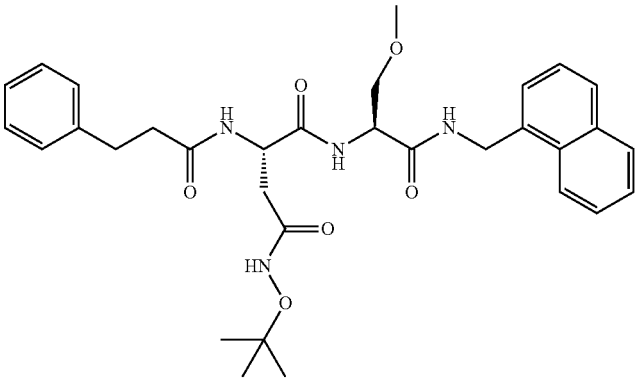 | 0.0038 | 0.23 | 60 | 0.46 |
| DPLG-2091 | 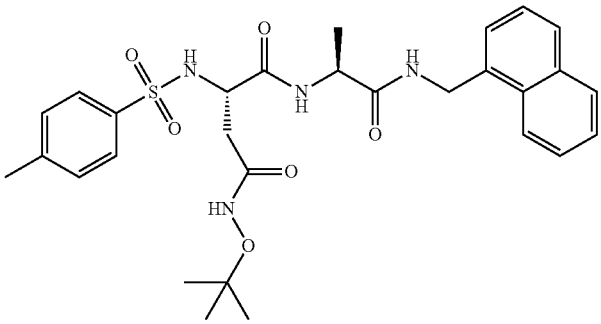 | 0.026 | 2.3 | 88 | 5.3 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2098 | 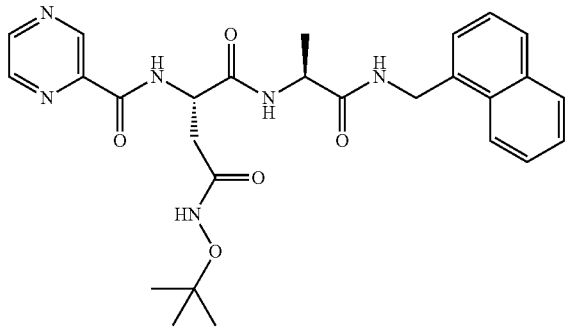 | 4.31 | >100 | >23 | >100 |
| DPLG-2099 | 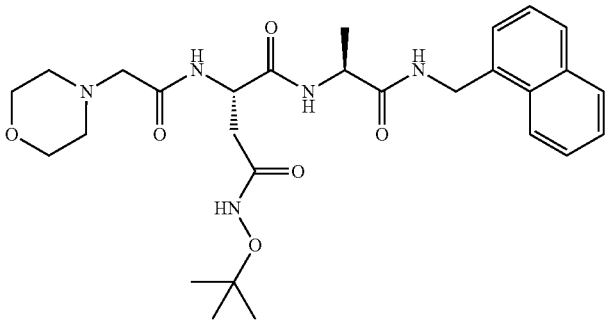 | 0.53 | 41.9 | 79 | >100 |
| DPLG-2102 | 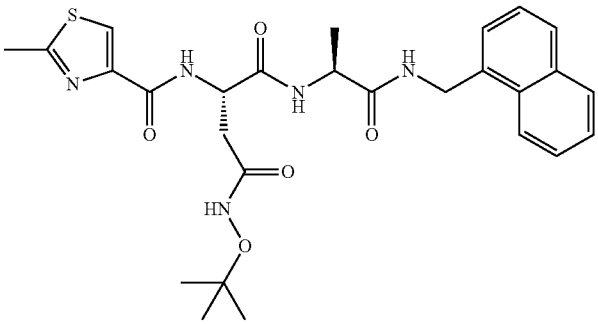 | 1.7 | 55.9 | 33 | 42 |
| DPLG-2105 | 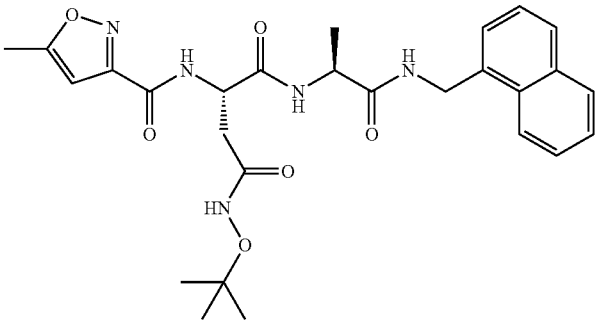 | 0.031 | 1.2 | 39 | 18 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2106 | 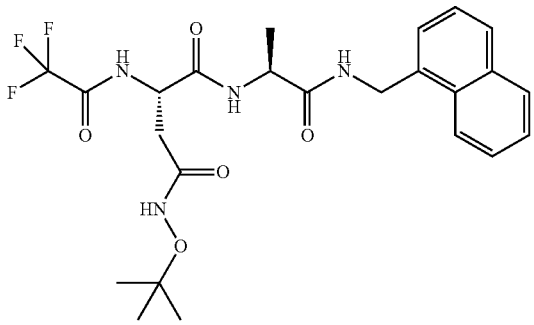 | 0.14 | 6.5 | 46 | 7.8 |
| DPLG-2109 | 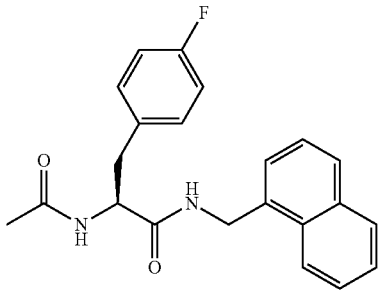 | 57.1 | >100 | >2 | >100 |
| DPLG-2127 | 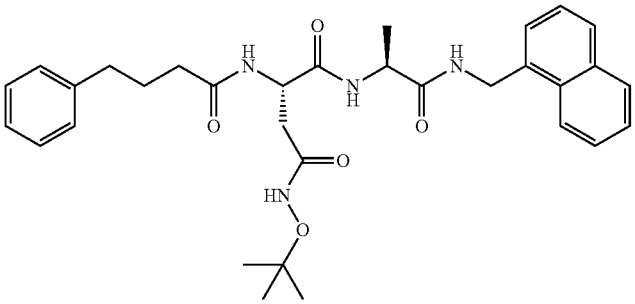 | 0.023 | 15.6 | 680 | >100 |
| DPLG-2130 | 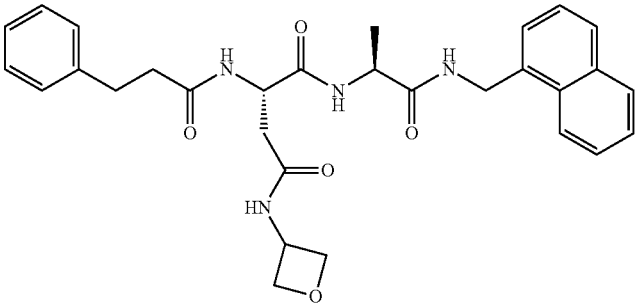 | 0.46 | 79 | 170 | 67.8 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2142 | 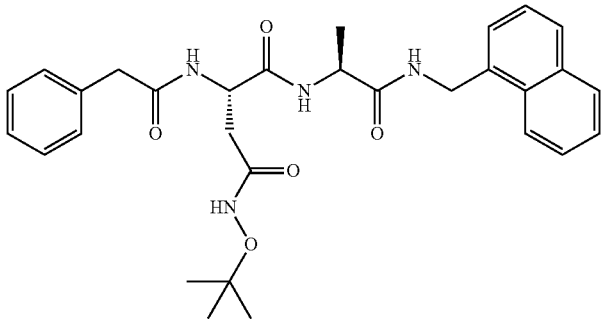 | 0.028 | 5.0 | 180 | 9.1 |
| DPLG-2143 | 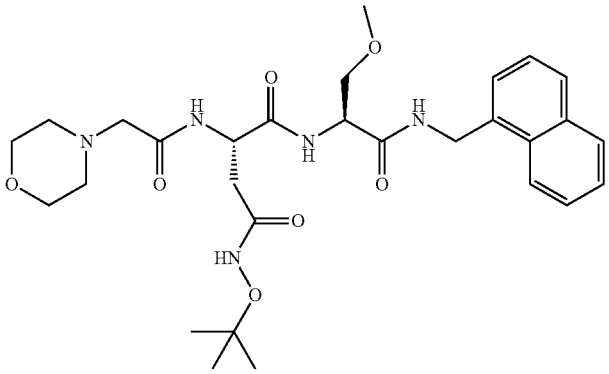 | 0.25 | 19.6 | 78 | >100 |
| DPLG-2144 | 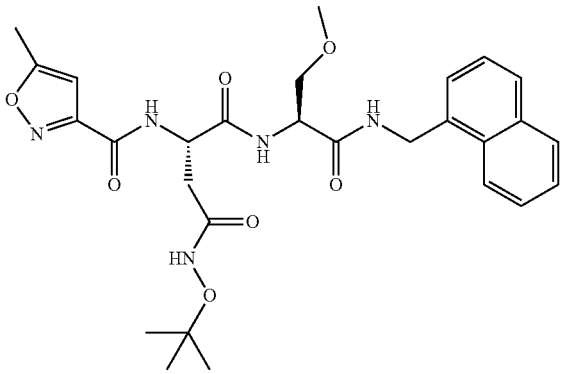 | 0.009 | 0.62 | 69 | 1.47 |
| DPLG-2150 | 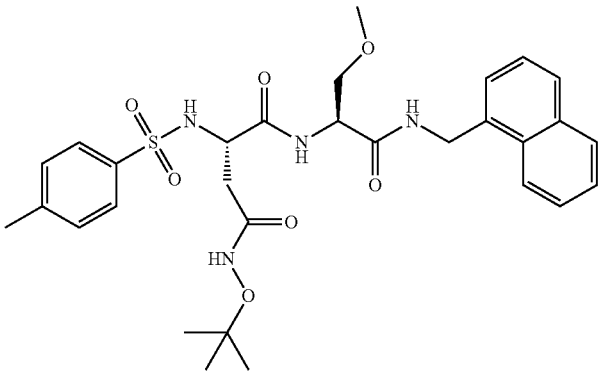 | 0.0044 | 0.61 | 139 | 0.8 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2160 | 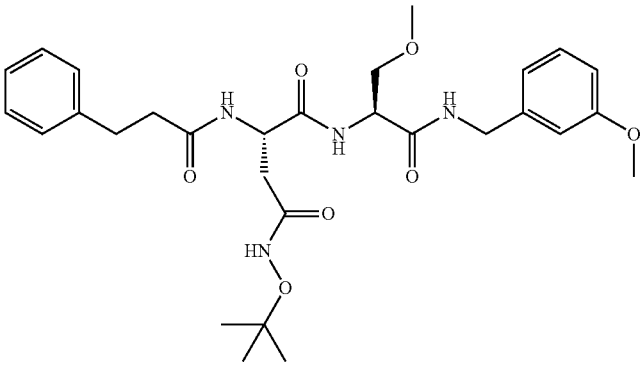 | 0.0094 | 0.098 | 10 | 0.05 |
| DPLG-2211 | 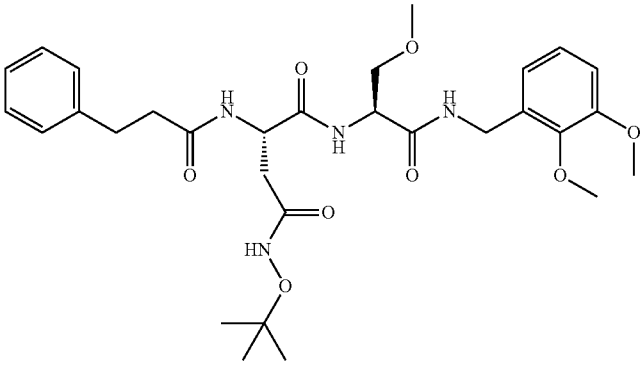 | 0.245 | 1.28 | 5 | 4.18 |
| DPLG-2219 | 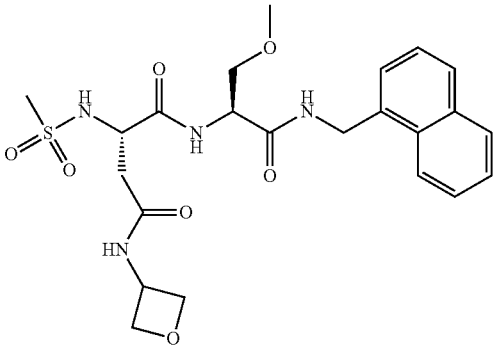 PKS2219 | 4.73 | >100 | >21 | >100 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2220 | 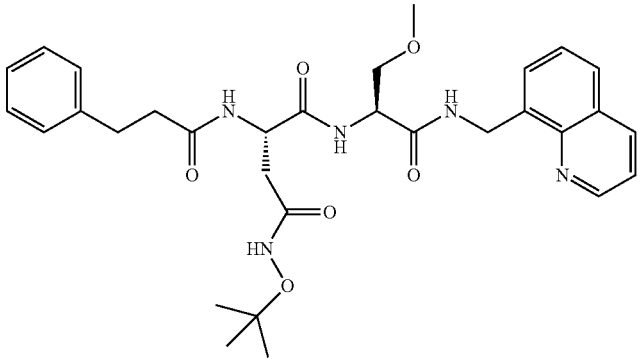 PKS2220 | 0.070 | 1.35 | 19 | 6.27 |
| DPLG-2224 | 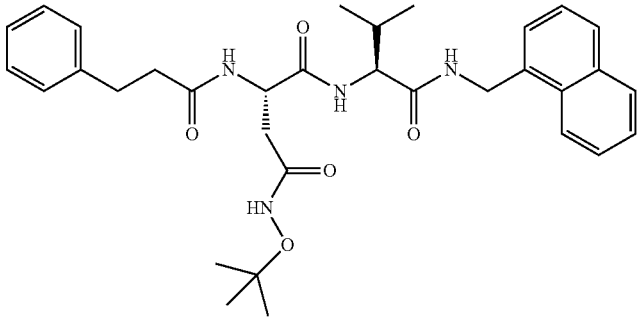 PKS2224 | 0.0043 | 0.228 | 53 | >100 |
| DPLG-2226 | 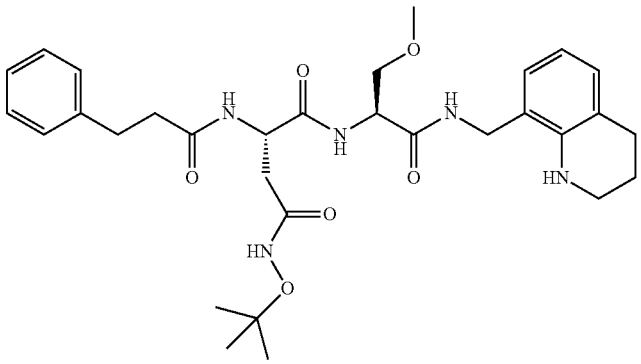 PKS2226 | 1.15 | 78.1 | 68 | >100 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2222 | 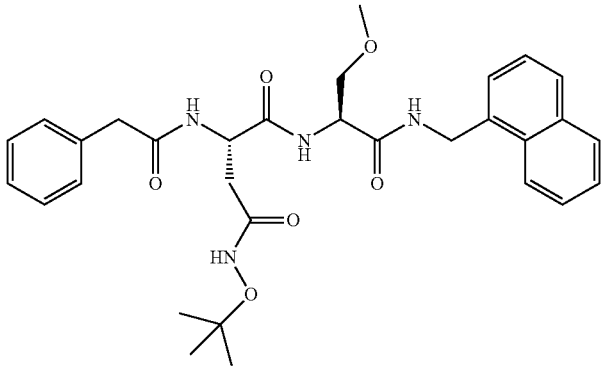 PKS2222 | 0.011 | 0.738 | 70 | >100 |
| DPLG-2223 | 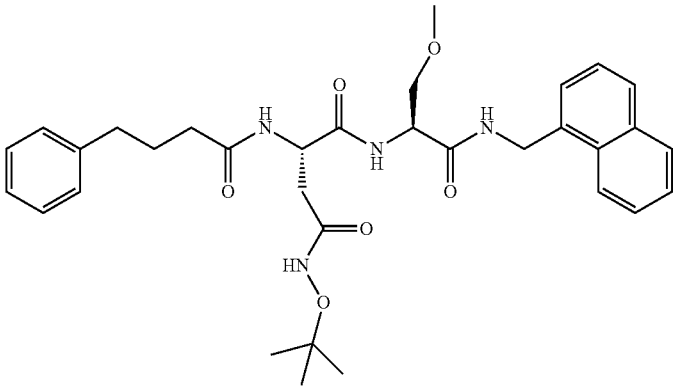 PKS2223 | 0.0065 | 0.767 | 118 | 4.47 |
| DPLG-2229 | 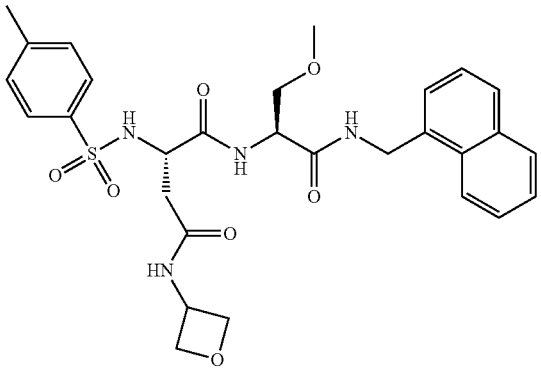 PKS2229 | 0.069 | 19.3 | 236 | >100 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2230 | 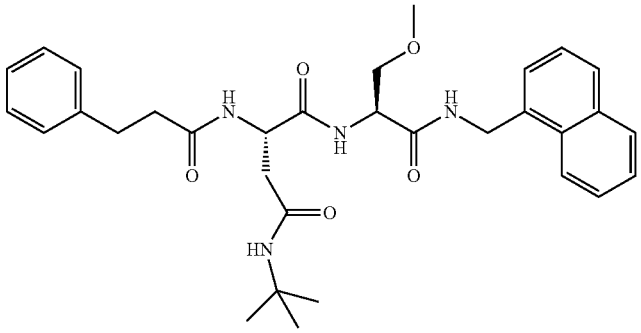 PKS2230 | 0.0055 | 0.498 | 90 | 1.11 |
| DPLG-2243 | 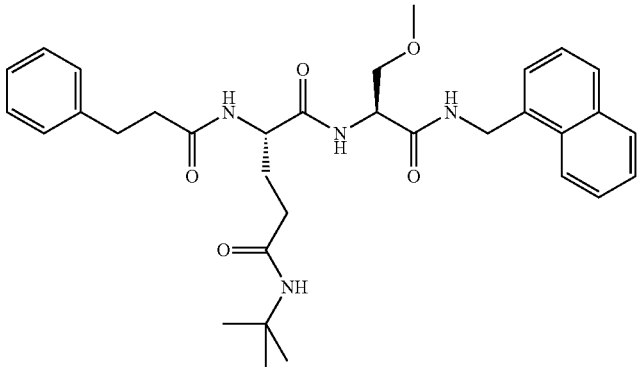 PKS2243 | 0.00012 | 0.0295 | 246 | 0.062 |
| DPLG-2244 | 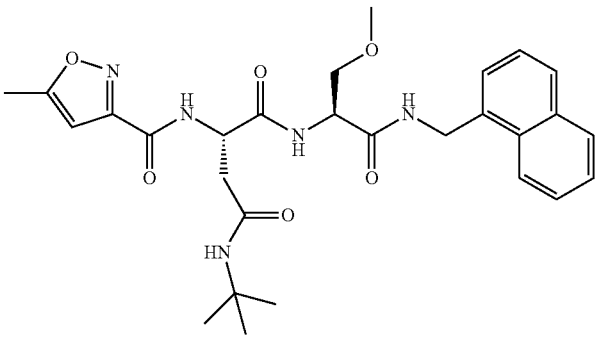 PKS2244 | 0.0125 | 0.82 | 66 | 2.20 |
| DPLG-2255 | 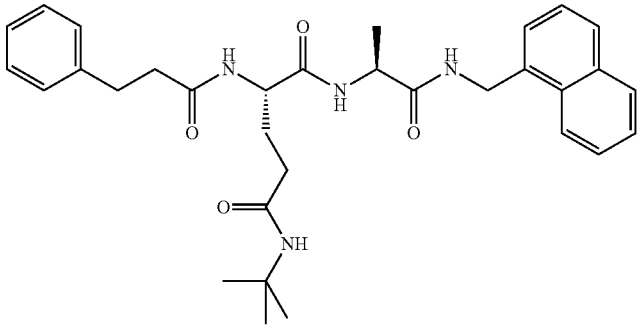 | 0.0015 | 0.12 | 80 | 0.028 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-2256 | 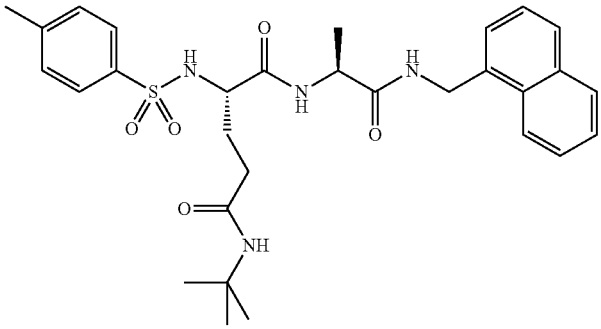 PKS2256 | 0.00009 | 0.031 | 343 | 0.034 |
| DPLG-3012 | 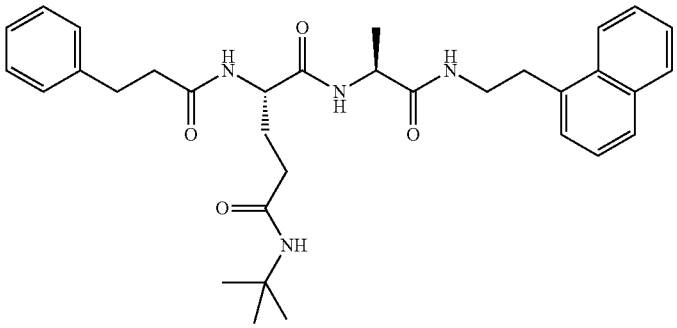 PKS3012 | 0.93 | 9.65 | 10.4 | 4.16 |
| DPLG-3013 | 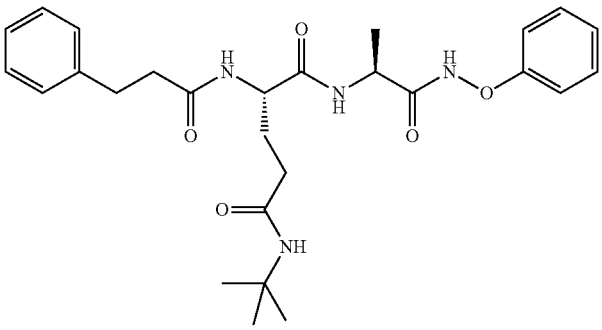 PKS3013 | 0.23 | 0.66 | 2.9 | 11.03 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-3014 | 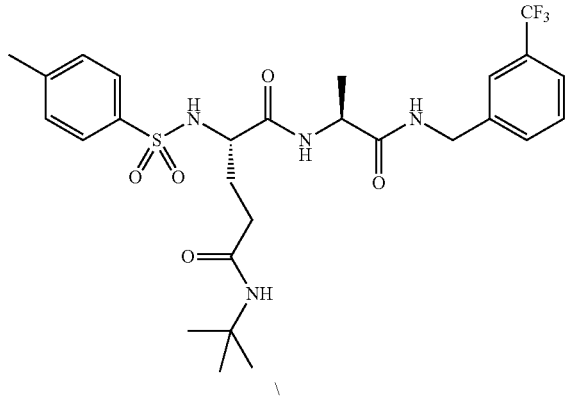 PKS3014 | 0.025 | 0.42 | 17 | 0.96 |
| DPLG-3016 | 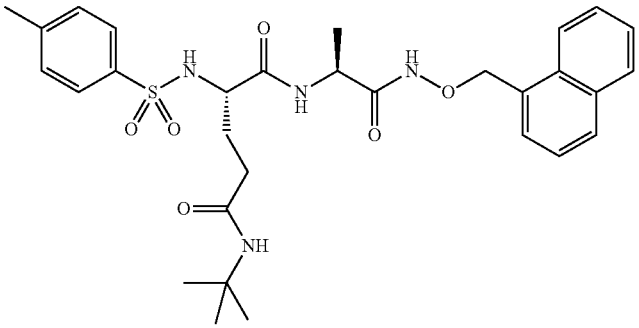 PKS3016 | 0.71 | 2.81 | 4 | 6.03 |
| DPLG-3017 | 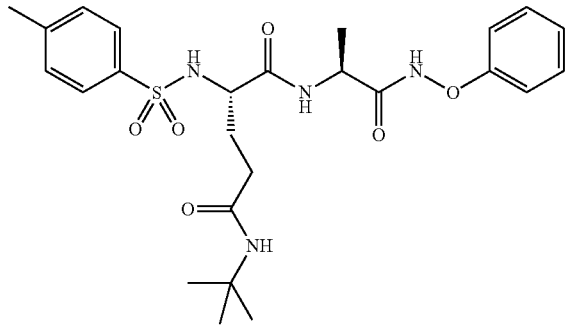 PKS3017 | 0.099 | 0.60 | 6 | 6.33 |
| DPLG-3053 | 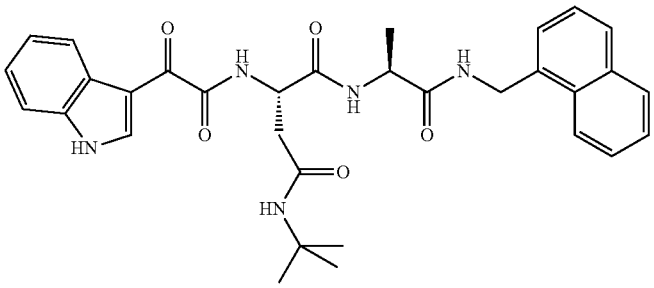 PKS3053 | 0.00075 | 0.075 | 100 | 0.22 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-3066 | 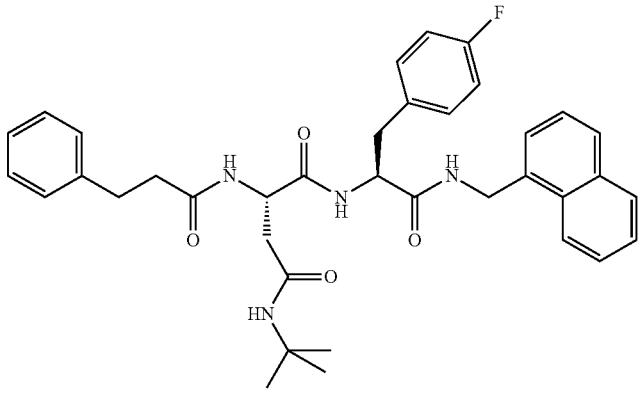 PKS3066 | 0.0053 | >100 | >19000 | 0.198 |
| DPLG-3083 | 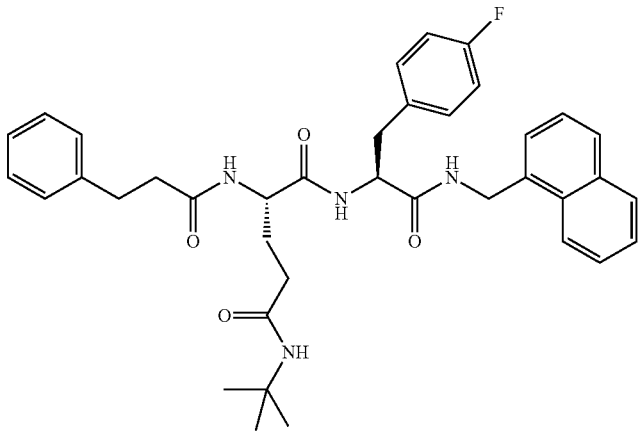 PKS3083 | 0.0033 | 0.3 | 90 | 1.20 |
| DPLG-3084 | 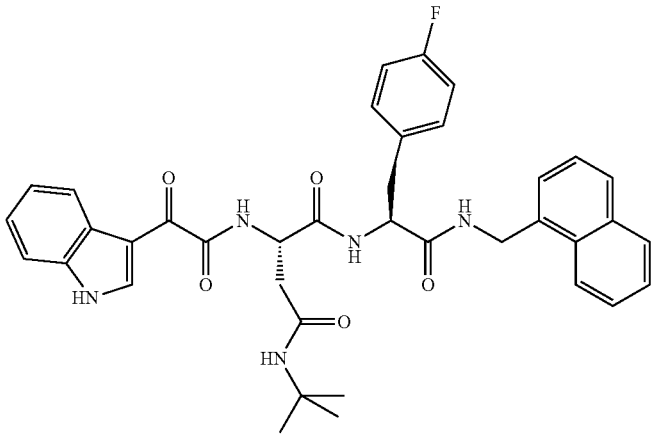 PKS3084 | 0.0014 | 0.037 | 26 | 0.084 |

TABLE 3-continued
Kinetic parameters and calculated logP for N,C-capped dipeptides
| ID | Structures | IC50 (μM) Hu i-20S | Hu c-20S | SI[a] | LD50 (μM) |
|---|---|---|---|---|---|
| DPLG-21033 | 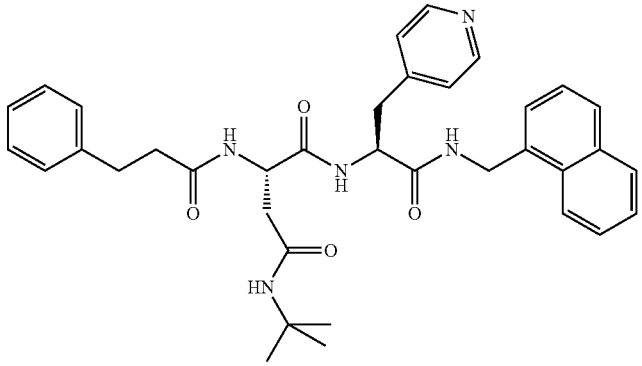 PKS21033 | 0.0053 | 0.438 | 83 | — |
| DPLG-21049 | 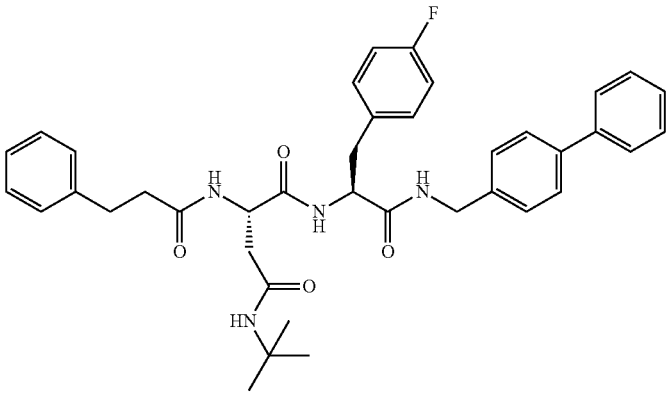 PKS21049 | 0.133 | 0.70 | 5 | — |
| DPLG-21050 | 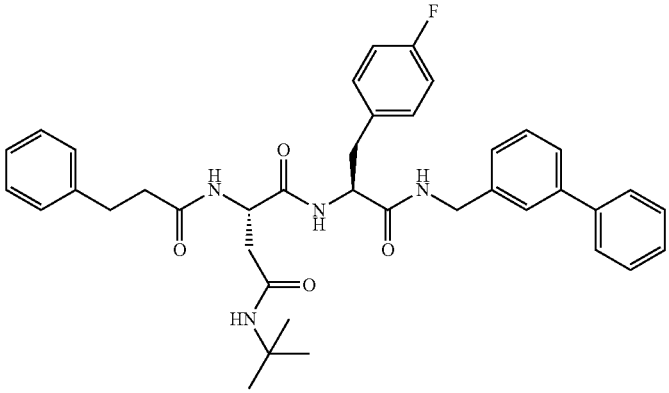 PKS21050 | 0.026 | >100 | >3846 | — |
[a]SI: selectivity index;
[b]logP: calculated with ChemDraw.

TABLE 4

IC50s of the N,C-dipeptides inhibiting proteasome inside the Karpas 1106p cells and their LD50 against Karpas.

| ID | Proteasome-glo ® β5-IC50 (μM) | LD50 (μM) Karpas |
|---|---|---|
| DPLG-3 | 0.11 | 2.04 |
| DPLG-2032 | >100 | >100 |
| DPLG-2058 | 0.009 | 34.4 |
| DPLG-2083 | 0.16 | 0.254 |
| DPLG-2086 | 0.005 | 0.46 |
| DPLG-2091 | 0.064 | 5.3 |
| DPLG-2106 | 1.46 | 7.8 |
| DPLG-2127 | 0.16 | >100 |
| DPLG-2130 | 1.13 | 67.8 |
| DPLG-2150 | 0.009 | 0.8 |
| DPLG-2160 | 0.019 | 0.05 |
| Bortezomib | 0.0006 | 0.0017 |

Karpas: subtype of lymphoma; Proteasome-glo ®: test of proteasome inhibition in intact cells.

Although the invention has been described in detail, for the purpose of illustration, it is understood that such detail is for that purpose and variations can be made therein by those skilled in the art without departing from the spirit and scope of the invention which is defined by the following claims.

What is claimed is:

1. A compound of Formula (Ia):

(Ia)

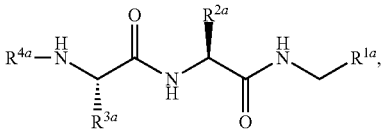

wherein $R^{1a}$ is selected from the group consisting of bicyclic aryl, monocyclic and bicyclic heteroaryl, and monocyclic and bicyclic non-aromatic heterocycle, wherein bicyclic aryl, monocyclic and bicyclic heteroaryl, and monocyclic and bicyclic non-aromatic heterocycle can be optionally substituted from 1 to 3 times with a substituent selected independently at each occurrence thereof from the group consisting of halogen, cyano, $C_{1-6}$ alkyl, and $C_{1-6}$ alkoxy;

$R^{2a}$ is selected from the group consisting of $C_{1-6}$ alkyl, —$CH_2OC_{1-6}$ alkyl, $CH_2Ar$, and heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^{3a}$ is selected from the group consisting of —$CH_2OC_{1-6}$ alkyl, —$(CH_2)_mC(O)NHR^{5a}$, and —$CH_2C(O)R^{5a}$;

$R^{4a}$ is selected from the group consisting of —C(O)$(CH_2)_n$ Ph, —$C(O)CH_2NR^{6a}R^{7a}$, —$SO_2Ar$, —$SO_2C_{1-6}$ alkyl, —C(O)$(CH_2)_n$Het, —$C(O)C_{1-6}$ alkyl, —C(O)$CF_3$, heteroaryl, and —$(CH_2)_nNR^{6a}R^{7a}$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^{5a}$ is selected from the group consisting of $C_{1-6}$ alkyl, $C_{1-6}$ alkoxy, non-aromatic heterocycle, —$NR^{6a}R^{7a}$, and —$CR^{8a}R^{9a}$;

$R^{6a}$, $R^{7a}$, $R^{8a}$, and $R^{9a}$ are each independently selected from the group consisting of H, $C_{1-6}$ alkyl, and —$(CH_2)_k$ OH;

or $R^{6a}$ and $R^{7a}$ are taken together with the nitrogen to which they are attached to form a piperidine, pyrrolidine, azepane, azetidine, or morpholine ring;

or $R^{8a}$ and $R^{9a}$ are taken together with the carbon to which they are attached to form an oxetane ring;

m is 1 or 2;

n is 0, 1, 2, or 3; and k is 1, 2, or 3.

2. A pharmaceutical composition comprising a therapeutically effective amount of the compound according to claim 1 and a pharmaceutically acceptable carrier.

3. The compound according to claim 1, wherein m is 1.

4. The compound according to claim 1, wherein m is 2.

5. The compound according to claim 1, wherein $R^{5a}$ is selected from the group consisting of $C_{1-6}$ alkyl, $C_{1-6}$ alkoxy, non-aromatic heterocycle, and —$CR^{8a}R^{9a}$.

6. The compound according to claim 3, wherein $R^{1a}$ is selected from the group consisting of

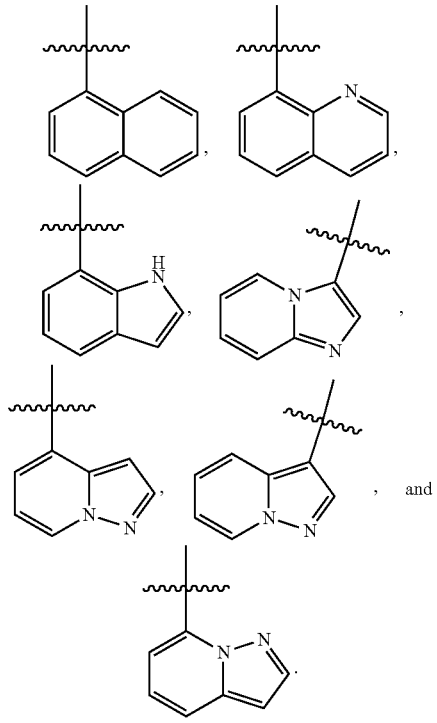

7. The compound according to claim 3, wherein $R^{2a}$ is selected from the group consisting of Me, —$CH_2OMe$, and

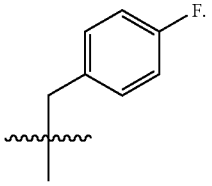

8. The compound according to claim 3, wherein $R^{3a}$ is selected from the group consisting of —$CH_2OMe$,

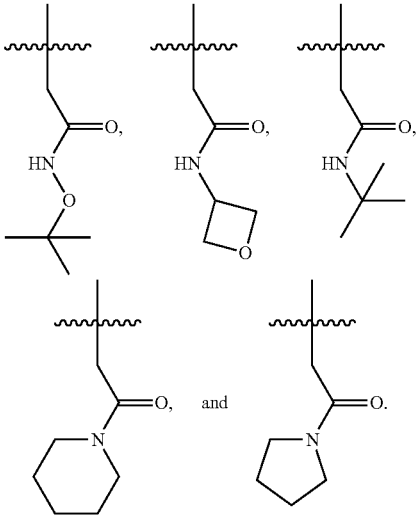
9. The compound according to claim 3, wherein $R^{4a}$ is selected from the group consisting of trifluoroacetyl,
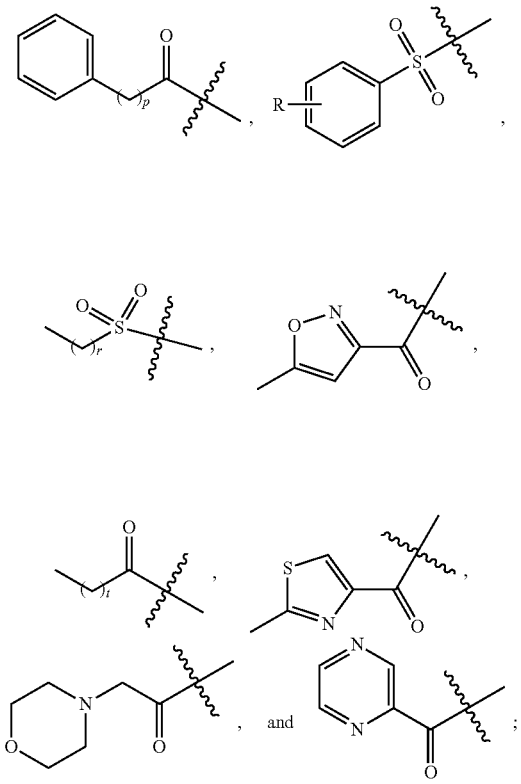
p is 0, 1, 2, or 3;
r is 0, 1, 2, 3, 4, or 5;
t is 0, 1, 2, 3, or 4; and
R is selected from the group consisting of H, halogen, cyano, $C_{1-6}$ alkyl, and $C_{1-6}$ alkoxy.
10. The compound according to claim 3, wherein the compound has a structure selected from the group consisting of:
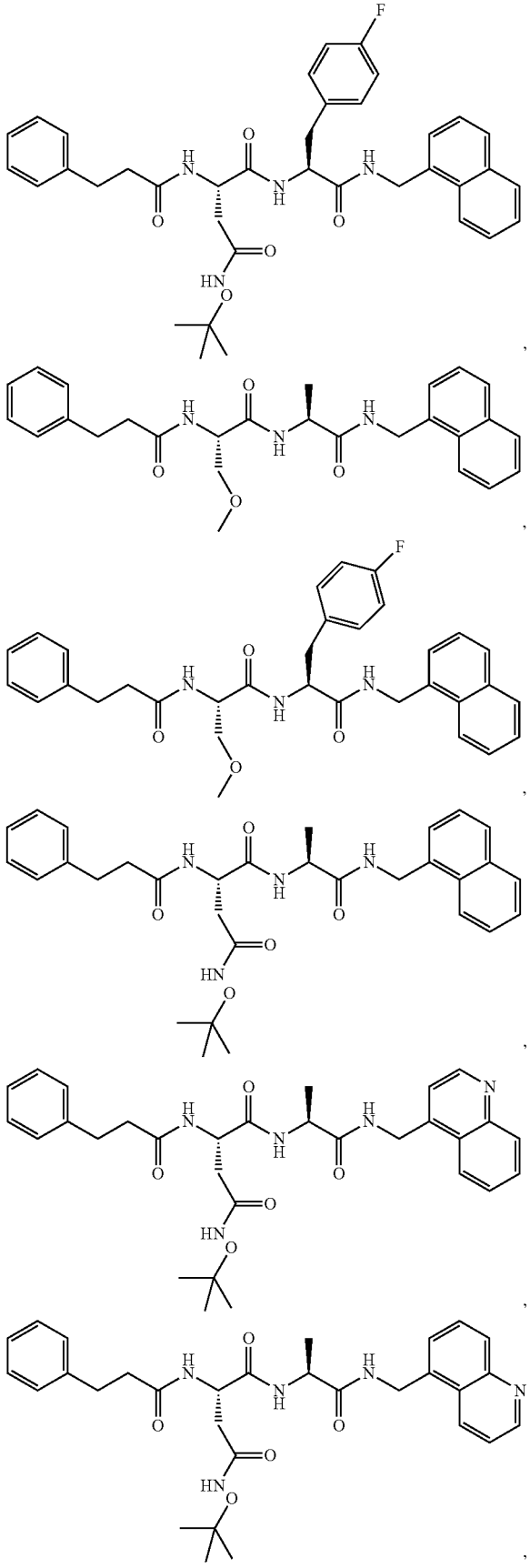

-continued
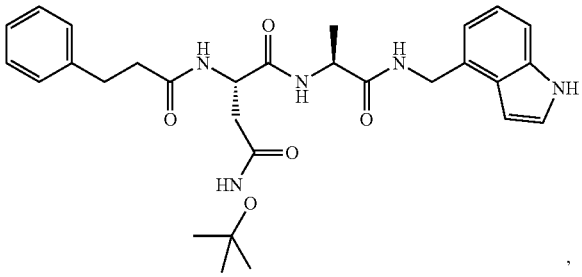
,
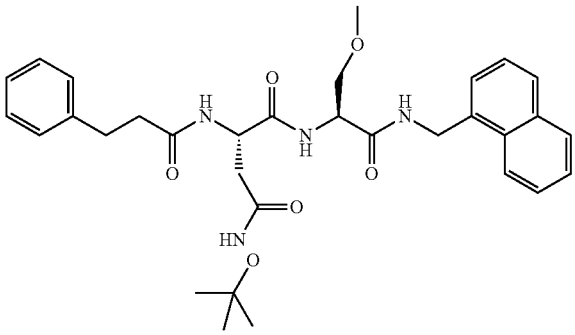
,
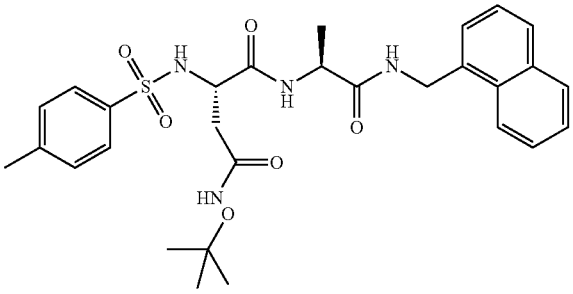
,
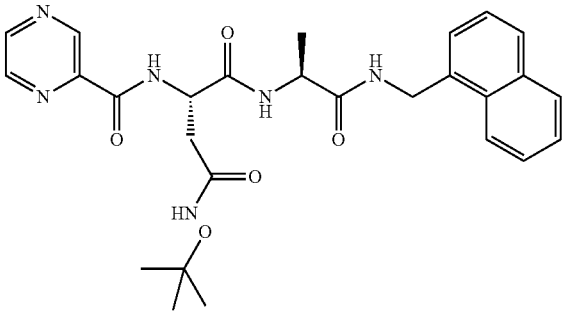
,
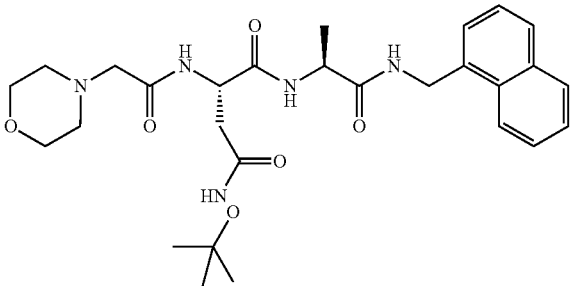
,
-continued
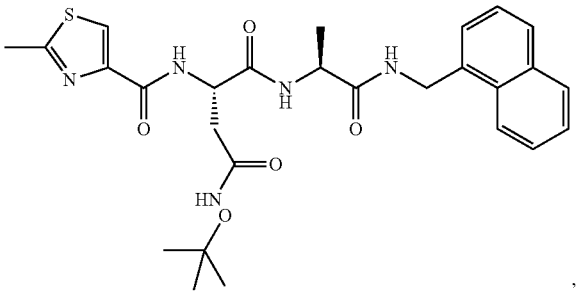
,
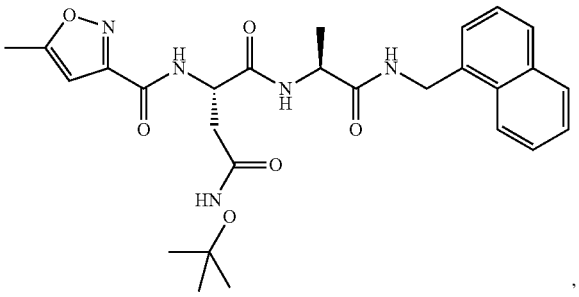
,
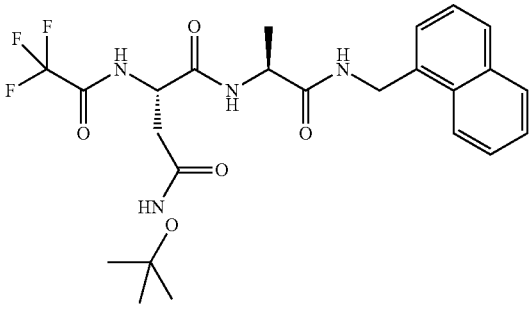
,
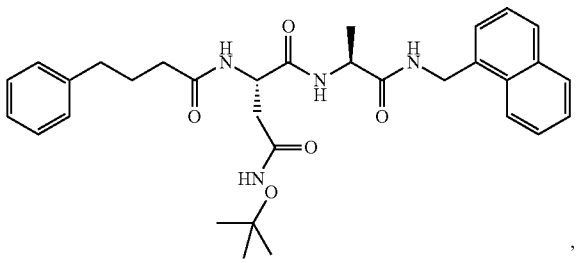
,
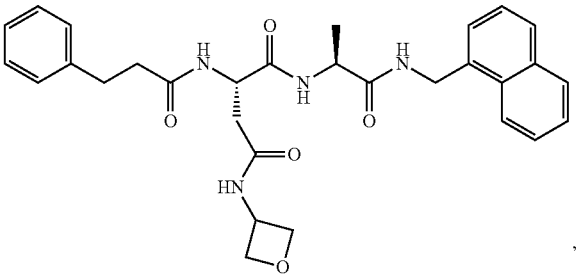
, -continued

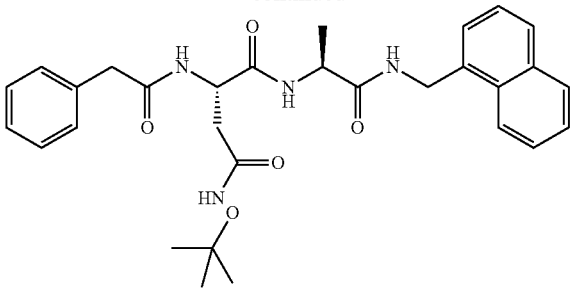

,

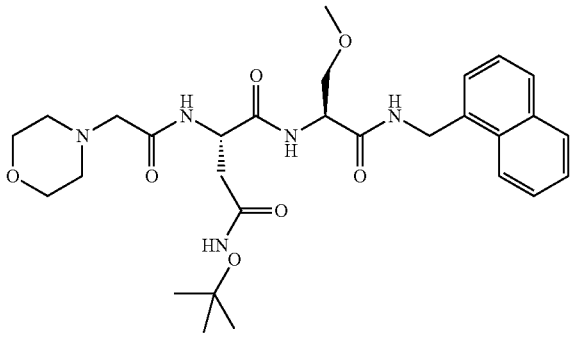

,

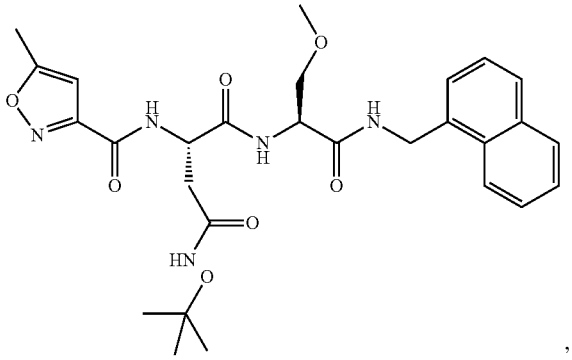

, and

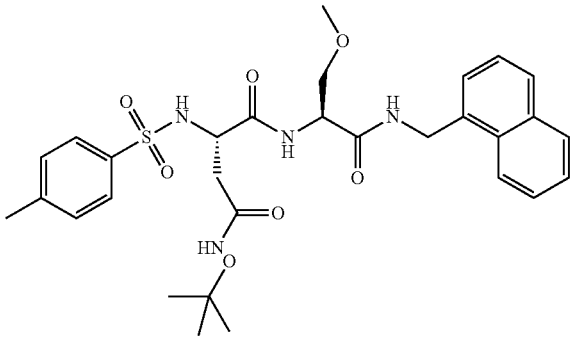

.

11. A method of treating cancer, immunologic disorders, autoimmune disorders, neurodegenerative disorders, or inflammatory disorders in a subject or for providing immunosuppression for transplanted organs or tissues in a subject, said method comprising:

administering to the subject in need thereof a compound of the Formula (Ia):

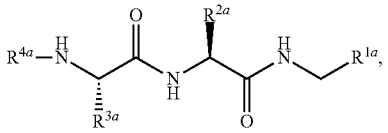

(Ia)

wherein $R^{1a}$ is selected from the group consisting of bicyclic aryl, monocyclic and bicyclic heteroaryl, and monocyclic and bicyclic non-aromatic heterocycle, wherein bicyclic aryl, monocyclic and bicyclic heteroaryl, and monocyclic and bicyclic non-aromatic heterocycle can be optionally substituted from 1 to 3 times with a substituent selected independently at each occurrence thereof from the group consisting of halogen, cyano, $C_{1-6}$ alkyl, and $C_{1-6}$ alkoxy;

$R^{2a}$ is selected from the group consisting of $C_{1-6}$ alkyl, —$CH_2OC_{1-6}$ alkyl, —$CH_2Ar$, and heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^{3a}$ is selected from the group consisting of —$CH_2OC_{1-6}$ alkyl, —$CH_mC(O)NHR^{5a}$, and —$CH_2C(O)R^{5a}$;

$R^{4a}$ is selected from the group consisting of —$C(O)(CH_2)_n$ Ph, —$C(O)CH_2NR^{6a}R^{7a}$, —$SO_2Ar$, —$SO_2C_{1-6}$ alkyl, —$C(O)(CH_2)_n$Het, —$C(O)C_{1-6}$ alkyl, —$C(O)CF_3$, heteroaryl, and —$(CH_2)_nNR^{6a}R^{7a}$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^{5a}$ is selected from the group consisting of $C_{1-6}$ alkyl, $C_{1-6}$ alkoxy, non-aromatic heterocycle, —$NR^{6a}R^{7a}$, and —$CR^{8a}R^{9a}$;

$R^{6a}$, $R^{7a}$, $R^{8a}$, and $R^{9a}$ are each independently selected from the group consisting of H, $C_{1-6}$ alkyl, and —$(CH_2)_kOH$;

or $R^{6a}$ and $R^{7a}$ are taken together with the nitrogen to which they are attached to form a piperidine, pyrrolidine, azepane, azetidine, or morpholine ring;

or $R^{8a}$ and $R^{9a}$ are taken together with the carbon to which they are attached to form an oxetane ring;

m is 1 or 2;

n is 0, 1, 2, or 3; and k is 1, 2, or 3.

12. The method of claim 11, wherein m is 1.

13. The method of claim 11, wherein m is 2.

14. The method of claim 11, wherein $R^{5a}$ is selected from the group consisting of $C_{1-6}$ alkyl, $C_{1-6}$ alkoxy, non-aromatic heterocycle, and —$CR^{8a}R^{9a}$.

15. The method of claim 12, wherein $R^{1a}$ is selected from the group consisting of

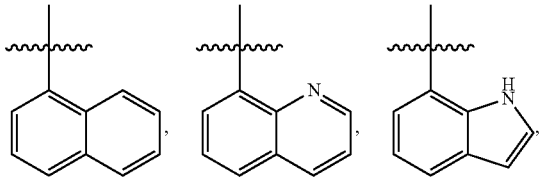

-continued

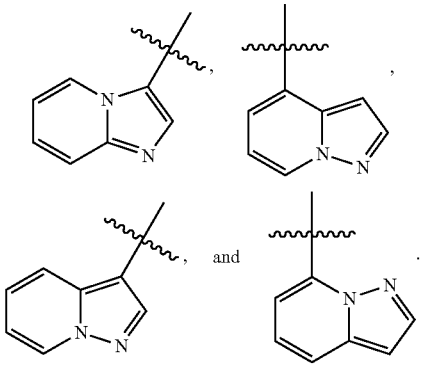

16. The method of claim 12, wherein $R^{2a}$ is selected from the group consisting of Me, —$CH_2OMe$, and

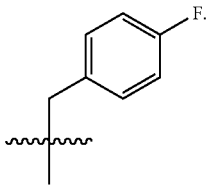

17. The method of claim 12, wherein $R^{3a}$ is selected from the group consisting of —$CH_2OMe$,

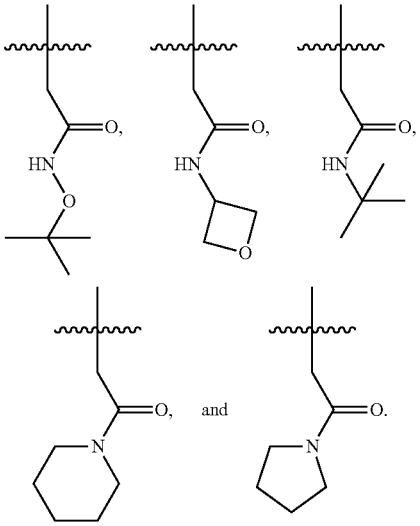

18. The method of claim 12, wherein $R^{4a}$ is selected from the group consisting of trifluoroacetyl,

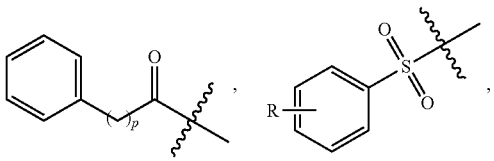

-continued

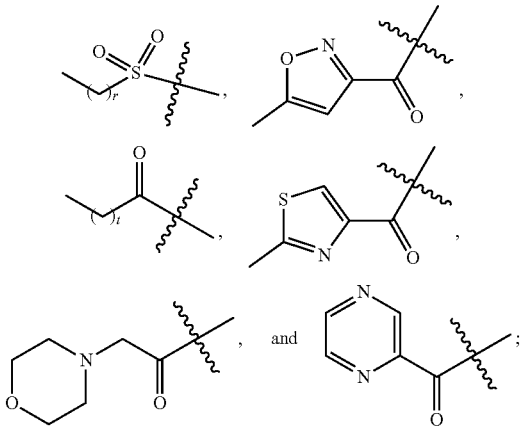

p is 0, 1, 2, or 3;

r is 0, 1, 2, 3, 4, or 5;

t is 0, 1, 2, 3, or 4; and

R is selected from the group consisting of H, halogen, cyano, $C_{1-6}$ alkyl, and $C_{1-6}$ alkoxy.

19. The method of claim 12, wherein the compound of Formula (I) is selected from the group consisting of:

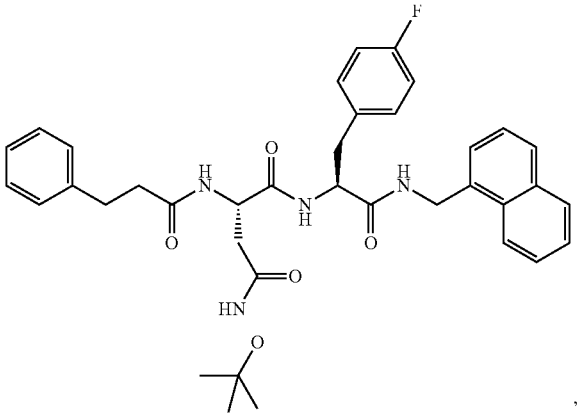

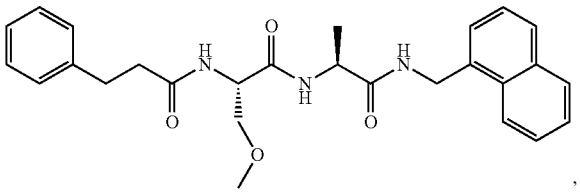

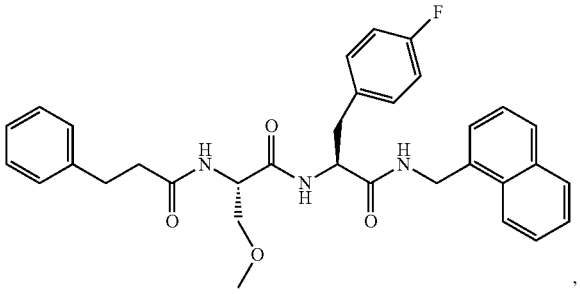

-continued
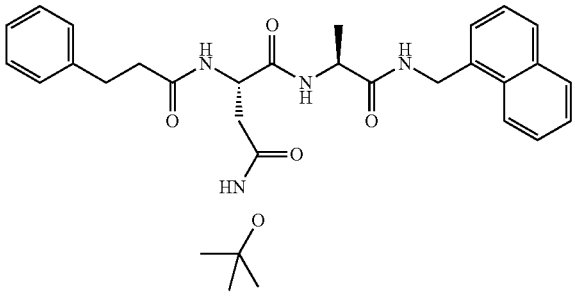
,
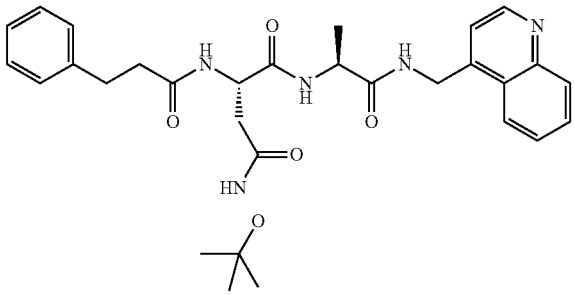
,
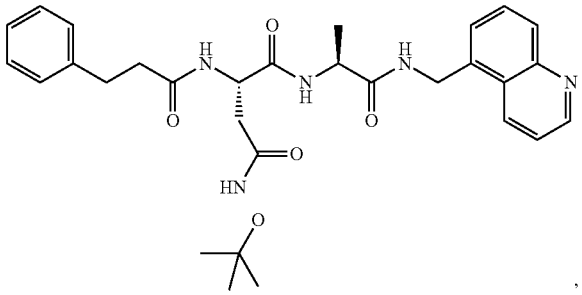
,
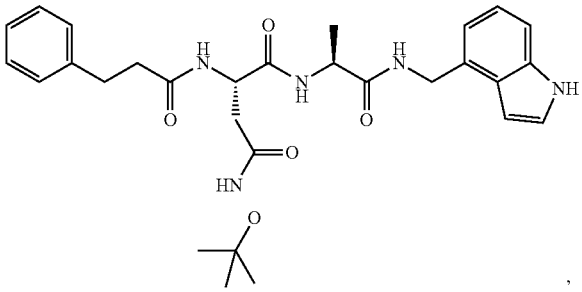
,
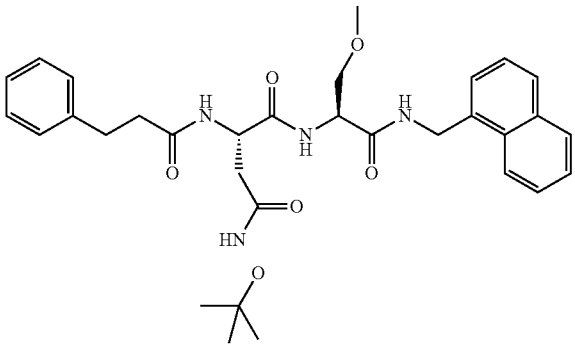
,
-continued
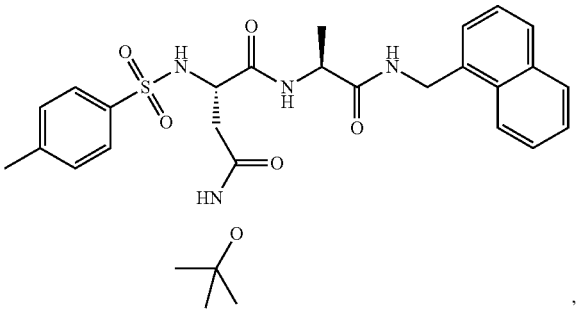
,
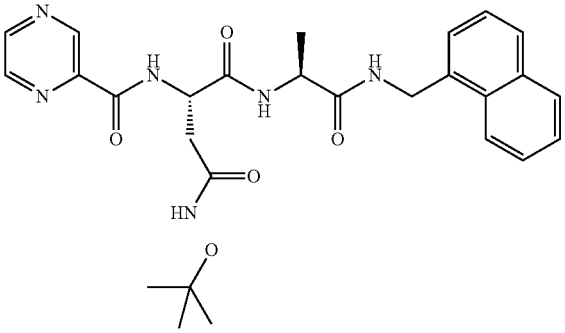
,
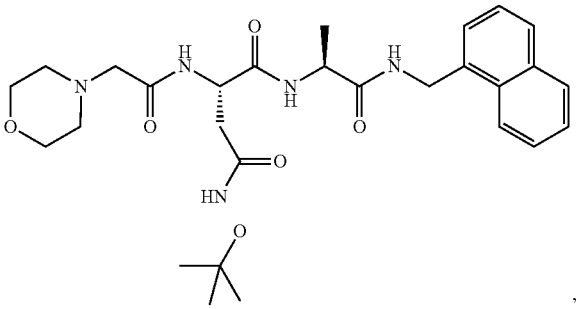
,
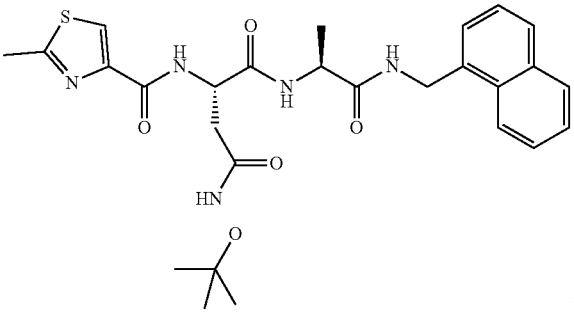
,
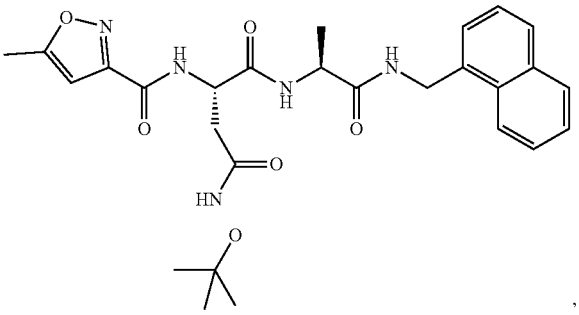
, -continued

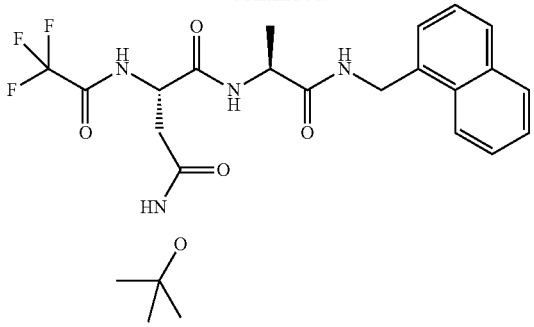

,

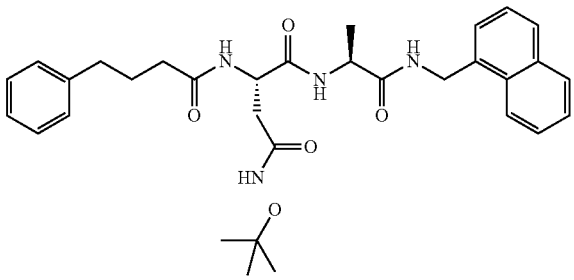

,

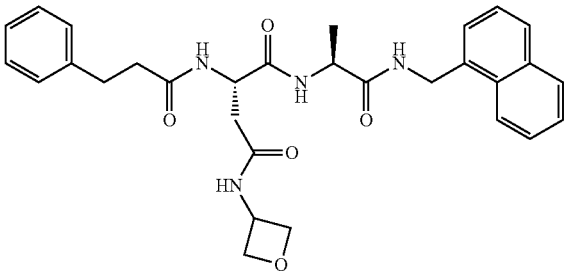

,

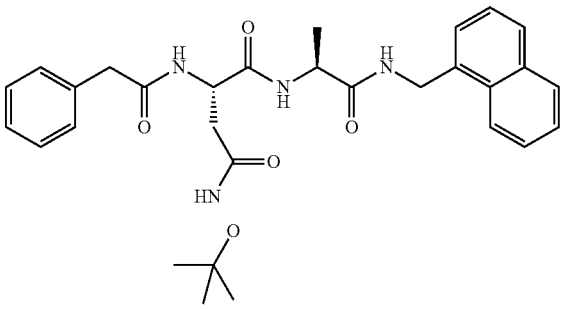

,

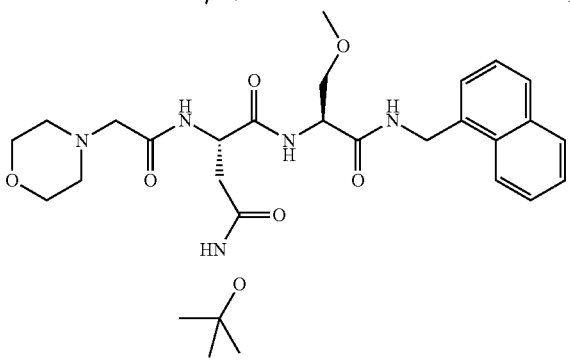

,

-continued

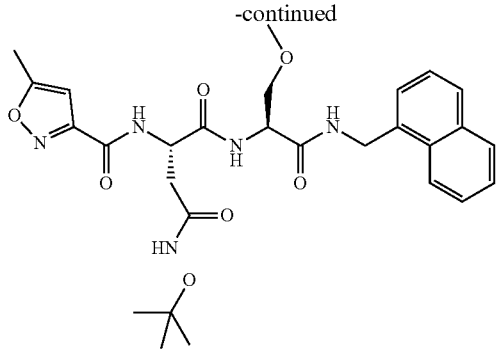

, and

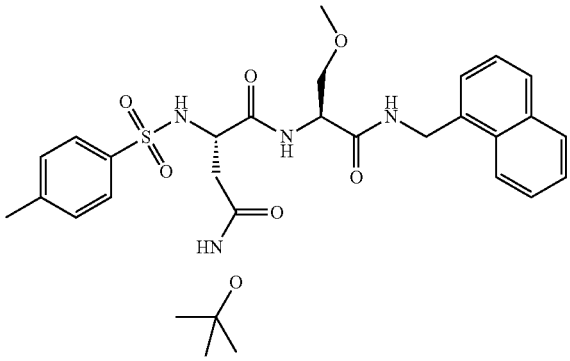

.

20. The method of claim 12, wherein an autoimmune disorder is treated, said autoimmune disorder being selected from the group consisting of arthritis, colitis, and lupus.

21. The method of claim 12, wherein immunosuppression is provided for transplanted organs or tissues, said immunosuppression being used to prevent transplant rejection.

22. The method of claim 12, wherein an inflammatory disorder is treated, said inflammatory disorder being Crohn's disease.

23. The method of claim 12, wherein cancer is treated, said cancer being selected from the group consisting of neoplastic disorders, hematologic malignancies, and lymphocytic malignancies.

*24. A compound of Formula (I):*

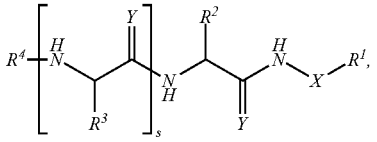

(I)

*wherein*

*$R^1$ is bicyclic aryl optionally substituted 1 time with a substituent selected independently at each occurrence thereof from the group consisting of halogen and $C_{1-6}$ alkyl;*

*$R^2$ is selected from the group consisting of $C_{1-6}$ alkyl, —$CH_2OC_{1-6}$ alkyl, and —$CH_2Ar$, wherein aryl (Ar) can be optionally substituted 1 time with halogen;*

*$R^3$ is independently selected at each occurrence thereof from the group consisting of —$CH_2OC_{1-6}$ alkyl and —$(CH_2)_mC(O)NHR^5$;*

*$R^4$ is selected from the group consisting of —$C(O)(CH_2)_nPh$, —$SO_2Ar$, —$SO_2C_{1-6}$ alkyl, —$C(O)(CH_2)_nHet$, and —$C(O)C(O)Het$, wherein aryl (Ar) and heteroaryl (Het) can be optionally substituted 1 time with $C_{1-6}$ alkyl;*

$R^5$ is selected from the group consisting of $C_{1-4}$ alkyl and —$CR^8R^9$;

$R^8$ and $R^9$ are taken together with the carbon to which the are attached to form an oxetane ring;

X is —$(CH_2)_q$—,

Y is O;

m is 1 or 2, n is 0 or 2;

q is 1; and s is 1.

25. The compound according to claim 24, wherein $R^1$ is

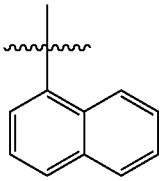

optionally substituted 1 time with a substituent selected independently at each occurrence thereof from the group consisting of halogen and $C_{1-6}$ alkyl.

26. The compound according to claim 24, wherein $R^2$ is selected from the group consisting of Me, —$CH_2OMe$, and

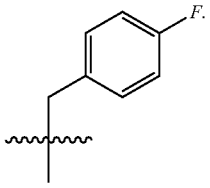

27. The compound according to claim 24, wherein $R^3$ is selected from the group consisting of

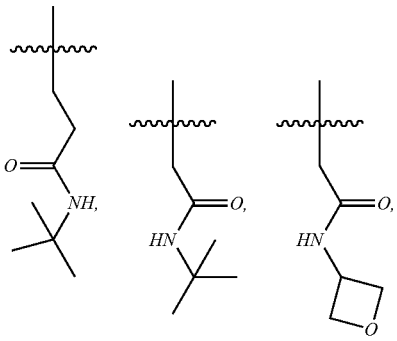

and —$CH_2OMe$.

28. The compound according to claim 24, wherein $R^4$ is selected from the group consisting of

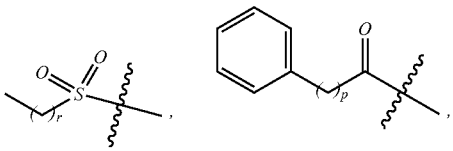

-continued

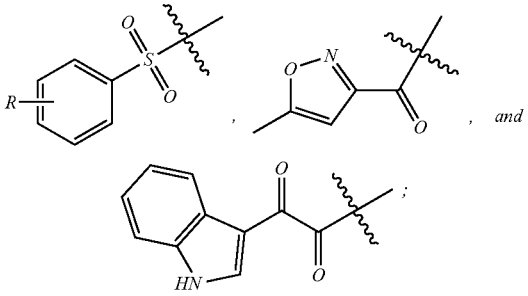

p is 2;

r is 0; and

R is $C_{1-6}$ alkyl.

29. The compound according to claim 24, wherein the compound has a structure selected from the group consisting of:

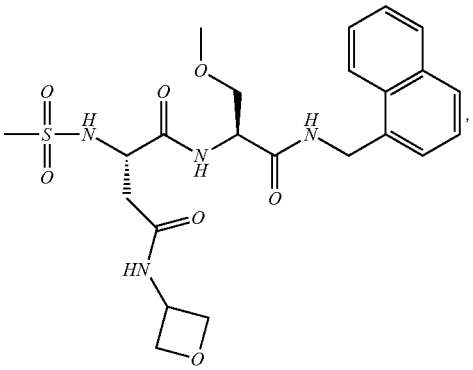

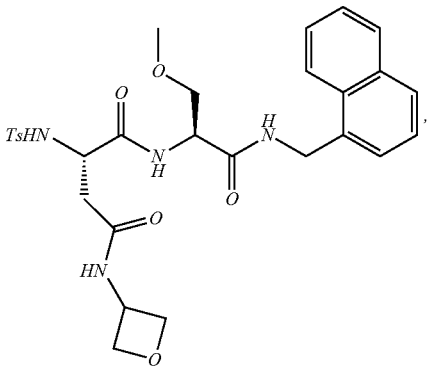

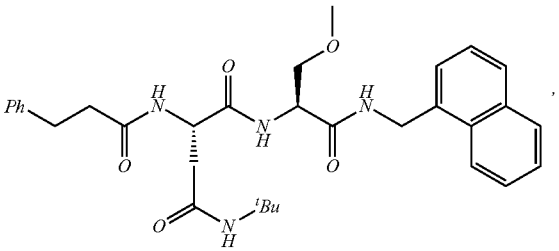

-continued
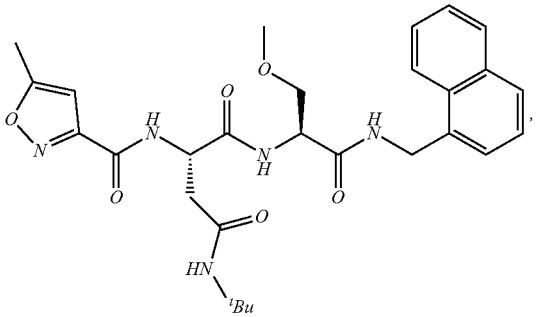
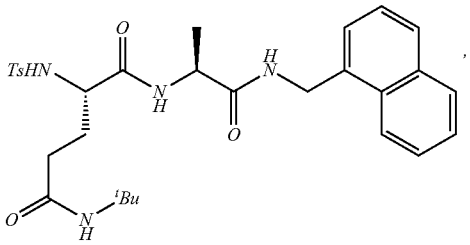
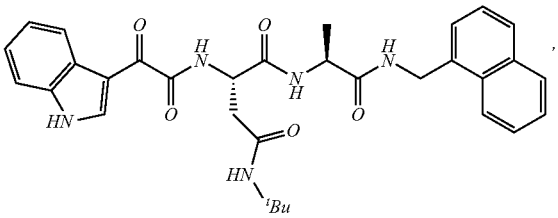
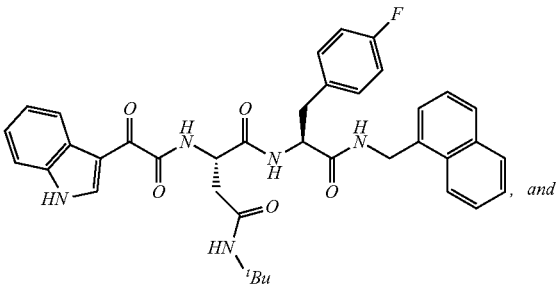
and
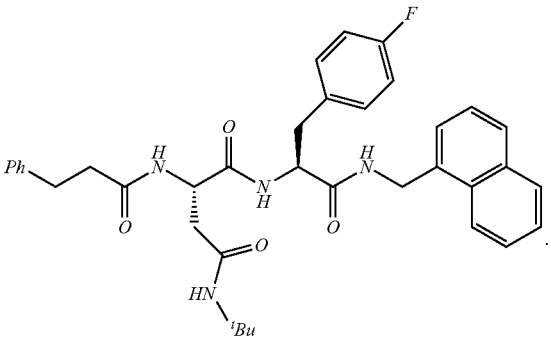
30. The compound according to claim 24, wherein the compound has a structure of:
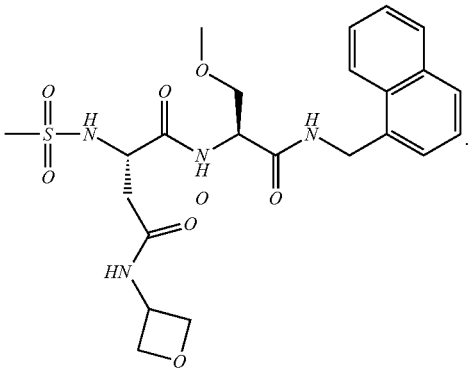
31. The compound according to claim 24, wherein the compound has a structure of:
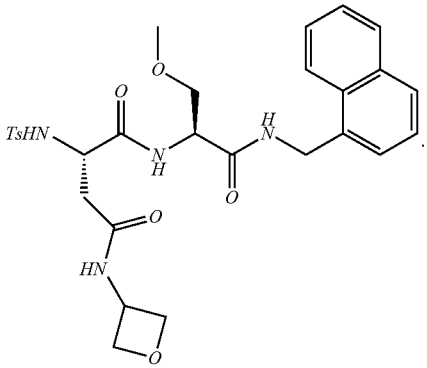
32. The compound according to claim 24, wherein the compound has a structure of:
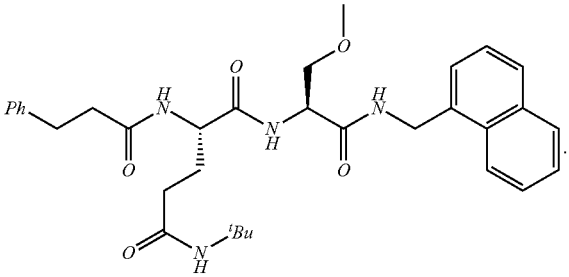
33. The compound according to claim 24, wherein the compound has a structure of:

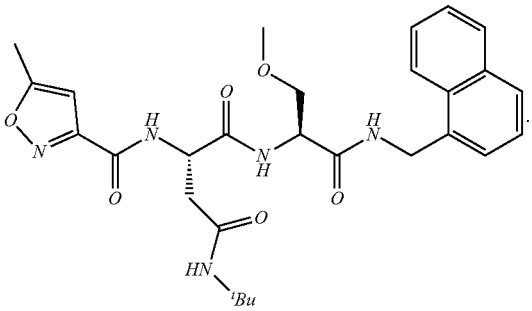

34. The compound according to claim 24, wherein the compound has a structure of:

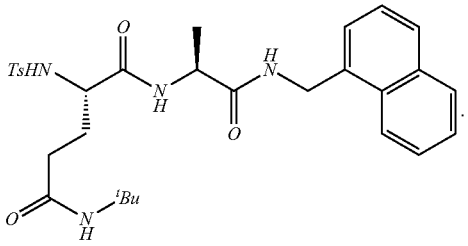

35. The compound according to claim 24, wherein the compound has a structure of:

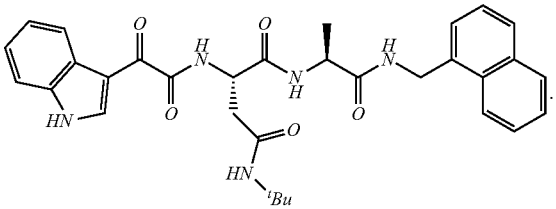

36. The compound according to claim 24, wherein the compound has a structure of:

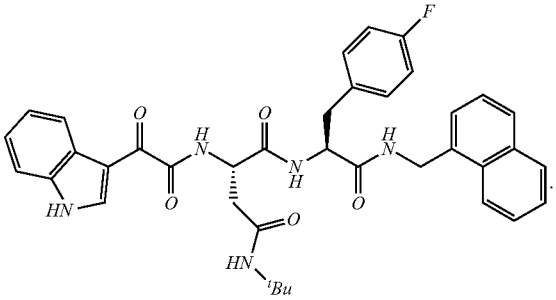

37. The compound according to claim 24, wherein the compound has a structure of:

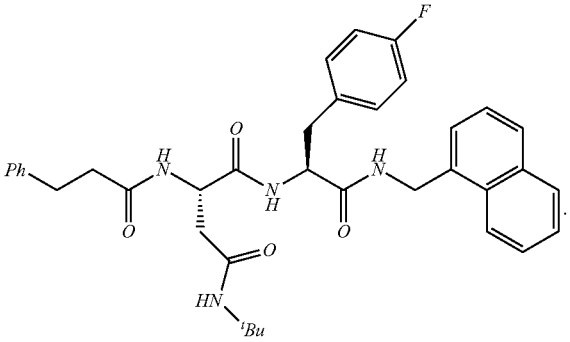

38. The compound according to claim 24, wherein $R^1$ is a bicyclic aryl substituted 1 time with fluoride, $R^2$ is $—CH_2OMe$, $R^3$ is

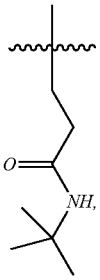

$R^4$ is

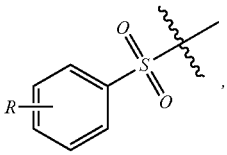

and R is Me.

39. The compound according to claim 24, wherein $R^1$ is a bicyclic aryl substituted 1 time with fluoride, $R^2$ is $—CH_2OMe$, $R^3$ is

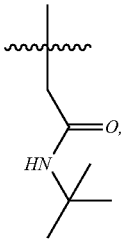

$R^4$ is

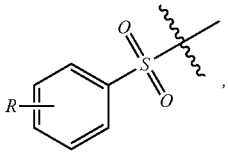

and R is Me.

40. The compound according to claim 24, wherein $R^1$ is a bicyclic aryl substituted 1 time with fluoride, $R^2$ is —$CH_2OMe$, $R^3$ is

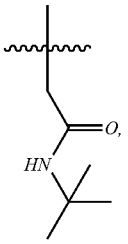

and $R^4$ is

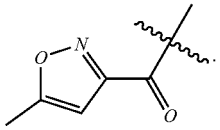

41. The compound according to claim 24, wherein $R^1$ is a bicyclic aryl substituted 1 time with fluoride, $R^2$ is Me, $R^3$ is

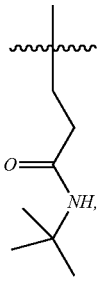

and $R^4$ is

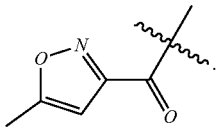

42. The compound according to claim 24, wherein $R^1$ is a bicyclic aryl substituted 1 time with fluoride, $R^2$ is —$CH_2OMe$, $R^3$ is

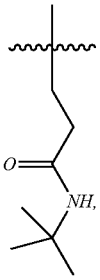

and $R^4$ is

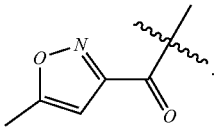

43. The compound according to claim 24, wherein $R^1$ is a bicyclic aryl substituted 1 time with fluoride, $R^2$ is Me, $R^3$ is

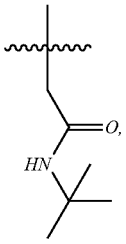

and $R^4$ is

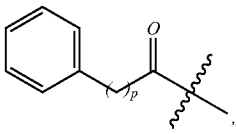

and p is 2.

44. A method of treating cancer, immunologic disorders, autoimmune disorders, neurodegenerative disorders, or inflammatory disorders in a subject or for providing immunosuppression for transplanted organs or tissues in a subject, said method comprising administering to the subject in need thereof a compound of the Formula (I):

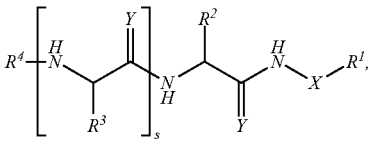

(I)

*wherein*

$R^1$ *is bicyclic aryl optionally substituted 1 time with a substituent selected independently at each occurrence thereof from the group consisting of halogen and* $C_{1-6}$ *alkyl;*

$R^2$ *is selected from the group consisting of* $C_{1-6}$ *alkyl,* $—CH_2OC_{1-6}$ *alkyl, and* $—CH_2Ar$*, wherein aryl (Ar) can be optionally substituted 1 time with halogen;*

$R^3$ *is independently selected at each occurrence thereof from the group consisting of* $—CH_2OC_{1-6}$ *alkyl and* $—(CH_2)_mC(O)NHR^5$*;*

$R^4$ *is selected from the group consisting of* $—C(O)(CH_2)_nPh$*,* $—SO_2Ar$*,* $—SO_2C_{1-6}$ *alkyl,* $—C(O)(CH_2)_nHet$*, and* $—C(O)C(O)Het$*, wherein aryl (Ar) and heteroaryl (Het) can be optionally substituted 1 time with* $C_{1-6}$ *alkyl;*

$R^5$ *is selected from the group consisting of* $C_{1-4}$ *alkyl and* $—CR^8R^9$*;*

$R^8$ *and* $R^9$ *are taken together with the carbon to which they are attached to form an oxetane ring;*

*X is* $—(CH_2)_q—$*;*

*Y is O;*

*m is 1 or 2;*

*n is 0 or 2;*

*q is 1; and*

*s is 1.*

*45. The method of claim 44, wherein* $R^1$ *is*

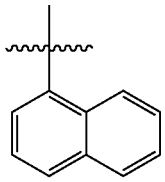

*optionally substituted 1 time with a substituent selected independently at each occurrence thereof from the group consisting of halogen and* $C_{1-6}$ *alkyl.*

*46. The method of claim 44, wherein* $R^2$ *is selected from the group consisting of Me,* $—CH_2OMe$*, and*

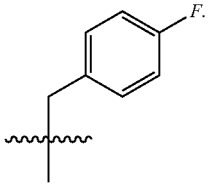

*47. The method of claim 44, wherein* $R^3$ *is selected from the group consisting of*

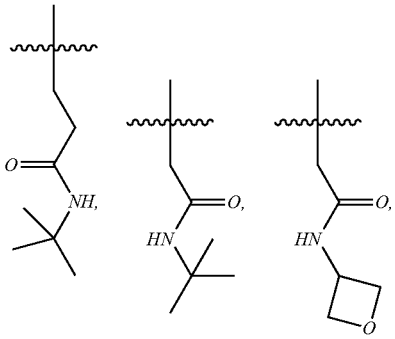

*and* $—CH_2OMe$*.*

*48. The method of claim 44, wherein* $R^4$ *is selected from the group consisting of*

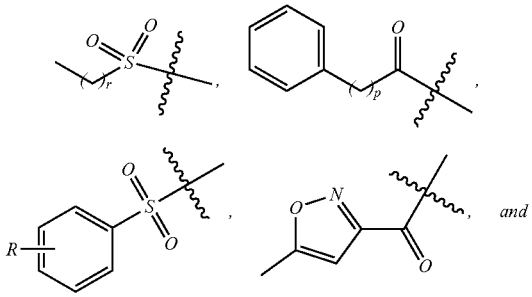

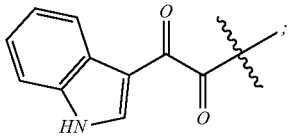

*p is 2;*

*r is 0; and*

*R is* $C_{1-6}$ *alkyl.*

*49. The method of claim 44, wherein the compound has a structure selected from the group consisting of:*

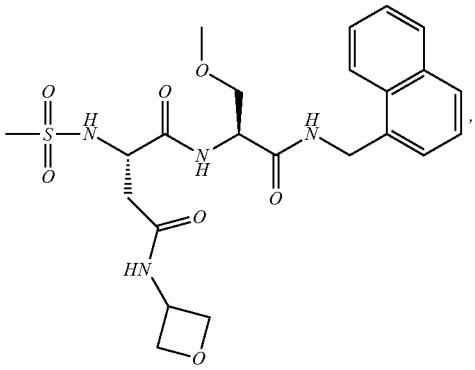

-continued
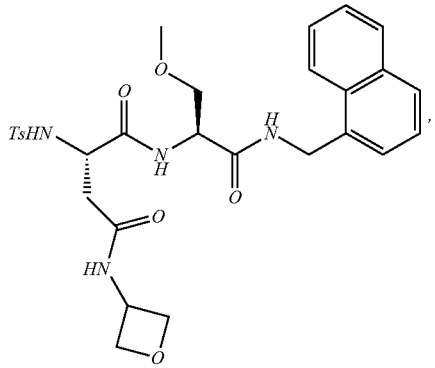
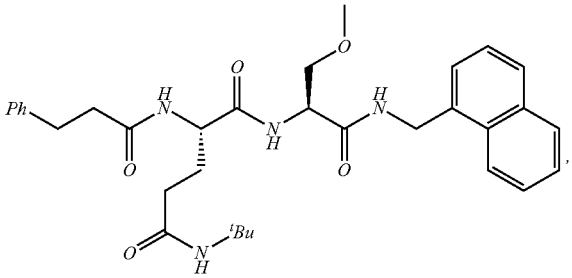
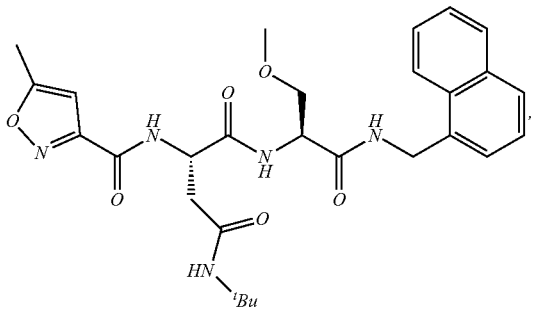
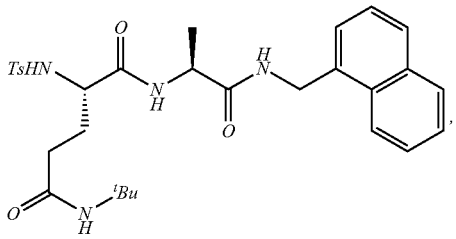
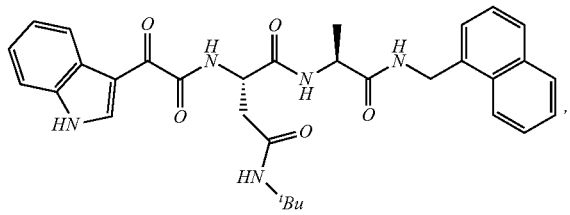
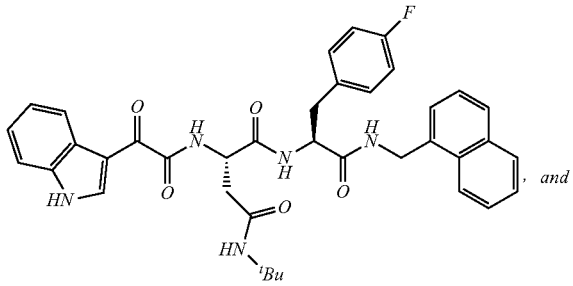
and
-continued
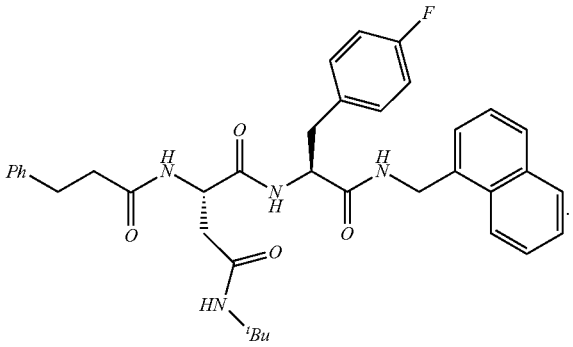
*50. The method of claim 44, wherein the compound has a structure of:*
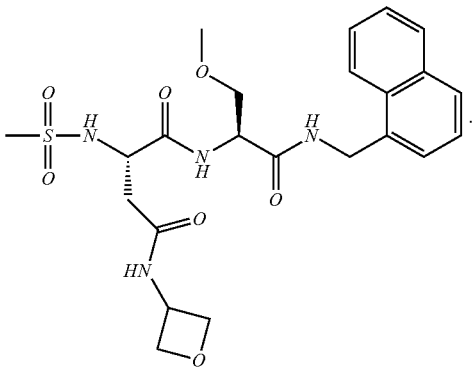
*51. The method of claim 44, wherein the compound has a structure of:*
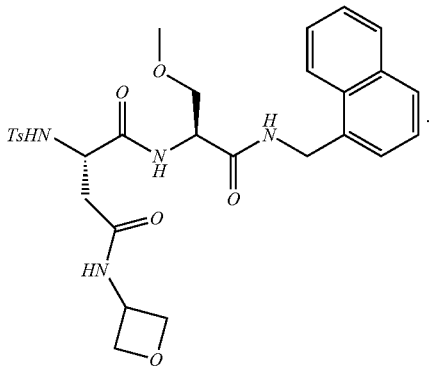
*52. The method of claim 44, wherein the compound has a structure of:*

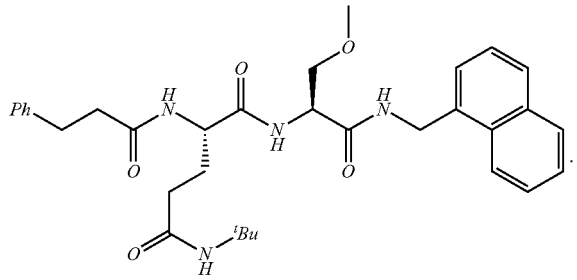

53. The method of claim 44, wherein the compound has a structure of:

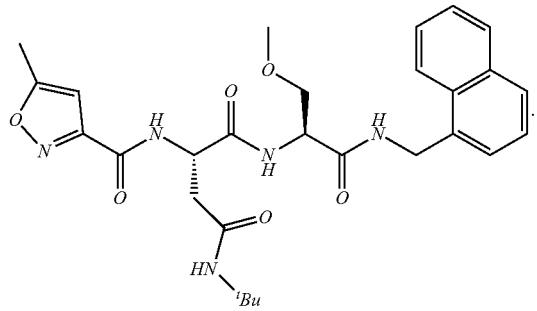

54. The method of claim 44, wherein the compound has a structure of:

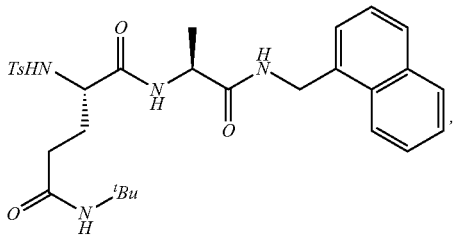

55. The method of claim 44, wherein the compound has a structure of:

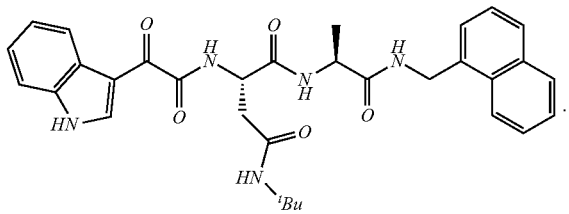

56. The method of claim 44, wherein the compound has a structure of:

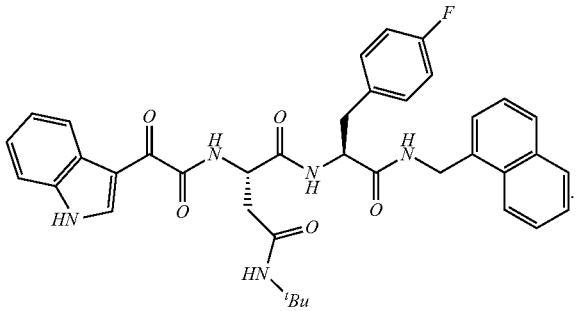

57. The method of claim 44, wherein the compound has a structure of:

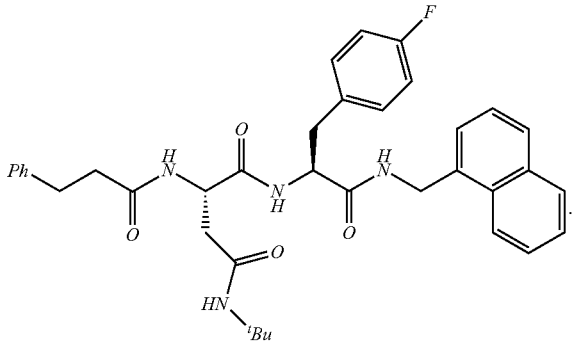

58. The method of claim 44, wherein $R^1$ is a bicyclic aryl substituted 1 time with fluoride, $R^2$ is —$CH_2OMe$, $R^3$ is

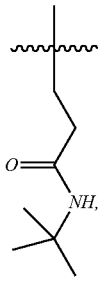

$R^4$ is

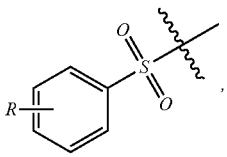

and R is Me.

59. The method of claim 44, wherein $R^1$ is a bicyclic aryl substituted 1 time with fluoride, $R^2$ is —$CH_2OMe$, $R^3$ is

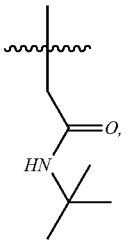

$R^4$ is

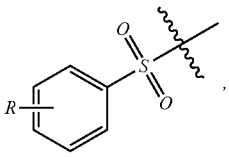

and R is Me.

60. The method of claim 44, wherein $R^1$ is a bicyclic aryl substituted 1 time with fluoride, $R^2$ is —$CH_2OMe$, $R^3$ is

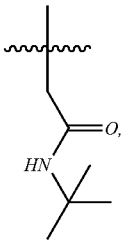

and $R^4$ is

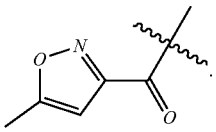

61. The method of claim 44, wherein $R^1$ is a bicyclic aryl substituted 1 time with fluoride, $R^2$ is Me, $R^3$ is

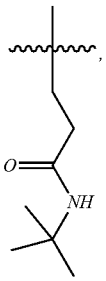

and $R^4$ is

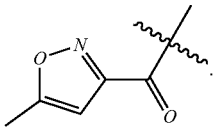

62. The method of claim 44, wherein $R^1$ is a bicyclic aryl substituted 1 time with fluoride, $R^2$ is —$CH_2Ome$, $R^3$ is

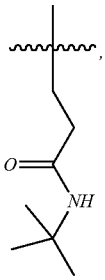

and $R^4$ is

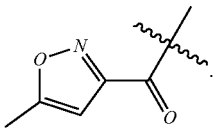

63. The method of claim 44, wherein $R^1$ is a bicyclic aryl substituted 1 time with fluoride, $R^2$ is Me, $R^3$ is

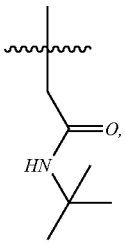

and $R^4$ is

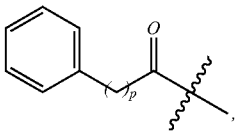

and p is 2.

64. The method of claim 44, wherein an autoimmune disorder is treated, said autoimmune disorder being selected from the group consisting of arthritis, colitis, and lupus.

65. The method of claim 44, wherein immunosuppression is provided for transplanted organs or tissues, said immunosuppression being used to prevent transplant rejection.

*66. The method of claim 44, wherein an inflammatory disorder is treated, said inflammatory disorder being Crohn's disease.*

*67. The method of claim 44, wherein cancer is treated, said cancer being selected from the group consisting of neoplastic disorders, hematologic malignancies, and lymphocytic malignancies.*

*68. A pharmaceutical composition comprising a therapeutically effective amount of the compound according to claim 24 and a pharmaceutically acceptable carrier.*

*69. The compound according to claim 24, wherein $R^1$ is a bicyclic aryl substituted 1 time with fluoride, $R^2$ is Me, $R^3$ is*

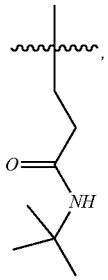

*$R^4$ is*

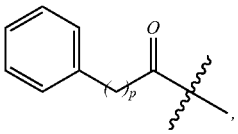

*and p is 2.*

*70. The compound according to claim 24, wherein $R^1$ is a bicyclic aryl substituted 1 time with fluoride, $R^2$ is Me, $R^3$ is*

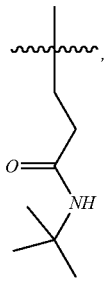

*$R^4$ is*

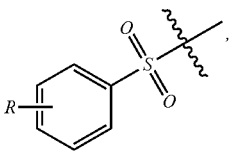

*and R is methyl.*

*71. The compound according to claim 24, wherein $R^1$ is*

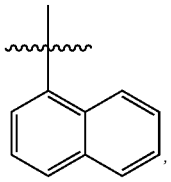

*$R^2$ is*

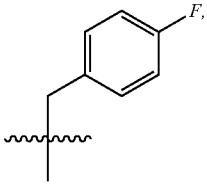

*$R^3$ is*

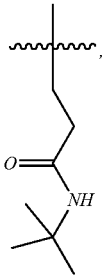

*and $R^4$ is*

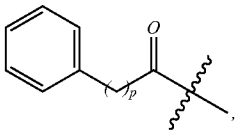

*and p is 2.*

*72. The compound according to claim 1, wherein $R^{1a}$ is*

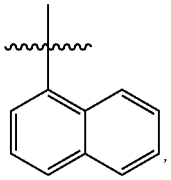

$R^{2a}$ is —$CH_2OMe$, $R^{3a}$ is
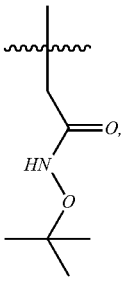
$R^{4a}$ is
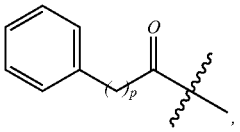
and p is 3.
73. The method of claim 44, wherein $R^1$ is a bicyclic aryl substituted 1 time with fluoride, $R^2$ is Me, $R^3$ is
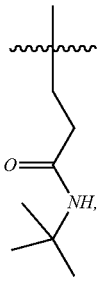
$R^4$ is
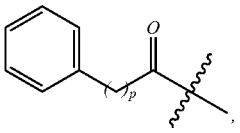
and p is 2.
74. The method of claim 44, wherein $R^1$ is a bicyclic aryl substituted 1 time with fluoride, $R^2$ is Me, $R^3$ is
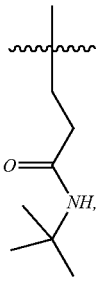
$R^4$ is
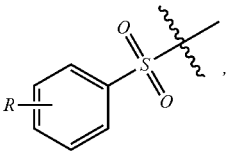
and R is methyl.
75. The method of claim 44, wherein $R^1$ is
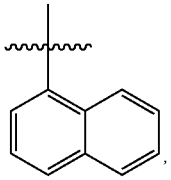
$R^2$ is
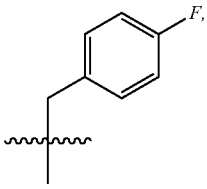
$R^3$ is
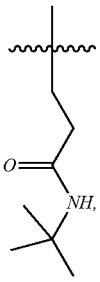

*and* $R^4$ *is*
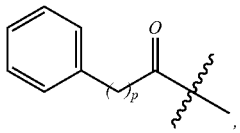
*and p is 2.*
*76. The method of claim 11, wherein* $R^{1a}$ *is*
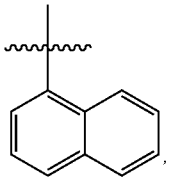
$R^{2a}$ *is* —$CH_2Ome$, $R^{3a}$ *is*
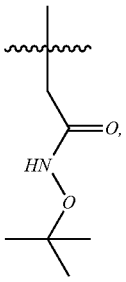
$R^{4a}$ *is*
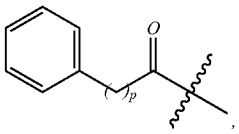
*and p is 3.*
* * * * *